US010370370B2

(12) United States Patent
Acharya et al.

(10) Patent No.: US 10,370,370 B2
(45) Date of Patent: Aug. 6, 2019

(54) AMINOBENZISOXAZOLE COMPOUNDS AS AGONISTS OF α7-NICOTINIC ACETYLCHOLINE RECEPTORS

(71) Applicant: FORUM PHARMACEUTICALS, INC., Waltham, MA (US)

(72) Inventors: Raksha Acharya, Bedford, MA (US); Duane A. Burnett, Wayland, MA (US); Matthew Gregory Bursavich, Needham, MA (US); Andrew Simon Cook, Stow, MA (US); Bryce Alden Harrison, Framingham, MA (US); Andrew J. McRiner, Melrose, MA (US)

(73) Assignee: Axovant Sciences GmbH, Basel (CH)

( * ) Notice: Subject to any disclaimer, the term of this patent is extended or adjusted under 35 U.S.C. 154(b) by 0 days.

(21) Appl. No.: 15/736,235

(22) PCT Filed: Jun. 9, 2016

(86) PCT No.: PCT/US2016/036689
§ 371 (c)(1),
(2) Date: Dec. 13, 2017

(87) PCT Pub. No.: WO2016/201096
PCT Pub. Date: Dec. 15, 2016

(65) Prior Publication Data
US 2018/0134696 A1    May 17, 2018

Related U.S. Application Data

(60) Provisional application No. 62/173,717, filed on Jun. 10, 2015.

(51) Int. Cl.
*C07D 453/02* (2006.01)
*A61P 25/00* (2006.01)

(52) U.S. Cl.
CPC ............ *C07D 453/02* (2013.01); *A61P 25/00* (2018.01)

(58) Field of Classification Search
CPC .................................................. C07D 453/02
USPC ......................................................... 546/18
See application file for complete search history.

(56) References Cited

U.S. PATENT DOCUMENTS

| | | | |
|---|---|---|---|
| 3,666,767 A | 5/1972 | Wittekind et al. |
| 3,835,142 A | 9/1974 | Wittekind et al. |
| 4,863,919 A | 9/1989 | Smith |
| 5,444,068 A | 8/1995 | Heitsch et al. |
| 5,635,525 A | 6/1997 | Heitsch et al. |
| 5,889,002 A | 3/1999 | Nielsen et al. |
| 5,935,585 A | 8/1999 | Bernardon et al. |
| 6,171,603 B1 | 1/2001 | Bernardon et al. |
| 6,225,310 B1 | 5/2001 | Nielsen et al. |
| 6,462,036 B1 | 10/2002 | Doyle et al. |
| 6,624,173 B1 | 9/2003 | Crooks et al. |
| 6,727,070 B2 | 4/2004 | Thomas et al. |
| 6,869,958 B2 | 3/2005 | Li |
| 6,911,543 B2 | 6/2005 | Walker et al. |
| 7,019,011 B2 | 3/2006 | Lesuisse et al. |
| 7,071,216 B2 | 7/2006 | Renhowe et al. |
| 7,166,629 B2 | 1/2007 | Lesuisse et al. |
| 7,176,198 B2 | 2/2007 | Piotrowski et al. |
| 7,196,109 B2 | 3/2007 | Lesuisse et al. |
| 7,214,686 B2 | 5/2007 | Bencherif et al. |
| 7,241,773 B2 | 7/2007 | Ji et al. |
| 7,253,196 B2 | 8/2007 | Henriksson et al. |
| 7,371,862 B2 | 5/2008 | Vanotti et al. |
| 7,388,118 B2 | 6/2008 | Romero et al. |
| 7,407,981 B2 | 8/2008 | Lesuisse et al. |
| 7,423,150 B2 | 9/2008 | Costales et al. |
| 7,455,978 B2 | 11/2008 | Thomas et al. |
| 7,514,450 B2 | 4/2009 | Peters et al. |
| 7,582,669 B2 | 9/2009 | Lesuisse et al. |
| 7,629,374 B2 | 12/2009 | Lesuisse et al. |
| 7,652,010 B2 | 1/2010 | Peters et al. |
| 7,674,899 B2 | 3/2010 | Peters et al. |
| 7,683,084 B2 | 3/2010 | Faghih et al. |
| 7,687,515 B2 | 3/2010 | Cai et al. |
| 7,696,238 B2 | 4/2010 | Merla et al. |
| 7,728,010 B2 | 6/2010 | Amiri et al. |
| 7,741,364 B2 | 6/2010 | Faghih et al. |
| 7,750,022 B2 | 7/2010 | Peters et al. |
| 7,786,171 B2 | 8/2010 | Schrimpf et al. |
| 7,795,453 B2 | 9/2010 | Flebner et al. |
| 7,807,700 B2 | 10/2010 | Henriksson et al. |
| 7,872,017 B2 | 1/2011 | Ji et al. |
| 7,897,766 B2 | 3/2011 | Schrimpf et al. |
| 7,902,217 B2 | 3/2011 | Xie et al. |
| 7,902,222 B2 | 3/2011 | Ji et al. |
| 7,994,223 B2 | 8/2011 | Schrimpf et al. |
| 8,076,350 B2 | 12/2011 | Ji et al. |

(Continued)

FOREIGN PATENT DOCUMENTS

EP    0327335    10/1992
JP    3087763    9/2000

(Continued)

OTHER PUBLICATIONS

International Search Report dated Feb. 19, 2016 for PCT/US2015/065497 (4 pages).

(Continued)

*Primary Examiner* — Nizal S Chandrakumar
(74) *Attorney, Agent, or Firm* — Jones Day

(57) ABSTRACT

The present invention relates to novel aminobenzisoxazole compounds, and pharmaceutical compositions of the same, that are suitable as agonists or partial agonists of Alpha7-nAChR, and methods of preparing these compounds and compositions, and the use of these compounds and compositions in methods of maintaining, treating and/or improving cognitive function. In particular, methods of administering the compound or composition to a patient in need thereof, for example a patient with a cognitive deficiency and/or a desire to enhance cognitive function, that may derive a benefit therefrom.

13 Claims, No Drawings

(56) References Cited

U.S. PATENT DOCUMENTS

| | | |
|---|---|---|
| 8,163,914 B2 | 4/2012 | Scanio et al. |
| 8,163,915 B2 | 4/2012 | Bunnelle |
| 8,163,916 B2 | 4/2012 | Schrimpf et al. |
| 8,168,791 B2 | 5/2012 | Shi et al. |
| 8,173,667 B2 | 5/2012 | Feuerback et al. |
| 8,273,891 B2 | 9/2012 | Schumacher et al. |
| 8,278,320 B2 | 10/2012 | McDonald et al. |
| 8,288,389 B2 | 10/2012 | Best et al. |
| 8,299,108 B2 | 10/2012 | Amiri et al. |
| 8,309,577 B2 | 11/2012 | Cook et al. |
| 8,314,119 B2 | 11/2012 | Schrimpf et al. |
| 8,383,657 B2 | 2/2013 | Faghih et al. |
| 8,415,382 B2 | 4/2013 | Costales et al. |
| 8,431,575 B2 | 4/2013 | Gohimukkula et al. |
| 8,445,690 B2 | 5/2013 | Bridgewater et al. |
| 8,470,813 B2 | 6/2013 | Faghih et al. |
| 8,481,555 B2 | 7/2013 | Lentz et al. |
| 8,507,516 B2 | 8/2013 | McDonald et al. |
| 8,536,221 B2 | 9/2013 | Mortell et al. |
| 8,541,592 B2 | 9/2013 | Henriksson et al. |
| 8,546,410 B2 | 10/2013 | Liu et al. |
| 8,586,746 B2 | 11/2013 | Schrimpf et al. |
| 8,609,713 B2 | 12/2013 | Faghih et al. |
| 8,614,330 B2 | 12/2013 | Amiri et al. |
| 8,648,085 B2 | 2/2014 | Mittelbiberach et al. |
| 8,686,011 B2 | 4/2014 | Henriksson et al. |
| 8,741,900 B2 | 6/2014 | Gohimukkula et al. |
| 8,778,939 B2 | 7/2014 | Nichols et al. |
| 8,841,289 B2 | 9/2014 | Ratcliffe et al. |
| 8,846,661 B2 | 9/2014 | Schrimpf et al. |
| 8,853,241 B2 | 10/2014 | Ji et al. |
| 8,946,432 B2 | 2/2015 | Sinha et al. |
| 8,980,888 B2 | 3/2015 | Okano et al. |
| 8,980,889 B2 | 3/2015 | Okano et al. |
| 8,987,453 B2 | 3/2015 | Schrimpf et al. |
| 9,012,447 B2 | 4/2015 | Hitchcock et al. |
| 9,045,461 B2 | 6/2015 | Gohimukkula et al. |
| 2002/0028808 A1 | 3/2002 | Hansen |
| 2002/0035106 A1 | 3/2002 | Hansen et al. |
| 2003/0109519 A1 | 3/2003 | Sturis |
| 2003/0125323 A1 | 7/2003 | Stuns |
| 2003/0235583 A1 | 12/2003 | Sturis et al. |
| 2004/0019053 A1 | 1/2004 | Roark |
| 2004/0043983 A1 | 3/2004 | Li |
| 2004/0147522 A1 | 7/2004 | Wong et al. |
| 2004/0192594 A1 | 9/2004 | Reid et al. |
| 2005/0186591 A1 | 8/2005 | Bumcrot et al. |
| 2005/0239853 A1 | 10/2005 | Barf et al. |
| 2005/0245567 A1 | 11/2005 | Peters et al. |
| 2006/0116395 A1 | 6/2006 | Piotrowski et al. |
| 2007/0082350 A1 | 4/2007 | Landfield et al. |
| 2007/0185086 A1 | 8/2007 | Bencherif et al. |
| 2007/0281938 A1 | 12/2007 | Henriksson et al. |
| 2008/0268044 A1 | 10/2008 | Appleby et al. |
| 2009/0005390 A1 | 1/2009 | Peters et al. |
| 2009/0099099 A1 | 4/2009 | Wang et al. |
| 2009/0170869 A1 | 7/2009 | Best et al. |
| 2009/0197860 A1 | 8/2009 | Ji et al. |
| 2009/0312356 A1 | 12/2009 | De Micheli et al. |
| 2010/0298289 A1 | 11/2010 | Raphy et al. |
| 2010/0305089 A1 | 12/2010 | Ji et al. |
| 2011/0014283 A1 | 1/2011 | Clarke et al. |
| 2011/0020447 A1 | 1/2011 | Clarke et al. |
| 2011/0082107 A1 | 4/2011 | Henriksson et al. |
| 2011/0189280 A1 | 8/2011 | Clarke et al. |
| 2011/0262407 A1 | 10/2011 | Bencherif et al. |
| 2012/0035178 A1 | 2/2012 | Cook et al. |
| 2012/0035189 A1 | 2/2012 | Cook et al. |
| 2012/0065219 A1 | 3/2012 | Ji et al. |
| 2012/0190704 A1 | 7/2012 | Schrimpf et al. |
| 2012/0190706 A1 | 7/2012 | Scanio et al. |
| 2012/0196890 A1 | 8/2012 | Bunnelle |
| 2012/0202804 A1 | 8/2012 | Hatfield et al. |
| 2012/0202828 A1 | 8/2012 | Hatfield et al. |
| 2012/0245195 A1 | 9/2012 | Chen et al. |
| 2012/0288501 A1 | 11/2012 | Amiri et al. |
| 2013/0123278 A1 | 5/2013 | Edwards et al. |
| 2013/0131064 A1 | 5/2013 | Cook et al. |
| 2013/0217683 A1 | 8/2013 | Xie et al. |
| 2013/0224195 A1 | 8/2013 | Costales et al. |
| 2013/0225584 A1 | 8/2013 | Andreotti et al. |
| 2013/0231365 A1 | 9/2013 | Koenig |
| 2013/0252901 A1 | 9/2013 | Mediannikov et al. |
| 2013/0310419 A1 | 11/2013 | Sinha et al. |
| 2013/0331387 A1 | 12/2013 | Sinha et al. |
| 2014/0018327 A1 | 1/2014 | Sinha et al. |
| 2014/0024644 A1 | 1/2014 | Hitchcock et al. |
| 2014/0221377 A1 | 8/2014 | Cook et al. |
| 2014/0234270 A1 | 8/2014 | Bencherif et al. |
| 2015/0094309 A1 | 4/2015 | Cook et al. |
| 2015/0132327 A1 | 5/2015 | Okano et al. |
| 2015/0133448 A1 | 5/2015 | Okano et al. |
| 2015/0158867 A1 | 6/2015 | Schrirrpf et al. |
| 2015/0166536 A1 | 6/2015 | Okano et al. |
| 2015/0275303 A1 | 10/2015 | Feuerbach et al. |
| 2017/0044155 A1* | 2/2017 | Acharya ............... C07D 453/00 |

FOREIGN PATENT DOCUMENTS

| | | |
|---|---|---|
| JP | 2003-267977 | 9/2003 |
| WO | WO 1993/009116 | 5/1993 |
| WO | WO 2001/066546 | 9/2001 |
| WO | WO 2002/100858 | 12/2002 |
| WO | WO 2004/022544 | 3/2004 |
| WO | WO 2004/039366 | 5/2004 |
| WO | WO 2004/039815 | 5/2004 |
| WO | WO 2004/062662 | 7/2004 |
| WO | WO 2007/080191 | 7/2007 |
| WO | WO 2008/000469 | 1/2008 |
| WO | WO 2009/017454 | 2/2009 |
| WO | WO 2009/050227 | 4/2009 |
| WO | WO 2009/083526 | 7/2009 |
| WO | WO 2011/036167 | 3/2011 |
| WO | WO 2012/108490 | 8/2012 |
| WO | WO 2013/132380 | 9/2013 |
| WO | WO 2013/174947 | 11/2013 |
| WO | WO 2013/177024 | 11/2013 |
| WO | WO 2014/072957 | 5/2014 |
| WO | WO 2014/083003 | 6/2014 |
| WO | WO 2014/111839 | 7/2014 |
| WO | WO 2014/141091 | 9/2014 |
| WO | WO 2014/195848 | 12/2014 |
| WO | WO 2014/203150 | 12/2014 |
| WO | WO 2015/066371 | 5/2015 |
| WO | WO 2016/100184 | 6/2016 |

OTHER PUBLICATIONS

International Search Report dated Aug. 16, 2016 for PCT/US2016/036689 (3 pages).

International Search Report dated Oct. 27, 2016 for PCT/US2016/046367 (3 pages).

International Search Report dated Jan. 10, 2017 for PCT/US2016/056607 (3 pages).

European Search Report dated Apr. 26, 2018 for EP 15870786.9 (7 pages).

Albuquerque, E. X. et al. "Modulation of Nicotinic Receptor Activity in the Central Nervous System: A Novel Approach to the Treatment of Alzheimer Disease," Alzheimer Disease and Associated Disorders, 15:1 (2001) S19-S25.

Compound Summary for CID 160186, *PubChem Open Chemistry Database*, NIH U.S. National Library of Medicine, National Center for Biotechnology Information, Entry Creation Date: Jul. 11, 2005.

D'Andrea, Michael R. et al. "Targeting the Alpha 7 Nicotinic Acetylcholine Receptor to Reduce Amyloid accumulation in Alzheimer's Disease Pyramidal Neurons," *Current Pharmaceutical Design*, 12 (2006) 677-684.

(56) References Cited

OTHER PUBLICATIONS

Deutsch, Stephen I. et al. "Progressive Worsening of Adaptive Functions in Down Syndrome May be Mediated by the Complexing of Soluble Aβ Peptides with the Alpha7 Nicotinic Acetylcholine Receptor: Therapeutic Implications," *Clinical Neuropharmacology*, 26:5 (2003) 277-283.

Haydar, Simon N. et al. "SAR and Biological Evaluation of SEN12333/WAY-317538: Novel Alpha7 Nicotinic Acetylcholine Receptor Agonist," *Bioorganic & Medicinal Chemistry*, 17 (2009) 5247-5258.

Jenkins, Jeremy L. et al. "A 3D Similarity Method for Scaffold Hopping from Known Drugs or Natural Ligands to New Chemotypes," J. Med. Chem., 47 (2004) 6144-6159.

Jeyarasasingam, G. et al. "Stimulation of Non-Alpha7 Nicotinic Receptors Partially Protects Dopaminergic Neurons from 1-Methyl-4-Phenylpyridinium-Induced Toxicity in Culture," *Neuroscience*, 109:2 (2002) 275-285.

Marrero, Mario B. et al. "An α7 Nicotinic Acetylcholine Receptor-Selective Agonist Reduces Weight Gain and Metabolic Changes in a Mouse Model of Diabetes," *The Journal of Pharmacology and Experimental Therapeutics*, 332:1 (Jan. 1, 2010) 173-180.

Mazurov, Anatoly et al. "2-(Arylmethyl)-3-substituted Quinuclidines as Selective α7 Nicotinic Receptor Ligands," *Bioorganic & Medicinal Chemistry Letters*, 15:8 (Apr. 15, 2005) 2073-2077.

Nagele, R. G. et al. "Intracellular Accumulation of β-Amyloid$^{1-42}$ in Neurons is Facilitated by the Alpha7 Nicotinic Acetylcholine Receptor in Alzheimer's Disease," *Neuroscience*, 11:2 (2002) 199-211.

Nordberg, Agneta "Neuroprotection in Alzheimer's Disease—New Strategies for Treatment," *Neurotoxicity Research*, 2 (2000) 157-165.

Wang, Hoau-Yan et al. "Dissociating β-Amyloid from Alpha7 Nicotinic Acetylcholine Receptor by a Novel Therapeutic Agent, S24795, Normalizes Alpha7 Nicotinic Acetylcholine and NMDA Receptor Function in Alzheimer's Disease Brain," *The Journal of Neuroscience*, 29:35 (Sep. 2, 2009) 10961-10973.

\* cited by examiner

AMINOBENZISOXAZOLE COMPOUNDS AS AGONISTS OF α7-NICOTINIC ACETYLCHOLINE RECEPTORS

CROSS REFERENCE TO RELATED APPLICATION

This application is the National Phase application of International Application No. PCT/US2016/036689, filed Jun. 9, 2017, which designates the United States and was published in English, and which further claims the benefit of priority from U.S. Provisional Application No. 62/173,717, filed Jun. 10, 2015. The foregoing related applications, in their entirety, are incorporated herein by reference.

FIELD OF THE INVENTION

The present invention relates to novel aminobenzisoxazole compounds, and pharmaceutical compositions of the same, that are suitable as agonists or partial agonists of the α7-nicotinic acetylcholine receptor, and methods of preparing these compounds and compositions, and the use of these compounds and compositions in methods of maintaining, treating and/or improving cognitive function. In particular, methods of administering the compound or composition to a patient in need thereof, for example a patient with a cognitive deficiency and/or a desire to enhance cognitive function, that may derive a benefit therefrom.

BACKGROUND OF THE INVENTION

The prevalence of cognitive disease, for example dementia in North America, is approximately 6 to 10% of the population, with Alzheimer's disease accounting for a substantial portion of these cases. Many forms of cognitive disease represent a steadily growing medical and social problem of our aging societies around the world. Some believe the main pathological features may relate to intraneuronal neurofibrillary tangles, formation of amyloid beta plaques and/or neurodegeneration of mainly cholinergic and, in later stages, also serotonergic, noradrenergic, and other neurons, resulting in deficiencies of acetylcholine and other neurotransmitters. Some theories suggest that the gradual development of an acetylcholine signaling deficiency may be responsible for the early clinical manifestations of cognitive disease. Consequently, some believe that compounds that improve cholinergic functioning, such as acetylcholine esterase inhibitors may ameliorate the cognitive deficits in patients with cognitive disease. The most widely used acetylcholine esterase inhibitor is donepezil hydrochloride (Aricept®).

Nicotinic acetylcholine receptors (nAChR) form a large family of ion channels which are activated by the messenger acetylcholine which is produced in the body (Galzi and Changeux, Neuropharmacol. 1995, 34, 563-582). A functional nAChR consists of five subunits which may be different (certain combinations of α1-9 and β1-4, γ, δ, ε subunits) or identical (α7-9). This leads to the formation of a diversity of subtypes which differ in the distribution in the muscles, the nervous system and other organs (McGehee and Role, Annu. Rev. Physiol. 1995, 57, 521-546). Activation of nAChR leads to influx of cations into the cell and to stimulation of nerve cells or muscle cells. Selective activation of individual nAChR subtypes restricts this stimulation to the cell types which have a corresponding subtype and is thus able to avoid unwanted side effects such as, for example, stimulation of nAChR in the muscles. Clinical experiments with nicotine and experiments in various animal models indicate that central nicotinic acetylcholine receptors are involved in learning and memory processes (e.g. Rezvani and Levin, Biol. Psychiatry 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Seguela et al., J. Neurosci. 1993, 13, 596-604). The α7 nAChR has a particularly high permeability for calcium ions, modulates neurotransmission, influences the growth of axons and, in this way, modulates neuronal plasticity (Broide and Leslie, Mol. Neurobiol. 1999, 20, 1-16).

WO 2003/055878 describes a variety of agonists of the α7 nAChR said to be useful for improving cognition. WO 2003/055878 suggests that certain agonists of the α7 nAChR are useful for improving perception, concentration, learning or memory, especially after cognitive impairments like those occurring for example in situations/diseases/syndromes such as mild cognitive impairment, age-associated learning and memory impairments, age-associated memory loss, Alzheimer's disease, schizophrenia and certain other cognitive disorders.

BRIEF SUMMARY OF THE INVENTION

An aspect of the invention provides an aminobenzisoxazole compound represented by Formula (Ia) or Formula (Ib):

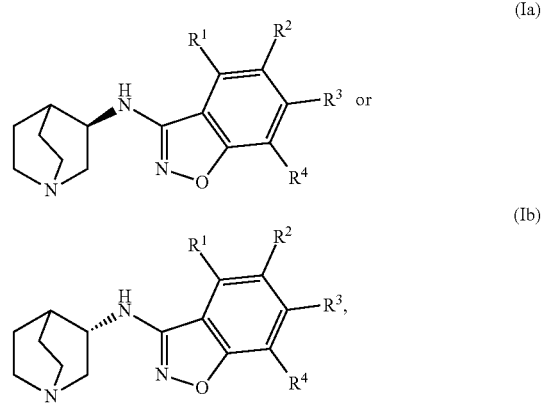

wherein:
$R^1$, $R^2$, $R^3$, and $R^4$ independently represent —H, -D, halogen radical, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —N($R^5$)($R^6$), —(CO)N($R^5$)($R^6$), —$NR^5$(CO)($R^6$), —$SO_2C_1$-$C_4$-alkyl, —$SO_2$N($R^5$)($R^6$), —$(CH_2)_m SO_2C_1$-$C_4$-alkyl, —$(CH_2)_m SO_2$N($R^5$)($R^6$), —N($R^5$)$SO_2C_1$-$C_4$-alkyl, an aryl radical, or a heteroaryl radical; wherein the alkyl portion of the unbranched $C_1$-$C_4$-alkyl radical, the branched $C_3$-$C_4$-alkyl radical, the $C_3$-$C_6$-cycloalkyl radical, the unbranched —$OC_1$-$C_4$-alkyl, the branched or cyclic —$OC_3$-$C_4$-alkyl, the —$SO_2C_1$-$C_4$-alkyl, the —$(CH_2)_m SO_2C_1$-$C_4$-alkyl, or the —N($R^5$)$SO_2C_1$-$C_4$-alkyl, may be independently substituted with up to 5 radical substituents comprising: -D, halogen radical, =O, —$OR^5$, —$(CH_2)_m OR^5$, —N($R^5$)($R^6$), —$NR^5$(CO)($R^6$), —$(CH_2)_m N(R^5)(R^6)$, —$SO_2C_1$-$C_4$-alkyl, —$SO_2$N($R^5$)($R^6$), —$(CH_2)_m SO_2C_1$-$C_4$-alkyl, —(CH₂)ₘSO₂N(R⁵)(R⁶), —N(R⁵)SO₂C₁-C₄-alkyl, —(CO)(CH₂)ₘR⁵, —(CO)N(R⁵)(R⁶), an unbranched C₁-C₆-alkyl radical, a branched C₃-C₆-alkyl radical, a C₃-C₆-cycloalkyl radical, a C₁-C₆-hydroxyalkyl radical, a C₁-C₂-haloalkyl radical, or —OC₁-C₂-haloalkyl radical; and wherein the aryl radical or the heteroaryl radical may be independently substituted with up to 5 radical substituents comprising: -D, halogen radical, —CN, —OR⁵, —(CH₂)ₘOR⁵, —N(R⁵)(R⁶), —NR⁵(CO)(R⁶), —(CH₂)ₘN(R⁵)(R⁶), —SO₂C₁-C₄-alkyl, —SO₂N(R⁵)(R⁶), —(CH₂)ₘSO₂C₁-C₄-alkyl, —(CH₂)ₘSO₂N(R⁵)(R⁶), —N(R⁵)SO₂C₁-C₄-alkyl, —(CO)(CH₂)ₘR⁵, —(CO)N(R⁵)(R⁶), an unbranched C₁-C₆-alkyl radical, a branched C₃-C₆-alkyl radical, a C₃-C₆-cycloalkyl radical, a C₁-C₆-hydroxyalkyl radical, a C₁-C₂-haloalkyl radical, or —OC₁-C₂-haloalkyl radical;

R⁵ and R⁶ independently represent —H; an unbranched C₁-C₆-alkyl radical, a branched C₃-C₆-alkyl radical; a C₃-C₆-cycloalkyl radical; or the N(R⁵)(R⁶) moiety forms a cycle, wherein R⁵ and R⁶ taken together represent a C₂-C₆-alkyl di-radical or a (3-6 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H, an unbranched C₁-C₄-alkyl radical, a branched C₃-C₄-alkyl radical, a C₃-C₄-cycloalkyl radical, —(CO)-unbranched C₁-C₄-alkyl, —(CO)-branched C₃-C₄-alkyl, —(SO₂)-unbranched C₁-C₄-alkyl, or —(SO₂)-branched C₃-C₄-alkyl, and with the further proviso that when the at least one ring atom is sulfur, the sulfur may be independently substituted with 0 to 2 =O; wherein the C₂-C₆-alkyl di-radical or the alkyl portion of said (3-6 membered)-heteroalkyl di-radical may be independently substituted with up to 5 radical substituents comprising: -D, halogen radical, =O, an unbranched C₁-C₆-alkyl radical, or a branched C₃-C₆-alkyl radical; and m independently represents an integer from 1 to 6; or a pharmaceutically acceptable salt thereof.

An aspect of the invention relates to the aminobenzisoxazole compound represented by Formula (Ia):

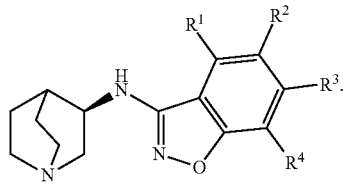

(Ia)

An aspect of the invention relates to the aminobenzisoxazole compound represented by Formula (Ib):

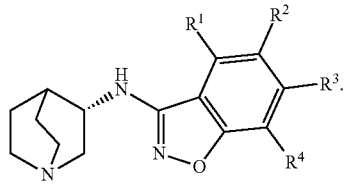

(Ib)

An aspect of the invention relates to a single stereoisomer of the aminobenzisoxazole compound represented by Formula (Ia) or Formula (Ib), or a pharmaceutically acceptable salt thereof.

An aspect of the invention relates to a single enantiomer or a single diastereomer of the aminobenzisoxazole compound represented by Formula (Ia) or Formula (Ib), or a pharmaceutically acceptable salt thereof.

An aspect of the invention relates to a pharmaceutical composition comprising the aminobenzisoxazole compound represented by Formula (Ia) or Formula (Ib), or a pharmaceutically acceptable salt thereof; and at least one pharmaceutically acceptable carrier, excipient or diluent.

An aspect of the invention relates to a method comprising administering to a patient in need thereof an effective dose of an aminobenzisoxazole compound represented by Formula (Ia) or Formula (Ib), or a pharmaceutically acceptable salt thereof, or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of treating a patient in need thereof, comprising: administering to the patient an effective dose of an aminobenzisoxazole compound represented by Formula (Ia) or Formula (Ib), or a pharmaceutically acceptable salt thereof, or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of maintaining, treating, curing and/or improving at least one cognitive function in a patient in need thereof, comprising: administering to the patient an effective dose of an aminobenzisoxazole compound represented by Formula (Ia) or Formula (Ib), or a pharmaceutically acceptable salt thereof, or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of maintaining, treating, curing and/or improving at least one cognitive function in a patient in need thereof, comprising: administering to the patient an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of treating a patient diagnosed as having a cognitive impairment, comprising: administering to the an effective dose of an aminobenzisoxazole compound represented by Formula (Ia) or Formula (Ib), or a pharmaceutically acceptable salt thereof; or administering to the patient an effective dose of a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of treating a patient in need thereof, comprising: administering to the patient, for example, a patient diagnosed with having a cognitive impairment, Limited Cognitive Impairment, Mild Cognitive Impairment, Alzheimer's disease, and/or schizophrenia, an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent; such that the patient may derive a benefit therefrom.

Another aspect of the invention provides a method of treating one or more symptoms associated with a cognitive impairment, comprising administering to a patient an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent; wherein the patient suffers from, or has been diagnosed as having, a cognitive impairment.

Another aspect of the invention provides a method of improving cognition of a patient in need thereof, comprising: administering to the patient an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of improving cognition in a patient suffering from a cognitive impairment, such as a cognitive impairment associated with either schizophrenia or Alzheimer's disease, for example mild Alzheimer's disease, moderate Alzheimer's disease, severe Alzheimer's disease, or mild-to-moderate Alzheimer's disease, comprising administering an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of treating a patient suffering from, diagnosed with having, or suffers from one or more symptoms associated with, a cognitive impairment, for example, Alzheimer's disease, dementia of an Alzheimer's type, MCI, LCI, or schizophrenia, comprising: administering to the patient an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent. For example, the method of treating a patient suffering from, diagnosed with having, or suffers from one or more symptoms associated with, a cognitive impairment, may provide said patient at least one of the following: (i) treats, minimizes progression of, prevents the deterioration of, or reduces the rate of detioraration of, one or more symptoms associated with the cognitive impairment; (ii) treats the cognitive impairment; (iii) improves cognition in said cognitively impaired patient; (iv) improves one or more behavioral symptoms associated with the cognitive impairment; (v) provides a pro-cognitive effect; (vi) provides a pro-cognitive effect in at least one of the following: visual motor, learning, delayed memory, or executive function, or (vii) provides a positive effect on clinical function in said cognitively impaired patient.

Another aspect of the invention provides a method of treating a patient previously treated, or currently being treated, with an AChEI, that is suffering from, or has been diagnosed with having, a cognitive impairment, for example, Alzheimer's disease, dementia of an Alzheimer's type, MCI, LCI, or schizophrenia, comprising: administering to the patient an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluents; wherein the method improves one or more symptoms associated with the cognitive impairment in the previously, or currently, AChEI treated patient.

Another aspect of the invention provides a method of treating a patient suffering from, or diagnosed with having a cognitive impairment, comprising: administering to the patient an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent; wherein the method provides a positive effect on cognition or a positive effect on clinical function in said cognitively impaired patient, and wherein said patient has been previously treated or is currently being treated with an AChEI.

Another aspect of the invention provides a method of improving cognition in a patient diagnosed as having a probable cognitive disease, comprising: administering to the patient an effective dose of an aminobenzisoxazole compound represented by Formula (Ia) or Formula (Ib), or a pharmaceutically acceptable salt thereof; or administering to the patient an effective dose of a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of improving or substantially improving one or more symptoms in a cognitive disease patient, comprising: administering to the patient an effective dose of an aminobenzisoxazole compound represented by Formula (Ia) or Formula (Ib), or a pharmaceutically acceptable salt thereof; or administering to the patient an effective dose of a pharmaceutical composition comprising the effective dose of the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of slowing the rate of deterioration of at least one symptom in a cognitive disease patient, comprising: administering to the patient an effective dose of an aminobenzisoxazole compound represented by Formula (Ia) or Formula (Ib), or a pharmaceutically acceptable salt thereof; or administering to the patient the pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of treating one or more symptoms associated with a cognitive disease in a patient suffering therefrom, comprising: administering to the patient an effective dose of an aminobenzisoxazole compound represented by Formula (Ia) or Formula (Ib), or a pharmaceutically acceptable salt thereof; or administering to the patient an effective dose of a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent Another aspect provides a method of minimizing or substantially halting the rate of progression of one or more cognitive diseases in a patient suffering from a cognitive disease, comprising: administering to the patient an effective dose of an aminobenzisoxazole compound represented by Formula (Ia) or Formula (Ib), or a pharmaceutically acceptable salt thereof; or administering to the patient an effective dose of a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of substantially stopping or reversing progression of one or more cognitive diseases, in a patient suffering therefrom, comprising: administering to the patient an effective dose of an aminobenzisoxazole compound represented by Formula (Ia) or Formula (Ib), or a pharmaceutically acceptable salt thereof; or administering to the patient an effective dose of a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of treating dementia, comprising: administering to a patient in need thereof an effective amount of an aminobenzisoxazole compound represented by Formula (Ia) or Formula (Ib), or a pharmaceutically acceptable salt thereof; or administering to the patient an effective dose of a pharmaceutical composition comprising the effective amount of the aminobenzisoxazole compound represented by Formula (Ia) or Formula (Ib), or a pharmaceutically acceptable salt thereof, and at least one pharmaceutically acceptable carrier, excipient or diluent; wherein said effective amount is administered in an effective dose.

Another aspect of the invention provides a method of treating dementia, comprising: administering to a patient in need thereof an effective amount of an aminobenzisoxazole compound represented by Formula (Ia) or Formula (Ib), or a pharmaceutically acceptable salt thereof; or administering to the patient an effective dose of a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

Another aspect of the invention provides a method of treating dementia, comprising: administering to a patient in need thereof an effective amount of an aminobenzisoxazole compound represented by Formula (Ia) or Formula (Ib), or a pharmaceutically acceptable salt thereof, wherein the aminobenzisoxazole compound represented by Formula (Ia) or Formula (Ib), or a pharmaceutically acceptable salt thereof, is administered in the form of a pharmaceutical composition comprising at least one pharmaceutically acceptable carrier, excipient or diluent.

Another aspect of the invention provides a method of treating dementia, comprising: administering to a patient in need thereof an effective amount of an aminobenzisoxazole compound represented by Formula (Ia) or Formula (Ib), or a pharmaceutically acceptable salt thereof; or administering to the patient an effective dose of a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent; wherein the pharmaceutical composition is in the form of a tablet.

Another aspect of the invention provides a method of treating a patient having a cognitive disease and being administered an acetylcholine esterase inhibitor, comprising: administering to a patient in need thereof an effective amount of an aminobenzisoxazole compound represented by Formula (Ia) or Formula (Ib), or a pharmaceutically acceptable salt thereof; or administering to the patient an effective dose of a pharmaceutical composition comprising an aminobenzisoxazole compound represented by Formula (Ia) or Formula (Ib), or a pharmaceutically acceptable salt thereof, and at least one pharmaceutically acceptable carrier, excipient or diluent; wherein the treatment comprises halting the administration of the acetylcholine esterase inhibitor prior to treating with the aminobenzisoxazole compound represented by Formula (Ia) or Formula (Ib), or a pharmaceutically acceptable salt thereof.

DETAILED DESCRIPTION OF THE INVENTION

An embodiment of the present invention provides an aminobenzisoxazole compound represented by Formula (Ia) or Formula (Ib):

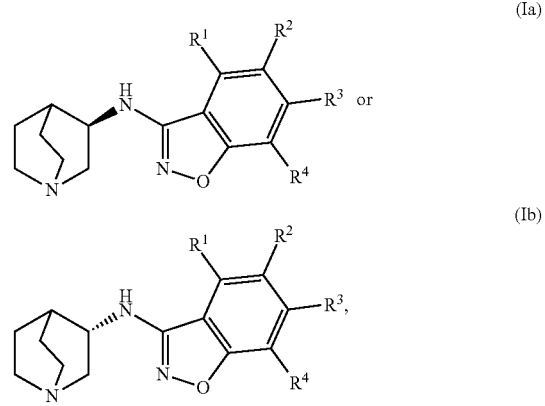

wherein:
$R^1$, $R^2$, $R^3$, and $R^4$ independently represent —H, -D, halogen radical, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —$N(R^5)(R^6)$, —(CO)$N(R^5)(R^6)$, —$NR^5$(CO)($R^6$), —$SO_2C_1$-$C_4$- alkyl, —SO$_2$N(R$^5$)(R$^6$), —(CH$_2$)$_m$SO$_2$C$_1$-C$_4$-alkyl, —(CH$_2$)$_m$SO$_2$N(R$^5$)(R$^6$), —N(R$^5$)SO$_2$C$_1$-C$_4$-alkyl, an aryl radical, or a heteroaryl radical; wherein the alkyl portion of the unbranched C$_1$-C$_4$-alkyl radical, the branched C$_3$-C$_4$-alkyl radical, the C$_3$-C$_6$-cycloalkyl radical, the unbranched —OC$_1$-C$_4$-alkyl, the branched or cyclic —OC$_3$-C$_4$-alkyl, the —SO$_2$C$_1$-C$_4$-alkyl, the —(CH$_2$)$_m$SO$_2$C$_1$-C$_4$-alkyl, or the —N(R$^5$)SO$_2$C$_1$-C$_4$-alkyl, may be independently substituted with up to 5 radical substituents comprising: -D, halogen radical, =O, —OR$^5$, —(CH$_2$)$_m$OR$^5$, —N(R$^5$)(R$^6$), —NR$^5$(CO)(R$^6$), —(CH$_2$)$_m$N(R$^5$)(R$^6$), —SO$_2$C$_1$-C$_4$-alkyl, —SO$_2$N(R$^5$)(R$^6$), —(CH$_2$)$_m$SO$_2$C$_1$-C$_4$-alkyl, —(CH$_2$)$_m$SO$_2$N(R$^5$)(R$^6$), —N(R$^5$)SO$_2$C$_1$-C$_4$-alkyl, —(CO)(CH$_2$)$_m$R$^5$, —(CO)N(R$^5$)(R$^6$), an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein the aryl radical or the heteroaryl radical may be independently substituted with up to 5 radical substituents comprising: -D, halogen radical, —CN, —OR$^5$, —(CH$_2$)$_m$OR$^5$, —N(R$^5$)(R$^6$), —NR$^5$(CO)(R$^6$), —(CH$_2$)$_m$N(R$^5$)(R$^6$), —SO$_2$C$_1$-C$_4$-alkyl, —SO$_2$N(R$^5$)(R$^6$), —(CH$_2$)$_m$SO$_2$C$_1$-C$_4$-alkyl, —(CH$_2$)$_m$SO$_2$N(R$^5$)(R$^6$), —N(R$^5$)SO$_2$C$_1$-C$_4$-alkyl, —(CO)(CH$_2$)$_m$R$^5$, —(CO)N(R$^5$)(R$^6$), an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical;

R$^5$ and R$^6$ independently represent —H; an unbranched C$_1$-C$_6$-alkyl radical, a branched C$_3$-C$_6$-alkyl radical; a C$_3$-C$_6$-cycloalkyl radical; or the N(R$^5$)(R$^6$) moiety forms a cycle, wherein R$^5$ and R$^6$ taken together represent a C$_2$-C$_6$-alkyl di-radical or a (3-6 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H, an unbranched C$_1$-C$_4$-alkyl radical, a branched C$_3$-C$_4$-alkyl radical, a C$_3$-C$_4$-cycloalkyl radical, —(CO)-unbranched C$_1$-C$_4$-alkyl, —(CO)-branched C$_3$-C$_4$-alkyl, —(SO$_2$)-unbranched C$_1$-C$_4$-alkyl, or —(SO$_2$)-branched C$_3$-C$_4$-alkyl, and with the further proviso that when the at least one ring atom is sulfur, the sulfur may be independently substituted with 0 to 2 =O; wherein the C$_2$-C$_6$-alkyl di-radical or the alkyl portion of said (3-6 membered)-heteroalkyl di-radical may be independently substituted with up to 5 radical substituents comprising: -D, halogen radical, =O an unbranched C$_1$-C$_6$-alkyl radical, or a branched C$_3$-C$_6$-alkyl radical; and m independently represents an integer from 1 to 6;

or a pharmaceutically acceptable salt thereof.

In certain embodiments, the aminobenzisoxazole compound represented by Formula (Ia) or Formula (Ib), may comprise R$^1$, R$^2$, R$^3$, and R$^4$ independently representing —H, -D, halogen radical, —CN, an unbranched C$_1$-C$_3$-alkyl radical, a branched C$_3$-C$_4$-alkyl radical, a C$_3$-C$_5$-cycloalkyl radical, an unbranched —OC$_1$-C$_4$-alkyl, a branched or cyclic —OC$_3$-C$_4$-alkyl, —N(R$^5$)(R$^6$), —(CO)N(R$^5$)(R$^6$), —NR$^5$(CO)(R$^6$), —SO$_2$C$_1$-C$_2$-alkyl, —SO$_2$N(R$^5$)(R$^6$), —(CH$_2$)$_m$SO$_2$C$_1$-C$_2$-alkyl, —(CH$_2$)$_m$SO$_2$N(R$^5$)(R$^6$), —N(R$^5$)SO$_2$C$_1$-C$_2$-alkyl, an aryl radical, or a heteroaryl radical; wherein the alkyl portion of the unbranched C$_1$-C$_3$-alkyl radical, the branched C$_3$-C$_4$-alkyl radical, the C$_3$-C$_5$-cycloalkyl radical, the unbranched —OC$_1$-C$_4$-alkyl, the branched or cyclic —OC$_3$-C$_4$-alkyl, the —SO$_2$C$_1$-C$_2$-alkyl, the —(CH$_2$)$_m$SO$_2$C$_1$-C$_2$-alkyl, or the —N(R$^5$)SO$_2$C$_1$-C$_2$-alkyl, may be independently substituted with up to 5 radical substituents, for example, up to 4 radical substituents or up to 3 radical substituents, comprising: -D, halogen radical, =O, —OR$^5$, —(CH$_2$)$_m$OR$^5$, —N(R$^5$)(R$^6$), —NR$^5$(CO)(R$^6$), —(CH$_2$)$_m$N(R$^5$)(R$^6$), —SO$_2$C$_1$-C$_2$-alkyl, —SO$_2$N(R$^5$)(R$^6$), —(CH$_2$)$_m$SO$_2$C$_1$-C$_2$-alkyl, —(CH$_2$)$_m$SO$_2$N(R$^5$)(R$^6$), —N(R$^5$)SO$_2$C$_1$-C$_2$-alkyl, —(CO)(CH$_2$)$_m$R$^5$, —(CO)N(R$^5$)(R$^6$), an unbranched C$_1$-C$_4$-alkyl radical, a branched C$_3$-C$_4$-alkyl radical, a C$_3$-C$_5$-cycloalkyl radical, a C$_1$-C$_4$-hydroxyalkyl radical, a C$_1$-C$_2$-haloalkyl radical, or —OC$_1$-C$_2$-haloalkyl radical; and wherein the aryl radical or the heteroaryl radical may be independently substituted with up to 5 radical substituents, for example, up to 4 radical substituents or up to 3 radical substituents, comprising: -D, halogen radical, —CN, —OR$^5$, —(CH$_2$)$_m$OR$^5$, —N(R$^5$)(R$^6$), —NR$^5$(CO)(R$^6$), —(CH$_2$)$_m$N(R$^5$)(R$^6$), —SO$_2$C$_1$-C$_2$-alkyl, —SO$_2$N(R$^5$)(R$^6$), —(CH$_2$)$_m$SO$_2$C$_1$-C$_2$-alkyl, —(CH$_2$)$_m$SO$_2$N(R$^5$)(R$^6$), —N(R$^5$)SO$_2$C$_1$-C$_2$-alkyl, —(CO)(CH$_2$)$_m$R$^5$, —(CO)N(R$^5$)(R$^6$), an unbranched C$_1$-C$_4$-alkyl radical, a branched C$_3$-C$_4$-alkyl radical, a C$_3$-C$_5$-cycloalkyl radical, a C$_1$-C$_4$-hydroxyalkyl radical, a C$_1$-C$_2$-haloalkyl radical, or —OC$_1$-C$_2$-haloalkyl radical; and wherein R$^5$ and R$^6$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^5$)(R$^6$) moiety forms a cycle, wherein R$^5$ and R$^6$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the aminobenzisoxazole compound represented by Formula (Ia) or Formula (Ib), may comprise R$^1$ and R$^2$ independently representing —H, -D, —F, —Cl, —Br, —CN, an unbranched C$_1$-C$_3$-alkyl radical, a branched C$_3$-C$_4$-alkyl radical, a C$_3$-C$_4$-cycloalkyl radical, —CHF$_2$, —CH$_2$F, —CF$_3$, an unbranched —OC$_1$-C$_3$-alkyl, a branched or cyclic —OC$_3$-alkyl, —OCF$_3$, —SO$_2$CH$_3$, —SO$_2$N(CH$_3$)$_2$, or —N(R$^5$)SO$_2$CH$_3$; wherein the alkyl portion of the unbranched C$_1$-C$_3$-alkyl radical, the branched C$_3$-C$_4$-alkyl radical, the C$_3$-C$_4$-cycloalkyl radical, the unbranched —OC$_1$-C$_3$-alkyl, or the branched or cyclic —OC$_3$-alkyl, may be independently substituted with up to 5 radical substituents, for example, up to 4 radical substituents or up to 3 radical substituents, comprising: -D, —F, —Cl, —OR$^5$, =O, —CH$_3$, —CHF$_2$, —CH$_2$F, —CF$_3$, cyclopropyl radical, cyclobutyl radical, or —OCF$_3$; and wherein R$^5$ may independently represent —H, —CH$_3$, or —CH$_2$CH$_3$.

In certain embodiments, the aminobenzisoxazole compound represented by Formula (Ia) or Formula (Ib), may comprise R$^1$ and R$^2$ independently representing —H, -D, —F, —Cl, —CH$_3$, —CH$_2$CH$_3$, a cyclopropyl radical, —CHF$_2$, —CH$_2$F, —CF$_3$, —OCH$_3$, —OCH$_2$CH$_3$, —OCH(CH$_3$)$_2$, —OCF$_3$, —SO$_2$CH$_3$, —SO$_2$N(CH$_3$)$_2$, or —N(H)SO$_2$CH$_3$.

In certain embodiments, the aminobenzisoxazole compound represented by Formula (Ia) or Formula (Ib), may comprise R$^1$ and R$^2$ independently representing —H, -D, or halogen radical, for example, —F, —Cl, or —Br. For example, in certain embodiments, R$^1$ and R$^2$ may independently represent —H, -D, —F, or —Cl, such as —H, -D, or —F. In certain embodiments, R$^1$ and R$^2$ may independently represent —H or -D. In certain embodiments, $R^1$ may independently represent —H or -D, and $R^2$ may independently represent —F or —Cl, such as —F. In certain embodiments, $R^1$ may independently represent —F or —Cl, such as —F, and $R^2$ may independently represent —H or -D.

In certain embodiments, the aminobenzisoxazole compound represented by Formula (Ia) or Formula (Ib), may comprise $R^3$ independently representing —F, —Cl, —Br, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —$N(R^5)(R^6)$, —$(CO)N(R^5)(R^6)$, —$NR^5(CO)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, an aryl radical, or a heteroaryl radical; wherein the alkyl portion of the unbranched $C_1$-$C_4$-alkyl radical, the branched $C_3$-$C_4$-alkyl radical, the $C_3$-$C_6$-cycloalkyl radical, the unbranched —$OC_1$-$C_4$-alkyl, the branched or cyclic —$OC_3$-$C_4$-alkyl, the —$SO_2C_1$-$C_4$-alkyl, the —$(CH_2)_mSO_2C_1$-$C_4$-alkyl, or the —$N(R^5)SO_2C_1$-$C_4$-alkyl, may be independently substituted with up to 5 radical substituents, for example, up to 4 radical substituents or up to 3 radical substituents, comprising: -D, —F, —Cl, —Br, =O, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein the aryl radical or the heteroaryl radical may be independently substituted with up to 5 radical substituents, for example, up to 4 radical substituents or up to 3 radical substituents, comprising: -D, —F, —Cl, —Br, —CN, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein $R^5$ and $R^6$ may independently represent —H, an unbranched $C_1$-$C_6$-alkyl radical, such as —$CH_3$ or —$CH_2CH_3$, a branched $C_3$-$C_6$-alkyl radical, such as —$CH(CH_3)_2$, or a $C_3$-$C_6$-cycloalkyl radical, such as a cyclopropyl radical, or the $N(R^5)(R^6)$ moiety forms a cycle, wherein $R^5$ and $R^6$ taken together represent a $C_2$-$C_6$-alkyl di-radical, such as a $C_2$-$C_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the aminobenzisoxazole compound represented by Formula (Ia) or Formula (Ib), may comprise $R^3$ independently representing —F, —Cl, —Br, —CN, an unbranched $C_1$-$C_4$-alkyl radical, a branched $C_3$-$C_4$-alkyl radical, a $C_3$-$C_4$-cycloalkyl radical, an unbranched —$OC_1$-$C_4$-alkyl, a branched or cyclic —$OC_3$-$C_4$-alkyl, —$OCHF_2$, —$OCH_2F$, —$OCF_3$, —$OCH_2CF_3$, —$N(R^5)(R^6)$, —$(CO)N(R^5)(R^6)$, —$NR^5(CO)(R^6)$, —$SO_2CH_3$, —$SO_2N(R^5)(R^6)$, —$CH_2CH_2SO_2C_1$-$C_4$-alkyl, or —$N(R^5)SO_2CH_3$, an aryl radical, or a heteroaryl radical; wherein the alkyl portion of the unbranched $C_1$-$C_4$-alkyl radical, the branched $C_3$-$C_4$-alkyl radical, the $C_3$-$C_4$-cycloalkyl radical, the unbranched —$OC_1$-$C_4$-alkyl, the branched or cyclic —$OC_3$-$C_4$-alkyl, or the —$CH_2CH_2SO_2C_1$-$C_4$-alkyl, may be independently substituted with up to 5 radical substituents, for example, up to 4 radical substituents or up to 3 radical substituents, comprising: -D, —F, —Cl, —Br, =O, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein the aryl radical or the heteroaryl radical may be independently substituted with up to 5 radical substituents, for example, up to 4 radical substituents or up to 3 radical substituents, comprising: -D, —F, —Cl, —Br, —CN, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein $R^5$ and $R^6$ may independently represent —H, an unbranched $C_1$-$C_6$-alkyl radical, such as —$CH_3$ or —$CH_2CH_3$, a branched $C_3$-$C_6$-alkyl radical, such as —$CH(CH_3)_2$, or a $C_3$-$C_6$-cycloalkyl radical, such as a cyclopropyl radical, or the $N(R^5)(R^6)$ moiety forms a cycle, wherein $R^5$ and $R^6$ taken together represent a $C_2$-$C_6$-alkyl di-radical, such as a $C_2$-$C_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the aminobenzisoxazole compound represented by Formula (Ia) or Formula (Ib), may comprise $R^3$ independently representing —F, —Cl, —Br, —CN, —$CH_3$, —$CH_2CH_3$, cyclopropyl radical, —$CHF_2$, —$CH_2F$, —$CF_3$, —$OCH_3$, —$OCH_2CH_3$, —$OCH(CH_3)_2$, —O-cyclopropyl, —$OCHF_2$, —$OCH_2F$, —$OCF_3$, —$OCH_2CF_3$, —$SO_2CH_3$, a phenyl radical or a heteroaryl radical, such as an N-pyrazole radical, a furan radical, a thiophene radical, an imidazole radical, an oxazole radical, a thiazole radical, a pyridyl radical, a pyrazine radical, a pyrimidine radical, or an oxadiazole radical; wherein the phenyl radical or the heteroaryl radical, such as the N-pyrazole radical, the furan radical, the thiophene radical, the imidazole radical, the oxazole radical, the thiazole radical, the pyridyl radical, the pyrazine radical, the pyrimidine radical, or the oxadiazole radical, may be independently substituted with up to 5 radical substituents, for example, up to 4 radical substituents or up to 3 radical substituents, comprising: -D, —F, —Cl, —Br, —CN, —$OR^5$, —$(CH_2)_mOR^5$, —$N(R^5)(R^6)$, —$NR^5(CO)(R^6)$, —$(CH_2)_mN(R^5)(R^6)$, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein $R^5$ and $R^6$ may independently represent —H, an unbranched $C_1$-$C_6$-alkyl radical, such as —$CH_3$ or —$CH_2CH_3$, a branched $C_3$-$C_6$-alkyl radical, such as —$CH(CH_3)_2$, or a $C_3$-$C_6$-cycloalkyl radical, such as a cyclopropyl radical, or the $N(R^5)(R^6)$ moiety forms a cycle, wherein $R^5$ and $R^6$ taken together represent a $C_2$-$C_6$-alkyl di-radical, such as a $C_2$-$C_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the aminobenzisoxazole compound represented by Formula (Ia) or Formula (Ib), may comprise $R^3$ independently representing —F, —Cl, —Br, —CN, —CH$_3$, —CH$_2$CH$_3$, cyclopropyl radical, —CHF$_2$, —CH$_2$F, —CF$_3$, —OCH$_3$, —OCH$_2$CH$_3$, —OCH(CH$_3$)$_2$, —O-cyclopropyl, —OCF$_3$, —SO$_2$CH$_3$, a phenyl radical or a heteroaryl radical, such as an N-pyrazole radical, a furan radical, a thiophene radical, an imidazole radical, an oxazole radical, a thiazole radical, a pyridyl radical, a pyrazine radical, a pyrimidine radical, or an oxadiazole radical; wherein the phenyl radical or the heteroaryl radical, such as the N-pyrazole radical, the furan radical, the thiophene radical, the imidazole radical, the oxazole radical, the thiazole radical, the pyridyl radical, the pyrazine radical, the pyrimidine radical, or the oxadiazole radical, may be substituted with up to 5 radical substituents, for example, up to 4 radical substituents or up to 3 radical substituents, comprising: -D, —F, —Cl, —Br, —CN, —OR$^5$, —CH$_3$, cyclopropyl radical, —CHF$_2$, —CH$_2$F, —CF$_3$, —OCF$_3$, or —OCH$_2$CF$_3$. For example, in certain embodiments, $R^3$ may independently represent —F, —Cl, —Br, —CN, —CH$_3$, —CH$_2$CH$_3$, cyclopropyl radical, —CHF$_2$, —CH$_2$F, —CF$_3$, —OCH$_3$, —OCH$_2$CH$_3$, —OCH(CH$_3$)$_2$, —O-cyclopropyl, or —OCF$_3$. In certain embodiments, $R^3$ may independently represent —F, —Cl, —Br, —CH$_3$, or —OCH$_3$, such as $R^3$ may independently represent —Cl, —CH$_3$, or —OCH$_3$.

In certain embodiments, the aminobenzisoxazole compound represented by Formula (Ia) or Formula (Ib), may comprise $R^4$ independently representing —H, -D, —F, —Cl, —Br, —CN, an unbranched C$_1$-C$_4$-alkyl radical, a branched C$_3$-C$_4$-alkyl radical, a C$_3$-C$_6$-cycloalkyl radical, an unbranched —OC$_1$-C$_4$-alkyl, a branched or cyclic —OC$_3$-C$_4$-alkyl, —N(R$^5$)(R$^6$), —(CO)N(R$^5$)(R$^6$), —NR$^5$(CO)(R$^6$), —SO$_2$C$_1$-C$_4$-alkyl, —SO$_2$N(R$^5$)(R$^6$), —(CH$_2$)$_m$SO$_2$C$_1$-C$_4$-alkyl, —(CH$_2$)$_m$SO$_2$N(R$^5$)(R$^6$), —N(R$^5$)SO$_2$C$_1$-C$_4$-alkyl, an aryl radical, or a heteroaryl radical; wherein the alkyl portion of the unbranched C$_1$-C$_4$-alkyl radical, the branched C$_3$-C$_4$-alkyl radical, the C$_3$-C$_6$-cycloalkyl radical, the unbranched —OC$_1$-C$_4$-alkyl, the branched or cyclic —OC$_3$-C$_4$-alkyl, the —SO$_2$C$_1$-C$_4$-alkyl, the —(CH$_2$)$_m$SO$_2$C$_1$-C$_4$-alkyl, or the —N(R$^5$)SO$_2$C$_1$-C$_4$-alkyl, may be independently substituted with up to 5 radical substituents, for example, up to 4 radical substituents or up to 3 radical substituents, comprising: -D, —F, —Cl, —Br, =O, —OR$^5$, —(CH$_2$)$_m$OR$^5$, —N(R$^5$)(R$^6$), —NR$^5$(CO)(R$^6$), —(CH$_2$)$_m$N(R$^5$)(R$^6$), —SO$_2$C$_1$-C$_4$-alkyl, —SO$_2$N(R$^5$)(R$^6$), —(CH$_2$)$_m$SO$_2$C$_1$-C$_4$-alkyl, —(CH$_2$)$_m$SO$_2$N(R$^5$)(R$^6$), —N(R$^5$)SO$_2$C$_1$-C$_4$-alkyl, —(CO)(CH$_2$)$_m$R$^5$, —(CO)N(R$^5$)(R$^6$), —OCF$_3$ an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein aryl radical or the heteroaryl radical may be independently substituted with up to 5 radical substituents, for example, up to 4 radical substituents or up to 3 radical substituents, comprising: -D, —F, —Cl, —Br, —CN, —OR$^5$, —(CH$_2$)$_m$OR$^5$, —N(R$^5$)(R$^6$), —NR$^5$(CO)(R$^6$), —(CH$_2$)$_m$N(R$^5$)(R$^6$), —SO$_2$C$_1$-C$_4$-alkyl, —SO$_2$N(R$^5$)(R$^6$), —(CH$_2$)$_m$SO$_2$C$_1$-C$_4$-alkyl, —(CH$_2$)$_m$SO$_2$N(R$^5$)(R$^6$), —N(R$^5$)SO$_2$C$_1$-C$_4$-alkyl, —(CO)(CH$_2$)$_m$R$^5$, —(CO)N(R$^5$)(R$^6$), —OCF$_3$, an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein R$^5$ and R$^6$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^5$)(R$^6$) moiety forms a cycle, wherein R$^5$ and R$^6$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the aminobenzisoxazole compound represented by Formula (Ia) or Formula (Ib), may comprise R$^4$ independently representing —H, -D, —F, —Cl, —CN, an unbranched C$_1$-C$_3$-alkyl radical, a branched C$_3$-C$_4$-alkyl radical, a C$_3$-C$_4$-cycloalkyl radical, unbranched —OC$_1$-C$_3$-alkyl, a branched or cyclic —OC$_3$-C$_4$-alkyl, —OCHF$_2$, —OCH$_2$F, —OCF$_3$, —OCH$_2$CF$_3$; wherein the alkyl portion of the unbranched C$_1$-C$_3$-alkyl radical, the branched C$_3$-C$_4$-alkyl radical, the C$_3$-C$_4$-cycloalkyl radical, the unbranched —OC$_1$-C$_3$-alkyl, or the branched or cyclic —OC$_3$-C$_4$-alkyl, may be independently substituted with up to 5 radical substituents, for example, up to 4 radical substituents or up to 3 radical substituents, comprising: -D, —F, —Cl, —Br, =O, —OR$^5$, —(CH$_2$)$_m$OR$^5$, —N(R$^5$)(R$^6$), —NR$^5$(CO)(R$^6$), —(CH$_2$)$_m$N(R$^5$)(R$^6$), —(CO)(CH$_2$)$_m$R$^5$, —(CO)N(R$^5$)(R$^6$), —OCF$_3$, an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein R$^5$ and R$^6$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^5$)(R$^6$) moiety forms a cycle, wherein R$^5$ and R$^6$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the aminobenzisoxazole compound represented by Formula (Ia) or Formula (Ib), may comprise R$^4$ independently representing —H, -D, —F, —Cl, —CN, —CH$_3$, cyclopropyl radical, cyclobutyl radical, —CH$_2$F, —CHF$_2$, —CF$_3$, —OCH$_3$, —OCH$_2$CH$_3$, —OCH(CH$_3$)$_2$, —O-cyclopropyl, —OCHF$_2$, —OCH$_2$F, —OCF$_3$, or —OCH$_2$CF$_3$. For example, in certain embodiments, R$^4$ may independently represent —H, -D, —F, —Cl, —CN, —CH$_3$, cyclopropyl radical, cyclobutyl radical, —CH$_2$F, —CHF$_2$, —CF$_3$, —OCH$_3$, —OCH$_2$CH$_3$, —OCH(CH$_3$)$_2$, —O-cyclopropyl, or —OCF$_3$, such as R$^4$ may independently represent —H, -D, —F, —Cl, —CH$_3$, —OCH$_3$, —OCH$_2$CH$_3$, or —CF$_3$.

In certain embodiments, the aminobenzisoxazole compound represented by Formula (Ia) or Formula (Ib), may comprise: R$^1$ and R$^2$ independently representing —H or -D, R$^2$ and R$^4$ independently representing —H or -D, R$^1$ and R$^4$ independently representing —H or -D, or R$^1$, R$^2$, and R$^4$ independently representing —H or -D; and R$^3$ independently representing —H, -D, —F, —Cl, —Br, —CN, an unbranched C$_1$-C$_3$-alkyl radical, for example, —CH$_3$ or —CH$_2$CH$_3$, a branched C$_3$-C$_4$-alkyl radical, a cyclopropyl radical, a cyclobutyl radical, —CHF$_2$, —CH$_2$F, —CF$_3$, an unbranched —OC$_1$-C$_3$-alkyl, such as —OCH$_3$ or —OCH$_2$CH$_3$, a branched or cyclic —OC$_3$-C$_4$-alkyl, such as —OCH(CH$_3$)$_2$ or —O-cyclopropyl, —OCHF$_2$, —OCH$_2$F, —OCF$_3$, —OCH$_2$CF$_3$, —SO$_2$CH$_3$, a phenyl radical or a heteroaryl radical, such as an N-pyrazole radical, a furan radical, a thiophene radical, an imidazole radical, an oxazole radical, a thiazole radical, a pyridyl radical, a pyrazine radical, a pyrimidine radical, or an oxadiazole radical; wherein the alkyl portion of the unbranched $C_1$-$C_3$-alkyl radical, branched $C_3$-$C_4$-alkyl radical, unbranched —O$C_1$-$C_3$-alkyl, or the branched or cyclic —O$C_3$-$C_4$-alkyl, may be independently substituted with up to 5 radical substituents, for example, up to 4 radical substituents or up to 3 radical substituents, comprising: -D, —F, —Cl, =O, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —OCF$_3$, or —OCH$_2$CF$_3$; and wherein the phenyl radical or the heteroaryl radical may be independently substituted with up to 5 radical substituents, for example, up to 4 radical substituents or up to 3 radical substituents, comprising: -D, —F, —Cl, —Br, —CN, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —OCF$_3$, or —OCH$_2$CF$_3$.

In certain embodiments, the aminobenzisoxazole compound represented by Formula (Ia) or Formula (Ib), may comprise $R^1$ independently representing —H, -D, or a halogen radical, for example —H, -D, —F, or —Cl, such as —H, -D, or —F; $R^2$ independently representing —H, -D, or a halogen radical, for example —H, -D, —F, or —Cl, such as —H, -D, or —F; $R^3$ independently representing —H, -D, —F, —Cl, —Br, —CN, an unbranched $C_1$-$C_3$-alkyl radical, for example, —CH$_3$ or —CH$_2$CH$_3$, —CH(CH$_3$)$_2$, a cyclopropyl radical, a cyclobutyl radical, —CHF$_2$, —CH$_2$F, —CF$_3$, an unbranched —O$C_1$-$C_3$-alkyl, such as —OCH$_3$ or —OCH$_2$CH$_3$, —OCH(CH$_3$)$_2$, —O-cyclopropyl, —OCHF$_2$, —OCH$_2$F, —OCF$_3$, —OCH$_2$CF$_3$, —SO$_2$CH$_3$, a phenyl radical or a heteroaryl radical, such as an N-pyrazole radical or an oxadiazole radical; and $R^4$ independently representing —H, -D, —F, —Cl, —CN, an unbranched $C_1$-$C_3$-alkyl radical, for example, —CH$_3$ or —CH$_2$CH$_3$, —CH(CH$_3$)$_2$, a cyclopropyl radical, a cyclobutyl radical, —CHF$_2$, —CH$_2$F, —CF$_3$, an unbranched —O$C_1$-$C_3$-alkyl, such as —OCH$_3$ or —OCH$_2$CH$_3$, —OCH(CH$_3$)$_2$, —O-cyclopropyl, —OCHF$_2$, —OCH$_2$F, —OCF$_3$, —OCH$_2$CF$_3$; wherein the alkyl portion of the unbranched $C_1$-$C_3$-alkyl radical, —CH(CH$_3$)$_2$, unbranched —O$C_1$-$C_3$-alkyl, —OCH(CH$_3$)$_2$, or —O-cyclopropyl, may be independently substituted with up to 5 radical substituents, for example, up to 4 radical substituents or up to 3 radical substituents, comprising: -D, —F, —Cl, =O, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —OCF$_3$, or —OCH$_2$CF$_3$; and wherein the phenyl radical or the heteroaryl radical may be independently substituted with up to 5 radical substituents, for example, up to 4 radical substituents or up to 3 radical substituents, comprising: -D, —F, —Cl, —Br, —CN, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —OCF$_3$, or —OCH$_2$CF$_3$.

In certain embodiments, the aminobenzisoxazole compound represented by Formula (Ia) or Formula (Ib), may comprise $R^1$ independently representing —H, -D, or a halogen radical, for example —H, -D, —F, or —Cl, such as —H, -D, or —F; $R^2$ independently representing —H, -D, or a halogen radical, for example —H, -D, —F, or —Cl, such as —H, -D, or —F; $R^3$ independently representing —H, -D, —F, —Cl, —Br, —CN, an unbranched $C_1$-$C_3$-alkyl radical, for example, —CH$_3$ or —CH$_2$CH$_3$, —CH(CH$_3$)$_2$, a cyclopropyl radical, a cyclobutyl radical, —CHF$_2$, —CH$_2$F, —CF$_3$, an unbranched —O$C_1$-$C_3$-alkyl, such as —OCH$_3$ or —OCH$_2$CH$_3$, —OCH(CH$_3$)$_2$, —O-cyclopropyl, —OCHF$_2$, —OCH$_2$F, —OCF$_3$, —OCH$_2$CF$_3$, or —SO$_2$CH$_3$; and $R^4$ independently representing —H, -D, —F, —Cl, —CN, an unbranched $C_1$-$C_3$-alkyl radical, for example, —CH$_3$ or —CH$_2$CH$_3$, —CH(CH$_3$)$_2$, a cyclobutyl radical, —CHF$_2$, —CH$_2$F, —CF$_3$, an unbranched —O$C_1$-$C_3$-alkyl, such as —OCH$_3$ or —OCH$_2$CH$_3$, —OCH (CH$_3$)$_2$, —O-cyclopropyl, —OCHF$_2$, —OCH$_2$F, —OCF$_3$, —OCH$_2$CF$_3$; wherein the alkyl portion of the unbranched $C_1$-$C_3$-alkyl radical, —CH(CH$_3$)$_2$, the cyclopropyl radical, the cyclobutyl radical, the unbranched —O$C_1$-$C_3$-alkyl, —OCH(CH$_3$)$_2$, or —O-cyclopropyl, may be independently substituted with up to 5 radical substituents, for example, up to 4 radical substituents or up to 3 radical substituents, comprising: -D, —F, —Cl, =O, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —OCF$_3$, or —OCH$_2$CF$_3$.

In certain embodiments, the aminobenzisoxazole compound represented by Formula (Ia) or Formula (Ib), may comprise $R^1$ independently representing —H, -D, or a halogen radical, for example —H, -D, —F, or —Cl, such as —H, -D, or —F; $R^2$ independently representing —H, -D, or a halogen radical, for example —H, -D, —F, or —Cl, such as —H, -D, or —F; $R^3$ independently representing —H, -D, —F, —Cl, —Br, —CN, —CH$_3$, —CH$_2$CH$_3$, —CH(CH$_3$)$_2$, a cyclopropyl radical, a cyclobutyl radical, —CHF$_2$, —CH$_2$F, —CF$_3$, —OCH$_3$, —OCH$_2$CH$_3$, —OCH(CH$_3$)$_2$, or —O-cyclopropyl, or —OCF$_3$; and $R^4$ independently representing —H, -D, —F, —Cl, —CN, —CH$_3$, —CH$_2$CH$_3$, a cyclopropyl radical, a cyclobutyl radical, —CHF$_2$, —CH$_2$F, —CF$_3$, —OCH$_3$, —OCH$_2$CH$_3$, —OCH(CH$_3$)$_2$, or —O-cyclopropyl, —OCF$_3$.

For example, in certain embodiments, $R^1$ may independently represent —H, -D, —F, or —Cl, such as —H, -D, or —F; $R^2$ may independently represent —H, -D, —F, or —Cl, such as —H, -D, or —F; $R^3$ may independently represent —F, —Cl, —Br, —CN, —CH$_3$, —CH$_2$CH$_3$, a cyclopropyl radical, —CHF$_2$, —CH$_2$F, —CF$_3$, —OCH$_3$, —OCH$_2$CH$_3$, —OCH(CH$_3$)$_2$, or —O-cyclopropyl, or —OCF$_3$, such as —F, —Cl, —Br, —CH$_3$, or —OCH$_3$, or such as —Cl, —CH$_3$, or —OCH$_3$; and $R^4$ may independently represent —H, -D, —F, —Cl, —CN, —CH$_3$, —CH$_2$CH$_3$, a cyclopropyl radical, a cyclobutyl radical, —CHF$_2$, —CH$_2$F, —CF$_3$, —OCH$_3$, —OCH$_2$CH$_3$, —OCH(CH$_3$)$_2$, or —O-cyclopropyl, —OCF$_3$, such as —H, -D, —F, —Cl, —CH$_3$, —OCH$_3$, —OCH$_2$CH$_3$, or —CF$_3$.

In certain embodiments, the aminobenzisoxazole compound represented by Formula (Ia) or Formula (Ib), at least one of $R^1$, $R^2$, $R^3$, and $R^4$ does not independently represent —H. For example, in certain embodiments, $R^1$ independently represents —H, and at least one of $R^2$, $R^3$, and $R^4$ does not independently represent —H; $R^2$ independently represents —H, and at least one of $R^1$, $R^3$, and $R^4$ does not independently represent —H; $R^3$ independently represents —H, and at least one of $R^1$, $R^2$, and $R^4$ does not independently represent —H; or $R^4$ independently represents —H, and at least one of $R^1$, $R^2$, and $R^3$ does not independently represent —H.

In certain embodiments, the aminobenzisoxazole compound represented by Formula (Ia) or Formula (Ib), may comprise $R^5$, $R^6$, or both $R^5$ and $R^6$, independently representing —H; an unbranched $C_1$-$C_6$-alkyl radical, such as —CH$_3$ or —CH$_2$CH$_3$, a branched $C_3$-$C_6$-alkyl radical, such as —CH(CH$_3$)$_2$; or a $C_3$-$C_6$-cycloalkyl radical, such as a cyclopropyl radical or a cyclobutyl radical. For example, $R^5$ and $R^6$ may independently represent —H, —CH$_3$, —CH$_2$CH$_3$, —CH(CH$_3$)$_2$, a cyclopropyl radical, or a cyclobutyl radical, such as independently represent —H, —CH$_3$, or —CH$_2$CH$_3$.

In certain embodiments, the aminobenzisoxazole compound represented by Formula (Ia) or Formula (Ib), may comprise an N($R^5$)($R^6$) moiety, wherein the N($R^5$)($R^6$) moiety forms a cycle, wherein $R^5$ and $R^6$ taken together represent a $C_2$-$C_6$-alkyl di-radical or a (3-6 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H, an unbranched $C_1$-$C_4$-alkyl radical, a branched $C_3$-$C_4$-alkyl radical, a $C_3$-$C_4$-cycloalkyl radical, —(CO)-unbranched $C_1$-$C_4$-alkyl, —(CO)-branched $C_3$-$C_4$-alkyl, —($SO_2$)-unbranched $C_1$-$C_4$-alkyl, or —($SO_2$)-branched $C_3$-$C_4$-alkyl, and with the further proviso that when the at least one ring atom is sulfur, the sulfur may be independently substituted with 0 to 2 =O; wherein the $C_2$-$C_6$-alkyl di-radical or the alkyl portion of said (3-6 membered)-heteroalkyl di-radical may be independently substituted with up to 5 radical substituents, for example, up to 4 radical substituents or up to 3 radical substituents, comprising: -D, halogen radical, =O, an unbranched $C_1$-$C_6$-alkyl radical, or a branched $C_3$-$C_6$-alkyl radical.

In certain embodiments, the N($R^5$)($R^6$) moiety may form a cycle, wherein $R^5$ and $R^6$ taken together represent a $C_2$-$C_6$-alkyl di-radical, such as a $C_2$-$C_5$-alkyl di-radical or $C_3$-$C_4$-alkyl di-radical; wherein the $C_2$-$C_6$-alkyl di-radical, such as a $C_2$-$C_5$-alkyl di-radical or $C_3$-$C_4$-alkyl di-radical, may be independently substituted with up to 5 radical substituents, for example, up to 4 radical substituents or up to 3 radical substituents, comprising: -D, halogen radical, =O, an unbranched $C_1$-$C_6$-alkyl radical, or a branched $C_3$-$C_6$-alkyl radical. For example, the N($R^5$)($R^6$) moiety may form a cycle, wherein $R^5$ and $R^6$ taken together represent a $C_2$-alkyl di-radical, a $C_3$-alkyl di-radical, $C_4$-alkyl di-radical, or $C_5$-alkyl di-radical, such as a $C_2$-alkyl di-radical.

In certain embodiments, the N($R^5$)($R^6$) moiety may, for example, form a cycle wherein the $R^5$ and $R^6$ taken together represent a (3-6 membered)-heteroalkyl di-radical, such as (4-5 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H; an unbranched $C_1$-$C_4$-alkyl radical, such as —$CH_3$, —$CH_2CH_3$, or —$CH_2CH_2CH_3$, a branched $C_3$-$C_4$-alkyl radical, such as —CH($CH_3$)$_2$; a $C_3$-$C_4$-cycloalkyl radical; —(CO)-unbranched $C_1$-$C_4$-alkyl; —(CO)-branched $C_3$-$C_4$-alkyl; —($SO_2$)-unbranched $C_1$-$C_4$-alkyl; or —($SO_2$)-branched $C_3$-$C_4$-alkyl; and with the further proviso that when the at least one ring atom is sulfur, the sulfur may be independently substituted with 0 to 2 =O; wherein the alkyl portion of said (3-6 membered)-heteroalkyl di-radical may be independently substituted with up to 5 radical substituents, for example, up to 4 radical substituents or up to 3 radical substituents, comprising: -D, halogen radical, =O, an unbranched $C_1$-$C_6$-alkyl radical, or a branched $C_3$-$C_6$-alkyl radical. For example, the N($R^5$)($R^6$) moiety may form a cycle, wherein $R^5$ and $R^6$ taken together represent a (4-5 membered)-heteroalkyl di-radical, wherein the (4-5 membered)-heteroalkyl di-radical comprises at least one ring atom selected from the group consisting of oxygen or nitrogen, with the proviso that when the at least one ring atom is nitrogen, the nitrogen is independently substituted with —H; —$CH_3$, —$CH_2CH_3$, —CH($CH_3$)$_2$, a cyclopropyl radical. —(CO)$CH_3$, —(CO)$CH_2CH_3$, —($SO_2$)$CH_3$, or —($SO_2$)$CH_2CH_3$.

In certain embodiments, the aminobenzisoxazole compound represented by Formula (Ia) or Formula (Ib), may comprise racemic mixture of enantiomers, a mixture of diastereomers, a single enantiomer, or a single diastereomer, of the compound, or a pharmaceutically acceptable salt thereof. In certain embodiments, the aminobenzisoxazole compound represented by Formula (Ia) or Formula (Ib), may comprise a mixture of tautomers, substantially a single tautomer form, or a single tautomer form, such as a tautomer contained within the aminobenzisoxazole ring system or a tautomer resulting from one or more substitutents substituted on the aminobenzisoxazole ring system, for example, a tautomer may be contained within the aminobenzisoxazole ring system or one or more substitutents substituted on the aminobenzisoxazole ring system containing a heteroaryl ring nitrogen adjacent to a heteroaryl ring carbon substituted with a hydroxyl group.

The chemical names and structure diagrams used herein to describe the compounds of the present invention, supra and infra, were created with the use of ChemBioDraw Ultra® Version 12.0 (available from CambridgeSoft Corp., Cambridge, Mass.).

In certain embodiments, specific examples of the aminobenzisoxazole compound represented by Formula (Ia) or Formula (Ib) may include, collectively or individually, the compounds listed below, and single enantiomers and pharmaceutically acceptable salts thereof:

N-(quinuclidin-3-yl)benzo[d]isoxazol-3-amine;
7-chloro-N-(quinuclidin-3-yl)benzo[d]isoxazol-3-amine;
6-chloro-N-(quinuclidin-3-yl)benzo[d]isoxazol-3-amine;
5-chloro-N-(quinuclidin-3-yl)benzo[d]isoxazol-3-amine;
6-methyl-N-(quinuclidin-3-yl)benzo[d]isoxazol-3-amine;
6-cyclopropyl-N-(quinuclidin-3-yl)benzo[d]isoxazol-3-amine;
6-methoxy-N-(quinuclidin-3-yl)benzo[d]isoxazol-3-amine;
N-(quinuclidin-3-yl)-6-(trifluoromethyl)benzo[d]isoxazol-3-amine;
6,7-dichloro-N-(quinuclidin-3-yl)benzo[d]isoxazol-3-amine;
4-chloro-N-(quinuclidin-3-yl)benzo[d]isoxazol-3-amine;
6-fluoro-N-(quinuclidin-3-yl)benzo[d]isoxazol-3-amine;
3-(quinuclidin-3-ylamino)benzo[d]isoxazole-6-carbonitrile;
6-(methylsulfonyl)-N-(quinuclidin-3-yl)benzo[d]isoxazol-3-amine;
6-(tert-butyl)-N-(quinuclidin-3-yl)benzo[d]isoxazol-3-amine;
5,6-dichloro-N-(quinuclidin-3-yl)benzo[d]isoxazol-3-amine;
N-(quinuclidin-3-yl)-6-(trifluoromethoxy)benzo[d]isoxazol-3-amine;
7-fluoro-N-(quinuclidin-3-yl)benzo[d]isoxazol-3-amine;
5-fluoro-N-(quinuclidin-3-yl)benzo[d]isoxazol-3-amine;
4-fluoro-N-(quinuclidin-3-yl)benzo[d]isoxazol-3-amine;
7-fluoro-6-methyl-N-(quinuclidin-3-yl)benzo[d]isoxazol-3-amine;
6,7-difluoro-N-(quinuclidin-3-yl)benzo[d]isoxazol-3-amine;
5-fluoro-6-methyl-N-(quinuclidin-3-yl)benzo[d]isoxazol-3-amine;
6-chloro-7-methyl-N-(quinuclidin-3-yl)benzo[d]isoxazol-3-amine;
6-chloro-7-methoxy-N-(quinuclidin-3-yl)benzo[d]isoxazol-3-amine;
6-chloro-N-(quinuclidin-3-yl)-7-(trifluoromethyl)benzo[d]isoxazol-3-amine;
6-chloro-7-cyclopropyl-N-(quinuclidin-3-yl)benzo[d]isoxazol-3-amine;

4-fluoro-6-chloro-N-(quinuclidin-3-yl)benzo[d]isoxazol-3-amine;
4,6-dichloro-N-(quinuclidin-3-yl)benzo[d]isoxazol-3-amine;
7-fluoro-6-methoxy-N-(quinuclidin-3-yl)benzo[d]isoxazol-3-amine;
7-chloro-6-methoxy-N-(quinuclidin-3-yl)benzo[d]isoxazol-3-amine;
7-chloro-6-methyl-N-(quinuclidin-3-yl)benzo[d]isoxazol-3-amine;
6-isopropoxy-N-(quinuclidin-3-yl)benzo[d]isoxazol-3-amine;
6-ethoxy-N-(quinuclidin-3-yl)benzo[d]isoxazol-3-amine;
6-chloro-3-(quinuclidin-3-ylamino)benzo[d]isoxazole-7-carbonitrile;
7-chloro-6-fluoro-N-(quinuclidin-3-yl)benzo[d]isoxazol-3-amine;
6-(1H-pyrazol-1-yl)-N-(quinuclidin-3-yl)benzo[d]isoxazol-3-amine;
6-(5-methyl-1,3,4-oxadiazol-2-yl)-N-(quinuclidin-3-yl)benzo[d]isoxazol-3-amine;
7-methoxy-6-methyl-N-(quinuclidin-3-yl)benzo[d]isoxazol-3-amine;
6-chloro-7-ethoxy-N-(quinuclidin-3-yl)benzo[d]isoxazol-3-amine;
6,7-dimethyl-N-(quinuclidin-3-yl)benzo[d]isoxazol-3-amine;
6-chloro-7-fluoro-N-(quinuclidin-3-yl)benzo[d]isoxazol-3-amine;
6-chloro-5-fluoro-N-(quinuclidin-3-yl)benzo[d]isoxazol-3-amine; and
6-bromo-N-(quinuclidin-3-yl)benzo[d]isoxazol-3-amine.

In certain embodiments, specific examples of the aminobenzisoxazole compound represented by Formula (Ia) or Formula (Ib) may include, collectively or individually, the compounds listed below, and single enantiomers and pharmaceutically acceptable salts thereof:
6-cyclopropoxy-N-(quinuclidin-3-yl)benzo[d]isoxazol-3-amine;
6-ethyl-N-(quinuclidin-3-yl)benzo[d]isoxazol-3-amine;
6-chloro-N-(quinuclidin-3-yl)-7-(trifluoromethoxy)benzo[d]isoxazol-3-amine;
6-chloro-7-cyclobutyl-N-(quinuclidin-3-yl)benzo[d]isoxazol-3-amine;
5-fluoro-6-methoxy-N-(quinuclidin-3-yl)benzo[d]isoxazol-3-amine;
6-methoxy-7-methyl-N-(quinuclidin-3-yl)benzo[d]isoxazol-3-amine;
6-methyl-N-(quinuclidin-3-yl)-7-(trifluoromethyl)benzo[d]isoxazol-3-amine;
6-chloro-5,7-difluoro-N-(quinuclidin-3-yl)benzo[d]isoxazol-3-amine;
6-chloro-7-(difluoromethyl)-N-(quinuclidin-3-yl)benzo[d]isoxazol-3-amine;
6-chloro-7-isopropoxy-N-(quinuclidin-3-yl)benzo[d]isoxazol-3-amine;
6-chloro-7-cyclopropoxy-N-(quinuclidin-3-yl)benzo[d]isoxazol-3-amine;
7-ethoxy-6-methyl-N-(quinuclidin-3-yl)benzo[d]isoxazol-3-amine;
7-ethoxy-6-fluoro-N-(quinuclidin-3-yl)benzo[d]isoxazol-3-amine;
6-fluoro-7-methoxy-N-(quinuclidin-3-yl)benzo[d]isoxazol-3-amine;
6-methoxy-N-(quinuclidin-3-yl)-7-(trifluoromethyl)benzo[d]isoxazol-3-amine;
5-fluoro-7-methyl-N-(quinuclidin-3-yl)benzo[d]isoxazol-3-amine;
5,6-difluoro-7-methyl-N-(quinuclidin-3-yl)benzo[d]isoxazol-3-amine;
5,7-difluoro-N-(quinuclidin-3-yl)benzo[d]isoxazol-3-amine;
6-chloro-5-fluoro-7-methyl-N-(quinuclidin-3-yl)benzo[d]isoxazol-3-amine;
6-chloro-5-fluoro-N-(quinuclidin-3-yl)-7-(trifluoromethyl)benzo[d]isoxazol-3-amine;
6-chloro-5-fluoro-7-methoxy-N-(quinuclidin-3-yl)benzo[d]isoxazol-3-amine;
5,7-difluoro-6-methyl-N-(quinuclidin-3-yl)benzo[d]isoxazol-3-amine;
6,7-dichloro-5-fluoro-N-(quinuclidin-3-yl)benzo[d]isoxazol-3-amine;
6-chloro-7-ethoxy-5-fluoro-N-(quinuclidin-3-yl)benzo[d]isoxazol-3-amine; and
5,7-difluoro-6-methoxy-N-(quinuclidin-3-yl)benzo[d]isoxazol-3-amine.

In certain embodiments, specific examples of the aminobenzisoxazole compound represented by Formula (Ia) or Formula (Ib) may include, collectively or individually, the single enantiomers listed below, and pharmaceutically acceptable salts thereof:
(R) N-(quinuclidin-3-yl)benzo[d]isoxazol-3-amine;
(S)—N-(quinuclidin-3-yl)benzo[d]isoxazol-3-amine;
(R)-7-chloro-N-(quinuclidin-3-yl)benzo[d]isoxazol-3-amine;
(S)-7-chloro-N-(quinuclidin-3-yl)benzo[d]isoxazol-3-amine;
(R)-6-chloro-N-(quinuclidin-3-yl)benzo[d]isoxazol-3-amine;
(S)-6-chloro-N-(quinuclidin-3-yl)benzo[d]isoxazol-3-amine;
(R)-5-chloro-N-(quinuclidin-3-yl)benzo[d]isoxazol-3-amine;
(S)-5-chloro-N-(quinuclidin-3-yl)benzo[d]isoxazol-3-amine;
(R)-6-methyl-N-(quinuclidin-3-yl)benzo[d]isoxazol-3-amine;
(S)-6-methyl-N-(quinuclidin-3-yl)benzo[d]isoxazol-3-amine;
(R)-6-cyclopropyl-N-(quinuclidin-3-yl)benzo[d]isoxazol-3-amine;
(S)-6-cyclopropyl-N-(quinuclidin-3-yl)benzo[d]isoxazol-3-amine;
(R)-6-methoxy-N-(quinuclidin-3-yl)benzo[d]isoxazol-3-amine;
(S)-6-methoxy-N-(quinuclidin-3-yl)benzo[d]isoxazol-3-amine;
(R) N-(quinuclidin-3-yl)-6-(trifluoromethyl)benzo[d]isoxazol-3-amine;
(S)—N-(quinuclidin-3-yl)-6-(trifluoromethyl)benzo[d]isoxazol-3-amine;
(R)-6,7-dichloro-N-(quinuclidin-3-yl)benzo[d]isoxazol-3-amine;
(S)-6,7-dichloro-N-(quinuclidin-3-yl)benzo[d]isoxazol-3-amine;
(R)-4-chloro-N-(quinuclidin-3-yl)benzo[d]isoxazol-3-amine;
(S)-4-chloro-N-(quinuclidin-3-yl)benzo[d]isoxazol-3-amine;
(R)-6-fluoro-N-(quinuclidin-3-yl)benzo[d]isoxazol-3-amine;
(S)-6-fluoro-N-(quinuclidin-3-yl)benzo[d]isoxazol-3-amine;

(R)-3-(quinuclidin-3-ylamino)benzo[d]isoxazole-6-carbonitrile;
(S)-3-(quinuclidin-3-ylamino)benzo[d]isoxazole-6-carbonitrile;
(R)-6-(methylsulfonyl)-N-(quinuclidin-3-yl)benzo[d]isoxazol-3-amine;
(S)-6-(methylsulfonyl)-N-(quinuclidin-3-yl)benzo[d]isoxazol-3-amine;
(R)-6-(tert-butyl)-N-(quinuclidin-3-yl)benzo[d]isoxazol-3-amine;
(S)-6-(tert-butyl)-N-(quinuclidin-3-yl)benzo[d]isoxazol-3-amine;
(R)-5,6-dichloro-N-(quinuclidin-3-yl)benzo[d]isoxazol-3-amine;
(S)-5,6-dichloro-N-(quinuclidin-3-yl)benzo[d]isoxazol-3-amine;
(R) N-(quinuclidin-3-yl)-6-(trifluoromethoxy)benzo[d]isoxazol-3-amine;
(S)—N-(quinuclidin-3-yl)-6-(trifluoromethoxy)benzo[d]isoxazol-3-amine;
(R)-7-fluoro-N-(quinuclidin-3-yl)benzo[d]isoxazol-3-amine;
(S)-7-fluoro-N-(quinuclidin-3-yl)benzo[d]isoxazol-3-amine;
(R)-5-fluoro-N-(quinuclidin-3-yl)benzo[d]isoxazol-3-amine;
(S)-5-fluoro-N-(quinuclidin-3-yl)benzo[d]isoxazol-3-amine;
(R)-4-fluoro-N-(quinuclidin-3-yl)benzo[d]isoxazol-3-amine;
(S)-4-fluoro-N-(quinuclidin-3-yl)benzo[d]isoxazol-3-amine;
(R)-7-fluoro-6-methyl-N-(quinuclidin-3-yl)benzo[d]isoxazol-3-amine;
(S)-7-fluoro-6-methyl-N-(quinuclidin-3-yl)benzo[d]isoxazol-3-amine;
(R)-6,7-difluoro-N-(quinuclidin-3-yl)benzo[d]isoxazol-3-amine;
(S)-6,7-difluoro-N-(quinuclidin-3-yl)benzo[d]isoxazol-3-amine;
(R)-5-fluoro-6-methyl-N-(quinuclidin-3-yl)benzo[d]isoxazol-3-amine;
(S)-5-fluoro-6-methyl-N-(quinuclidin-3-yl)benzo[d]isoxazol-3-amine;
(R)-6-chloro-7-methyl-N-(quinuclidin-3-yl)benzo[d]isoxazol-3-amine;
(S)-6-chloro-7-methyl-N-(quinuclidin-3-yl)benzo[d]isoxazol-3-amine;
(R)-6-chloro-7-methoxy-N-(quinuclidin-3-yl)benzo[d]isoxazol-3-amine;
(S)-6-chloro-7-methoxy-N-(quinuclidin-3-yl)benzo[d]isoxazol-3-amine;
(R)-6-chloro-N-(quinuclidin-3-yl)-7-(trifluoromethyl)benzo[d]isoxazol-3-amine;
(S)-6-chloro-N-(quinuclidin-3-yl)-7-(trifluoromethyl)benzo[d]isoxazol-3-amine;
(R)-6-chloro-7-cyclopropyl-N-(quinuclidin-3-yl)benzo[d]isoxazol-3-amine;
(S)-6-chloro-7-cyclopropyl-N-(quinuclidin-3-yl)benzo[d]isoxazol-3-amine;
(R)-4-fluoro-6-chloro-N-(quinuclidin-3-yl)benzo[d]isoxazol-3-amine;
(S)-4-fluoro-6-chloro-N-(quinuclidin-3-yl)benzo[d]isoxazol-3-amine;
(R)-4,6-dichloro-N-(quinuclidin-3-yl)benzo[d]isoxazol-3-amine;
(S)-4,6-dichloro-N-(quinuclidin-3-yl)benzo[d]isoxazol-3-amine;
(R)-7-fluoro-6-methoxy-N-(quinuclidin-3-yl)benzo[d]isoxazol-3-amine;
(S)-7-fluoro-6-methoxy-N-(quinuclidin-3-yl)benzo[d]isoxazol-3-amine;
(R)-7-chloro-6-methoxy-N-(quinuclidin-3-yl)benzo[d]isoxazol-3-amine;
(S)-7-chloro-6-methoxy-N-(quinuclidin-3-yl)benzo[d]isoxazol-3-amine;
(R)-7-chloro-6-methyl-N-(quinuclidin-3-yl)benzo[d]isoxazol-3-amine;
(S)-7-chloro-6-methyl-N-(quinuclidin-3-yl)benzo[d]isoxazol-3-amine;
(R)-6-isopropoxy-N-(quinuclidin-3-yl)benzo[d]isoxazol-3-amine;
(S)-6-isopropoxy-N-(quinuclidin-3-yl)benzo[d]isoxazol-3-amine;
(R)-6-ethoxy-N-(quinuclidin-3-yl)benzo[d]isoxazol-3-amine;
(S)-6-ethoxy-N-(quinuclidin-3-yl)benzo[d]isoxazol-3-amine;
(R)-6-chloro-3-(quinuclidin-3-ylamino)benzo[d]isoxazole-7-carbonitrile;
(S)-6-chloro-3-(quinuclidin-3-ylamino)benzo[d]isoxazole-7-carbonitrile;
(R)-7-chloro-6-fluoro-N-(quinuclidin-3-yl)benzo[d]isoxazol-3-amine;
(S)-7-chloro-6-fluoro-N-(quinuclidin-3-yl)benzo[d]isoxazol-3-amine;
(R)-6-(1H-pyrazol-1-yl)-N-(quinuclidin-3-yl)benzo[d]isoxazol-3-amine;
(S)-6-(1H-pyrazol-1-yl)-N-(quinuclidin-3-yl)benzo[d]isoxazol-3-amine;
(R)-6-(5-methyl-1,3,4-oxadiazol-2-yl)-N-(quinuclidin-3-yl)benzo[d]isoxazol-3-amine;
(S)-6-(5-methyl-1,3,4-oxadiazol-2-yl)-N-(quinuclidin-3-yl)benzo[d]isoxazol-3-amine;
(R)-7-methoxy-6-methyl-N-(quinuclidin-3-yl)benzo[d]isoxazol-3-amine;
(S)-7-methoxy-6-methyl-N-(quinuclidin-3-yl)benzo[d]isoxazol-3-amine;
(R)-6-chloro-7-ethoxy-N-(quinuclidin-3-yl)benzo[d]isoxazol-3-amine;
(S)-6-chloro-7-ethoxy-N-(quinuclidin-3-yl)benzo[d]isoxazol-3-amine;
(R)-6,7-dimethyl-N-(quinuclidin-3-yl)benzo[d]isoxazol-3-amine;
(S)-6,7-dimethyl-N-(quinuclidin-3-yl)benzo[d]isoxazol-3-amine;
(R)-6-chloro-7-fluoro-N-(quinuclidin-3-yl)benzo[d]isoxazol-3-amine;
(S)-6-chloro-7-fluoro-N-(quinuclidin-3-yl)benzo[d]isoxazol-3-amine;
(R)-6-chloro-5-fluoro-N-(quinuclidin-3-yl)benzo[d]isoxazol-3-amine;
(S)-6-chloro-5-fluoro-N-(quinuclidin-3-yl)benzo[d]isoxazol-3-amine;
(R)-6-bromo-N-(quinuclidin-3-yl)benzo[d]isoxazol-3-amine; and
(S)-6-bromo-N-(quinuclidin-3-yl)benzo[d]isoxazol-3-amine.

In certain embodiments, specific examples of the aminobenzisoxazole compound represented by Formula (Ia) or Formula (Ib) may include, collectively or individually, the single enantiomers listed below, and pharmaceutically acceptable salts thereof:

(R)-6-cyclopropoxy-N-(quinuclidin-3-yl)benzo[d]isoxazol-3-amine;
(S)-6-cyclopropoxy-N-(quinuclidin-3-yl)benzo[d]isoxazol-3-amine;
(R)-6-ethyl-N-(quinuclidin-3-yl)benzo[d]isoxazol-3-amine;
(S)-6-ethyl-N-(quinuclidin-3-yl)benzo[d]isoxazol-3-amine;
(R)-6-chloro-N-(quinuclidin-3-yl)-7-(trifluoromethoxy)benzo[d]isoxazol-3-amine;
(S)-6-chloro-N-(quinuclidin-3-yl)-7-(trifluoromethoxy)benzo[d]isoxazol-3-amine;
(R)-6-chloro-7-cyclobutyl-N-(quinuclidin-3-yl)benzo[d]isoxazol-3-amine;
(S)-6-chloro-7-cyclobutyl-N-(quinuclidin-3-yl)benzo[d]isoxazol-3-amine;
(R)-5-fluoro-6-methoxy-N-(quinuclidin-3-yl)benzo[d]isoxazol-3-amine;
(S)-5-fluoro-6-methoxy-N-(quinuclidin-3-yl)benzo[d]isoxazol-3-amine;
(R)-6-methoxy-7-methyl-N-(quinuclidin-3-yl)benzo[d]isoxazol-3-amine;
(S)-6-methoxy-7-methyl-N-(quinuclidin-3-yl)benzo[d]isoxazol-3-amine;
(R)-6-methyl-N-(quinuclidin-3-yl)-7-(trifluoromethyl)benzo[d]isoxazol-3-amine;
(S)-6-methyl-N-(quinuclidin-3-yl)-7-(trifluoromethyl)benzo[d]isoxazol-3-amine;
(R)-6-chloro-5,7-difluoro-N-(quinuclidin-3-yl)benzo[d]isoxazol-3-amine;
(S)-6-chloro-5,7-difluoro-N-(quinuclidin-3-yl)benzo[d]isoxazol-3-amine;
(R)-6-chloro-7-(difluoromethyl)-N-(quinuclidin-3-yl)benzo[d]isoxazol-3-amine;
(S)-6-chloro-7-(difluoromethyl)-N-(quinuclidin-3-yl)benzo[d]isoxazol-3-amine;
(R)-6-chloro-7-isopropoxy-N-(quinuclidin-3-yl)benzo[d]isoxazol-3-amine;
(S)-6-chloro-7-isopropoxy-N-(quinuclidin-3-yl)benzo[d]isoxazol-3-amine;
(R)-6-chloro-7-cyclopropoxy-N-(quinuclidin-3-yl)benzo[d]isoxazol-3-amine;
(S)-6-chloro-7-cyclopropoxy-N-(quinuclidin-3-yl)benzo[d]isoxazol-3-amine;
(R)-7-ethoxy-6-methyl-N-(quinuclidin-3-yl)benzo[d]isoxazol-3-amine;
(S)-7-ethoxy-6-methyl-N-(quinuclidin-3-yl)benzo[d]isoxazol-3-amine;
(R)-7-ethoxy-6-fluoro-N-(quinuclidin-3-yl)benzo[d]isoxazol-3-amine;
(S)-7-ethoxy-6-fluoro-N-(quinuclidin-3-yl)benzo[d]isoxazol-3-amine;
(R)-6-fluoro-7-methoxy-N-(quinuclidin-3-yl)benzo[d]isoxazol-3-amine;
(S)-6-fluoro-7-methoxy-N-(quinuclidin-3-yl)benzo[d]isoxazol-3-amine;
(R)-6-methoxy-N-(quinuclidin-3-yl)-7-(trifluoromethyl)benzo[d]isoxazol-3-amine;
(S)-6-methoxy-N-(quinuclidin-3-yl)-7-(trifluoromethyl)benzo[d]isoxazol-3-amine;
(R)-5-fluoro-7-methyl-N-(quinuclidin-3-yl)benzo[d]isoxazol-3-amine;
(S)-5-fluoro-7-methyl-N-(quinuclidin-3-yl)benzo[d]isoxazol-3-amine;
(R)-5,6-difluoro-7-methyl-N-(quinuclidin-3-yl)benzo[d]isoxazol-3-amine;
(S)-5,6-difluoro-7-methyl-N-(quinuclidin-3-yl)benzo[d]isoxazol-3-amine;
(R)-5,7-difluoro-N-(quinuclidin-3-yl)benzo[d]isoxazol-3-amine;
(S)-5,7-difluoro-N-(quinuclidin-3-yl)benzo[d]isoxazol-3-amine;
(R)-6-chloro-5-fluoro-7-methyl-N-(quinuclidin-3-yl)benzo[d]isoxazol-3-amine;
(S)-6-chloro-5-fluoro-7-methyl-N-(quinuclidin-3-yl)benzo[d]isoxazol-3-amine;
(R)-6-chloro-5-fluoro-N-(quinuclidin-3-yl)-7-(trifluoromethyl)benzo[d]isoxazol-3-amine;
(S)-6-chloro-5-fluoro-N-(quinuclidin-3-yl)-7-(trifluoromethyl)benzo[d]isoxazol-3-amine;
(R)-6-chloro-5-fluoro-7-methoxy-N-(quinuclidin-3-yl)benzo[d]isoxazol-3-amine;
(S)-6-chloro-5-fluoro-7-methoxy-N-(quinuclidin-3-yl)benzo[d]isoxazol-3-amine;
(R)-5,7-difluoro-6-methyl-N-(quinuclidin-3-yl)benzo[d]isoxazol-3-amine;
(S)-5,7-difluoro-6-methyl-N-(quinuclidin-3-yl)benzo[d]isoxazol-3-amine;
(R)-6,7-dichloro-5-fluoro-N-(quinuclidin-3-yl)benzo[d]isoxazol-3-amine;
(S)-6,7-dichloro-5-fluoro-N-(quinuclidin-3-yl)benzo[d]isoxazol-3-amine;
(R)-6-chloro-7-ethoxy-5-fluoro-N-(quinuclidin-3-yl)benzo[d]isoxazol-3-amine;
(S)-6-chloro-7-ethoxy-5-fluoro-N-(quinuclidin-3-yl)benzo[d]isoxazol-3-amine;
(R)-5,7-difluoro-6-methoxy-N-(quinuclidin-3-yl)benzo[d]isoxazol-3-amine; and
(S)-5,7-difluoro-6-methoxy-N-(quinuclidin-3-yl)benzo[d]isoxazol-3-amine.

In certain embodiments, specific examples of the aminobenzisoxazole compound represented by Formula (Ia) or Formula (Ib) may include, collectively or individually, the single enantiomers listed below, and pharmaceutically acceptable salts thereof:
(R)-6-chloro-N-(quinuclidin-3-yl)benzo[d]isoxazol-3-amine;
(S)-6-chloro-N-(quinuclidin-3-yl)benzo[d]isoxazol-3-amine;
(R)-6-methyl-N-(quinuclidin-3-yl)benzo[d]isoxazol-3-amine;
(R)-6-methoxy-N-(quinuclidin-3-yl)benzo[d]isoxazol-3-amine;
(S)-6-methoxy-N-(quinuclidin-3-yl)benzo[d]isoxazol-3-amine;
(R)-6,7-dichloro-N-(quinuclidin-3-yl)benzo[d]isoxazol-3-amine;
(R)-7-fluoro-6-methyl-N-(quinuclidin-3-yl)benzo[d]isoxazol-3-amine;
(R)-5-fluoro-6-methyl-N-(quinuclidin-3-yl)benzo[d]isoxazol-3-amine;
(R)-6-chloro-7-methyl-N-(quinuclidin-3-yl)benzo[d]isoxazol-3-amine;
(R)-6-chloro-7-methoxy-N-(quinuclidin-3-yl)benzo[d]isoxazol-3-amine;
(R)-6-chloro-N-(quinuclidin-3-yl)-7-(trifluoromethyl)benzo[d]isoxazol-3-amine;
(R)-6-chloro-7-fluoro-N-(quinuclidin-3-yl)benzo[d]isoxazol-3-amine; and
(R)-6-chloro-5-fluoro-N-(quinuclidin-3-yl)benzo[d]isoxazol-3-amine.

In certain embodiments, specific examples of the aminobenzisoxazole compound represented by Formula (Ia) or Formula (Ib) may include, collectively or individually, the single enantiomers listed below, and pharmaceutically acceptable salts thereof:

(R)-6-chloro-N-(quinuclidin-3-yl)benzo[d]isoxazol-3-amine;

(R)-6-methyl-N-(quinuclidin-3-yl)benzo[d]isoxazol-3-amine;

(R)-6,7-dichloro-N-(quinuclidin-3-yl)benzo[d]isoxazol-3-amine;

(R)-7-fluoro-6-methyl-N-(quinuclidin-3-yl)benzo[d]isoxazol-3-amine;

(R)-6-chloro-7-methyl-N-(quinuclidin-3-yl)benzo[d]isoxazol-3-amine;

(R)-6-chloro-7-methoxy-N-(quinuclidin-3-yl)benzo[d]isoxazol-3-amine;

(R)-6-chloro-N-(quinuclidin-3-yl)-7-(trifluoromethyl)benzo[d]isoxazol-3-amine; and (R)-6-chloro-7-fluoro-N-(quinuclidin-3-yl)benzo[d]isoxazol-3-amine.

In certain embodiments, specific examples of the aminobenzisoxazole compound represented by Formula (Ia) or Formula (Ib) may include, collectively or individually, the single enantiomers listed below, and pharmaceutically acceptable salts thereof:

(S)-6-chloro-N-(quinuclidin-3-yl)benzo[d]isoxazol-3-amine;

(R)-6-methoxy-N-(quinuclidin-3-yl)benzo[d]isoxazol-3-amine;

(S)-6-methoxy-N-(quinuclidin-3-yl)benzo[d]isoxazol-3-amine;

(R)-5-fluoro-6-methyl-N-(quinuclidin-3-yl)benzo[d]isoxazol-3-amine; and (R)-6-chloro-5-fluoro-N-(quinuclidin-3-yl)benzo[d]isoxazol-3-amine.

In certain embodiments, the aminobenzisoxazole compounds of the present invention represented by Formula (Ia) or Formula (Ib), or a pharmaceutically acceptable salt thereof, may be more potent against α7 nAChR (according to the α7 nAChR Binding Assay (Ki)) than against a 5-HT$_3$ serotonin receptor (according to the [$^3$H]BRL 43694 competition binding (Ki)). For example, the aminobenzisoxazole compounds of the present invention represented by Formula (Ia) or Formula (Ib), or a pharmaceutically acceptable salt thereof, may be at least 1.5 times more potent against α7 nAChR than against a 5-HT$_3$ serotonin receptor, as determined by the α7 nAChR Binding Assay and the [$^3$H]BRL 43694 competition binding assay, respectively, such as at least 2 times more potent, at least 3 times more potent, at least 4 times more potent, at least 5 times more potent, at least 6 times more potent, at least 7 times more potent, at least 8 times more potent, at least 9 times more potent, at least 10 times more potent, at least 15 times more potent, at least 20 times more potent, or at least 25 times more potent against α7 nAChR than against a 5-HT$_3$ serotonin receptor, as determined by the α7 nAChR Binding Assay and the [$^3$H]BRL 43694 competition binding assay, respectively.

As used herein, the term "treating" (or "treat" or "treatment"), unless otherwise specified, includes the generally accepted meaning which encompasses improving, modifying, decreasing, prohibiting, preventing, restraining, minimizing, slowing, halting, stopping, curing, and/or reversing a symptom associated with a disease and/or a disease. Treatment may include both therapeutic and prophylactic administration. For example, treatment of a cognitive impairment, in a patient diagnosed as having a cognitive impairment, may include, but is not limited to, curing the cognitive impairment, preventing the deterioration of one or more symptoms associated with the cognitive impairment; improving cognition in a patient suffering from the cognitive impairment, slowing the progression of the cognitive impairment and/or modifying the cognitive impairment.

As used herein, the term "effective dose" (or "dose"), unless otherwise specified, is understood to include a therapeutically acceptable dose, a thereapeutically acceptable amount, a thereapeutically effective dose, a thereapeutically effective amount, a pharmaceutically acceptable dose, a pharmaceutically acceptable amount, a pharmaceutically effective dose, or a pharmaceutically effective amount.

As used herein, the term "cognitive impairment," unless otherwise specified, includes at least one of the following: Limited Cognitive Impairment (LCI), Mild Cognitive Impairment (MCI), Alzheimer's disease (or dementia of an Alzheimer's-type) or a particular stage of Alzheimer's disease, inclusive of pre-Alzheimer's disease, early Alzheimer's disease, mild Alzheimer's disease, moderate Alzheimer's disease, severe Alzheimer's disease, pre-Alzheimer's-to-mild Alzheimer's disease, mild-to-moderate Alzheimer's disease, moderate-to-severe Alzheimer's disease, schizophrenia (for example, paranoid type schizophrenia, disorganized type schizophrenia, catatonic type schizophrenia, undifferentiated type schizophrenia), schizophreniform disorder, schizoaffective disorder, delusional disorder, positive symptoms of schizophrenia, negative symptoms of schizophrenia, or schizophrenia with dementia.

Alzheimer's disease may include, unless otherwise specified, any of the sub-diagnostic categories used to characterize the type or degree of cognitive impairment in a patient for treatment purposes. A commonly referenced diagnostic scale for characterizing the degree of cognitive impairment for a patient with Alzheimer's disease includes the 3-stage Alzheimer Disease Model. The 3-stages consist of: mild stage (also referred to as "early Alzheimer's disease" or "mild Alzheimer's disease" or "early stage Alzheimer's disease" or "mild dementia of an Alzheimer's-type"), moderate stage (also referred to as "middle Alzheimer's disease" or "moderate Alzheimer's disease" or "middle stage Alzheimer's disease" or "moderate dementia of an Alzheimer's-type"), and severe stage (also referred to as "late Alzheimer's disease" or "severe Alzheimer's disease" or "late stage Alzheimer's disease" or "severe dementia of an Alzheimer's-type"). For patients with a condition that has not progressed to the point of mild stage Alzheimer's disease, they may be diagnosed as having pre-Alzheimer's disease. It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. Another useful diagnostic scale that is used in characterizing the degree of cognitive impairment for a patient having Alzheimer's disease is the Seven Stage Alzheimer's Disease Model (sometimes known as the "Seven Stage Global Deterioration Scale" or the "Reisberg Scale"). This diagnostic scale divides the progression of the cognitive disorder associated with Alzheimer's disease as follows: Stage 1-no Alzheimer's disease (generally characterized by absence of impairment, no impairment, or normal function), Stage 2-pre-Alzheimer's disease (generally characterized by minimal impairment, normal forgetfulness, or very mild cognitive decline), Stage 3-early-stage Alzheimer's disease (generally characterized by a noticeable cognitive decline, early confusional/mild cognitive impairment, or mild cognitive decline), Stage 4-early-stage/mild Alzheimer's disease (also referred to as late confusional/mild Alzheimer's, and generally characterized by moderate cognitive decline), Stage 5-middle-stage/moderate Alzheimer's (also referred to as early dementia/moderate Alzheimer's disease and generally characterized by moderately severe cognitive decline), Stage 6-middle dementia/moderately severe Alzheimer's disease (also referred to as middle-stage/moderate to late-stage/severe Alzheimer's disease and generally characterized by severe cognitive decline), and Stage 7-late-stage/severe Alzheimer's disease (also referred to as severe dementia or failure-to-thrive, and generally characterized by very severe cognitive decline). It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. As used herein, unless otherwise specified, Alzheimer's disease includes all of the above named diagnostic catagories or disease characterizations. It is also not uncommon for a physician to categorize any one or more of the above noted states of Alzheimer's disease as being probable, for example, probable mild-to-moderate Alzheimer's disease or probable severe Alzheimer's disease, when their diagnosis does not include, for example a physical biopsy or other definitive analysis.

Mild Cognitive Impairment (MCI) is considered by some to be an intermediate stage between normal aging and the onset of Alzheimer's disease. For example, MCI may be characterized by persistent forgetfulness, but may lack some or many of the more debilitating symptoms of Alzheimer's disease. Another set of criteria that may characterize a patient as having mild cognitive impairment suitable for treatment includes a patient that meets the following: 1) memory complaints corroborated by an informant, 2) objective memory impairment for age and education, 3) normal general cognitive function, 4) intact activities of daily living, and 5) the patient does not meet criteria for dementia. In general, a patient characterized as having mild cognitive impairment may not yet have a clinical cognitive deficit. Mild cognitive impairment may also be distinguished from senile dementia in that mild cognitive impairment involves a more persistent and troublesome problem of memory loss for the age of the patient. On the clinical diagnostic scale, mild cognitive impairment is followed, in increased severity, by Alzheimer's disease.

Limited Cognitive Impairment (LCI) describes a cognitive impairment (i.e., symptoms or conditions), which precedes mild cognitive impairment on a clinical diagnostic scale, and includes any chronic or temporary impairment in cognition, learning or memory that prevents or reduces the ability of a patient from achieving their individual potential in these areas. For example, LCIs may include minor impairments to memory associated with focus and concentration (e.g., accuracy and speed of learning and recalling information), working memory (e.g., used in decision making and problem solving), cognition, focus, mental quickness, and mental clarity.

The term "stereoisomer" refers to a molecule capable of existing in more than one spatial atomic arrangement for a given atomic connectivity (e.g., enantiomers, meso compounds, and diastereomers). As used herein, the term "stereoisomer" means either or both enantiomers and diastereomers.

The aminobenzisoxazole compounds of the present invention represented by Formula (Ia) or Formula (Ib), or a pharmaceutically acceptable salt thereof, may contain one or more stereogenic centers. Accordingly, compounds of this invention can exist as either individual stereoisomers or mixtures of two or more stereoisomers. A compound of the present invention will include both mixtures (e.g., racemic mixtures) and also individual respective stereoisomers that are substantially free from another possible stereoisomer. The term "substantially free of other stereoisomers" as used herein means less than 25% of other stereoisomers, less than 10% of other stereoisomers, less than 5% of other stereoisomers, less than 2% of other stereoisomers, or less than "X"% of other stereoisomers (wherein X is a number between 0 and 100, inclusive) are present.

The aminobenzisoxazole compounds of the present invention represented by Formula (Ia) or Formula (Ib), or a pharmaceutically acceptable salt thereof, may contain one or more tautomeric forms. Accordingly, compounds of this invention can exist as either individual tautomers or mixtures of tautomeric forms. A compound of the present invention will include both mixtures (e.g., mixtures of tautomeric forms) and also individual respective tautomers that are substantially free from another possible tautomer.

The aminobenzisoxazole compounds of the present invention represented by Formula (Ia) or Formula (Ib), or a pharmaceutically acceptable salt thereof, may contain one or more geometric isomers. Accordingly, compounds of this invention can exist as either geometric isomers or mixtures of geometric isomers. A compound of the present invention will include both mixtures (e.g., mixtures of geometric isomers) and also individual respective geometric isomers that are substantially free from another possible geometric isomer.

The term "haloalkyl" refers to an alkyl group having from 1 to 5 halogen substituents independently selected from —F, —Cl, —Br, and —I. For example, a haloalkyl may represent a —$CF_3$ group, a —$CCl_3$ group, a —$CH_2CF_3$ group, or a —$CF_2CF_3$ group.

The term "heteroaryl" refers to an aromatic ring system comprising at least one or more hetero-ring atoms, such as two, three, four, or five hetero-ring atoms, independently selected from N, O, and S. Suitable heteroaryl groups may include a single ring, for example, thienyl, pyridyl, thiazolyl, pyrazinyl, pyrimidyl, imidazolyl, furanyl, isothiazolyl, pyrazolyl, triazolyl, tetrazolyl, isoxazolyl, oxazolyl, pyrrolyl, pydridazinyl, triazinyl, oxadiazolyl, and furazanyl. Suitable heteroaryl groups may include a fused ring system, for example, a six-six fused ring system, a six-five fused ring system, or a five-six fused ring system, such as benzothienyl, quinolyl, benzofuranyl, benzothiazolyl, benzisothiazolyl, benzisoxazolyl, benzimidazolyl, indolyl, benzoxazolyl, isoquinolinyl, cinnolinyl, indazolyl, indolizinyl, phthalazinyl, isoindolyl, purinyl, benzofurazanyl, benzothiophenyl, benzothiazolyl, quinazolinyl, quinoxalinyl, naphthridinyl, and furopyridinyl.

Suitable "heterocycloalkyl" groups include those having at least one or more hetero-ring atoms, such as two or three hetero-ring atoms, independently selected from at least one ring atom selected from the group consisting of oxygen, nitrogen, and sulfur, with the proviso that when the at least one ring atom is nitrogen, the nitrogen is independently substituted with —H, an unbranched $C_1$-$C_4$-alkyl radical, a branched $C_3$-$C_4$-alkyl radical, a $C_3$-$C_4$-cycloalkyl radical, —(CO)-unbranched $C_1$-$C_4$-alkyl, —(CO)-branched $C_3$-$C_4$-alkyl, —($SO_2$)-unbranched $C_1$-$C_4$-alkyl, or —($SO_2$)-branched $C_3$-$C_4$-alkyl, and with the further proviso that when the at least one ring atom is sulfur, the sulfur may be independently substituted with 0 to 2=O. Suitable heterocycloalkyl groups may include, for example, tetrahydrofurano, tetrahydropyrano, morpholino, pyrrolidino, piperidino, piperazino, azetidino, azetidinono, oxindolo, oxetano, dihydroimidazolo, and pyrrolidinono.

The pharmaceutically acceptable salt of the aminobenzisoxazole compounds represented by Formula (Ia) or Formula (Ib), according to the present invention may be acid addition salts with inorganic or organic acids. Specific examples of these salts include acid addition salts with, for instance, mineral acids such as hydrochloric acid, hydrobromic acid, hydriodic acid, sulfuric acid, nitric acid or phosphoric acid; organic acids, for example carboxylic acids or sulfonic acids, such as formic acid, acetic acid, propionic acid, oxalic acid, malonic acid, succinic acid, fumaric acid, maleic acid, lactic acid, malic acid, tartaric acid, citric acid, benzoic acid, p-toluenesulfonic acid, benzenesulfonic acid, naphthalenedisulfonic acid, isethionic acid, glucuronic acid, gluconic acid, methanesulfonic acid or ethanesulfonic acid; or acidic amino acids such as aspartic acid or glutamic acid.

In certain embodiments, a pharmaceutical composition may comprise an aminobenzisoxazole compound represented by Formula (Ia) or Formula (Ib), or a pharmaceutically acceptable salt thereof, and at least one pharmaceutically acceptable carrier, excipient or diluent.

In certain embodiments, the aminobenzisoxazole compounds represented by Formula (Ia) or Formula (Ib), or a pharmaceutically acceptable salt thereof, are suitable for use as medicaments for the treatment and/or prophylaxis of diseases in humans and/or animals.

In certain embodiments, the invention relates to a method comprising administering to a patient in need thereof an effective dose of an aminobenzisoxazole compound represented by Formula (Ia) or Formula (Ib), or a pharmaceutically acceptable salt thereof, or administering to the patient a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

In certain embodiments, the aminobenzisoxazole compound represented by Formula (Ia) or Formula (Ib), or a pharmaceutically acceptable salt thereof, act as ligands, in particular as α7-nAChR agonists.

In certain embodiments, a method of treating a patient in need thereof, comprising administering an aminobenzisoxazole compound represented by Formula (Ia) or Formula (Ib), or a pharmaceutically acceptable salt thereof. In certain embodiments, a method of treating a patient in need thereof, comprising administering a pharmaceutical composition comprising an aminobenzisoxazole compound represented by Formula (Ia) or Formula (Ib), or a pharmaceutically acceptable salt thereof. For example, the patient may suffer from a cognitive impairment or suffers from one or more symptoms associated with a cognitive impairment, such as Limited Cognitive Impairment (LCI), Mild Cognitive Impairment (MCI), Alzheimer's disease, dementia of an Alzheimer's-type, schizophrenia, schizophreniform disorder, schizoaffective disorder, delusional disorder, positive symptoms of schizophrenia, negative symptoms of schizophrenia, or schizophrenia with dementia.

In certain embodiments, the aminobenzisoxazole compounds represented by Formula (Ia) or Formula (Ib), or a pharmaceutically acceptable salt thereof, can, because of their pharmacological properties, be employed alone or in combination with other active ingredients for the treatment and/or prevention of cognitive impairments, for example, Alzheimer's disease or schizophrenia. Because of their selective effect as α7-nAChR agonists, the aminobenzisoxazole compounds represented by Formula (Ia) or Formula (Ib), or a pharmaceutically acceptable salt thereof, are particularly suitable for improving cognition, providing procognitive effects, improving perception, improving concentration, improving learning or memory, improving one or more aspects of cognition, e.g., one or more of: executive function, memory (e.g., working memory), social cognition, visual learning, verbal learning and speed of processing, especially after or associated with cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic brain syndrome, general concentration impairments, concentration impairments in children with learning and memory problems, attention deficit hyperactivity disorder, Alzheimer's disease, Lewy body dementia, dementia with degeneration of the frontal lobes, including Pick's syndrome, Parkinson's disease, dyskinesias associated with dopamine agonist therapy in Parkinson's Disease, progressive nuclear palsy, dementia with corticobasal degeneration, amyotrophic lateral sclerosis (ALS), Huntington's disease, multiple sclerosis, thalamic degeneration, Creutzfeld-Jakob dementia, HIV dementia, schizophrenia (e.g., paranoid type, disorganized type, catatonic type, and undifferentiated type), schizophreniform disorder, schizoaffective disorder, delusional disorder, positive symptoms of schizophrenia, negative symptoms of schizophrenia, schizophrenia with dementia, Korsakoff s psychosis, depression, anxiety, mood and affective disorders, traumatic brain injury, withdrawal symptoms associated with smoking cessation and dependent drug cessation, Gilles de la Tourette's Syndrome, age-related macular degeneration, glaucoma, neurodegeneration associated with glaucoma, treatment (including amelioration, prevention or delay of progression) of sleep disorders (e.g., narcolepsy, excessive daytime sleepiness, nocturnal sleep disruption and/or cataplexy), treatment (including amelioration, prevention or delay) of progression of fatigue, or use for facilitation of emergence from general anesthesia.

In certain embodiments, the aminobenzisoxazole compounds represented by Formula (Ia) or Formula (Ib), or a pharmaceutically acceptable salt thereof, can be employed alone or in combination with other active ingredients for the prophylaxis and treatment of acute and/or chronic pain (for a classification, see "Classification of Chronic Pain, Descriptions of Chronic Pain Syndromes and Definitions of Pain Terms", $2^{nd}$ edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache, or rheumatic pain. In addition, these active ingredients are also suitable for the therapy of primary acute pain of any origin and of secondary states of pain resulting therefrom, and for the therapy of states of pain which were formerly acute and have become chronic.

In certain embodiments, the invention relates to a method comprising administering to a patient in need thereof, such as a patient suffering from, or diagnosed as having, a cognitive impairment or having one or more symptoms associated with a cognitive impairment, an effective dose of an aminobenzisoxazole compound represented by Formula (Ia) or Formula (Ib), or a pharmaceutically acceptable salt thereof; or administering to the patient a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent. For example, the method may treat and/or improve the one or more symptoms associated with a cognitive impairment and/or the cognitive impairment.

A certain embodiment of the present invention provides a method of improving one or more cognitive symptoms, improving one or more behavioral symptoms, or both, associated with a cognitive impairment, comprising: administering to a patient in need thereof an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent.

In a certain embodiment of the present invention, the method provides a pro-cognitive effect in a patient suffering from, or diagnosed as having, a cognitive disease or dementia, comprising: administering to a patient in need thereof an effective dose of an aminobenzisoxazole compound represented by Formula (Ia) or Formula (Ib), or a pharmaceutically acceptable salt thereof; or administering to the patient a pharmaceutical composition comprising an effective dose of the aminobenzisoxazole compound represented by Formula (Ia) or Formula (Ib), or a pharmaceutically acceptable salt thereof, and at least one pharmaceutically acceptable carrier, excipient or diluent; wherein the method provides at least one of the following: visual motor, learning, delayed memory, or executive function; for example provides a pro-cognitive effect, exclusive of attention, in said patient; for example provides a pro-cognitive effect in at least one of the following: visual motor, learning, delayed memory, or executive function.

A certain embodiment of the present invention provides a method of treating a patient with a cognitive disease, comprising: administering to the patient a daily dose of a pharmaceutical composition comprising an aminobenzisoxazole compound represented by Formula (Ia) or Formula (Ib), or a pharmaceutically acceptable salt thereof, and at least one pharmaceutically acceptable carrier, excipient or diluent.

In a certain embodiment of the present invention, the method provides a pro-cognitive effect in a patient suffering from, or diagnosed as having, schizophrenia, for example, paranoid type schizophrenia, disorganized type schizophrenia, catatonic type schizophrenia, undifferentiated type schizophrenia, schizophreniform disorder, schizoaffective disorder, delusional disorder, positive symptoms of schizophrenia, negative symptoms of schizophrenia, or schizophrenia with dementia, comprising: administering to a patient in need thereof an effective dose of an aminobenzisoxazole compound represented by Formula (Ia) or Formula (Ib), or a pharmaceutically acceptable salt thereof; or administering to a patient in need thereof, a pharmaceutical composition comprising an effective dose of an aminobenzisoxazole compound represented by Formula (Ia) or Formula (Ib), or a pharmaceutically acceptable salt thereof, and at least one pharmaceutically acceptable carrier, excipient or diluents; wherein the method provides at least one of the following: visual motor, learning, delayed memory, or executive function; for example provides a pro-cognitive effect, exclusive of attention, in said patient; for example provides a pro-cognitive effect in at least one of the following: visual motor, learning, delayed memory, or executive function.

In an embodiment of the present invention, any one of the above-noted embodiments, includes wherein the daily dose is an initial daily dose.

In a certain embodiment of the present invention provides a method of improving cognition of a patient in need thereof, comprising: administering to the patient an aminobenzisoxazole compound represented by Formula (Ia) or Formula (Ib), or a pharmaceutically acceptable salt thereof; or administering to the patient a pharmaceutical composition comprising an effective dose of an aminobenzisoxazole compound represented by Formula (Ia) or Formula (Ib), or a pharmaceutically acceptable salt thereof, and at least one pharmaceutically acceptable carrier, excipient or diluents.

In a certain embodiment of the present invention provides a method of treating or improving one or more symptoms associated with a cognitive disease and/or a cognitive impairment in a patient in need thereof, comprising: administering to the patient an effective dose of an aminobenzisoxazole compound represented by Formula (Ia) or Formula (Ib), or a pharmaceutically acceptable salt thereof; or administering to the patient a pharmaceutical composition comprising the aminobenzisoxazole compound represented by Formula (Ia) or Formula (Ib), or a pharmaceutically acceptable salt thereof, and at least one pharmaceutically acceptable carrier, excipient or diluent.

In an embodiment of the present invention, any one of the above-noted embodiments, wherein the method specifically includes treating a symptom associated with a cognitive disease.

In an embodiment of the present invention, any one of the above-noted embodiments, wherein the method specifically includes improving a symptom associated with a cognitive disease.

In an embodiment of the present invention, any one of the above-noted embodiments, wherein the method specifically includes preventing progression of a cognitive disease.

In an embodiment of the present invention, any one of the above-noted embodiments, wherein the patient has been diagnosed as having a cognitive disease.

In an embodiment of the present invention, any one of the above-noted embodiments, wherein the patient has been diagnosed as having Alzheimer's disease.

In an embodiment of the present invention, any one of the above-noted embodiments, wherein the method specifically includes treating a symptom associated with Alzheimer's disease.

In an embodiment of the present invention, any one of the above-noted embodiments, wherein the method specifically includes improving a symptom associated with Alzheimer's disease.

In an embodiment of the present invention, any one of the above-noted embodiments, wherein the method specifically includes preventing progression of Alzheimer's disease.

In an embodiment of the present invention, any one of the above-noted embodiments, wherein the patient has been diagnosed as having mild-to-moderate Alzheimer's disease.

In an embodiment of the present invention, any one of the above-noted embodiments, wherein the method specifically includes treating a symptom associated with schizophrenia.

In an embodiment of the present invention, any one of the above-noted embodiments, wherein the method specifically includes improving a symptom associated with schizophrenia.

In an embodiment of the present invention, any one of the above-noted embodiments, wherein the method specifically includes preventing progression of schizophrenia.

In an embodiment of the present invention, any one of the above-noted embodiments, wherein the patient has been diagnosed as having schizophrenia.

In an embodiment of the present invention, any one of the above-noted embodiments, wherein the method specifically includes treating a symptom associated with positive symptoms of schizophrenia.

In an embodiment of the present invention, any one of the above-noted embodiments, wherein the method specifically includes improving a symptom associated with positive symptoms of schizophrenia.

In an embodiment of the present invention, any one of the above-noted embodiments, wherein the method specifically includes preventing progression of positive symptoms of schizophrenia.

In an embodiment of the present invention, any one of the above-noted embodiments, wherein the method specifically includes the patient has been diagnosed as having positive symptoms of schizophrenia.

In an embodiment of the present invention, any one of the above-noted embodiments, wherein the method specifically includes treating a symptom associated with negative symptoms of schizophrenia.

In an embodiment of the present invention, any one of the above-noted embodiments, wherein the method specifically includes improving a symptom associated with negative symptoms of schizophrenia.

In an embodiment of the present invention, any one of the above-noted embodiments, wherein the method specifically includes preventing progression of negative symptoms of schizophrenia.

In an embodiment of the present invention, any one of the above-noted embodiments, wherein the method specifically includes the patient has been diagnosed as having negative symptoms of schizophrenia.

In an embodiment of the present invention, any one of the above-noted embodiments, wherein the method specifically includes treating a symptom associated with schizophrenia with dementia.

In an embodiment of the present invention, any one of the above-noted embodiments, wherein the method specifically includes improving a symptom associated with schizophrenia with dementia.

In an embodiment of the present invention, any one of the above-noted embodiments, wherein the method specifically includes preventing progression of schizophrenia with dementia.

In an embodiment of the present invention, any one of the above-noted embodiments, wherein the method specifically includes the patient has been diagnosed as having schizophrenia with dementia.

In an embodiment of the present invention, any one of the above-noted embodiments, wherein the method specifically includes the patient has been diagnosed as having a disease associated with chronic inflammation, including atherosclerosis, rheumatoid arthritis and inflammatory bowel diseases.

In an embodiment of the present invention, any one of the above-noted embodiments, wherein the pharmaceutical composition is in the form of a tablet.

Pharmaceutical Compositions

In certain embodiments, the invention also includes pharmaceutical preparations which, besides inert, nontoxic, pharmaceutically suitable excipients, adjuvants and carriers, contain one or more aminobenzisoxazole compounds represented by Formula (Ia) or Formula (Ib), or a pharmaceutically acceptable salt thereof, or consist of one or more aminobenzisoxazole compounds represented by Formula (Ia) or Formula (Ib), or a pharmaceutically acceptable salt thereof, and processes for producing these preparations.

An aminobenzisoxazole compound represented by Formula (Ia) or Formula (Ib), or a pharmaceutically acceptable salt thereof, may be formulated for administration in solid or liquid form. For example, an aminobenzisoxazole compound represented by Formula (Ia) or Formula (Ib), or a pharmaceutically acceptable salt thereof, may be formulated for administration in a capsule, a tablet, or a powder form. For example, an aminobenzisoxazole compound represented by Formula (Ia) or Formula (Ib), or a pharmaceutically acceptable salt thereof, may be formulated alone or as part of a pharmaceutical composition, suitable for oral administration, such as in a capsule or tablet, intravenous administration, parenteral administration, topical administration, or transdermal administration, such as in a patch, to a patient in need thereof.

An aminobenzisoxazole compound represented by Formula (Ia) or Formula (Ib), or a pharmaceutically acceptable salt thereof, may be administered as a pharmaceutical composition, for example, in the presence of carriers, adjuvants, excipients, diluents, fillers, buffers, stabilizers, preservatives, lubricants, and the like, for example, administered as a pharmaceutical composition (e.g., formulation) comprising at least an aminobenzisoxazole compound represented by Formula (Ia) or Formula (Ib), or a pharmaceutically acceptable salt thereof, together with one or more pharmaceutically acceptable carriers, adjuvants, excipients, diluents, or other materials well known to those skilled in the art. As used herein, the term "pharmaceutically acceptable", unless otherwise specified, includes the generally accepted meaning which encompasses combinations, compounds, materials, compositions, and/or dosage forms which are, within the scope of sound medical judgment, suitable for consumption by humans without excessive toxicity, irritation, allergic response, or other problem or complication, commensurate with a reasonable benefit/risk ratio.

Suitable pharmaceutically acceptable carriers, adjuvants, excipients, and diluents, can include, but are not limited to, lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The formulations can additionally include, but are not limited to, pharmaceutically acceptable lubricating agents, glidants, wetting agents, emulsifying and suspending agents, preserving agents, sweetening agents, and/or flavoring agents. The pharmaceutical compositions of the present invention may be formulated so as to provide quick release, immediate release, sustained release, or delayed release of an aminobenzisoxazole compound represented by Formula (Ia) or Formula (Ib), or a pharmaceutically acceptable salt thereof, after administration to the patient by employing procedures well-known in the art.

Another embodiment of the invention further comprises methods of making Pharmaceutical Composition, comprising admixing at least an aminobenzisoxazole compound represented by Formula (Ia) or Formula (Ib), or a pharmaceutically acceptable salt thereof, together with one or more pharmaceutically acceptable carriers, excipients, buffers, adjuvants, stabilizers, or other materials.

In certain embodiments, the aminobenzisoxazole compounds represented by Formula (Ia) or Formula (Ib), or a pharmaceutically acceptable salt thereof, are to be present in these preparations in a concentration of from 0.1 to 99.5% by weight, preferably from 0.5 to 95% by weight, of the complete mixture. Besides the aminobenzisoxazole compounds represented by Formula (Ia) or Formula (Ib), or a pharmaceutically acceptable salt thereof, the pharmaceutical preparations may also contain other active pharmaceutical ingredients.

In certain embodiments, the novel active ingredients can be converted in a known manner into conventional formulations such as tablets, coated tablets, pills, granules, aerosols, syrups, emulsions, suspensions and solutions, using inert, nontoxic, pharmaceutically suitable excipients or solvents. In these cases, the therapeutically active compound should in each case be present in a concentration of about 0.5 to 90% by weight of the entire mixture, i.e., in amounts which are sufficient to reach the stated dose range.

In certain embodiments, the formulations are produced, for example, by extending the active ingredients with solvents and/or excipients, where appropriate with use of emulsifiers and/or dispersants, it being possible for example when water is used as diluent where appropriate to use organic solvents as auxiliary solvents.

In certain embodiments, administration may take place in a conventional way, for example, orally, transdermally or parenterally, especially perlingually or intravenously. In certain embodiments, administration may also take place by inhalation through the mouth or nose, for example, with the aid of a spray, or topically via the skin.

In certain embodiments, the aminobenzisoxazole compounds represented by Formula (Ia) or Formula (Ib), or a pharmaceutically acceptable salt thereof, may be administered in amounts of about 0.01 to 10 mg/kg, on oral administration, for example, about 0.05 to 5 mg/kg, of body weight to achieve effective results.

EXAMPLES

Analytical Instrument Model:

TABLE 1

| | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| | Agilent Technologies 1100 |
| | Agilent Technologies 1260 |
| NMR | BRUKER ADVANCE III/400 (400 MHz) |
| | BRUKER ADVANCE 400 (400 MHz) |
| | BRUKER DMX300 (300 MHz) |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

LCMS:

LCMS Conditions A ("LCMS (A)"): Instrument: Shimadzu LCMS 2020; Mobile phase A: 4 L H2O\1.5 mL TFA, Mobile phase B: 4 L ACN\0.75 mL TFA; Method name: 10-80AB_4MIN_2W; Flow Rate: 0.8 mL/min.; Gradient: 10%-80%; Column: Boston Green ODS 2.1×30 mm, 3 µm; Column temperature: 50° C.; Wavelength: 220 nm & 254 nm.

LCMS Conditions B ("LCMS (B)"): Instrument: Agilent 1200 Series; Mobile phase A: 4 L H2O\1.5 ml TFA, Mobile phase B: 4 L ACN\0.75 mL TFA; Method name: 5-95AB_R_2W; Flow Rate: 1.5 mL/min.; Gradient: 5%-95%; Column: Chromolith@Flash RP-18e 25×2 mm; Column temperature: 50° C.; Wavelength: 220 nm & 254 nm.

LCMS Conditions C ("LCMS (C)"): Instrument: Agilent 1200 Series; Mobile phase A: 4 L H2O\2 mL NH3H2O; Mobile phase B: Acetonitrile; Method name: 5-95CD_4.5MIN_2W; Flow Rate: 0.8 mL/min.; Gradient: 5%-95%; Column: Chromolith@Flash RP-18e 25×2 mm; Column temperature 50° C.; Wavelength: 220 nm & 254 nm.

LCMS Conditions D ("LCMS (D)"): Instrument: Agilent 1200 Series; Mobile phase A: 4 L H2O\1.5 mL TFA, Mobile phase B: 4 L ACN\0.75 mL TFA; Method name: 5-95AB_R4MIN_2W; Flow Rate: 0.8 mL/min.; Gradient: 5%-95%; Column: Chromolith@Flash RP-18e 25×2 mm; Column temperature: 50° C.; Wavelength: 220 nm & 254 nm.

LCMS Conditions E ("LCMS (E)"): Instrument: Agilent 1200 Series; Mobile phase A: 4 L H2O\1.5 ml TFA, Mobile phase B: 4 L ACN\0.75 mL TFA; Method name: 5-95AB_R; Flow Rate: 1.5 mL/min.; Gradient: 5%-95%; Column: Chromolith@Flash RP-18e 25×2 mm; Column temperature: 50° C.; Wavelength: 220 nm & 254 nm.

LCMS Conditions F ("LCMS (F)"): Instrument: Agilent 1200 Series; Mobile phase A: 4 L H2O\2 ml NH3H2O, Mobile phase B: Acetonitrile; Method name: 5-95CD_2MIN_2W; Flow Rate: 1.2 mL/min.; Gradient: 5%-95%; Column: XBrige Shield RP-18 2.1×50 mm, 5 µm; Column temperature: 30° C.; Wavelength: 220 nm & 254 nm.

LCMS Conditions G ("LCMS (G)"): Instrument: Agilent 1200 Series; Mobile phase A: 4 L H2O\2 mL NH3H2O, Mobile phase B: Acetonitrile; Method name: 10-80CD_4MIN_2W; Flow Rate: 0.8 mL/min.; Gradient: 10%-80%; Column: XBridge C-18 2.1×50 mm, 5 µm; Column temperature: 40° C.; Wavelength: 220 nm & 254 nm.

LCMS Conditions H ("LCMS (H)"): Instrument: Agilent 1200 Series; Mobile phase A: 4 L H2O\1.5 mL TFA, Mobile phase B: 4 L ACN\0.75 mL TFA; Method name: 10-80AB_4MIN_2W; Flow Rate: 0.8 mL/min.; Gradient: 10%-80%; Column: Xtimate C-18, 2.1×30 mm, 3 µm; Column temperature: 50° C.; Wavelength: 220 nm & 254 nm.

LCMS Conditions I ("LCMS (I)"): Instrument: Agilent 1200 Series; Mobile phase A: 4 L H2O\2 mL NH3H2O, Mobile phase B: Acetonitrile; Method name: 0-60CD_4.5MIN_2W; Flow Rate: 0.8 ml/min.; Gradient: 0%-60%; Column: XBrige Shield RP-18 2.1×50 mm, 5 µm; Column temperature 50° C.; Wavelength: 220 nm & 254 nm.

LCMS Conditions J ("LCMS (J)"): Instrument: Agilent 1200 Series; Mobile phase A: 4 L H2O\2 mL NH3H2O, Mobile phase B: Acetonitrile; Method name: 10-80CD_2MIN_POS_2W; Flow Rate: 1.2 ml/min.; Gradient: 10%-80%; Column: Xbridge C-18 2.1×50 mm, 5 μm; Column temperature: 40° C.; Wavelength: 220 nm & 254 nm.

LCMS Conditions K ("LCMS (K)"): Instrument: Shimadzu LCMS 2020; Mobile phase A: 4 L H2O\1.5 mL TFA, Mobile phase B: 4 L ACN\0.75 mL TFA; Method name: 0-30AB_2MIN_2W; Flow Rate: 1.2 mL/min.; Gradient: 0%-30%; Column: Chromolith@Flash RP-18E 25×2 mm; Column temperature: 50° C.; Wavelength: 220 nm & 254 nm.

LCMS Conditions L ("LCMS (L)"): Instrument: Shimadzu LCMS 2020; Mobile phase A: 4 L H2O\1.5 mL TFA, Mobile phase B: 4 L ACN\0.75 mL TFA; Method name: 0-30AB_4MIN_2W; Flow Rate: 0.8 mL/min.; Gradient: 0%-30%; Column: Chromolith@Flash RP-18E 25×2 mm; Column temperature: 50° C.; Wavelength: 220 nm & 254 nm.

LCMS Conditions M ("LCMS (M)"): Instrument: Shimadzu LCMS 2020; Mobile phase A: 4 L H2O\1.5 mL TFA, Mobile phase B: 4 L ACN\0.75 mL TFA; Method name: 0-60AB_2MIN_2W; Flow Rate: 1.2 mL/min.; Gradient: 0%-60%; Column: Chromolith@Flash RP-18E 25×2 mm; Column temperature: 50° C.; Wavelength: 220 nm & 254 nm.

LCMS Conditions N ("LCMS (N)"): Instrument: Shimadzu LCMS 2020; Mobile phase A: 4 L H2O\1.5 mL TFA, Mobile phase B: 4 L ACN\0.75 mL TFA; Method name: 0-60AB_4MIN_2W; Flow Rate: 0.8 mL/min.; Gradient: 0%-60%; Column: Chromolith@Flash RP-18E 25×2 mm; Column temperature: 50° C.; Wavelength: 220 nm & 254 nm.

LCMS Conditions O ("LCMS(O)"): Instrument: Agilent 1200 Series LCMS; Mobile phase A: 4 L H2O\2 mL NH3H2O, Mobile phase B: CAN; Method name: 0-30CD_2MIN_POS_2W; Flow Rate: 1.0 mL/min.; Gradient: 0%-30%; Column: Xbridge C18 2.1×50 mm, 5 um; Column temperature: 40° C.; Wavelength: 220 nm & 254 nm.

LCMS Conditions P ("LCMS (P)"): Instrument: Agilent 1200 Series LCMS; Mobile phase A: 4 L H2O\2 mL NH3H2O, Mobile phase B: CAN; Method name: 0-60CD_2MIN_POS_2W; Flow Rate: 1.0 mL/min.; Gradient: 0%-60%; Column: Xbridge C18 2.1×50 mm, 5 um; Column temperature: 40° C.; Wavelength: 220 nm & 254 nm.

LCMS Conditions Q ("LCMS (Q)"): Instrument: Agilent 1200 Series LCMS; Mobile phase A: 4 L H2O\2 mL NH3H2O, Mobile phase B: CAN; Method name: 0-60CD_4MIN_2W; Flow Rate: 0.8 mL/min.; Gradient: 0%-60%; Column: Xbridge C18 2.1×50 mm, 5 um; Column temperature: 40° C.; Wavelength: 220 nm & 254 nm.

LCMS Conditions R ("LCMS (R)"): Instrument: Agilent 1200 Series LCMS; Mobile phase A: 4 L H2O\1.5 mL TFA, Mobile phase B: 4 L ACN\0.75 mL TFA; Method name: 10-80AB_2MIN_2W; Flow Rate: 1.2 mL/min.; Gradient: 10%-80%; Column: Xtimate C18, 2.1×30 mm, 3 um; Column temperature: 50° C.; Wavelength: 220 nm & 254 nm.

LCMS Conditions S ("LCMS (S)"): Instrument: Agilent 1200 Series LCMS; Mobile phase A: 4 L H2O\2 mL NH3H2O, Mobile phase B: CAN; Method name: 30-90CD_4MIN_POS_2W; Flow Rate: 0.8 mL/min.; Gradient: 30%-90%; Column: Xbridge C18 2.1×50 mm, 5 um; Column temperature: 40° C.; Wavelength: 220 nm & 254 nm.

LCMS Conditions T ("LCMS (T)"): Instrument: Agilent 1200 Series LCMS; Mobile phase A: 4 L H2O\1.5 mL TFA, Mobile phase B: 4 L ACN\0.75 mL TFA; Method name: 5-95AB_15MIN_YMC; Flow Rate: 1.0 mL/min.; Gradient: 5%-95%; Column: YMC-Pack ODS-A 5 μm 150×4.6 mm; Column temperature: 50° C.; Wavelength: 220 nm & 254 nm.

LCMS Conditions U ("LCMS (U)"): Instrument: Agilent 1200 Series LCMS; Mobile phase A: 4 L H2O\1.5 mL TFA, Mobile phase B: 4 L ACN\0.75 mL TFA; Method name: 0-30AB_2MIN_2W; Flow Rate: 1.2 mL/min.; Gradient: 0%-30%; Column: Chromolith@Flash RP-18E 25×2 mm; Column temperature: 50° C.; Wavelength: 220 nm & 254 nm.

LCMS Conditions V ("LCMS (V)"): Instrument: Agilent 1200 Series LCMS; Mobile phase A: 4 L H2O\1.5 mL TFA, Mobile phase B: 4 L ACN\0.75 mL TFA; Method name: 0-30AB_4MIN_2W; Flow Rate: 0.8 mL/min.; Gradient: 0%-30%; Column: Chromolith@Flash RP-18E 25×2 mm; Column temperature: 50° C.; Wavelength: 220 nm & 254 nm.

LCMS Conditions W ("LCMS (W)"): Instrument: Agilent 1200 Series LCMS; Mobile phase A: 4 L H2O\1.5 mL TFA, Mobile phase B: 4 L ACN\0.75 mL TFA; Method name: 0-60AB_2MIN_2W; Flow Rate: 1.2 mL/min.; Gradient: 0%-60%; Column: Chromolith@Flash RP-18E 25×2 mm; Column temperature: 50° C.; Wavelength: 220 nm & 254 nm.

LCMS Conditions X ("LCMS (X)"): Instrument: Agilent 1200 Series LCMS; Mobile phase A: 4 L H2O\1.5 mL TFA, Mobile phase B: 4 L ACN\0.75 mL TFA; Method name: 0-60AB_4MIN_2W; Flow Rate: 0.8 mL/min.; Gradient: 0%-60%; Column: Chromolith@Flash RP-18E 25×2 mm; Column temperature: 50° C.; Wavelength: 220 nm & 254 nm.

LCMS Conditions Y ("LCMS (Y)"): Instrument: Shimadzu LCMS 2020; Mobile phase A: 4 L H2O\1.5 ml TFA, Mobile phase B: 4 L ACN\0.75 mL TFA; Method name: 5-95AB_R_2W; Flow Rate: 1.5 mL/min.; Gradient: 5%-95%; Column: Chromolith@Flash RP-18e 25×2 mm; Column temperature: 50° C.; Wavelength: 220 nm & 254 nm.

LCMS Conditions Z ("LCMS (Z)"): Instrument: Shimadzu LCMS 2020; Mobile phase A: 4 L H2O\1.5 mL TFA, Mobile phase B: 4 L ACN\0.75 mL TFA; Method name: 5-95AB_R_4MIN_2W; Flow Rate: 0.8 mL/min.; Gradient: 5%-95%; Column: Chromolith@Flash RP-18e 25×2 mm; Column temperature: 50° C.; Wavelength: 220 nm & 254 nm.

LCMS Conditions AA ("LCMS (AA)"): Instrument: Agilent 1200 Series LCMS; Mobile phase A: 4 L H2O\2 mL $NH_3.H_2O$, Mobile phase B: ACN; Method name: 10-80CD_2MIN_NEG; Flow Rate: 1.2 mL/min.; Gradient: 10%-80%; Column: Xbridge C18 2.1×50 mm, 5 μm; Column temperature: 40° C.; Wavelength: 220 nm & 254 nm.

LCMS Conditions BB ("LCMS (BB)"): Instrument: Agilent 1200 Series LCMS; Mobile phase A: 4 L H2O\1.5 mL TFA, Mobile phase B: 4 L ACN\0.75 mL TFA; Method name: 0-60AB_R_2W; Flow Rate: 1.5 mL/min.; Gradient: 0%-60%; Column: Chromolith@Flash RP-18E 25×2 mm; Column temperature: 50° C.; Wavelength: 220 nm & 254 nm.

LCMS Conditions CC ("LCMS (CC)"): Instrument: Agilent 1200 Series LCMS; Mobile phase A: 4 L H2O\1.5 mL TFA, Mobile phase B: 4 L ACN\0.75 mL TFA; Method name: 0-30AB_R_2W; Flow Rate: 1.5 mL/min.; Gradient: 0%-30%; Column: Chromolith@Flash RP-18E 25×2 mm; Column temperature: 50° C.; Wavelength: 220 nm & 254 nm.

LCMS Conditions DD ("LCMS (DD)"): Instrument: Agilent 1200 Series LCMS; Mobile phase A: 4 L H2O\1.5 mL TFA, Mobile phase B: 4 L ACN\0.75 mL TFA; Method name: 10-80AB_R_2W; Flow Rate: 1.5 mL/min.; Gradient: 10%-80%; Column: Chromolith@Flash RP-18E 25×2 mm; Column temperature: 50° C.; Wavelength: 220 nm & 254 nm.

LCMS Conditions EE ("LCMS (EE)"): Instrument: Agilent 1200 Series; Mobile phase A: 1 L H2O\0.375 mL TFA, Mobile phase B: 4 L ACN\0.75 mL TFA; Method name: WUXIAB00; Flow Rate: 0.6-1.0 mL/min; Gradient: 0%-80%-100%; Column: Agilent 5 TC-C18 50×2.1 mm; Column temperature: 50° C.; Wavelength: 220 nm & 254 nm.

LCMS Conditions FF ("LCMS (FF)"): Instrument: Agilent 1200 Series; Mobile phase A: 1 L H2O\0.375 mL TFA, Mobile phase B: 4 L ACN\0.75 mL TFA; Method name: WUXIAB01; Flow Rate: 0.8-1.0 mL/min; Gradient: 1%-90%-100%; Column: Agilent 5 TC-C18 50×2.1 mm; Column temperature: 50° C.; Wavelength: 220 nm & 254 nm.

LCMS Conditions GG ("LCMS (GG)"): Instrument: Agilent 1200 Series; Mobile phase A: 1 L H2O\0.375 mL TFA, Mobile phase B: 4 L ACN\0.75 mL TFA; Method name: WUXIAB10; Flow Rate: 0.8-1.0 mL/min; Gradient: 10%-100%; Column: Agilent 5 TC-C18 50×2.1 mm; Column temperature: 50° C.; Wavelength: 220 nm & 254 nm.

LCMS Conditions 1 ("LCMS (1)"): Instrument: Agilent 1100 Bin. Pump: G1312A, degasser; autosampler, ColCom, DAD: Agilent G1315B, 210 nm, MSD: Agilent LC/MSD G1956B ESI, pos/neg 100-800; MS parameters: Source: ESI, Capillary voltage: 3000V, Drying gas flow: 12 L/min., Nebulizer Pressure 60 psig, Drying Gas Temperature: 350° C., Fragmentor 70, MS scan: MS range 100-800 (positive and negative mode), Flow into MS 0.4 mL/min.; Mobile phase A: 95% acetonitrile+5% 10 mM ammonium bicarbonate in water; Mobile phase B: 10 mM ammonium bicarbonate in water pH=9.0; Flow Rate: 0.8 mL/min; Linear Gradient: t=0 min 5% A, t=3.5 min 98% A, t=6 min 98% A; Column: Phenomenex Gemini NX (C18, 50×2.0 mm, particle size: 3 μm); Column temperature: 25° C.; Detection DAD: Wavelength 220-320 nm.

LCMS Conditions 2 ("LCMS (2)"): Instrument Apparatus: Agilent 1260 Bin. Pump: G1312B, degasser; autosampler, ColCom, DAD: Agilent G1315D, 220-320 nm, MSD: Agilent LC/MSD G6130B ESI, pos/neg 100-800, ELSD Alltech 3300 gas flow 1.5 mL/min., Gas Temperature: 40° C.; MS parameters: Source: ESI, Capillary voltage: 3000V, Drying gas flow: 12 L/min., Nebulizer Pressure 60 psig, Drying Gas Temperature: 350° C., Fragmentor 70, MS scan: MS range 100-800 (positive and negative mode), Flow into MS 0.4 mL/min.; Mobile phase A: 0.1% formic acid in acetonitrile; Mobile phase B: 0.1% formic acid in water; Flow Rate: 1 mL/min; Linear gradient: t=0 min 5% A, t=1.6 min 98% A, t=3 min 98% A; Column: Waters XSelect (C18, 30×2.1 mm, particle size 3.5 μm); Column temperature: 35° C.; Detection DAD: Wavelength 220-320 nm.

GCMS:

GCMS Conditions Instrument: SHIMADZU GCMS-QP2010 Ultra; Carrier gas: He; Column Flow: 1.5 mL/min; Injector: 250° C.; Split Ratio:100:1; Column: HP-5MS 15 m×0.25 mm×0.25 um; FILM From: 40° C. (holding 3 min) to 250° C. (holding 3 min) at the rate of 25° C./min.

cSFC Analytical:

cSFC Analytical Conditions: Flow rate: 3 mL/min; Wavelength: 220 nm; and Column temperature: 35° C., were used for each of the specified conditions below:

cSFC Analytical Conditions A ("cSFC analytical (A)"): Column: Chiralpak OD-3 100×4.6 mm I.D., 3 um; Mobile phase: ethanol (0.05% diethylamine ("DEA") in $CO_2$ from 5% to 40%.

cSFC Analytical Conditions B ("cSFC analytical (B)"): Column: Chiralpak OD-3 100×4.6 mm I.D., 3 um; Mobile phase: methanol (0.05% DEA) in $CO_2$ from 5% to 40%.

cSFC Analytical Conditions C ("cSFC analytical (C)"): Column: Chiralpak OD-3 100×4.6 mm I.D., 3 um; Mobile phase: 40% ethanol (0.05% DEA) in $CO_2$.

cSFC Analytical Conditions D ("cSFC analytical (D)"): Column: Chiralpak AY-3 100×4.6 mm I.D., 3 um; Mobile phase: ethanol (0.05% DEA) in $CO_2$ from 5% to 40%.

cSFC Analytical Conditions E ("cSFC analytical (E)"): Column: Chiralpak OJ-3 100×4.6 mm I.D., 3 um; Mobile phase: ethanol (0.05% DEA) in $CO_2$ from 5% to 40%.

cSFC Analytical Conditions F ("cSFC analytical (F)"): Column: Chiralpak OJ-3 100×4.6 mm I.D., 3 um; Mobile phase: methanol (0.05% DEA) in $CO_2$ from 5% to 40%.

cSFC Analytical Conditions G ("cSFC analytical (G)"): Column: Chiralpak AD-3 100×4.6 mm I.D., 3 um; Mobile phase: ethanol (0.05% DEA) in $CO_2$ from 5% to 40%.

cSFC Analytical Conditions H ("cSFC analytical (H)"): Column: Chiralpak AD-3 100×4.6 mm I.D., 3 um; Mobile phase: methanol (0.05% DEA) in $CO_2$ from 5% to 40%.

For each final compound prepared below that indicates the presence of a salt associated with the final compound (i.e., a salt complex), the specific molar equivalence of salt included in the final compound, unless specified, was not determined.

General Procedure A1: Synthesis of N-hydroxyimidoyl Chloride.

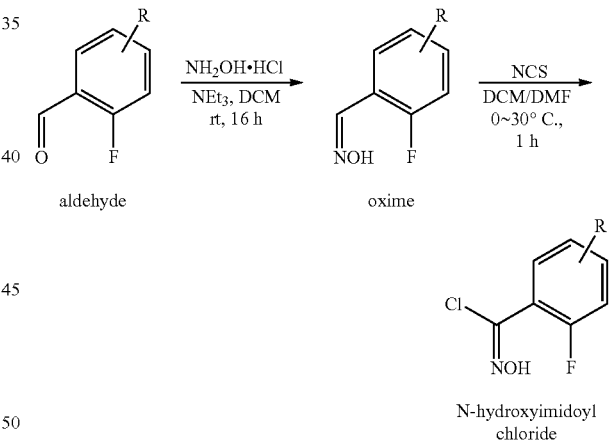

A mixture of aldehyde (1 eq.), hydroxylamine hydrochloride (1.3-2 eq.) and triethylamine (2 eq.) in dichloromethane (1.2-2.5 mL/mmol aldehyde) was stirred at room temperature for 16 hours. On completion, the reaction mixture was diluted with water and extracted with dichloromethane (3×20 mL). The combined organic layers were washed with water and brine, dried over anhydrous sodium sulfate and concentrated in vacuo to give the oxime intermediate. This intermediate was either purified by silica gel chromatography or used without further purification in the next step.

To a solution of oxime intermediate (1 eq.) in dichloromethane (10 mL) at 0° C. was added a solution of N-chlorosuccinimide (1.2 eq.) in N,N-dimethylformamide (0.5 mL). The mixture was stirred at 30° C. for 1 hour. On completion, the reaction mixture was diluted with water and extracted with dichloromethane (3×10 mL). The combined organic layers were washed with water and brine, dried over anhydrous sodium sulfate, filtered and concentrated in vacuo to give N-hydroxyimidoyl chloride intermediate, which was used crude in the next reaction without further purification.

General Procedure A2: Synthesis of N-hydroxyimidoyl Chloride.

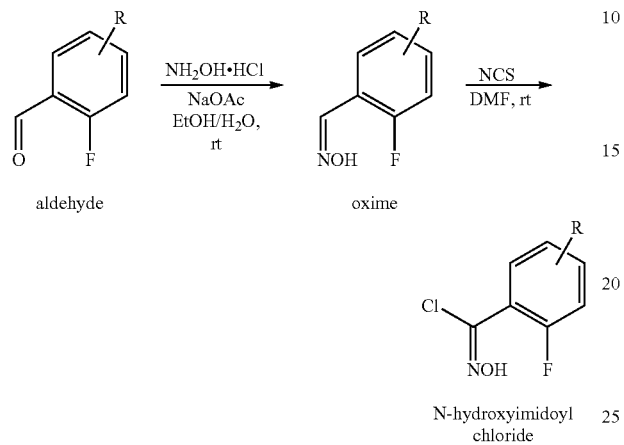

aldehyde oxime

N-hydroxyimidoyl chloride

To a solution of aldehyde in ethanol/water (8/1, v/v) at room temperature was added hydroxylamine hydrochloride (2 eq.) and sodium acetate (3 eq.). The reaction was stirred for 1-2 hour until TLC showed the reaction was complete. The mixture was concentrated in vacuo, and the residue was triturated from water, collected by filtration, washed with water and dried in vacuo to afford the oxime product, which was used as such in the next step.

To a solution of oxime in N,N-dimethylformamide at room temperature was added N-chlorosuccinimide (1 eq.). The reaction was stirred for 1 or more hours until TLC showed the reaction was complete. The solution was diluted with ethyl acetate and water and filtered through Celite to remove particles. The layers were separated, and the organic layer was washed with water and brine (2×), dried with sodium sulfate, filtered, and concentrated in vacuo to afford the N-hydroxybenzimidoyl chloride product, which was used as such in the next step.

Example 1A 7-chlorobenzo[d]isoxazol-3-amine (A-1)

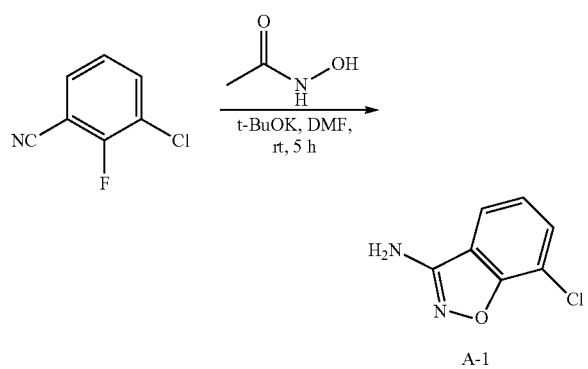

To a solution of N-hydroxyacetamide (3.6 g, 48 mmol) in dry N,N-dimethylformamide (60 mL) at room temperature was added potassium t-butoxide (5.4 g, 48 mmol). After stirring for 30 minutes, 3-chloro-2-fluorobenzonitrile (5.0 g, 32 mmol) was added, and stirring was continued for another 4.5 hours. On completion, the reaction mixture was poured into a mixture of brine (60 mL) and ethyl acetate (60 mL). The organic phase was separated, dried over anhydrous sodium sulfate, filtered and concentrated to dryness. The residue was purified by silica gel chromatography [petroleum ether:ethyl acetate=3:1] to afford compound A-1 (3.9 g, 73% yield) as a pale yellow solid. $^1$H-NMR (DMSO-$d_6$, 400 MHz): δ 7.82-7.80 (d, J=7.6 Hz, 1H), 7.65-7.63 (d, J=7.2 Hz, 1H), 7.30-7.26 (m, 1H), 6.61 (s, 2H).

Example 2A 6-chlorobenzo[d]isoxazol-3-amine (A-2)

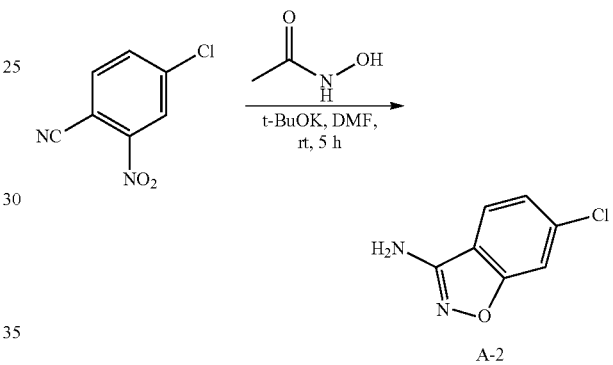

To a solution of N-hydroxyacetamide (3.1 g, 41 mmol) in dry N,N-dimethylformamide (60 mL) at room temperature was added potassium t-butoxide (4.6 g, 41 mmol). After stirring for 30 minutes, 4-chloro-2-nitrobenzonitrile (5.0 g, 27 mmol) was added, and stirring was continued for another 4.5 hours. On completion, the reaction mixture was poured into a mixture of brine (60 mL) and ethyl acetate (60 mL). The organic phase was separated, dried over anhydrous sodium sulfate, filtered and concentrated to dryness. The residue was purified by silica gel chromatography [petroleum ether:ethyl acetate=3:1] to afford compound A-2 (3.1 g, 66% yield) as a pale yellow solid. $^1$H-NMR (DMSO-$d_6$, 400 MHz): δ 7.84-7.82 (d, J=8.8 Hz, 1H), 7.65-7.64 (d, J=1.2 Hz, 1H), 7.33-7.31 (dd, J=1.2 Hz, J=8.8 Hz, 1H), 6.52 (s, 2H).

Example 3A 5-chlorobenzo[d]isoxazol-3-amine (A-3)

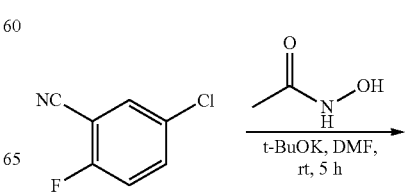

-continued

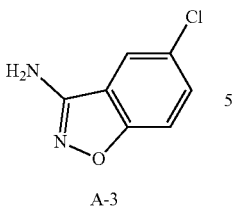

A-3

To a solution of N-hydroxyacetamide (2.2 g, 29 mmol) in dry N,N-dimethylformamide (30 mL) at room temperature was added potassium t-butoxide (3.2 g, 29 mmol). After stirring for 30 minutes, 5-chloro-2-fluorobenzonitrile (3.0 g, 19 mmol) was added, and stirring was continued for another 4.5 hours. On completion, the reaction mixture was quenched with water and extracted with ethyl acetate (3×20 mL). The combined organic layers were washed with water and brine (5×50 mL), dried over anhydrous sodium sulfate and concentrated in vacuo. The residue was purified by silica gel chromatography [petroleum ether:ethyl acetate=1:1] to afford compound A-3 (1.5 g, 31% yield) as a white solid.

Example 4A 6-cyclopropylbenzo[d]isoxazol-3-amine (A-4)

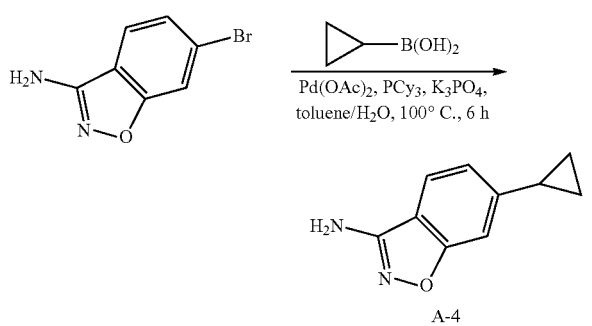

To a solution of 6-bromobenzo[d]isoxazol-3-amine (1.0 g, 4.7 mmol) and cyclopropylboronic acid (0.81 g, 9.4 mmol) in a mixture of toluene (10 mL) and water (1.0 mL) under nitrogen at room temperature were added potassium phosphate (1.0 g, 9.4 mmol), palladium acetate (53 mg, 0.2 mmol) and tricyclohexylphosphine (0.11 g, 0.4 mmol). The resulting mixture was stirred at 100° C. for 6 hours, then diluted with water (10 mL) and extracted with ethyl acetate (3×10 mL). The combined organic layers were dried over anhydrous sodium sulfate, filtered and concentrated in vaccuo. The residue was purified by silica gel chromatography [petroleum ether:ethyl acetate=5:1] to afford compound A-4 (0.59 g, 72% yield) as a off-white solid. LCMS (B): tR=0.684 min., (ES+) m/z (M+H)+=175.1. $^1$H-NMR (CD$_3$OD, 400 MHz): δ 7.40-7.38 (d, J=8.0 Hz, 1H), 7.09 (s, 1H), 6.99-6.97 (d, J=8.4 Hz, 1H), 4.37 (s, 2H), 2.05-2.01 (m, 1H), 1.10-1.05 (m, 2H), 0.81-0.77 (m, 2H).

Example 5A 6-methoxybenzo[d]isoxazol-3-amine (A-5)

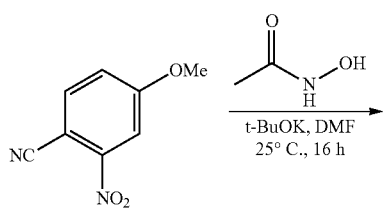

-continued

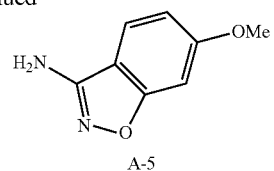

A-5

To a solution of N-hydroxyacetamide (3.2 g, 42 mmol) in dry N,N-dimethylformamide (50 mL) at room temperature was added potassium t-butoxide (6.6 g, 59 mmol). After stirring for 30 minutes, 4-methoxy-2-nitrobenzonitrile (3.0 g, 17 mmol) was added, and stirring was continued for another 16 hours. On completion, the reaction mixture was quenched with water and extracted with ethyl acetate (3×100 mL). The combined organic layers were washed with water and brine, dried over anhydrous sodium sulfate, concentrated in vacuo and purified by silica gel chromatography [petroleum ether:ethyl acetate=1:1] to give compound A-5 (2.0 g, 72% yield) as a yellow solid. LCMS (J): (ES$^+$) m/z (M+H)$^+$=165.1, tR=1.164 min.

Example 6A 3,4-dichloro-2-fluorobenzaldehyde oxime (A-6)

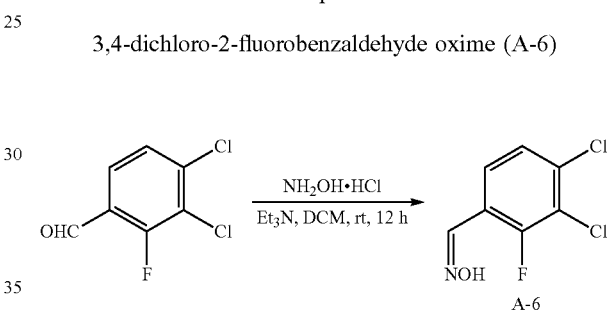

A mixture of 3,4-dichloro-2-fluorobenzaldehyde (2.0 g, 9.5 mmol), hydroxylamine hydrochloride (0.98 g, 14 mmol.) and triethylamine (2.0 mL, 14 mmol.) in dichloromethane (10 mL) was stirred at room temperature for 12 hours. On completion, the reaction mixture was diluted with water and extracted with dichloromethane (3×20 mL). The combined organic layers were washed with water and brine, dried over anhydrous sodium sulfate and concentrated in vacuo to give compound A-6 (1.5 g, white solid, 69% yield). LCMS (B): (ES$^+$) m/z (M+H)$^+$=208.0. tR=0.81 min.

Example 7A 3,4-dichloro-2-fluorobenzonitrile (A-7)

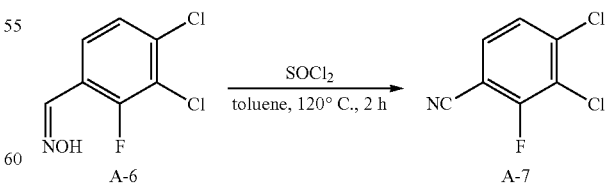

To a solution of compound A-6 (1.5 g, 7.2 mmol) in toluene (50 mL) was added slowly thionyl chloride (0.90 g, 7.6 mmol). The mixture was stirred at 120° C. for 2 hours, then concentrated in vacuo. The residue was purified by silica gel chromatography [petroleum ether:ethyl acetate=10:1] to give compound A-7 (0.80 g, 58% yield) as a white solid. $^1$H-NMR (CD$_3$OD, 400 MHz): δ 7.81-7.73 (m, 1H), 7.62-7.60 (m, 1H).

Example 8A 6,7-dichlorobenzo[d]isoxazol-3-amine (A-8)

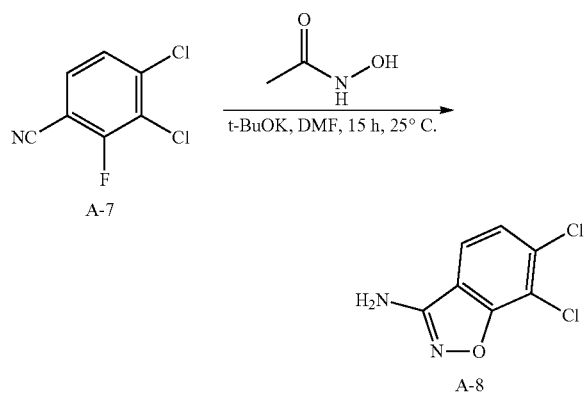

To a solution of N-hydroxyacetamide (1.4 g, 19 mmol) in dry N,N-dimethylformamide (20 mL) at room temperature was added potassium t-butoxide (2.1 g, 19 mmol). After stirring for 0.5 hour, compound A-7 was added, and stirring was continued for another 12 hours. On completion the reaction mixture was poured into brine and extracted with ethyl acetate (2×25 mL). The combined organic layers were washed with water and brine, dried over anhydrous sodium sulfate and concentrated in vacuo. The resulting solid was recrystallized from dichloromethane/petroleum ether to give compound A-8 (1.0 g, 50% yield) as a white solid. LCMS (B): (ES$^+$) m/z (M+H)$^+$=203.1. tR=0.73 min.

Example 9A 2-chloro-6-fluoro-N-hydroxybenzimidoyl chloride (A-10)

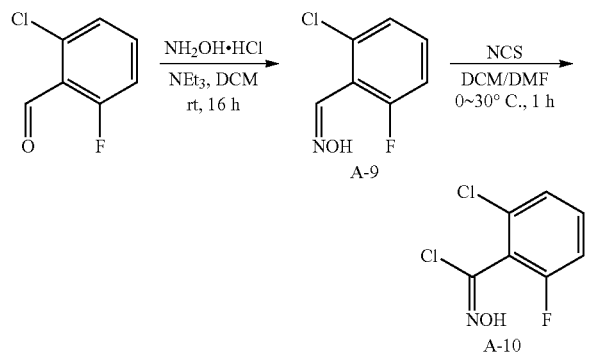

Following general procedure A1, compound A-10 was prepared from 2-chloro-6-fluorobenzaldehyde:

Compound A-9 (790 mg, white solid, 72% yield) was prepared from 2-chloro-6-fluorobenzaldehyde (1.0 g, 6.37 mmol) and purified by silica gel chromatography [petroleum ether: ethyl acetate=10:1].

Compound A-10 (0.3 g, white solid, crude) was prepared from compound A-9 (0.4 g, 2.3 mmol). TLC [petroleum ether:ethyl acetate=5:1]: Rf=0.7.

Example 10A 2,4-difluoro-N-hydroxybenzimidoyl chloride (A-12)

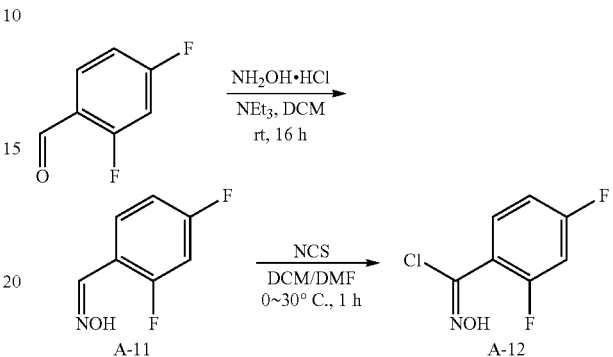

Following general procedure A1, compound A-12 was prepared from 2,4-difluorobenzaldehyde:

Compound A-11 (2.0 g, white solid, 90% yield) was prepared from 2,4-difluorobenzaldehyde (2.0 g, 14 mmol) and purified by silica gel chromatography [petroleum ether: ethyl acetate=10:1]. LCMS (B): (ES$^+$) m/z (M+H)$^+$=158.1, tR=0.598 min.

Compound A-12 (1.4 g, white solid, crude) was prepared from compound A-11 (1.0 g, 6.4 mmol). TLC [petroleum ether:ethyl acetate=5:1]: Rf=0.6.

Example 11A 4-cyano-2-fluoro-N-hydroxybenzimidoyl chloride (A-14)

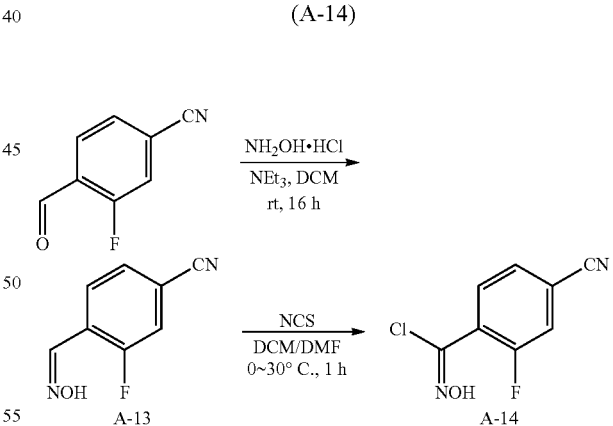

Following general procedure A1, compound A-14 was prepared from 3-fluoro-4-formylbenzonitrile:

Compound A-13 (2.7 g, white solid, 82% yield) was prepared from 3-fluoro-4-formylbenzonitrile (3.0 g, 20 mmol) and purified by silica gel chromatography [petroleum ether:ethyl acetate=10:1]. LCMS (B): (ES$^+$) m/z (M+H)$^+$=165.1, tR=0.538 min.

Compound A-14 (0.30 g, white solid, crude) was prepared from compound A-13 (0.40 g, 2.4 mmol). TLC [petroleum ether:ethyl acetate=5:1]: Rf=0.6.

Example 12A

2-fluoro-N-hydroxy-4-(methylsulfonyl)benzimidoyl chloride (A-16)

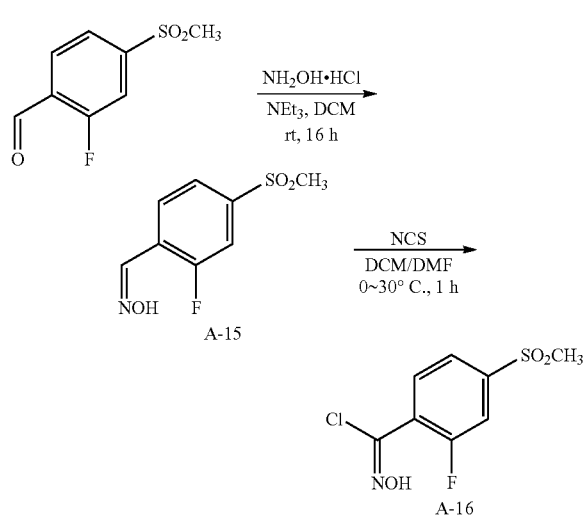

Following general procedure A1, compound A-16 was prepared from 2-fluoro-4-(methylsulfonyl) benzaldehyde:

Compound A-15 (1.8 g, white solid, 81% yield) was prepared from 2-fluoro-4-(methylsulfonyl) benzaldehyde (2.0 g, 9.9 mmol) and purified by silica gel chromatography [petroleum ether:ethyl acetate=8:1]. LCMS (B): (ES$^+$) m/z (M+H)$^+$=218.1, tR=0.798 min.

Compound A-16 (0.6 g, white solid, crude) was prepared from compound A-15 (1.0 g, 4.6 mmol). TLC [petroleum ether:ethyl acetate=10:1]: Rf=0.5.

Example 13A

1-(tert-butyl)-3-fluorobenzene (A-17)

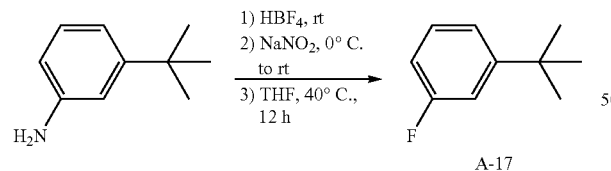

To 40% fluoroboric acid (40 mL) was added 3-tert-butylaniline (5.5 g, 37 mmol) portion-wise. The mixture was stirred at 25° C. for 0.5 hour and then cooled to 0° C. Sodium nitrite (4.1 g, 59 mmol) in water (10 mL) was added, and the solution was stirred at 0° C. for 0.5 hour and at 25° C. for 20 mins, resulting in formation of a sold. The solid was collected by filtration, washed with 40% fluoroboric acid (10 mL), ethanol (5 mL) and n-hexane (10 mL), dried, dissolved in tetrahydrofuran (60 mL) and stirred at 40° C. for 12 hours. On completion, the mixture was concentrated, and the residue was purified by silica gel chromatography [petroleum ether:ethyl acetate=1:0] to afford compound A-17 (4.0 g, 71% yield) as a yellow oil.

Example 14A

4-(tert-butyl)-2-fluorobenzaldehyde (A-18)

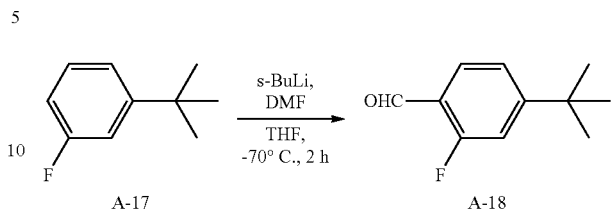

To a solution of compound A-17 (1.9 g, 12 mmol) in anhydrous tetrahydrofuran (25 mL) at −70° C. was added dropwise sec-butyllithium (12 mL, 1.3 N in pentane, 15 mmol). The reaction was stirred at −70° C. for 1 h. Then N,N-dimethylformamide (3.6 g, 49 mmol) was added, and stirring was continued at −70° C. for another 1 h. On completion, the mixture was poured into aqueous ammonium chloride (20 mL) and extracted with ethyl acetate (3×20 mL). The combined organic layers were washed with brine, dried over anhydrous sodium sulfate, filtered and concentrated. The reside was purified by silica gel chromatography [petroleum ether:ethyl acetate=15:1] to give compound A-18 (2.0 g, 91% yield) as a yellow oil.

Example 15A

4-(tert-butyl)-2-fluoro-N-hydroxybenzimidoyl chloride (A-20)

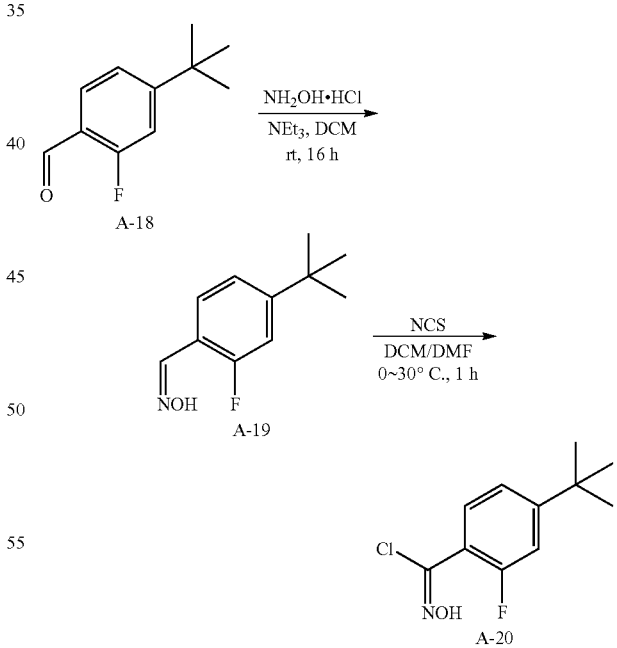

Following general procedure A1, compound A-20 was prepared from compound A-18:

Compound A-19 (0.35 g, white solid, 73% yield) was prepared from compound A-18 (0.45 g, 2.5 mmol) and purified by silica gel chromatography [petroleum ether:ethyl acetate=10:1]. LCMS (DD): (ES$^+$) m/z (M+H)$^+$=196.2, tR=0.835 min.

Compound A-20 (0.30 g, white solid, crude) was prepared from compound A-19 (0.35 g, 1.8 mmol).

Example 16A (4,5-dichloro-2-fluorophenyl)methanol (A-21)

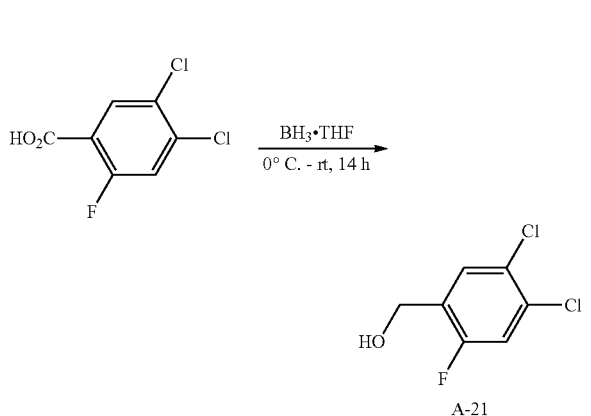

To a solution of 4, 5-dichloro-2-fluoro-benzoic acid (5.0 g, 24 mmol) in tetrahydrofuran (50 mL) at 0° C. was added borane-tetrahydrofuran complex (1 M, 60 mL, 60 mmol) dropwise over 30 minutes. The resulting solution was stirred at 30° C. for 14 hours until TLC analysis showed the reaction was complete. The reaction was quenched carefully with methanol (10 mL) and then concentrated in vacuo to give compound A-21 (4.50 g, 85% yield) as a yellow oil, which was used in the next step without further purification. LCMS (DD): (ES$^+$) m/z (M+H)$^+$=176.9, tR=0.859 min.

Example 17A 4,5-dichloro-2-fluorobenzaldehyde (A-22)

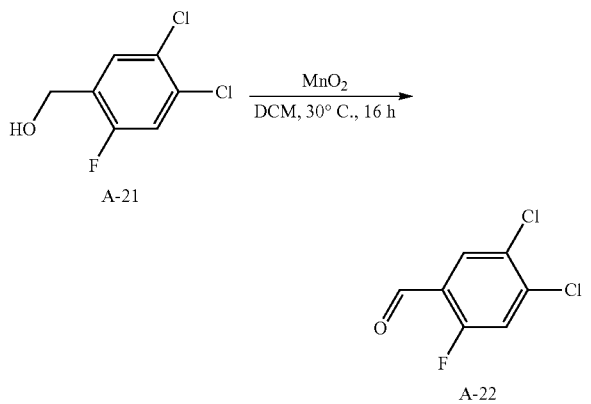

A mixture of compound A-21 (2.8 g, 14 mmol) and manganese dioxide (12 g, 143 mmol) in dichloromethane (40 mL) was stirred at 30° C. for 16 hours until TLC analysis showed the starting material was consumed. The reaction mixture was filtered, and the filtrate was concentrated in vacuo. The residue was purified by silica gel chromatography [petroleum ether:ethyl acetate=5:1] to afford compound A-22 (2.0 g, 73% yield) as a white solid.

Example 18A 4,5-dichloro-2-fluoro-N-hydroxybenzimidoyl chloride (A-24)

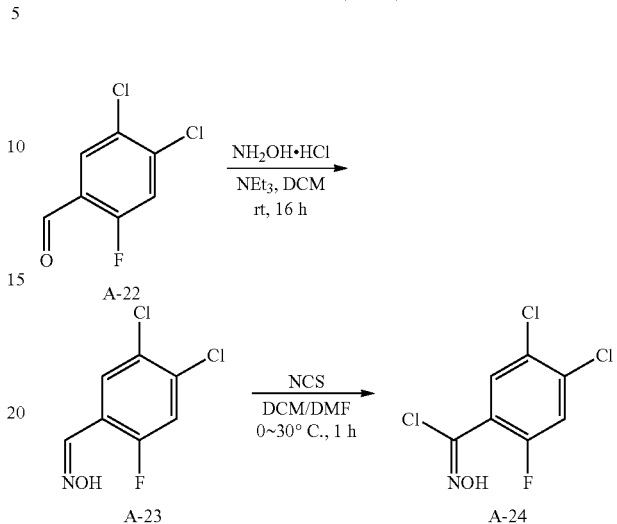

Following general procedure A1, compound A-24 was prepared from compound A-22:

Compound A-23 (3.0 g, white solid, 80% yield) was prepared from compound A-22 (3.5 g, 18 mmol) and purified by silica gel chromatography [petroleum ether:ethyl acetate=10:1]. LCMS (DD): (ES$^+$) m/z (M+H)$^+$=207.9, tR=0.931 min.

Compound A-24 (0.30 g, white solid, crude) was prepared from compound A-23 (0.30 g, 1.4 mmol).

Example 19A 2-fluoro-N-hydroxy-4-(trifluoromethoxy)benzimidoyl chloride (A-26)

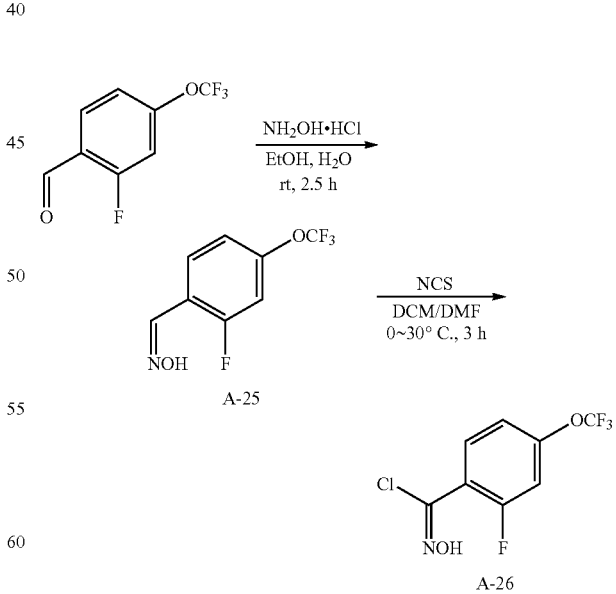

Following general procedure A1, compound A-26 was prepared from 2-fluoro-4-(trifluoromethoxy) benzaldehyde:

Compound A-25 (0.93 g, white solid, crude) was prepared from 2-fluoro-4-(trifluoromethoxy)benzaldehyde (1.0 g, 4.8 mmol) and hydroxylamine hydrochloride (1.0 g, 14 mmol) using a mixture of ethanol (12 mL) and water (2.4 mL) without triethylamine as the solvent instead of dichloromethane. The reaction time was 2.5 hours. The product was used directly for the next step without further purification. LCMS (DD): (ES$^+$) m/z (M+H)$^+$=224.0, tR=0.953 min.

Compound A-26 (0.63 g of yellow oil, crude) was prepared from compound A-25 (0.55 g, 2.5 mmol) and N-chlorosuccinimide (0.40 g, 3.0 mmol). The reaction time was 3 hours. LCMS (B): tR=0.836 min, (ES$^+$) m/z (M+H)$^+$=258.0.

Example 20A 2,3-difluoro-N-hydroxybenzimidoyl chloride (A-28)

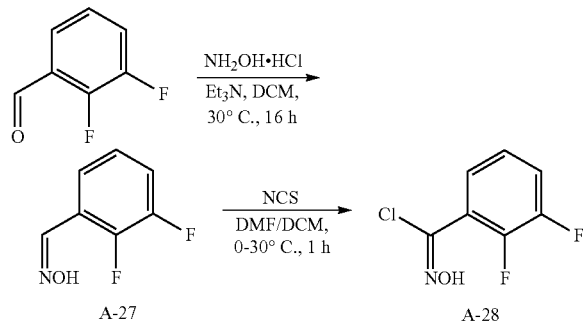

Following general procedure A1, compound A-28 was prepared from 2,3-difluorobenzaldehyde:

Compound A-27 (1.0 g, white solid, 90% yield) was prepared from 2,3-difluorobenzaldehyde (1.0 g, 7.0 mmol) and purified by silica gel chromatography [petroleum ether: ethyl acetate=10:1].

Compound A-28 (1.2 g, white solid, crude) was prepared from compound A-27 (1.0 g, 6.4 mmol).

Example 21A 2,5-difluoro-N-hydroxybenzimidoyl chloride (A-30)

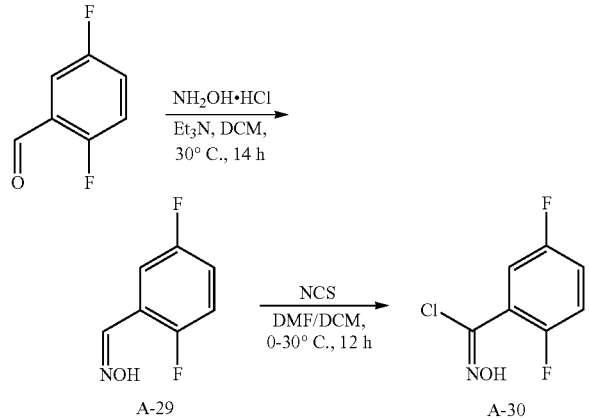

Following general procedure A1, compound A-30 was prepared from 2,5-difluorobenzaldehyde:

Compound A-29 (1.0 g, white solid, crude) was prepared from 2,5-difluorobenzaldehyde (1.0 g, 7.0 mmol) with a reaction time of 14 hours and used in next step without further purification. LCMS (B): (ES$^+$) m/z (M+H)$^+$=158.0, tR=0.559 min.

Compound A-30 (1.0 g, white solid, crude) was prepared from compound A-29 (1.0 g, 6.4 mmol) with a reaction time of 12 hours. [petroleum ether:ethyl acetate=5:1]: Rf=0.7.

Example 22A 2,6-difluoro-N-hydroxybenzimidoyl chloride (A-32)

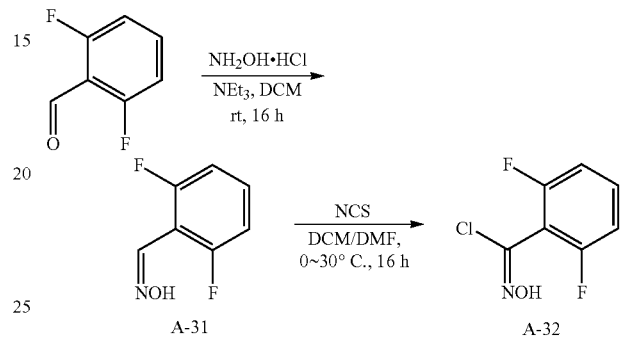

Following general procedure A1, compound A-32 was prepared from 2,6-difluorobenzaldehyde:

Compound A-31 (1.1 g, white solid, 99% yield) was prepared from 2,4-difluorobenzaldehyde (1.0 g, 7.0 mmol) and purified by silica gel chromatography [petroleum ether: ethyl acetate=10:1]. LCMS (J): (ES$^+$) m/z (M+H)$^+$=158.1, tR=0.838 min.

Compound A-32 (0.60 g, white solid, crude) was prepared from compound A-31 (0.50 g, 3.2 mmol). The reaction time was 16 hours. TLC [petroleum ether:ethyl acetate=10:1]: Rf=0.45.

Example 23A 2,3-difluoro-N-hydroxy-4-methylbenzimidoyl chloride (A-34)

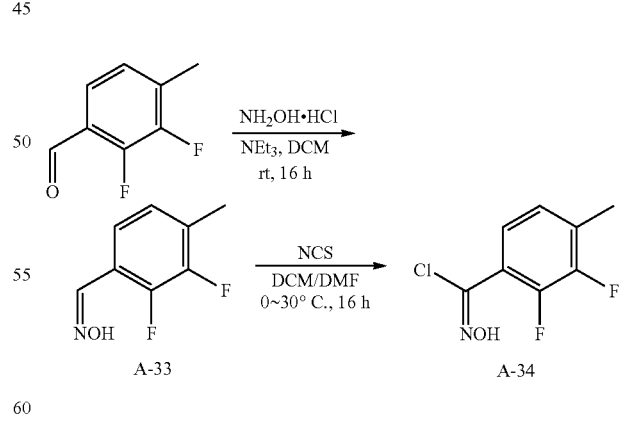

Following general procedure A1, compound A-34 was prepared from 2,3-difluoro-4-methylbenzaldehyde:

Compound A-33 (1.0 g, white solid, 91% yield) was prepared from 2,3-difluoro-4-methylbenzaldehyde (1.0 g, 6.4 mmol) and purified by silica gel chromatography [petroleum ether: ethyl acetate=10:1]. LCMS (J): (ES$^+$) m/z (M+H)$^+$=172.1, tR=1.279 min.

Compound A-34 (0.60 g, white solid, crude) was prepared from compound A-33 (0.50 g, 3.2 mmol). The reaction time was 16 hours. TLC [petroleum ether:ethyl acetate=10:1]: Rf=0.5.

Example 24A 2,3,4-trifluoro-N-hydroxybenzimidoyl chloride (A-36)

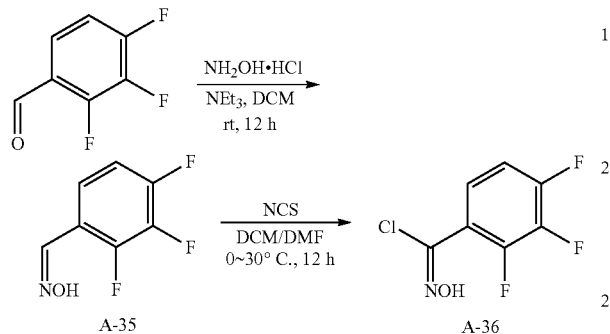

Following general procedure A1, compound A-36 was prepared from 2, 3, 4-trifluorobenzaldehyde:

Compound A-35 (0.80 g, white solid, 73% yield) was prepared from 2,3,4-trifluorobenzaldehyde (1.0 g, 6.3 mmol) (reaction time was 12 hours), and purified by silica gel chromatography [petroleum ether:ethyl acetate=10:1]. LCMS (B): (ES+) m/z (M+H)+=176.1, tR=0.68 min.

Compound A-36 (0.35 g, white solid, crude) was prepared from compound A-35 (0.40 g, 2.3 mmol) with a reaction time of 12 hours. TLC [petroleum ether:ethyl acetate=7:1]: Rf=0.6.

Example 25A (2,5-difluoro-4-methylphenyl)methanol (A-37)

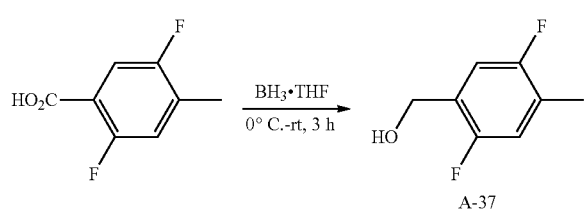

To a solution of 4, 5-dichloro-2-fluoro-benzoic acid (2.75 g, 16 mmol) in tetrahydrofuran (30 mL) at 0° C. was added borane-tetrahydrofuran complex (1 M, 40 mL, 40 mmol) drop-wise over 30 minutes. The resulting solution was stirred at 30° C. for 2.5 hours. On completion, the reaction was quenched carefully with methanol (10 mL) and then concentrated in vacuo to give compound A-37 (2.0 g, crude) as a yellow solid, which was used in next step without further purification. LCMS (J): (ES+) m/z (M+H)+=159.1, tR=1.12 min.

Example 26A 2, 5-difluoro-4-methylbenzaldehyde (A-38)

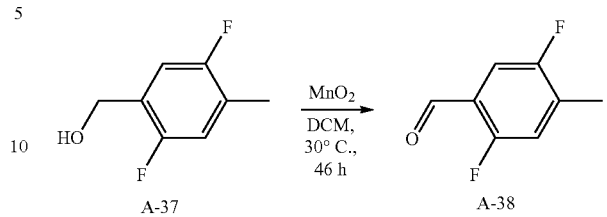

A mixture of compound A-37 (2.5 g, 16 mmol) and manganese dioxide (14 g, 0.16 mol) in dichloromethane (20 mL) was stirred at 30° C. for 46 hours. On completion, the reaction mixture was filtered, and the filtrate was concentrated in vacuo to give compound A-38 (2.0 g, crude) as a white solid. LCMS (J): (ES+) m/z (M+H)+=157.1, tR=1.28 min.

Example 27A 2,5-difluoro-N-hydroxy-4-methylbenzimidoyl chloride (A-40)

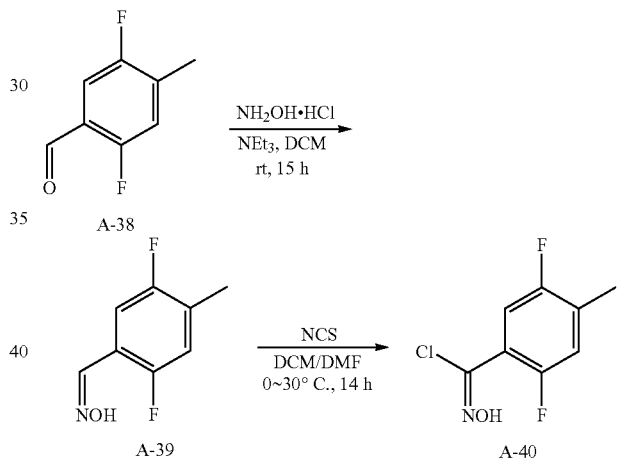

Following general procedure A1, compound A-40 was prepared from compound A-38.

Compound A-39 (2.3 g, crude) was prepared from compound A-38 (2.5 g, 16 mmol). The reaction time was 15 hours.

Compound A-40 (1.2 g, white solid, crude) was prepared from compound A-39 (1.0 g, 5.8 mmol). The reaction time was 14 hours. TLC [petroleum ether:ethyl acetate=8:1]: Rf=0.5.

Example 28A 4-chloro-2-fluoro-3-methylbenzaldehyde (A-41)

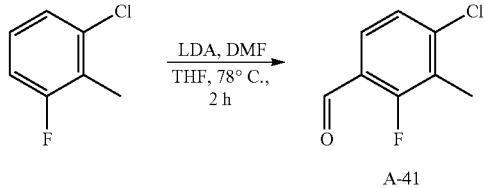

To a solution of 1-chloro-3-fluoro-2-methylbenzene (10 g, 69 mmol) in anhydrous tetrahydrofuran (20 mL) at −78° C. was added lithium diisopropylamide (2 M in tetrahydrofuran, 0.10 mol, 50 mL). The reaction was stirred for 0.5 hr, then N,N-dimethylformamide (0.21 mol, 15 g) was added, and stirring was continued −78° C. for 1.5 hrs. On completion, the reaction mixture was quenched with water and extracted with ethyl acetate (3×200 mL). The combined organic layers were washed with water and brine, dried over anhydrous sodium sulfate and concentrated in vacuo to give A-41 (12 g, crude) as a white solid.

Example 29A 4-chloro-2-fluoro-N-hydroxy-3-methylbenzimidoyl chloride (A-43)

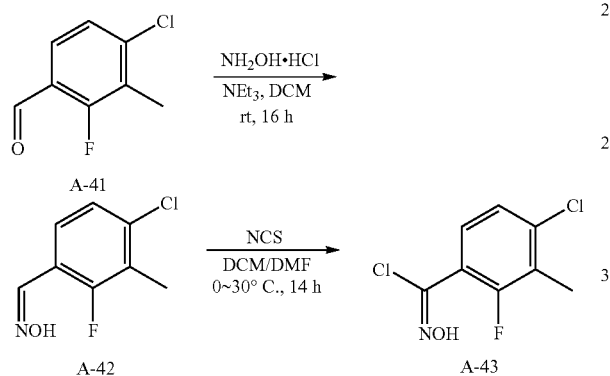

Following general procedure A1, compound A-43 was prepared from compound A-41.

Compound A-42 (1.1 g crude) was prepared from compound A-41 (12 g, 70 mmol). 1H-NMR (CD$_3$OD, 400 MHz): δ 11.68 (m, 1H), 8.21-8.19 (m, 1H), 7.61-7.57 (m, 1 H), 7.34-7.32 (m, 1H), 2.28 (s, 3H).

Compound A-43 (0.52 g, white solid, crude) was prepared from compound A-42 (0.50 g, 2.7 mmol). The reaction time was 14 hours. TLC [petroleum ether:ethyl acetate=8:1]: Rf=0.5.

Example 30A 4-chloro-2-fluoro-N-hydroxy-3-methoxybenzimidoyl chloride (A-45)

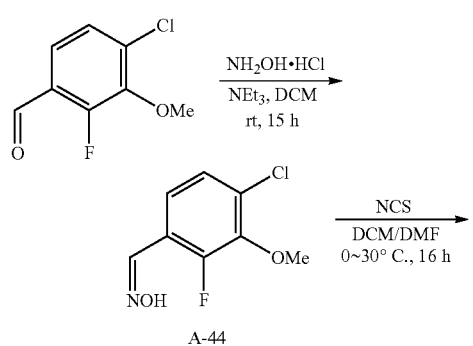

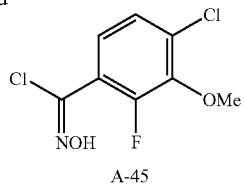

Following general procedure A1, compound A-45 was prepared from 4-chloro-2-fluoro-3-methoxybenzaldehyde:

Compound A-44 (0.49 g, white solid, crude) was prepared from 4-chloro-2-fluoro-3-methoxybenzaldehyde (0.50 g, 2.7 mmol) with a reaction time of 15 hours.

Compound A-45 (0.47 g, white solid, crude) was prepared from compound A-44 (0.45 g, 2.2 mmol) with a reaction time of 16 hours. TLC [petroleum ether:ethyl acetate=5:1]: Rf=0.7.

Example 31A 4-chloro-2-fluoro-3-(trifluoromethyl)benzaldehyde (A-46)

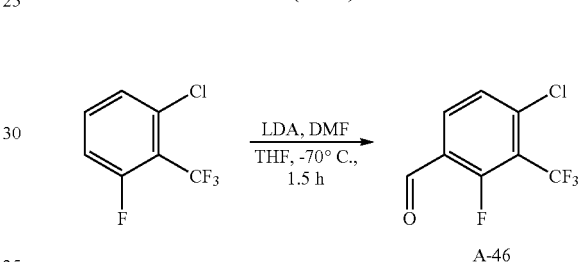

To a solution of 1-chloro-3-fluoro-2-(trifluoromethyl)benzene (0.50 g, 2.5 mmol) at −70° C. was added dropwise lithium diisopropylamide (2 M in tetrahydrofuran, 3.8 mmol, 1.9 mL). The reaction was stirred at −70° C. for 0.5 hour, then N,N-dimethylformamide (0.55 g, 7.6 mmol) was added slowly, and stirring was continued at −70° C. for another hour. The reaction was quenched with water (10 mL) and extracted with ethyl acetate (3×10 mL). The combined organic layers were concentrated in vacuo, and the residue was purified by silica gel chromatography [petroleum ether:ethyl acetate=10:1] to give A-46 (0.40 g, 70% yield) as a yellow solid. 1H-NMR (CDCl$_3$, 400 MHz): δ10.28 (s, 1H), 7.95-7.90 (t, J=10.0 Hz, 1H), 7.40-7.37 (d, J=11.2 Hz, 1H).

Example 32A 4-chloro-2-fluoro-N-hydroxy-3-(trifluoromethyl)benzimidoyl chloride (A-48)

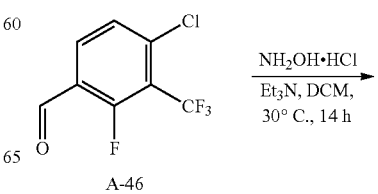

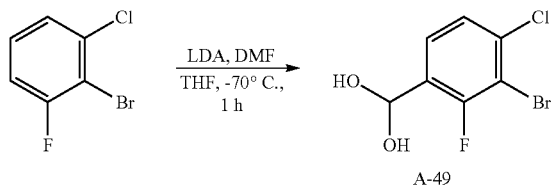

Following general procedure A1, compound A-48 was prepared from compound A-46:

Compound A-47 (0.40 g, yellow solid, 62% yield) was prepared from compound A-46 (0.60 g, 2.7 mmol) with a reaction time of 14 hours and used in next step without further purification.

Compound A-48 (0.40 g, white solid, crude) was prepared from compound A-47 (0.38 g, 1.6 mmol). TLC [petroleum ether:ethyl acetate=8:1]. Rf=0.6.

Example 33A (3-bromo-4-chloro-2-fluorophenyl)methanediol (A-49)

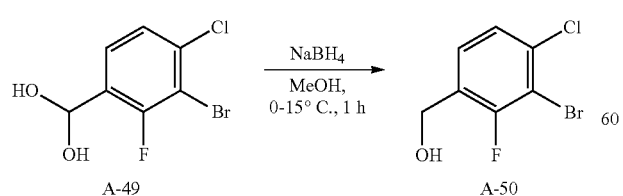

To a solution of 2-bromo-1-chloro-3-fluorobenzene (6.0 g, 29 mmol) in tetrahydrofuran (30 mL) at −70° C. was added dropwise lithium diisopropylamide (2 M in tetrahydrofuran/n-heptane, 22 mL, 43 mmol). The resulting solution was stirred at −70° C. for 0.5 hour. Then N,N-dimethylformamide (4.2 g, 57 mmol) was added slowly, and stirring was continued at −70° C. for another 0.5 hour. On completion of the reaction by TLC [petroleum ether:ethyl acetate=10:1, Rf=0.6], the reaction was quenched with saturated aqueous ammonium chloride (2 mL) at 0° C. and extracted with acetate ethyl (3×20 mL). The combined organic extracts were concentrated to give compound A-49 (4.0 g, 58% yield) as a yellow solid. $^1$H-NMR (CD$_3$OD, 400 MHz): δ 7.64-7.57 (m, 1H), 7.21-7.17 (m, 1H), 6.02 (s, 1H).

Example 34A (3-bromo-4-chloro-2-fluorophenyl)methanol (A-50)

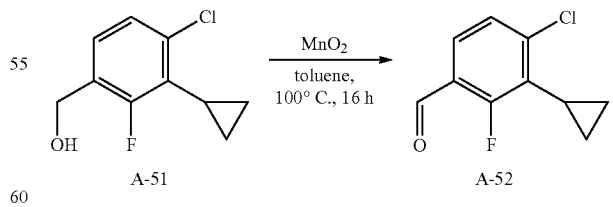

To a solution of compound A-49 (2.0 g, 8.4 mmol) in methanol (10 mL) at 0° C. was added sodium borohydride (0.64 g, 17 mmol). The reaction was allowed to warm to room temperature and stirred for another 1 hour, until TLC showed the reaction was complete [petroleum ether:ethyl acetate=10:1, Rf=0.4]. The reaction was quenched at 0° C. with 2 N hydrochloric acid (2 mL) and extracted with ethyl acetate (3×200 mL). The combined organic phase was dried over anhydrous sodium sulfate and concentrated to afford compound A-50 (2.0 g, crude) as a yellow oil. $^1$H-NMR (CD$_3$OD, 400 MHz): δ 7.50-7.46 (m, 1H), 7.17-7.13 (m, 1H), 4.89 (s, 2H).

Example 35A (4-chloro-3-cyclopropyl-2-fluorophenyl)methanol (A-51)

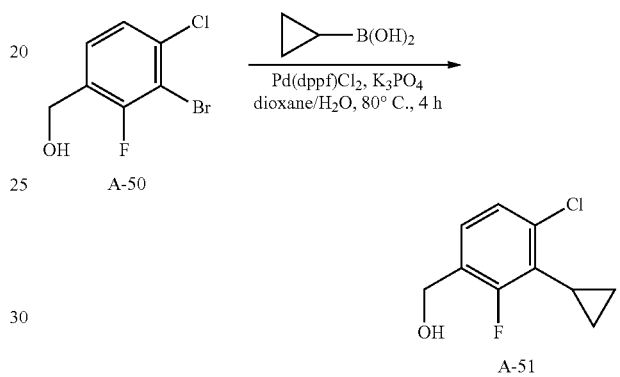

To a solution of compound A-50 (2.0 g, 8.4 mmol) in dioxane (8.0 mL) and water (1.0 mL) was added potassium phosphate (5.3 g, 25 mmol), [1,1'-bis(diphenylphosphino)ferrocene]dichloropalladium(II) (0.61 g, 0.84 mmol) and cyclopropylboronic acid (1.1 g, 13 mmol). The mixture was stirred at 80° C. for 4 hours, then concentrated and purified by silica gel chromatography [petroleum ether:ethyl acetate=5:1] to afford compound A-51 (1.2 g, 72% yield over two steps) as a yellow oil. GCMS: tR=9.103 min, 199.9, (EI) m/z (M)$^+$.

Example 36A 4-chloro-3-cyclopropyl-2-fluorobenzaldehyde (A-52)

A mixture of compound A-51 (1.2 g, 6.0 mmol) and manganese dioxide (11 g, 0.12 mol) in toluene (40 mL) was stirred at 100° C. for 16 hours until TLC analysis showed the starting material was consumed. The reaction mixture was filtered, and the filtrate was concentrated in vacuo. The residue was purified by silica gel chromatography [petroleum ether:ethyl acetate=5:1] to afford compound A-52 (0.6 g, crude) as a yellow oil. LCMS (B): (ES+) m/z (M+H)+=199.0, tR=0.827 min.

Example 37A 4-chloro-3-cyclopropyl-2-fluoro-N-hydroxybenzimidoyl chloride (A-54)

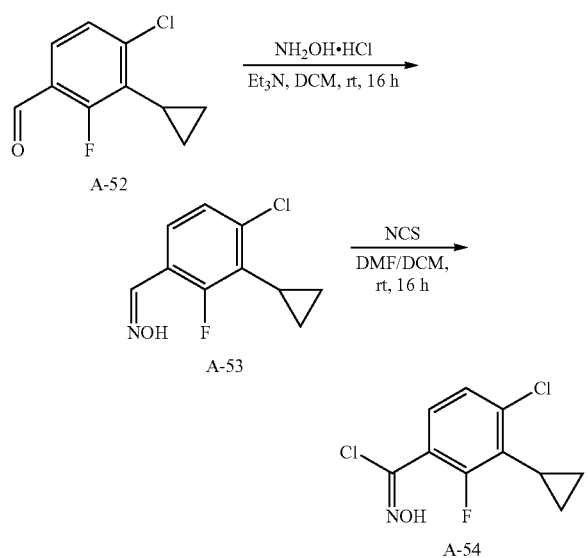

Following general procedure A1, compound A-54 was prepared from compound A-52:

Compound A-53 (0.45 g, white solid, 93% yield over two steps) was prepared from compound A-52 (0.45 g, 2.3 mmol). 1H-NMR (CDCl3, 400 MHz): δ9.23 (s, 1H), 8.47 (s, 1H), 7.15-7.12 (d, J=8.4 Hz, 1H), 6.87-6.83 (d, J=8.0 Hz, 1H), 2.16-2.07 (m, 1H), 1.05-0.97 (m, 2H), 0.73-0.68 (m, 2H).

Compound A-54 (0.50 g, colorless oil, crude) was prepared from compound A-53 (0.40 g, 1.7 mmol) with a reaction time of 16 hours. TLC [petroleum ether:ethyl acetate=10:1]: Rf=0.5.

Example 38A 4-chloro-2,6-difluoro-N-hydroxybenzimidoyl chloride (A-56)

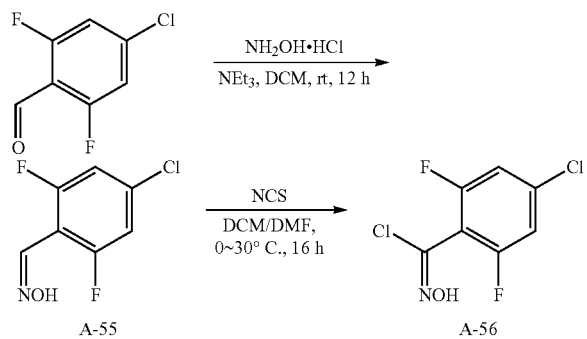

Following general procedure A1, compound A-56 was prepared from 4-chloro-2,6-difluorobenzaldehyde:

Compound A-55 (0.50 g, white solid, 92% yield) was prepared from 4-chloro-2,6-difluorobenzaldehyde (0.50 g, 2.8 mmol) with a reaction time of 12 hours and purified by silica gel chromatography [petroleum ether:ethyl acetate=10:1]. LCMS (B): tR=0.678 min., 192.1 m/z (M+1); 1H-NMR (CDCl3, 400 MHz): δ 8.27 (s, 1H), 8.21 (s, 1H), 7.03-7.00 (m, 2H).

Compound A-56 (0.80 g of colorless oil, crude) was prepared from compound A-55 (0.80 g, 4.2 mmol) with a reaction time of 16 hours. TLC [petroleum ether:ethyl acetate=5:1]: Rf=0.70.

Example 39A 2,4-dichloro-6-fluorobenzaldehyde (A-57)

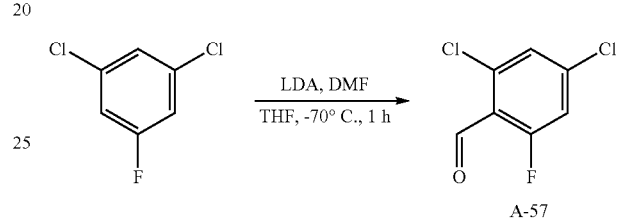

To a solution of 1,3-dichloro-5-fluorobenzene (2.0 g, 12 mmol) in tetrahydrofuran (20 mL) at −70° C. was added dropwise lithium diisopropylamide (2 M in tetrahydrofuran, 18 mmol., 9.1 mL). The reaction was stirred at −70° C. for 0.5 hr, then N,N-dimethylformamide (1.8 g, 24 mmol) was added slowly, and stirring was continued at −70° C. for another 0.5 hr. The reaction was quenched with water (20 mL) and extracted with acetate ethyl (3×20 mL). The combined organic layers were concentrated in vacuo and purified by silica gel chromatography [petroleum ether:ethyl acetate=30:1] to give A-57 (1.5 g, 64% yield) as a yellow solid. 1H-NMR (CDCl3, 400 MHz): δ10.41 (s, 1H), 7.934 (s, 1H), 7.18-7.16 (d, J=10.0 Hz, 1H).

Example 40A 2,4-dichloro-6-fluoro-N-hydroxybenzimidoyl chloride (A-59)

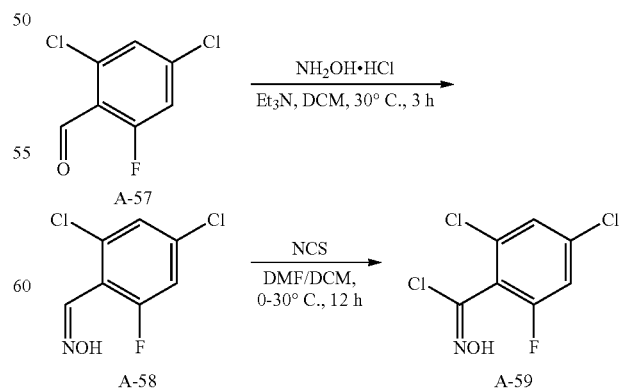

Following general procedure A1, compound A-59 was prepared from compound A-57:

Compound A-58 (0.75 g, white solid, 90% yield) was prepared from compound A-57 (0.77 g, 7.0 mmol) with a reaction time of 3 hours and used in the next step without further purification. LCMS (B): (ES$^+$) m/z (M+H)$^+$=207.9, tR=0.628 min.

Compound A-59 (0.35 g, white solid, crude) was prepared from compound A-58 (0.30 g, 1.4 mmol) with a reaction time of 12 hours. TLC [petroleum ether:ethyl acetate=5:1]: Rf=0.8.

Example 41A 2,3-difluoro-N-hydroxy-4-methoxybenzimidoyl chloride (A-61)

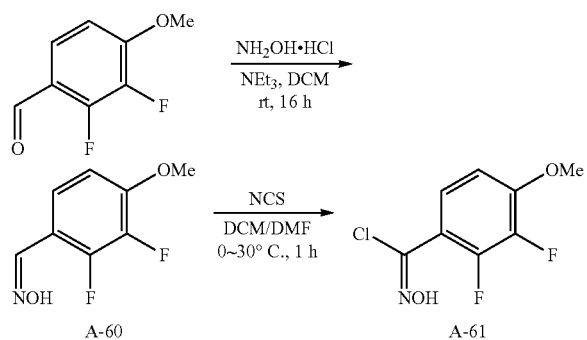

Following general procedure A1, compound A-61 was prepared from 2,3-difluoro-4-methoxybenzaldehyde:

Compound A-60 (0.50 g, white solid, 92% yield) was prepared from 2,3-difluoro-4-methoxyben zaldehyde (0.50 g, 2.9 mmol) and purified by silica gel chromatography [petroleum ether:ethyl acetate=8:1].

Compound A-61 (0.50 g, white solid, crude) was prepared from compound A-60 (0.40 g, 2.1 mmol). TLC [petroleum ether:ethyl acetate=3:1]: Rf=0.5.

Example 42A 3-chloro-2-fluoro-4-methoxybenzaldehyde (A-62)

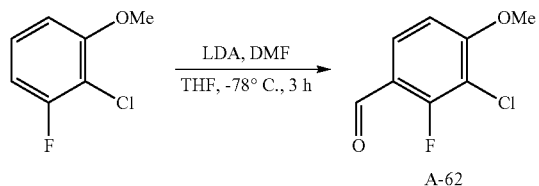

To a solution of 2-chloro-1-fluoro-3-methoxy-benzene (1.5 g, 9.3 mmol) in tetrahydrofuran (10 mL) at −78° C. was added lithium diisopropylamide (2M in tetrahydrofuran, 7.0 mL, 14 mmol). The reaction was stirred for 0.5 hour, then N,N-dimethylformamide (2.1 g, 28 mmol) was added, and stirring was continued at −78° C. for 2.5 hours. On completion, the reaction mixture was quenched with water (20 mL) and extracted with ethyl acetate (3×20 mL). The combined organic layers were washed with water and brine, dried over anhydrous sodium sulfate and concentrated in vacuo to give compound A-62 (0.40 g, 23% yield) as a white solid.

Example 43A 3-chloro-2-fluoro-N-hydroxy-4-methoxybenzimidoyl chloride (A-64)

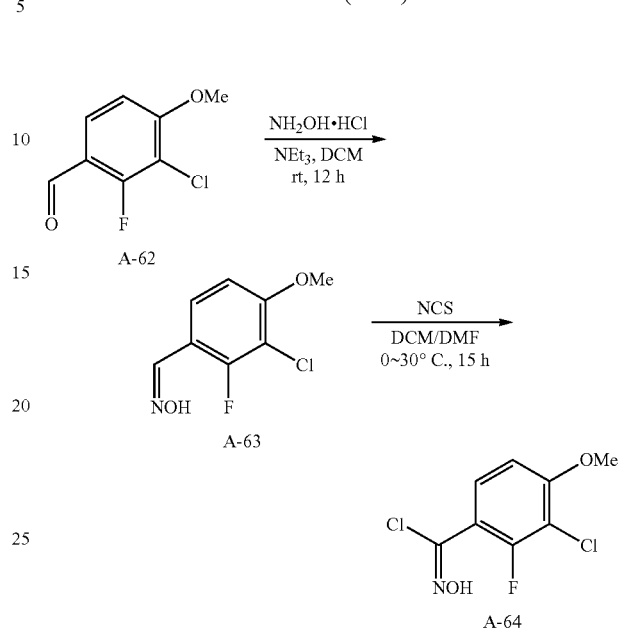

Following general procedure A1, compound A-64 was prepared from compound A-62:

Compound A-63 (0.43 g, white solid, crude) was prepared from compound A-62 (0.40 g, 2.1 mmol) with a reaction time is 12 hours.

Compound A-64 (0.45 g, white solid, crude) was prepared from compound A-63 (0.43 g, 2.1 mmol) with a reaction time is 15 hours. TLC [petroleum ether:ethyl acetate=5:1]: Rf=0.7.

Example 44A 3-chloro-2-fluoro-4-methylbenzaldehyde (A-65)

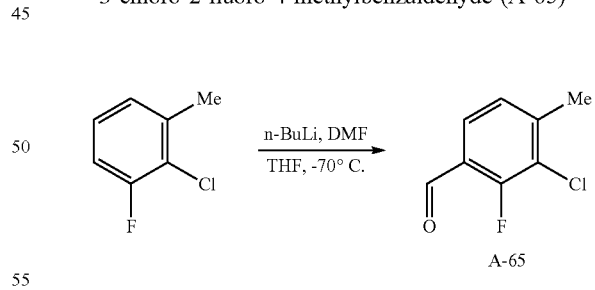

To a solution of 2-chloro-1-fluoro-3-methyl-benzene (1.0 g, 6.9 mmol) in tetrahydrofuran (30 mL) at −70° C. was added dropwise n-butyllithium (2.5 N in hexane, 3.3 mL, 8.3 mmol). The reaction was stirred at −70° C. for 0.5 h, then N,N-dimethylformamide (2.0 g, 28 mmol) was added, and stirring was continued at −70° C. for another 0.5 h. On completion, the mixture was poured into ammonium chloride (40 mL) solution and extracted with ethyl acetate (3×50 mL). The combined organic layers were washed with brine, dried over anhydrous sodium sulfate, filtered and concentrated in vacuo to give compound A-65 (1.2 g, 86% yield) as yellow solid, which was used in the next step without further purification. LCMS (J): (ES+) m/z (M+H)+=173.0, tR=0.508 min.

Example 45A 3-chloro-2-fluoro-N-hydroxy-4-methylbenzimidoyl chloride (A-67)

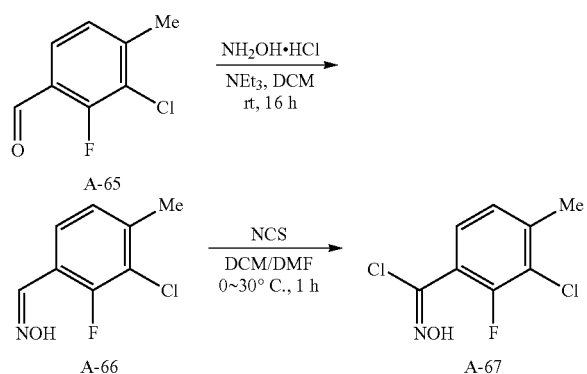

Following general procedure A1, compound A-67 was prepared from compound A-65:

Compound A-66 (1.1 g, white solid, 85% yield) was prepared from compound A-65 (1.2 g, 7.0 mmol) and purified by silica gel chromatography [petroleum ether:ethyl acetate=8:1]. 1H-NMR (CD₃OD, 400 MHz): δ 8.20 (s, 1H), 7.61-7.57 (t, J=7.2 Hz, 1H), 7.09-7.07 (d, J=8.0 Hz, 1H).

Compound A-67 (0.60 g, white solid, crude) was prepared from compound A-66 (0.50 g, 2.7 mmol). TLC [petroleum ether:ethyl acetate=3:1]: Rf=0.5.

Example 46A 1-bromo-2-fluoro-4-isopropoxybenzene (A-68)

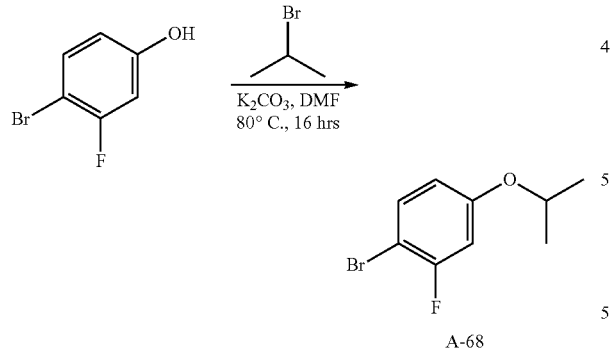

A mixture of 4-bromo-3-fluoro-phenol (5.0 g, 26 mmol), 2-bromopropane (6.4 g, 52 mmol) and potassium carbonate (29 g, 0.21 mol) in N,N-dimethylformamide (50 mL) was stirred at 80° C. for 16 hrs. On completion, the reaction was diluted with water (50 mL) and extracted with ethyl acetate (3×50 mL). The combined organic layers were concentrated in vacuo, and the residue was purified by silica gel chromatography [petroleum ether:ethyl acetate=30:1] to give compound A-68 (5.0 g, 82% yield) as colourless oil. 1H-NMR (CDCl₃, 400 MHz): δ7.42-7.38 (t, J=8.8 Hz, 1H), 6.71-6.68 (dd, J=10.8 Hz, J=2.8 Hz, 1H), 6.62-6.59 (dd, J=8.8 Hz, J=1.6 Hz, 1H), 4.55-4.46 (m, 1H), 1.36-1.34 (d, J=6.0 Hz, 6H).

Example 47A 2-fluoro-4-isopropoxybenzaldehyde (A-69)

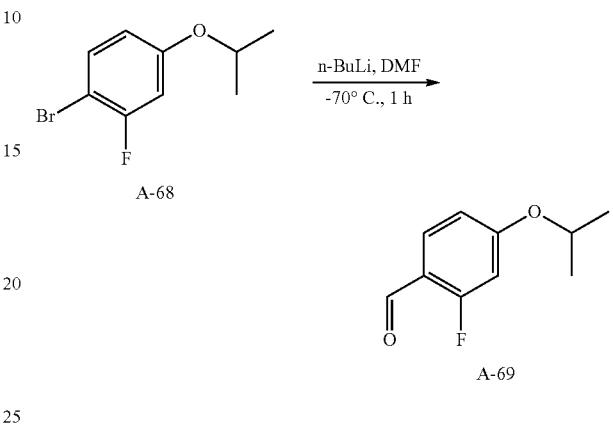

To a solution of A-68 (1.5 g, 6.4 mmol) in tetrahydrofuran (20 mL) at −70° C. was added dropwise n-butyllithium (2.5 M in hexanes, 3.1 mL, 7.8 mmol). The reaction was stirred at −70° C. for 0.5 hr., then N,N-dimethylformamide (1.4 g, 19 mmol) was added slowly, and stirring was continued at −70° C. for another 0.5 hr. On completion, the reaction was quenched slowly with saturated aqueous ammonium chloride (30 mL) and extracted with ethyl acetate (3×30 mL). The combined organic phases were concentrated in vacuo to give compound A-69 (1.0 g, 85% yield) as a light yellow solid.

Example 48A 2-fluoro-N-hydroxy-4-isopropoxybenzimidoyl chloride (A-71)

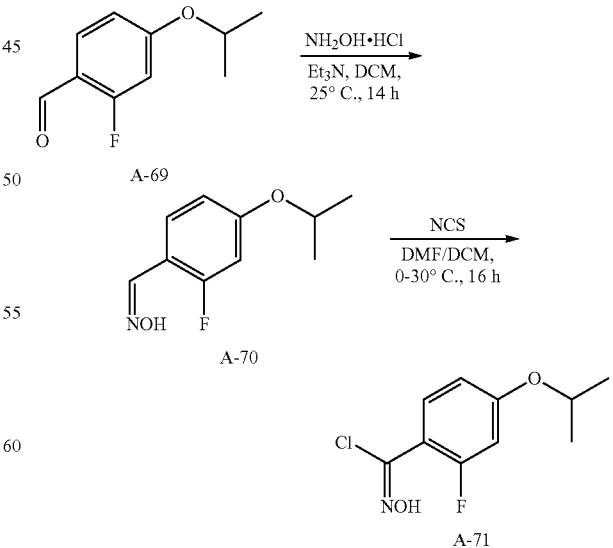

Following general procedure A1, compound A-71 was prepared from compound A-69:

Compound A-70 (0.90 g, light yellow solid, 83% yield) was prepared from compound A-69 (1.0 g, 5.5 mmol) with a reaction time of 14 hours and purified by silica gel chromatography [petroleum ether:ethyl acetate=20:1]. 1H-NMR (CDCl$_3$, 400 MHz): δ8.31 (s, 1H), 7.83 (s, 1H), 7.67-7.62 (t, J=8.4 Hz, 1H), 6.72-6.69 (dd, J=8.4 Hz, J=2.4 Hz, 1H), 6.64-6.60 (m, 1H), 4.62-4.52 (m, 1H), 1.38-1.37 (m, 6H).

Compound A-71 (0.80 g, yellow solid, crude) was prepared from compound A-70 (0.60 g, 3.0 mmol) with a reaction time of 16 hours. TLC [petroleum ether:ethyl acetate=5:1]: Rf=0.5.

Example 49A 4-ethoxy-2-fluorobenzaldehyde (A-72)

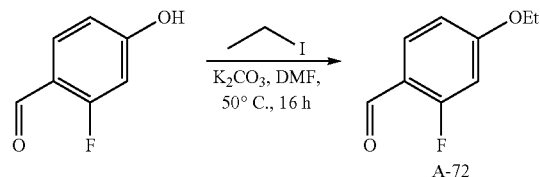

To a mixture of 2-fluoro-4-hydroxybenzaldehyde (3.0 g, 21 mmol) and iodoethane (5.0 g, 32 mmol) in N,N-dimethylformamide (0.5 mL) was added potassium carbonate (4.4 g, 32 mmol). The reaction mixture was stirred at 50° C. for 16 hours. On completion, the reaction mixture was diluted with water and extracted with ethyl acetate (3×150 mL). The combined organic layers were washed with water and brine, dried over anhydrous sodium sulfate, filtered and concentrated in vacuo to give compound A-72 (3.4 g, crude) as a yellow solid. LCMS (B): (ES$^+$) m/z (M+H)$^+$=169.2, tR=0.649 min.

Example 50A 4-ethoxy-2-fluoro-N-hydroxybenzimidoyl chloride (A-74)

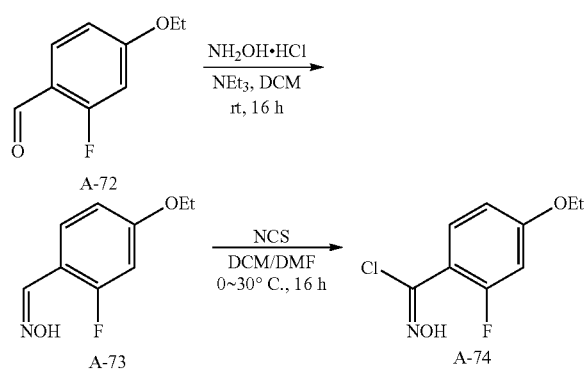

Following general procedure A1, compound A-74 was prepared from compound A-72:

Compound A-73 (1.0 g, white solid, 92% yield over two steps) was prepared from compound A-72 (1.0 g, 6.0 mmol) and purified by silica gel chromatography [petroleum ether:ethyl acetate=10:1]. LCMS (B): (ES$^+$) m/z (M+H)$^+$=184.2, tR=0.757 min.

Compound A-74 (0.60 g, white solid, crude) was prepared from compound A-73 (0.50 g, 2.9 mmol) with a reaction time of 16 hours. TLC [petroleum ether:ethyl acetate=5:1]: Rf=0.7.

Example 51A 6-chloro-2-fluoro-3-formylbenzonitrile (A-75)

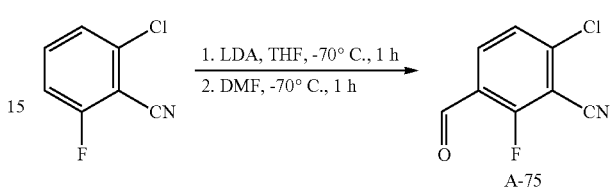

To a mixture of 2-chloro-6-fluorobenzonitrile (5.0 g, 32 mmol) in anhydrous tetrahydrofuran (50 mL) at −70° C. under nitrogen was added dropwise lithium diisopropylamide (2.0 M in tetrahydrofuran/n-heptane, 24 mL, 48 mmol). The mixture was stirred at −70° C. for 0.5 hour, and N,N-dimethylformamide (3.5 g, 48 mmol) was added dropwise. The reaction was stirred at −70° C. for another 0.5 hour, then quenched with saturated ammonium chloride solution (500 mL) at 0° C. and extracted with ethyl acetate (2×200 mL). The combined organic layers were dried with anhydrous sodium sulfate, filtered and concentrated in vacuo. The residue was purified by silica gel chromatography [petroleum ether:ethyl acetate=30:1] to give compound A-75 (1.0 g, 17% yield) as a yellow solid. $^1$H-NMR (CDCl$_3$, 400 MHz): δ 10.33 (s, 1H), 8.07 (t, J=8.0 Hz, 1H), 7.50 (d, J=8.4 Hz, 1H).

Example 52A 4-chloro-3-cyano-2-fluoro-N-hydroxybenzimidoyl chloride (A-77)

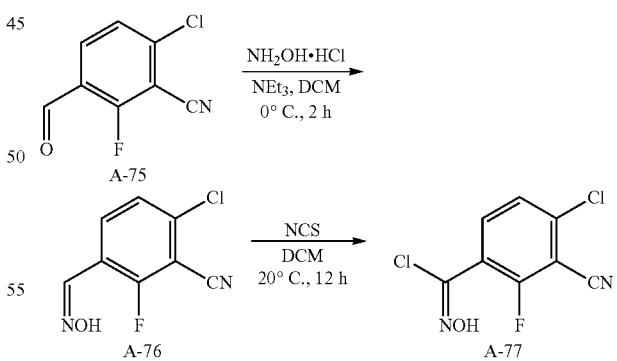

Following general procedure A1, compound A-77 was prepared from compound A-75:

Compound A-76 (0.36 g, white solid, 33% yield) was prepared from compound A-75 (0.20 g, 1.1 mmol, 5 batches) with a reaction time of 2 hours and 0° C. and purified by prep-TLC [petroleum ether:ethyl acetate=5:1]. 1H-NMR (CDCl$_3$, 400 MHz): δ 8.31 (s, 1H), 8.00 (t, J=8.0 Hz, 1H), 7.71 (s, 1H), 7.36 (d, J=8.8 Hz, 1H).

Compound A-77 (0.50 g of yellow oil, crude) was prepared from compound A-76 (0.31 g, 1.3 mmol), in dichloromethane and stirred at 20° C. for 12 hours. TLC [petroleum ether:ethyl acetate=5:1]: Rf=0.61.

Example 53A 3-chloro-2,4-difluoro-N-hydroxybenzimidoyl chloride (A-79)

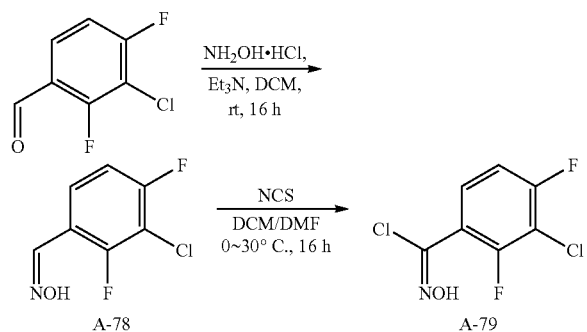

Following general procedure A1, compound A-79 was prepared from 3-chloro-2,4-difluorobenzaldehyde:

Compound A-78 (0.90 g, white solid, 83% yield) was prepared from 3-chloro-2,4-difluorobenzaldehyde (1.0 g, 5.7 mmol) and used in the next step without further purification.

Compound A-79 (0.80 g, white solid, crude) was prepared from compound A-78 (0.90 g, 4.7 mmol) with a reaction of 16 hours. TLC [petroleum ether:ethyl acetate=8:1]: Rf=0.75.

Example 54A 2-fluoro-4-(1H-pyrazol-1-yl)benzaldehyde (A-80)

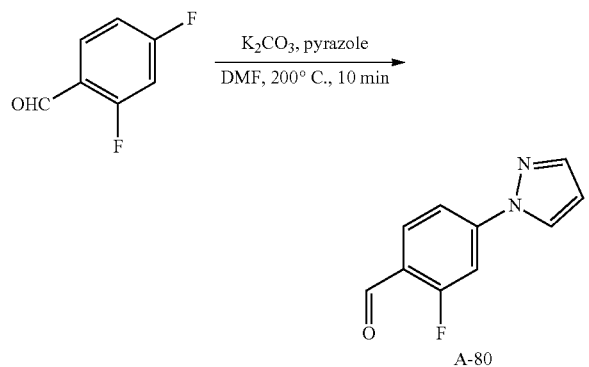

A mixture of 2,4-difluorobenzaldehyde (14 g, 1.0 mol), 1H-pyrazole (6.8 g, 1.0 mmol) and potassium carbonate (14 g, 1.0 mmol) in N,N-dimethylacetamide (200 mL) was stirred at 200° C. for 10 mins. TLC [petroleum ether:ethyl acetate=5:1] showed starting material consumed and two new spots formed. The reaction mixture was diluted with water (200 mL) and extracted with ethyl acetate (2×150 mL). The combined organic phases were washed with water (5×150 mL) and brine (150 mL), dried over sodium sulfate, filtered and concentrated. The residue was purified by Prep-HPLC (TFA, Instrument: HPLC-B. column:Phenomenex Synergi Max-RP 250×50 mm×10 µm. Condition: 0.1% TFA-ACN) and lyophilization to give compound A-80 (3.5 g, 18% yield) as a white solid. LCMS (D): (ES$^+$) m/z (M+H)$^+$=191.1, tR=1.271 min.

Example 55A 2-fluoro-N-hydroxy-4-(1H-pyrazol-1-yl)benzimidoyl chloride (A-82)

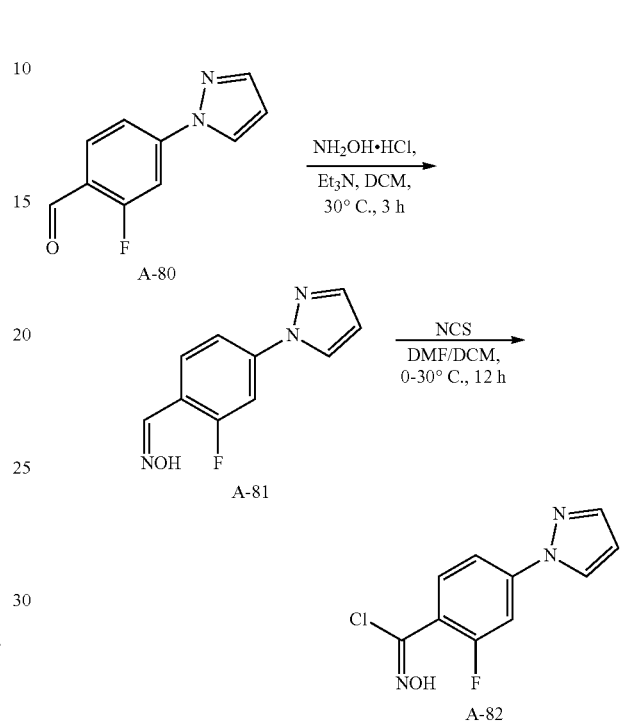

Following general procedure A1, compound A-82 was prepared from compound A-80:

Compound A-81 (0.75 g, white solid, 90% yield) was prepared from compound A-80 (1.0 g, 5.3 mmol) with a reaction time of 3 hours and purified by silica gel chromatography [petroleum ether:ethyl acetate=10:1]. LCMS (Y): (ES$^+$) m/z (M+H)$^+$=206.2, tR=0.666 min.

Compound A-82 (0.40 g, white solid, crude) was prepared from compound A-81 (0.30 g, 1.5 mmol) with a reaction time of 12 hours. [petroleum ether:ethyl acetate=5:1]: Rf=0.62.

Example 56A methyl 4-bromo-3-fluorobenzoate (A-83)

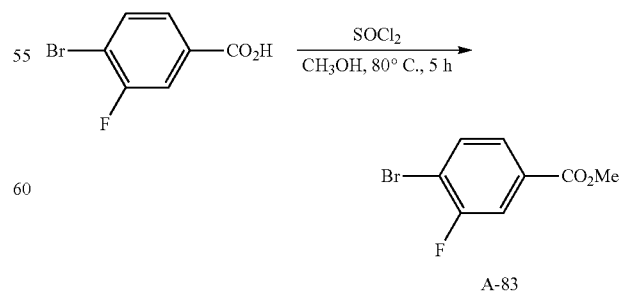

To a solution of 4-bromo-3-fluoro-benzoic acid (10 g, 46 mmol) in methanol (120 mL) was added thionyl chloride (33 g, 0.28 mol). The reaction was stirred at 80° C. for 5 hours, then concentrated in vacuo to give compound A-83 (11 g, crude) as yellow solid, which was used in the next step without further purification. TLC [petroleum ether:ethyl acetate=10:1]: Rf=0.80.

Example 57A 4-bromo-3-fluorobenzohydrazide (A-84)

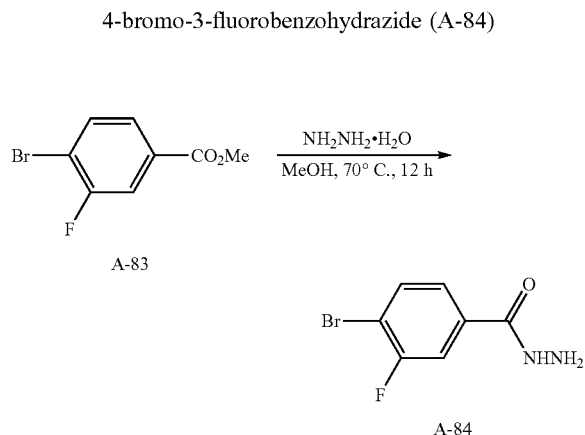

A mixture of compound A-83 (11 g, crude) and hydrazine hydrate (23 g, 0.46 mol) in methanol (200 mL) was stirred at 70° C. for 12 hours. On completion, the mixture was concentrated in vacuo, diluted with ethyl acetate (60 mL), washed with water (50 mL) and brine (2×20 mL), dried over anhydrous sodium sulfate, filtered and concentrated in vacuo to afford compound A-84 (5.0 g, crude) as a yellow solid.

Example 58A 2-(4-bromo-3-fluorophenyl)-5-methyl-1,3,4-oxadiazole (A-85)

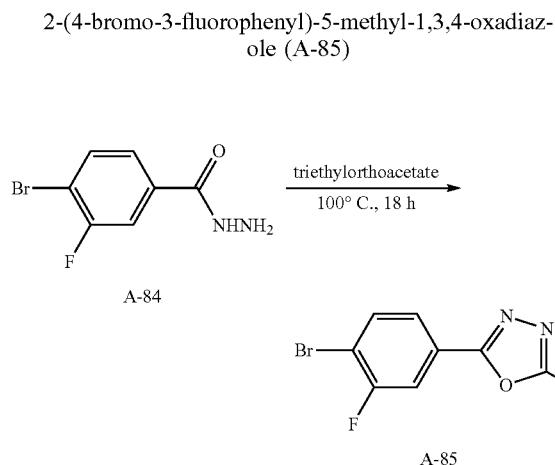

A mixture of compound A-84 (4.0 g, crude) and triethylorthoacetate (2.5 g, 17 mmol) was stirred at 100° C. for 18 hours. On completion, the mixture was poured into water (40 mL) and extracted with ethyl acetate (2×50 mL). The combined organic phase was washed with brine (2×20 mL), dried with anhydrous sodium sulfate and concentrated in vacuo. The residue was purified by silica gel chromatography [petroleum ether:ethyl acetate=3:1] to give compound A-85 (3.7 g, 39% yield over three steps) as a yellow solid. $^1$H-NMR (CD$_3$OD, 400 MHz): δ 7.88-7.85 (m, 2H), 7.79-7.77 (m, 1H), 2.65 (m, 3H).

Example 59A 2-(3-fluoro-4-vinylphenyl)-5-methyl-1,3,4-oxadiazole (A-86)

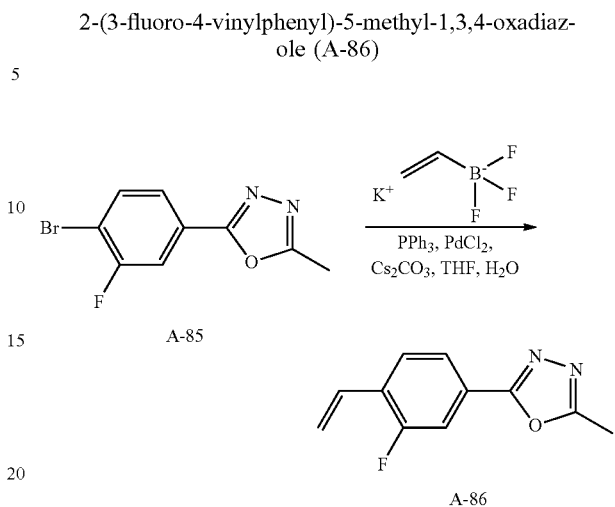

To a solution of compound A-85 (3.3 g, 13 mmol), potassium trifluoro(vinyl)boranuide (2.1 g, 15 mmol) and cesium carbonate (13 g, 39 mmol) in tetrahydrofuran (9.0 mL) and water (1.0 mL) was added triphenylphosphine (0.34 g, 1.3 mmol) and palladium chloride (0.23 g, 1.3 mmol). The reaction was stirred at 80-90° C. for 16 hours, then poured into water (20 mL) and extracted with ethyl acetate (2×20 mL). The combined organic phase was washed with brine, dried with anhydrous sodium sulfate and concentrated in vacuo. The residue was purified by silica gel chromatography [petroleum ether:ethyl acetate=3:1] to give compound A-86 (2.3 g, 88% yield) as a yellow solid. LCMS (B): (ES$^+$) m/z (M+H)$^+$=205.1, tR=0.730 min.

Example 60A 2-fluoro-4-(5-methyl-1,3,4-oxadiazol-2-yl)benzaldehyde (A-87)

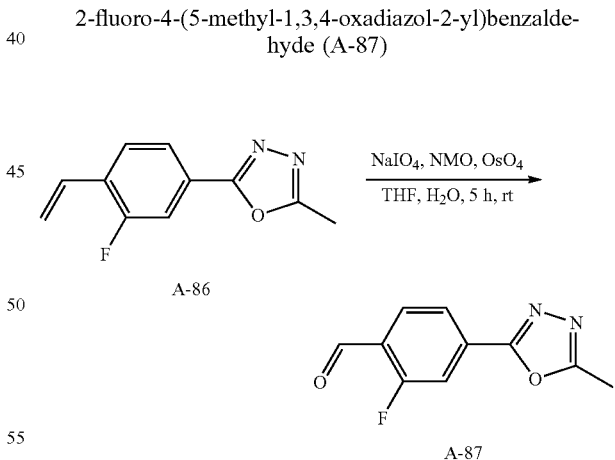

To a solution of compound A-86 (1.5 g, 7.2 mmol), sodium periodate (3.1 g, 14 mmol) and 4-methylmorpholine (2.5 g, 21 mmol) in tetrahydrofuran (50 mL) and water (25 mL) was added osmium tetroxide (18 mg, 72 μmol). The reaction was stirred at 25° C. for 5 hours, then poured into aqueous sodium thiosulfate (20 mL) and extracted with ethyl acetate (2×20 mL). The combined organic phase was washed with brine, dried with anhydrous sodium sulfate and concentrated in vacuo. The residue was purified by silica gel chromatography [petroleum ether:ethyl acetate=3:1] to give compound A-87 (1.3 g, 88% yield) as a yellow solid. LCMS (M): (ES+) m/z (M+H)+=207.1, tR=0.705 min.

Example 61A 2-fluoro-N-hydroxy-4-(5-methyl-1,3,4-oxadiazol-2-yl)benzimidoyl chloride (A-89)

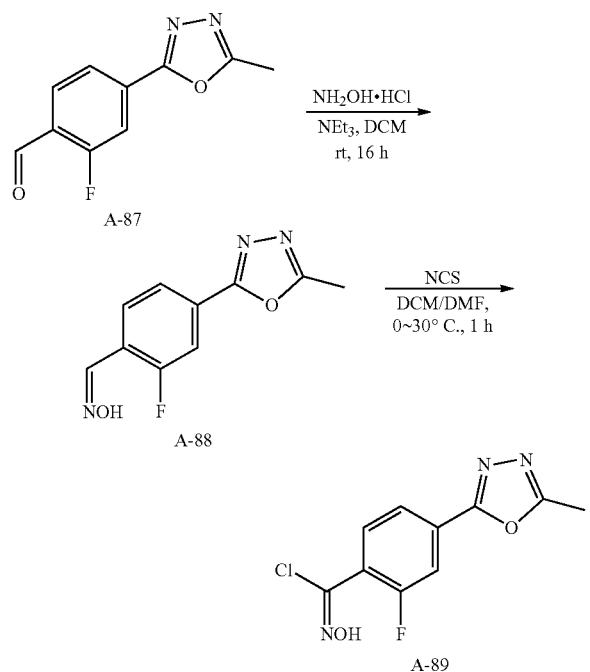

Following general procedure A1, compound A-89 was prepared from compound A-87:

Compound A-88 (0.50 g, yellow solid, 34% yield) was prepared from compound A-87 (1.4 g, 6.6 mmol) and purified by silica gel chromatography [petroleum ether:ethyl acetate=2:1]. LCMS (B): (ES+) m/z (M+H)+=222.1, tR=0.657 min.

Compound A-89 (0.60 g, yellow solid, crude) was prepared from compound A-88 (0.50 g, 2.3 mmol). TLC [petroleum ether:ethyl acetate=3:1]: Rf=0.60.

Example 62A 2-fluoro-3-methoxy-4-methylbenzaldehyde (A-90)

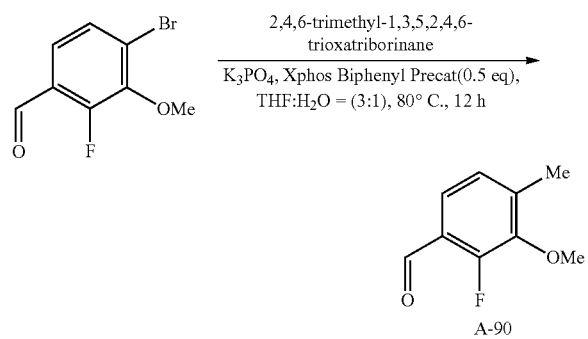

To a solution of 4-bromo-2-fluoro-3-methoxy-benzaldehyde (3.0 g, 13 mmol), 2,4,6-trimethyl-1,3,5,2,4,6-trioxatriborinane (2.1 g, 17 mmol) and potassium phosphate (5.5 g, 26 mmol) in water (10 mL) and tetrahydrofuran (30 mL) was added dicyclohexyl-[3-(2,4,6-triisopropylphenyl)phenyl]phosphane [2-(2-aminophenyl)phenyl]-chloro-palladium (0.51 g, 0.64 mmol). The mixture was stirred at 80° C. for 12 hours. On completion, the mixture was poured into water (20 mL) and extracted with ethyl acetate (2×20 mL). The combined organic phase was washed with brine (2×20 mL), dried with anhydrous sodium sulfate, filtered and concentrated in vacuo to give compound A-90 (1.60 g, crude) as a yellow solid, which was used in the next step without further purification. LCMS (B): (ES+) m/z (M+H)+=169.2, tR=0.640 min.

Example 63A 2-fluoro-N-hydroxy-3-methoxy-4-methylbenzimidoyl chloride (A-92)

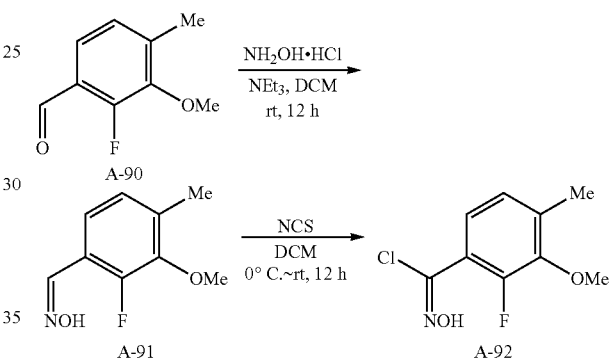

Following general procedure A1, compound A-92 was prepared from compound A-90:

Compound A-91 (0.70 g, yellow solid, 40% yield over two steps) was prepared from compound A-90 (1.6 g, 9.5 mmol) with a reaction time of 12 hours and purified by silica gel chromatography [petroleum ether:ethyl acetate=5:1]. LCMS (B): (ES+) m/z (M+H)+=184.2, tR=0.641 min.

Compound A-92 (0.50 g, yellow solid, crude) was prepared from compound A-91 (0.50 g, 2.7 mmol) with a reaction time of 12 hours and dichloromethane as the solvent. TLC [petroleum ether:ethyl acetate=3:1]: Rf=0.70.

Example 64A 1-chloro-2-ethoxy-3-fluorobenzene (A-93)

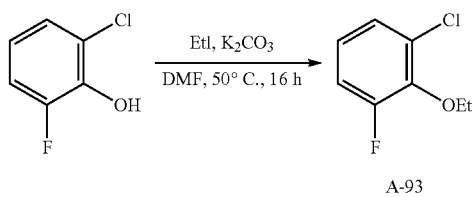

A mixture of 2-chloro-6-fluoro-phenol (2.0 g, 14 mmol, iodoethane (4.3 g, 27 mmol) and potassium carbonate (3.8 g, 27 mmol) in N,N-dimethylformamide (20 mL) was stirred at 50° C. for 16 hrs. On completion, the reaction was diluted with water (30 mL) and extracted with methyl t-butyl ether (3×20 mL). The combined organic phases were washed with water (10 mL) and brine (10 mL), dried with anhydrous sodium sulfate and concentrated in vacuo. The residue was purified by silica gel chromatography [petroleum ether:ethyl acetate=30:1] to give compound A-93 (1.5 g, 63% yield) as light yellow oil.

Example 65A 1-chloro-2-ethoxy-3-fluorobenzene (A-94)

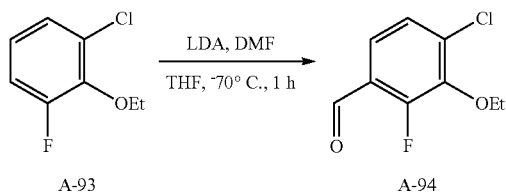

To a solution of Compound A-93 (1.0 g, 5.7 mmol) at −70° C. was added dropwise lithium diisopropylamide (2 M in tetrahydrofuran, 4.3 mL, 8.6 mmol). The reaction was stirred at −70° C. for 0.5 hr. Then N,N-dimethylformamide (1.7 g, 23 mmol) was added slowly, and stirring was continued at −70° C. for another 0.5 hr. The reaction was quenched with water (20 mL) and extracted with ethyl acetate (3×20 mL). The combined organic extracts were concentrated in vacuo and purified by silica gel chromatography [petroleum ether:ethyl acetate=8:1] to give compound A-94 (0.80 g, 69% yield) as a yellow solid.

Example 66A 4-chloro-3-ethoxy-2-fluoro-N-hydroxybenzimidoyl chloride (A-96)

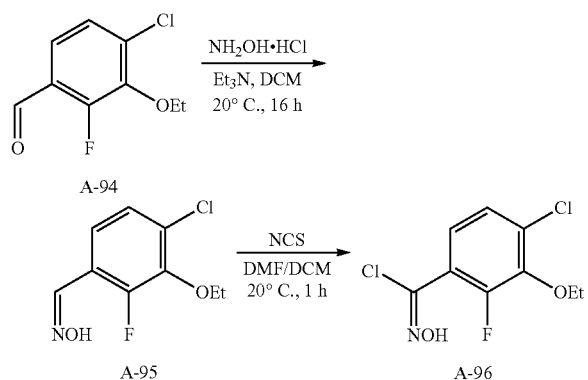

Following general procedure A1, compound A-96 was prepared from compound A-94:

Compound A-95 (90 mg, yellow solid, 84% yield) was prepared from compound A-94 (0.10 g, 0.49 mmol), reaction was stirred at 20° C., and purified by silica gel chromatography [petroleum ether:ethyl acetate=20:1]. 1H-NMR (CDCl$_3$, 400 MHz): δ8.33 (s, 1H), 7.79 (s, 1H), 7.45-7.41 (dd, J=7.2 Hz, J=1.2 Hz, 1H), 7.20-7.17 (dd, J=8.4 Hz, J=1.6 Hz, 1H), 4.23-4.18 (dd, J=14 Hz, J=7.2 Hz, 1H), 1.47-1.44 (t, J=7.2 Hz, 1H).

Compound A-96 (0.60 g, white solid, crude) was prepared from compound A-95 (0.45 g, 2.1 mmol), reaction was stirred at 20° C. TLC [petroleum ether:ethyl acetate=8:1]: Rf=0.52.

Example 67A 2-fluoro-3,4-dimethylbenzaldehyde (A-97)

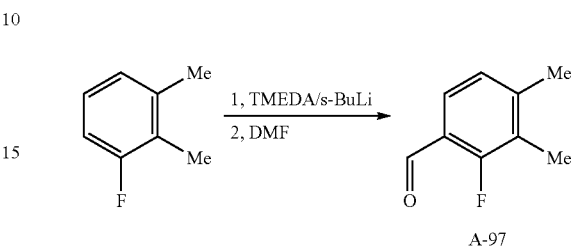

To a mixture of tetramethylethylenediamine (2.1 g, 18 mmol) in anhydrous tetrahydrofuran (20 mL) at −70° C. under nitrogen was added tert-butyllithium (1.3 M in pentane solution, 14 mL, 18 mmol) dropwise. The resulting yellow solution was stirred at −70° C. for 0.5 hour. Then a solution of 1-fluoro-2,3-dimethyl-benzene (2.0 g, 16 mmol) in anhydrous tetrahydrofuran (12 mL) was added dropwise. The mixture was stirred at −70° C. for 1 hour. Then a solution of N,N-dimethylformamide (1.3 g, 18 mmol) in anhydrous tetrahydrofuran (8.0 mL) was added, and the reddish-brown mixture was stirred at −70° C. for an additional 1 hour. On completion, the reaction mixture was quenched with acetic acid (2.0 mL) and water (20 mL) at 0° C. and extracted with ethyl acetate (3×30 mL). The combined organic layers were washed with water (2×20 mL), dried with anhydrous sodium sulfate, filtered and concentrated under reduced pressure to give compound A-97 (1.5 g, 61% yield) as a yellow oil. TLC [petroleum ether:ethyl acetate=5:1]: Rf=0.61.

Example 68A 2-fluoro-N-hydroxy-3,4-dimethylbenzimidoyl chloride (A-99)

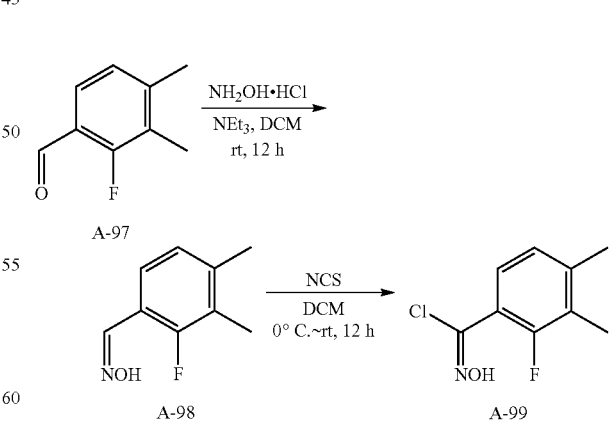

Following general procedure A1, compound A-99 was prepared from compound A-97:

Compound A-98 (1.5 g, yellow solid, 90% yield) was prepared from compound A-97 (1.5 g, 9.9 mmol) with a reaction time of 12 hours and purified by silica gel chromatography [petroleum ether:ethyl acetate=50:1~5:1]. $^1$H-NMR (CDCl$_3$, 400 MHz): δ 8.35 (s, 1H), 7.44 (t, J=8.0 Hz, 1H), 6.95 (d, J=8.0 Hz, 1H), 2.30 (s, 3H), 2.20 (s, 3H).

Compound A-99 (1.9 g, yellow solid, crude) was prepared from compound A-98 (1.0 g, 6.0 mmol) using dichloromethane and a reaction time of 12 hours. TLC [petroleum ether:ethyl acetate=10:1]: Rf=0.43.

Example 69A 4-chloro-2,3-difluoro-N-hydroxybenzimidoyl chloride (compound-A-101)

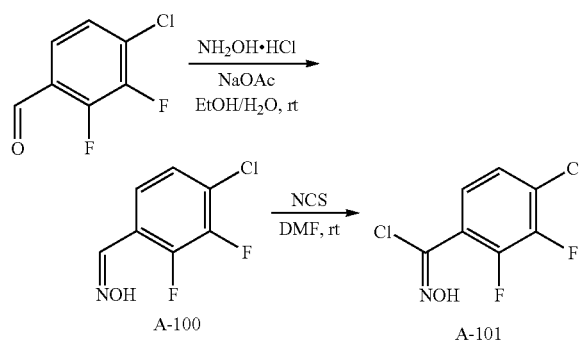

Following general procedure A2, compound A-101 was prepared from 4-chloro-2,3-difluorobenzaldehyde:

Compound A-100 (0.5 g, 92% yield, 11:1 mixture of (E)/(Z) isomers) was prepared as a white solid from 4-chloro-2,3-difluorobenzaldehyde (0.5 g, 2.8 mmol) using 9 mL of ethanol/water and a reaction time of 2 hours. LCMS (2): tR=1.910 min., (ES$^+$) m/z (M+H)$^+$=191.9. $^1$H NMR (300 MHz, DMSO-d$_6$, major isomer) δ 11.90 (s, 1H), 8.21 (s, 1H), 7.61-7.51 (m, 1H), 7.51-7.42 (m, 1H).

Compound A-101 (99 mg, 95% yield) was prepared as a white solid from compound A-100 (100 mg, 0.5 mmol) using 1 mL of N,N-dimethylformamide and a reaction time of 2 hours. 1H NMR (300 MHz, DMSO-d$_6$) δ 12.91 (s, 1H), 7.61-7.53 (m, 2H).

Example 70A 4-chloro-2,5-difluoro-N-hydroxybenzimidoyl chloride (compound-A-103)

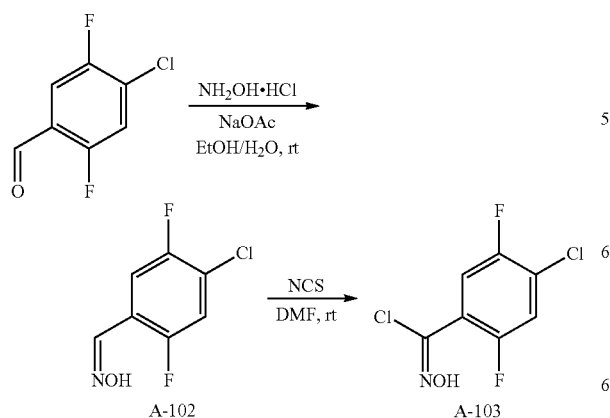

Following general procedure A2, compound A-103 was prepared from 4-chloro-2,5-difluorobenzaldehyde:

Compound A-102 (0.5 g, 92% yield, 8:1 mixture of (E)/(Z) isomers) was prepared as a white solid from 4-chloro-2,5-difluorobenzaldehyde (0.5 g, 2.8 mmol) using 7 mL of ethanol/water and a reaction time of 2 hours. LCMS (2): tR=1.907 min., (ES$^+$) m/z (M+H)$^+$=192.0. $^1$H NMR (300 MHz, DMSO-d$_6$, major isomer) δ 11.89 (s, 1H), 8.15 (s, 1H), 7.84-7.58 (m, 2H).

Compound A-103 (99 mg, 84% yield) was prepared as a white solid from compound A-102 (100 mg, 0.5 mmol) using 1 mL of N,N-dimethylformamide and a reaction time of 16 hours. 1H NMR (300 MHz, DMSO-d$_6$) δ 12.87 (s, 1H), 7.89-7.74 (m, 2H).

Example 71A 4-bromo-2-fluoro-N-hydroxybenzimidoyl chloride (compound-A-105)

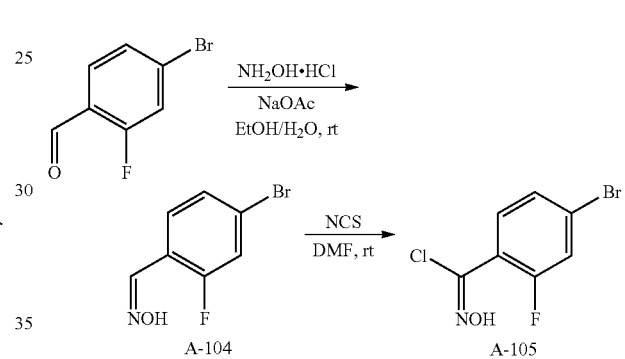

Following general procedure A2, compound A-105 was prepared from 4-bromo-2-fluorobenzaldehyde:

Compound A-104 (2.5 g, 93% yield, 9:1 mixture of (E)/(Z) isomers) was prepared as a white solid from 4-bromo-2-fluorobenzaldehyde (2.5 g, 12.3 mmol) using 45 mL of ethanol/water and a reaction time of 2 hours. 1H NMR (300 MHz, DMSO-d$_6$, major isomer) δ 11.69 (s, 1H), 8.15 (s, 1H), 7.69-7.60 (m, 2H), 7.48-7.42 (m, 1H).

Compound A-105 (2.3 g, 82% yield) was prepared as a white solid from compound A-104 (2.4 g, 11.0 mmol) using 20 mL of N,N-dimethylformamide and a reaction time of 3 days. 1H NMR (300 MHz, DMSO-d$_6$) δ 12.73 (s, 1H), 7.73 (dd, J=10.4, 1.8 Hz, 1H), 7.66-7.52 (m, 2H).

Example 72A 4-chloro-2-fluoro-N-hydroxybenzimidoyl chloride (compound-A-107)

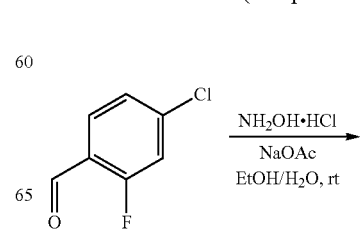

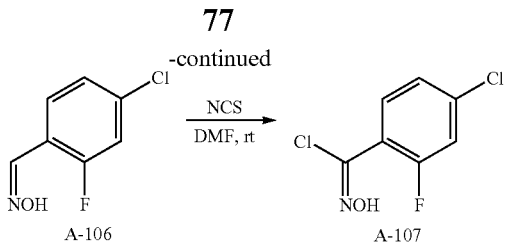

Following general procedure A2, compound A-107 was prepared from 4-chloro-2-fluorobenzaldehyde:

Compound A-106 (2.7 g, 96% yield) was prepared as a white solid from 4-chloro-2-fluorobenzaldehyde (2.6 g, 16.4 mmol) using 45 mL of ethanol/water and a reaction time of 1 hour. LCMS (2): tR=1.856 min., (ES$^+$) m/z (M+H)$^+$=174.0. $^1$H NMR (300 MHz, DMSO-d$_6$) δ 11.83 (s, 1H), 8.16 (s, 1H), 7.87-7.63 (m, 1H), 7.62-7.41 (m, 1H), 7.31 (d, J=7.9 Hz, 1H).

Compound A-107 (2.7 g, 84% yield) was prepared as a white solid from A-106 (2.7 g, 15.6 mmol) using 25 mL of N,N-dimethylformamide and a reaction time of 1.5 hours. 1H NMR (300 MHz, DMSO-d$_6$) δ 12.73 (s, 1H), 7.75-7.65 (m, 1H), 7.65-7.57 (m, 1H), 7.47-7.37 (m, 1H).

General Procedure B1: Synthesis and Chiral Separation of Amino-benzoisoxazoles.

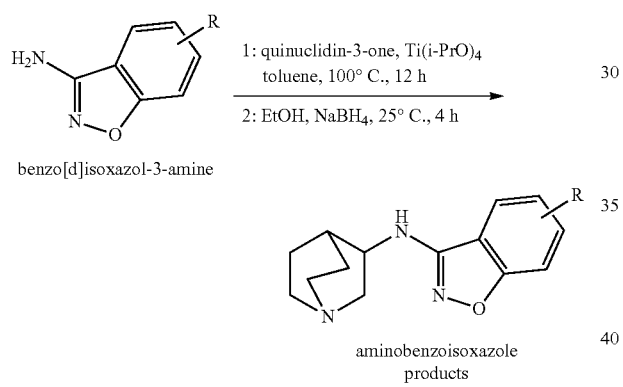

To a solution of benzo[d]isoxazol-3-amine (1 eq.) and quinuclidin-3-one (1.1 eq.) in toluene (7 mL/mmol benzo[d]isoxazol-3-amine) at 25° C. was added portion-wise titanium(IV) isopropoxide (9 eq.). The resulting solution was stirred at 100° C. for 12 hours. On completion, the mixture was cooled to 0° C., and ethanol (1 mL/mmol benzo[d]isoxazol-3-amine) was added via syringe, followed by sodium borohydride (3.7 eq.) in portions. The reaction was stirred at 25° C. for 3 hours, then quenched with saturated aqueous potassium carbonate solution, resulting in the formation of a solid. The mixture was filtered, and the filtrate was extracted with dichloromethane (5×50 mL). The combined organic layers were washed with brine, dried over anhydrous sodium sulfate, filtered and concentrated in vacuo. The filter cake from the original filtration was slurried with methanol, and the mixture was filtered. The filtrate was directly evaporated to dryness. The combined residue from both batches was dissolved in 4N hydrochloric acid (20 mL) and stirred at room temperature for 4 hours. The mixture was made basic by addition of saturated potassium carbonate solution and extracted with dichloromethane (5×50 mL). The combined organic layers were washed with brine, dried over anhydrous sodium sulfate, filtered and concentrated in vacuo. The residue was purified by prep-HPLC to give the racemic aminobenzoisoxazole product.

Chiral Separation: A solution of racemic aminobenzoisoxazole product in 3-5 mL of methanol was separated by cSFC (Waters SFC Prep 80, Column temperature: 25° C., back pressure: 100 bar, and wavelength: 220 nm). Each set of collected fractions was concentrated at room temperature. The residue was dissolved in 0.2 M hydrochloric acid and lyophilized to give each enantiomer of the aminobenzoisoxazole product.

General Procedure C1: Synthesis of Aminobenzoisoxazoles.

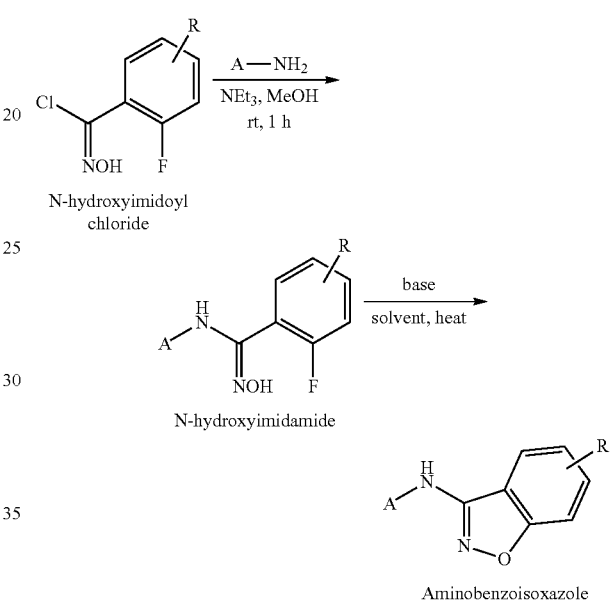

N-hydroxybenzimidoyl chloride intermediate (1 eq.) in methanol (7 mL/mmol imidoyl chloride intermediate) was added dropwise over 30 min. to a solution of amine A-NH$_2$ (1.2-2 eq.) and triethylamine (2 eq) in methanol (5-10 mL/mmol imidoyl chloride intermediate) at room temperature. The resulting mixture was stirred at room temperature for 30 min. On completion, the reaction mixture was concentrated in vacuo and purified by prep-HPLC to give the N-hydroxyimidamide intermediate.

A mixture of N-hydroxyimidamide intermediate and base, in an appropriate solvent, was heated until the reaction was judged complete by LCMS. The mixture was filtered, concentrated in vacuum and purified by prep-HPLC to give the aminobenzoisoxazole product.

General Procedure C2: Synthesis of Aminobenzoisoxazoles.

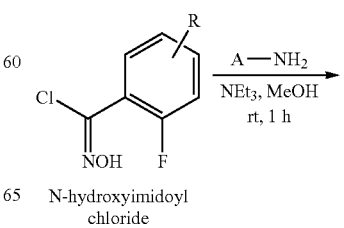

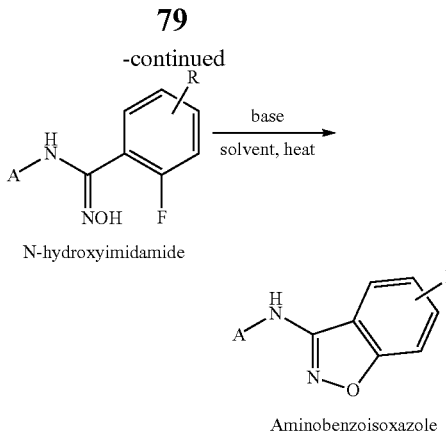

N-hydroxyimidamide

Aminobenzoisoxazole

To a solution of amine A-NH$_2$ (1 eq.) and triethylamine (1 eq.) in methanol (3-5 mL/mmol amine A-NH$_2$) at room temperature was added dropwise a solution of —N-hydroxybenzimidoyl chloride (1 eq) in methanol (3-5 mL/mmol N-hydroxybenzimidoyl chloride). The mixture was stirred for 1 or more hours, then filtered and concentrated in vacuo. The residue was purified by silica gel column chromatography to afford the N-hydroxyimidamide intermediate.

A mixture of N-hydroxyimidamide intermediate and base, in an appropriate solvent, was heated until the reaction was judged complete by LCMS. The mixture was filtered, concentrated in vacuum and purified by silica gel column chromatography to give the aminobenzoisoxazole product.

Example 1

N-(quinuclidin-3-yl)benzo[d]isoxazol-3-amine (rac-1)

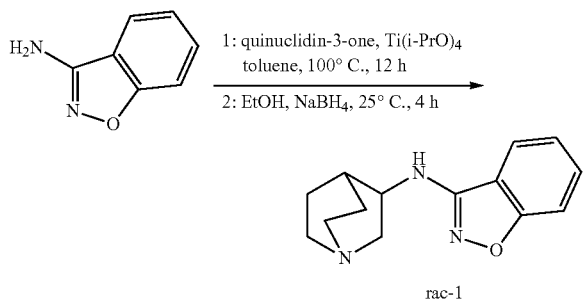

Following general procedure B1, rac-1 was prepared from benzo[d]isoxazol-3-amine (0.40 g, 3.0 mmol). The product was purified by prep-HPLC [Instrument: GX-A; Column: Phenomenex Gemini C18 150×25 mm, particle size: 10 μm; Mobile phase: 44-74% acetonitrile in H$_2$O (add 0.5% NH$_3$.H2O, v/v)] to give rac-1 (70 mg, 9% yield) as a yellow solid. LCMS (B): tR=1.179 min., (ES$^+$) m/z (M+H)$^+$=244.2.

Chiral Separation:

rac-1 (27 mg, 0.11 mmol) was separated by SFC (Column: Chiralpak AY-H-150×4.6 mm, I.D., 5 μm; Mobile phase: ethanol (0.05% DEA) in CO$_2$) according to the chiral separation of general procedure B1 to give:

N-(quinuclidin-3-yl)benzo[d]isoxazol-3-amine-enantiomer1 hydrochloride (compound 1-P1) (11 mg, 41% yield) as a white solid: cSFC analytical (A) tR=5.521 min., purity: 100.00%; LCMS (B): tR=0.115 min., (ES$^+$) m/z (M+H)$^+$=244.1; $^1$H-NMR (CD$_3$OD, 400 MHz): δ 7.88-7.86 (d, J=7.6 Hz, 1H), 7.58-7.54 (m, 1H), 7.42-7.40 (d, J=8.4 Hz, 1H), 7.30-7.26 (t, J=7.6 Hz, 1H), 4.20-4.18 (m, 1H), 3.87-3.84 (m, 1H), 3.43-3.35 (m, 5H), 2.58-2.56 (m, 1H), 2.38-2.35 (m, 1H), 2.16-2.10 (m, 2H), 1.99-1.93 (m, 1H); and N-(quinuclidin-3-yl)benzo[d]isoxazol-3-amine-enantiomer2 hydrochloride (compound 1-P2) (11 mg, 41% yield) as a white solid: cSFC analytical (A) tR=7.926 min., purity: 98.82%; LCMS (J): tR=1.150 min., (ES$^+$) m/z (M+H)$^+$=244.1; $^1$H-NMR (CD$_3$OD, 400 MHz): δ 7.90-7.88 (d, J=8.0 Hz, 1H), 7.61-7.57 (t, J=7.6 Hz, 1H), 7.45-7.43 (d, J=8.4 Hz, 1H), 7.32-7.29 (t, J=8.0 Hz, 1H), 4.20-4.18 (m, 1H), 3.90-3.86 (m, 1H), 3.48-3.33 (m, 5H), 2.58-2.56 (m, 1H), 2.38-2.36 (m, 1H), 2.16-2.10 (m, 2H), 1.97-1.96 (m, 1H).

Example 2

7-chloro-N-(quinuclidin-3-yl)benzo[d]isoxazol-3-amine (rac-2)

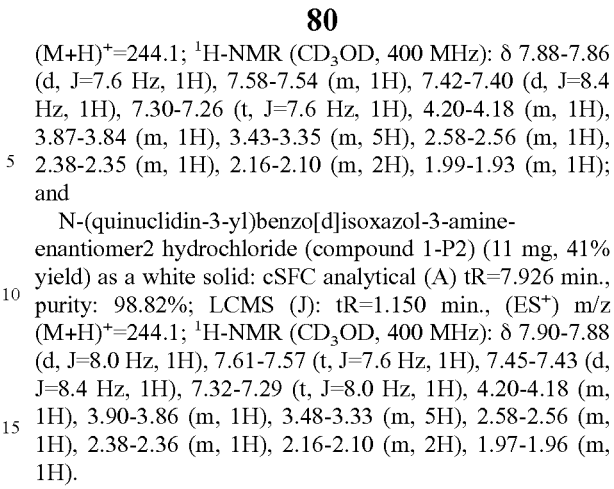

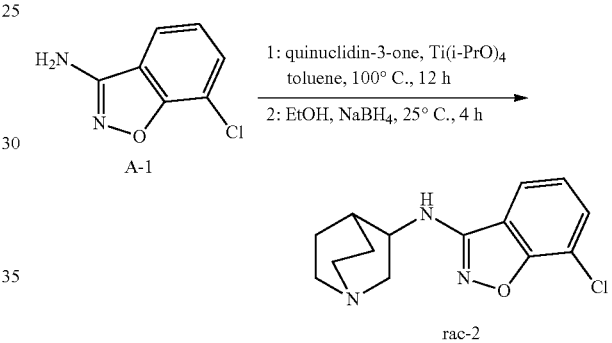

Following general procedure B1, rac-2 was prepared from A-1 (0.30 g, 1.8 mmol). The product was purified by prep-HPLC [Instrument: GX-A; Column: Phenomenex Gemini C18 150×25 mm, particle size: 10 μm; Mobile phase: 40-70% acetonitrile in H$_2$O (add 0.5% NH$_3$.H$_2$O, v/v)] to give rac-2 (170 mg, 34% yield) as an off-white solid. LCMS (B): tR=0.617 min., (ES$^+$) m/z (M+H)$^+$=278.1. $^1$H-NMR (CD$_3$OD, 400 MHz): δ 7.81-7.78 (d, J=8.4 Hz, 1H), 7.55 (m, 1H), 7.34-7.32 (d, J=7.2 Hz, 1H), 4.18-4.15 (m, 1H), 3.90-3.84 (td, J=2.0 Hz, J=13.2 Hz, 1H), 3.44-3.38 (m, 4H), 3.29-3.26 (m, 1H), 2.55-2.53 (m, 1H), 2.35-2.34 (m, 1H), 2.16-2.12 (m, 2H), 2.09-1.97 (m, 1H).

Chiral Separation:

rac-2 (170 mg, 0.6 mmol) was separated by SFC (Column: Chiralpak AY-H-150×4.6 mm, I.D., 5 μm; Mobile phase: ethanol (0.05% DEA) in CO$_2$) according to the chiral separation of general procedure B1 to give:

7-chloro-N-(quinuclidin-3-yl)benzo[d]isoxazol-3-amine-enantiomer1 hydrochloride (compound 2-P1) (40 mg, 47% yield) as a white solid: cSFC analytical (A) tR=6.113 min., purity: 100%; LCMS (B): tR=0.633 min., (ES$^+$) m/z (M+H)$^+$=278.1; $^1$H-NMR (CD$_3$OD, 400 MHz): δ 7.80-7.78 (d, J=8.0 Hz, 1H), 7.61-7.59 (d, J=7.6 Hz, 1H), 7.69-7.67 (t, J=8.0 Hz, 1H), 4.19-4.17 (m, 1H), 3.89-3.83 (m, 1H), 3.44-3.35 (m, 4H), 3.28-3.27 (m, 1H), 2.56-2.54 (m, 1H), 2.34-2.33 (m, 2H), 2.14-2.10 (m, 1H), 2.08-1.96 (m, 1H); and 7-chloro-N-(quinuclidin-3-yl)benzo[d]isoxazol-3-amine-enantiomer2 hydrochloride (compound 2-P2) (35 mg, 41% yield) as a white solid: cSFC analytical (A) tR=7.304 min., purity: 100.00%; LCMS (B): tR=0.636 min., (ES$^+$) m/z (M+H)$^+$=278.1; $^1$H-NMR (CD$_3$OD, 400 MHz): δ 7.81-7.79 (d, J=8.0 Hz, 1H), 7.61-7.59 (d, J=7.2 Hz, 1H), 7.69-7.67 (t, J=8.0 Hz, 1H), 4.19-4.17 (m, 1H), 3.89-3.83 (m, 1H), 3.45-3.35 (m, 4H), 3.29-3.28 (m, 1H), 2.55-2.53 (m, 1H), 2.34-2.33 (m, 2H), 2.14-2.11 (m, 1H), 1.99-1.96 (m, 1H).

Example 3

Preparation of 6-chloro-N-(quinuclidin-3-yl)benzo[d]isoxazol-3-amine (rac-3)

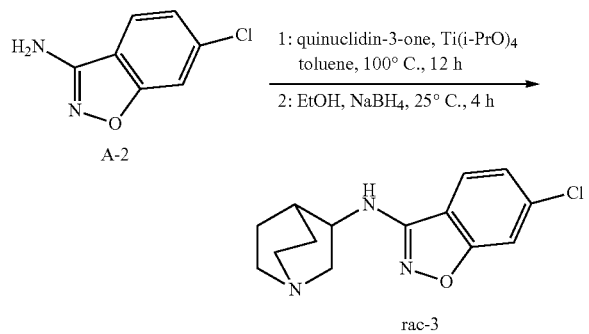

Following general procedure B1, rac-3 was prepared from A-2 (0.30 g, 1.8 mmol). The product was purified by prep-HPLC [Instrument: PREP-A; Column: Phenomenex Gemini C18 150×21.2 mm, particle size: 5 μm; Mobile phase: 30-55% acetonitrile in H$_2$O (add 0.05% NH$_3$.H$_2$O, v/v)] to give rac-3 (210 mg, 43% yield) as an off-white solid. LCMS (B): tR=0.631 min., (ES$^+$) m/z (M+H)$^+$=278.1. $^1$H-NMR (CD$_3$OD, 400 MHz): δ 7.79-7.77 (d, J=8.0 Hz, 1H), 7.63-7.61 (d, J=7.6 Hz 1H), 7.32-7.28 (m, 1H), 4.21-4.18 (m, 1H), 3.92-3.88 (m, 1H), 3.45-3.37 (m, 4H), 3.33-3.30 (m, 1H), 2.58-2.55 (m, 1H), 2.36-2.34 (m, 1H), 2.16-2.12 (m, 2H), 2.10-1.98 (m, 1H);

Chiral Separation:

rac-3 (170 mg, 0.6 mmol) was separated by SFC (Column: Chiralpak AY-H-150×4.6 mm, I.D., 5 μm; Mobile phase: ethanol (0.05% DEA) in CO$_2$) according to the chiral separation of general procedure B1 to give:

6-chloro-N-(quinuclidin-3-yl)benzo[d]isoxazol-3-amine-enantiomer1 hydrochloride (compound 3-P1) (50 mg, 59% yield) as a white solid: cSFC analytical (A) tR=5.617 min., purity: 99.33%; LCMS (B): tR=0.683 min., (ES$^+$) m/z (M+H)$^+$=278.1; $^1$H-NMR (CD$_3$OD, 400 MHz): δ 7.85-7.83 (d, J=8.8 Hz, 1H), 7.52-7.51 (d, J=1.6 Hz, 1H), 7.32-7.29 (dd, J=1.6 Hz, J=8.8 Hz, 1H), 4.20-4.18 (m, 1H), 3.87-3.84 (m, 1H), 3.43-3.35 (m, 5H), 2.58-2.56 (m, 1H), 2.38-2.35 (m, 1H), 2.16-2.10 (m, 2H), 1.99-1.93 (m, 1H); and 6-chloro-N-(quinuclidin-3-yl)benzo[d]isoxazol-3-amine-enantiomer2 hydrochloride (compound 3-P2) (32 mg, 38% yield) as a white solid: cSFC analytical (A) tR=8.069 min., purity: 100.00%; LCMS (B): tR=0.681 min., (ES$^+$) m/z (M+H)$^+$=278.1; $^1$H-NMR (CD$_3$OD, 400 MHz): δ 7.85-7.83 (d, J=8.4 Hz, 1H), 7.54-7.53 (d, J=1.6 Hz, 1H), 7.34-7.31 (dd, J=1.6 Hz, J=8.4 Hz, 1H), 4.18-4.16 (m, 1H), 3.90-3.83 (m, 1H), 3.36-3.33 (m, 4H), 3.46-3.37 (m, 1H), 2.56-2.54 (m, 1H), 2.36 (m, 1H), 2.15-2.11 (m, 2H), 1.98-1.97 (m, 1H).

Preparation of (R)-6-chloro-N-(quinuclidin-3-yl)benzo[d]isoxazol-3-amine ((R)-3)

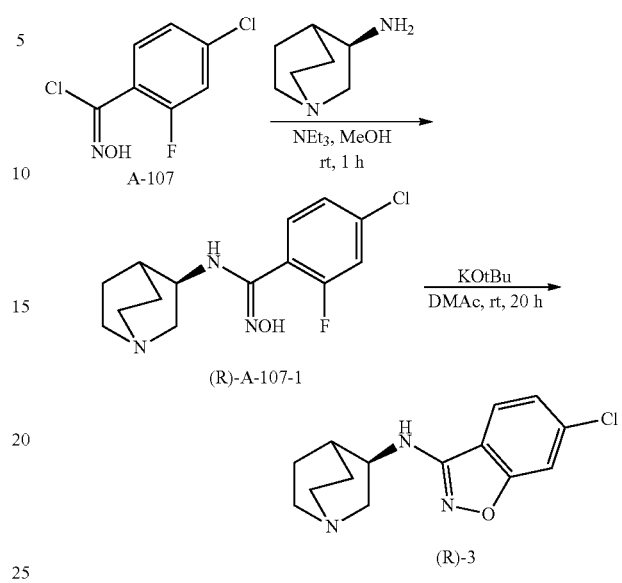

Following general procedure C2, compound (R)-3 was prepared from compound A-107:

Compound (R)-A-107-1 (144 mg, 61% yield) was prepared as a white solid from A-107 (165 mg, 0.8 mmol) and (R)-quinuclidin-3-amine (100 mg, 0.8 mmol) using 5 mL of methanol and a reaction time of 1 hour. The product was purified by silica gel column chromatography [chloroform:methanol=1:0 to 17:3]. LCMS (1): tR=2.965 min., (ES$^+$) m/z (M+H)$^+$=298.1.

To a solution of compound (R)-A-107-1 (101 mg, 0.3 mmol) in N,N-dimethylacetamide (5 mL) was added potassium tertbutoxide (57 mg, 0.5 mmol). The mixture was stirred at room temperature for 20 hours. The solution was put on an SCX column and eluted with methanol. The product was eluted from the column using 3.5 M ammonia in methanol, concentrated and purified by silica gel column chromatography [chloroform: 7M NH$_3$ in methanol=1/0 to 9/1]. The resulting product was lyophilized to afford:

Compound (R)-3 (23 mg, 24% yield) as a white solid: cHPLC analytical [cHPLC analytical conditions: Column: Chiralcel OD-H, 250×4.6 mm, particle size: 5 μm; Flow: 1.0 mL/min; Column temp: 25° C.; Mobile phase: 0.1% diethylamine in Heptane/Ethanol=8/2; detection: DAD (220-320 nm)] tR=4.505 min., purity: 100%; LCMS (1): tR=3.132 min., (ES+) m/z (M+H)+=278.0; 1H NMR (400 MHz, CDCl$_3$), δ 7.48-7.40 (m, 2H), 7.24-7.19 (m, 1H), 4.28 (d, J=4.6 Hz, 1H), 3.90-3.81 (m, 1H), 3.55-3.45 (m, 1H), 3.01-2.78 (m, 4H), 2.70-2.60 (m, 1H), 2.28-2.21 (m, 1H), 1.88-1.63 (m, 3H), 1.58-1.38 (m, 1H).

Example 4

5-chloro-N-(quinuclidin-3-yl)benzo[d]isoxazol-3-amine (rac-4)

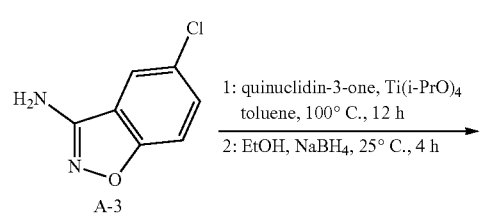

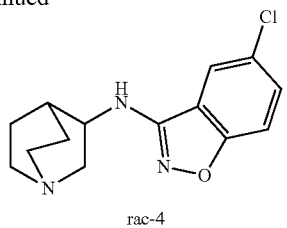

Following general procedure B1, rac-4 was prepared from A-3 (0.20 g, 1.2 mmol). The product was purified by prep-HPLC [Instrument: GX-A; Column: Phenomenex Gemini C18 150×25 mm, particle size: 10 μm; Mobile phase: 44-74% acetonitrile in $H_2O$ (add 0.5% $NH_3.H_2O$, v/v)] to give rac-4 (45 mg, 14% yield) as a white solid. LCMS (J): tR=1.346 min., (ES$^+$) m/z (M+H)$^+$=278.1.

Chiral Separation:

rac-4 (45 mg, 0.16 mmol) was separated by SFC (Column: Chiralpak AY-H-150×4.6 mm, I.D., 5 μm; Mobile phase: ethanol (0.05% DEA) in $CO_2$) according to the chiral separation of general procedure B1 to give:

5-chloro-N-(quinuclidin-3-yl)benzo[d]isoxazol-3-amine-enantiomer1 hydrochloride (compound 4-P1) (13 mg, 29% yield) as a white solid: cSFC analytical (D) tR=5.053 min., purity: 100%; LCMS (B): tR=0.615 min., (ES$^+$) m/z (M+H)$^+$=278.1; $^1$H-NMR (CD$_3$OD, 400 MHz): δ 7.94 (s, 1H), 7.56-7.50 (m, 1H), 7.44-7.38 (m, 1H), 4.19-4.17 (m, 1H), 3.89-3.83 (m, 1H), 3.49-3.36 (m, 5H), 2.56-2.55 (m, 1H), 2.36-2.36 (m, 1H), 2.13-2.12 (m, 2H), 1.99-1.96 (m, 1H); and 5-chloro-N-(quinuclidin-3-yl)benzo[d]isoxazol-3-amine-enantiomer2 hydrochloride (compound 4-P2) (10 mg, 22% yield) as a white solid: cSFC analytical (D) tR=6.445 min., purity: 98.3%; LCMS (B): tR=0.616 min., (ES$^+$) m/z (M+H)$^+$=2278.1; $^1$H-NMR (CD$_3$OD, 400 MHz): δ 7.92-7.92 (d, J=1.6 Hz, 1H), 7.57-7.55 (dd, J=8.8 Hz, J=1.6 Hz, 1H), 7.45-7.43 (d, J=8.8 Hz, 1H), 4.19-4.17 (m, 1H), 3.89-3.83 (m, 1H), 3.51-3.36 (m, 5H), 2.56-2.55 (m, 1H), 2.36-2.33 (m, 1H), 2.15-2.11 (m, 2H), 2.10-1.97 (m, 1H).

Example 5

6-methyl-N-(quinuclidin-3-yl)benzo[d]isoxazol-3-amine (rac-5)

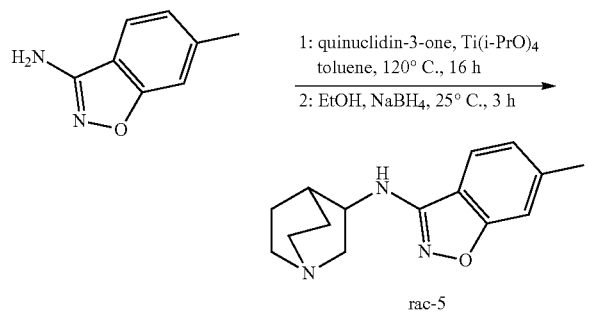

Following general procedure B1, rac-5 was prepared from 6-methylbenzo[d]isoxazol-3-amine (0.50 g, 3.4 mmol) using 4 equivalents sodium borohydride and a reaction time of 16 hours for the first step. The product was purified by prep-HPLC [Instrument: GX-A; Column: Phenomenex Gemini C18 150×25 mm, particle size: 10 μm; Mobile phase: 44-74% acetonitrile in $H_2O$ (add 0.5% $NH_3.H_2O$, v/v)] to give rac-5 (0.70 g, 14% yield) as a white solid. LCMS (G): (ES$^+$) m/z (M+H)$^+$=258.0, tR=2.749 min.

Chiral Separation:

rac-5 (0.10 g, 0.46 mmol) was separated by SFC (Column: Chiralpak AY-H-150×4.6 mm, I.D., 5 μm; Mobile phase: ethanol (0.05% DEA) in $CO_2$) according to the chiral separation of general procedure B1 to give:

6-methyl-N-(quinuclidin-3-yl)benzo[d]isoxazol-3-amine-enantiomer1 hydrochloride (compound 5-P1) (40 mg, 40% yield) as a white solid: cSFC analytical (G) tR=2.61 min., purity: 96.98%; LCMS (J): tR=1.21 min., (ES$^+$) m/z (M+H)$^+$=258; $^1$H-NMR (CD$_3$OD, 400 MHz): δ 7.72 (d, J=8.4 Hz, 1H), 7.24 (s, 1H), 7.14 (d, J=8.4 Hz, 1H), 4.17-4.15 (m, 1H), 3.88-3.82 (m, 1H), 3.48-3.27 (m, 5H), 2.56-2.53 (m, 1H), 2.50 (m, 3H), 2.37-2.34 (m, 1H), 2.15-2.09 (m, 2H), 1.98-1.92 (m, 1H); and 6-methyl-N-(quinuclidin-3-yl)benzo[d]isoxazol-3-amine-enantiomer2 hydrochloride (compound 5-P2) (45 mg, 45% yield) as a white solid: cSFC analytical (G) tR=3.05 min., purity: 96.94%; LCMS (J): tR=1.22 min., (ES$^+$) m/z (M+H)$^+$=258; $^1$H-NMR (CD$_3$OD, 400 MHz): δ 7.71 (d, J=8.4 Hz, 1H), 7.25 (s, 1H), 7.14 (d, J=8.4 Hz, 1H), 4.17-4.16 (m, 1H), 3.87-3.82 (m, 1H), 3.48-3.27 (m, 5H), 2.56-2.53 (m, 1H), 2.50 (m, 3H), 2.37-2.34 (m, 1H), 2.15-2.09 (m, 2H), 1.98-1.93 (m, 1H).

Example 6

6-cyclopropyl-N-(quinuclidin-3-yl)benzo[d]isoxazol-3-amine (rac-6)

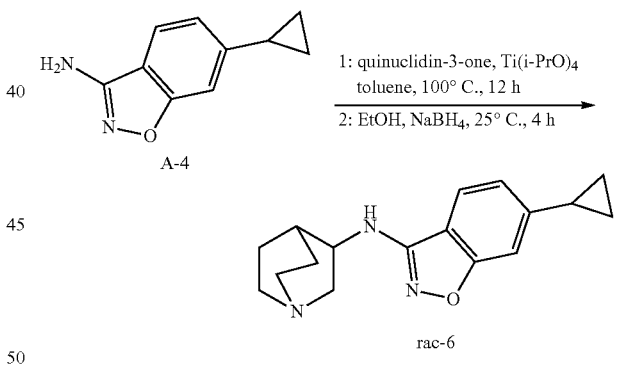

Following general procedure B1, rac-6 was prepared from A-4 (0.20 g, 1.1 mmol) using 10 eq. of titanium(IV) isopropoxide. The product was purified by prep-HPLC [Instrument: GX-I; Column: Xtimate C18 150×25 mm, particle size: 5 μm; Mobile phase: 25-55% acetonitrile in $H_2O$ (add 0.1% TFA, v/v)] to give rac-6 (150 mg, 40% yield) as a white solid. LCMS (J): tR=1.425 min., (ES$^+$) m/z (M+H)$^+$=278.1. $^1$H-NMR (CD$_3$OD, 400 MHz): δ 7.70-7.68 (d, J=8.4 Hz, 1H), 7.06 (m, 1H), 7.00-6.98 (d, J=8.4 Hz, 1H), 3.79-3.77 (m, 1H), 3.39-3.35 (m, 1H), 2.98-2.95 (m, 1H), 2.88-2.81 (m, 3H), 2.77-2.72 (m, 1H), 2.21-2.19 (m, 1H), 2.07-2.03 (m, 2H), 1.97-1.95 (m, 1H), 1.78-1.76 (m, 1H), 1.55-1.49 (m, 1H), 1.07-1.05 (m, 2H), 0.79-0.77 (m, 2H);

Chiral Separation:

rac-6 (60 mg, 0.2 mmol) was separated by SFC (Column: Chiralpak AD-3-100×4.6 mm, I.D., 3 μm; Mobile phase:

ethanol (0.05% DEA) in $CO_2$) according to the chiral separation of general procedure B1 to give:

6-cyclopropyl-N-(quinuclidin-3-yl)benzo[d]isoxazol-3-amine-enantiomer1 hydrochloride (compound 6-P1) (21 mg, 67% yield) as a white solid: cSFC analytical (A) tR=1.010 min., purity: 98.24%; LCMS (B): tR=0.649 min., (ES$^+$) m/z (M+H)$^+$=284.2; $^1$H-NMR (CD$_3$OD, 400 MHz): δ 7.73-7.70 (m, 1H), 7.09 (s, 1H), 7.02-7.00 (d, J=8.0 Hz, 1H), 4.15-4.12 (m, 1H), 3.86-3.83 (m, 1H), 3.46-3.33 (m, 5H), 2.53-2.52 (m, 1H), 2.29 (m, 1H), 2.10-2.06 (m, 3H), 2.04 (m, 1H), 1.07-1.05 (m, 2H), 0.79-0.78 (m, 2H); and 6-cyclopropyl-N-(quinuclidin-3-yl)benzo[d]isoxazol-3-amine-enantiomer2 hydrochloride (compound 6-P2) (22 mg, 73% yield) as a white solid: cSFC analytical (A) tR=1.633 min., purity: 95.20%; LCMS (B): tR=0.652 min., (ES$^+$) m/z (M+H)$^+$=284.2; $^1$H-NMR (CD$_3$OD, 400 MHz): δ 7.73-7.71 (d, J=8.4 Hz, 1H), 7.09 (s, 1H), 7.02-7.00 (d, J=8.0 Hz, 1H), 4.15-4.12 (m, 1H), 3.85-3.80 (m, 1H), 3.46-3.33 (m, 5H), 2.53-2.52 (m, 1H), 2.34-2.33 (m, 1H), 2.10-2.06 (m, 3H), 1.93 (m, 1H), 1.08-1.04 (m, 2H), 0.80-0.77 (m, 2H).

Example 7

6-methoxy-N-(quinuclidin-3-yl)benzo[d]isoxazol-3-amine (rac-7)

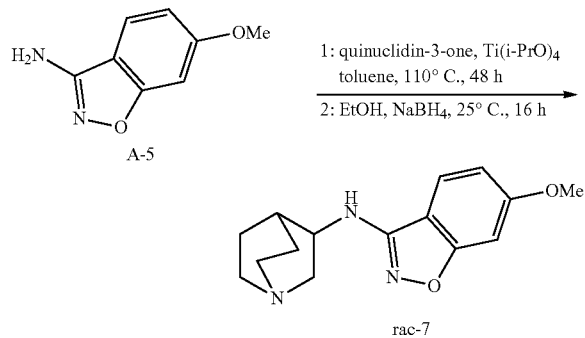

Following general procedure B1, rac-7 was prepared from compound A-5 (0.50 g, 3.1 mmol). The first step was run at 110° C. for 48 hours, and the second step at 25° C. for 16 hours. The product was purified by prep-HPLC [Instrument: GX-B; Column: YMC-pack ODS-AQ 150×30 mm, particle size: 5 μm; Mobile phase: 10-40% acetonitrile in H$_2$O (add 0.1% TFA, v/v)] to give rac-7 (0.60 g, 70% yield) as a white solid. LCMS (J): tR=1.135 min., (ES$^+$) m/z (M+H)$^+$=274.1.

Chiral Separation:

rac-7 (0.30 g, 1.1 mmol) was separated by SFC (Column: Chiralpak AD-3 100×4.6 mm, I.D., 10 μm; Mobile phase: 40% ethanol (0.05% DEA) in $CO_2$) according to the chiral separation of general procedure B1 to give:

6-methoxy-N-(quinuclidin-3-yl)benzo[d]isoxazol-3-amine-enantiomer1 hydrochloride (compound 7-P1) (40 mg, 13% yield) as a white solid: cSFC analytical (B) tR=2.479 min., purity: 98.09%; LCMS (Q): tR=2.777 min., (ES$^+$) m/z (M+H)$^+$=274.1; $^1$H-NMR (CD$_3$OD, 400 MHz): δ 7.73-7.71 (d, J=8.4 Hz, 1H), 6.97-6.96 (d, J=1.6 Hz, 1H), 6.91-6.88 (dd, J$_1$=8.8 Hz, J$_2$=2.0 Hz, 1H), 4.16-4.12 (m, 1H), 3.89 (s, 3H), 3.85-3.82 (m, 1H), 3.51-3.37 (m, 4H), 3.33-3.30 (m, 1H), 2.54-2.52 (m, 1H), 2.36-2.35 (m, 1H), 2.15-2.09 (m, 2H), 1.96-1.92 (m, 1H); and 6-methoxy-N-(quinuclidin-3-yl)benzo[d]isoxazol-3-amine-enantiomer2 hydrochloride (compound 7-P2) (40 mg, 13% yield) as a white solid: cSFC analytical (B) tR=2.771 min., purity: 97.76%; LCMS (Q): tR=2.770 min., (ES$^+$) m/z (M+H)$^+$=2740.1; $^1$H-NMR (CD$_3$OD, 400 MHz): δ 7.75-7.73 (d, J=8.8 Hz, 1H), 6.97-6.96 (d, J=2.0 Hz, 1H), 6.91-6.88 (dd, J$_1$=8.8 Hz, J$_2$=2.0 Hz, 1H), 4.15-4.13 (m, 1H), 3.89 (s, 3H), 3.85-3.82 (m, 1H), 3.52-3.37 (m, 4H), 3.33-3.30 (m, 1H), 2.55-2.52 (m, 1H), 2.39-2.35 (m, 1H), 2.15-2.08 (m, 2H), 1.98-1.92 (m, 1H).

Example 8

N-(quinuclidin-3-yl)-6-(trifluoromethyl)benzo[d]isoxazol-3-amine (rac-8)

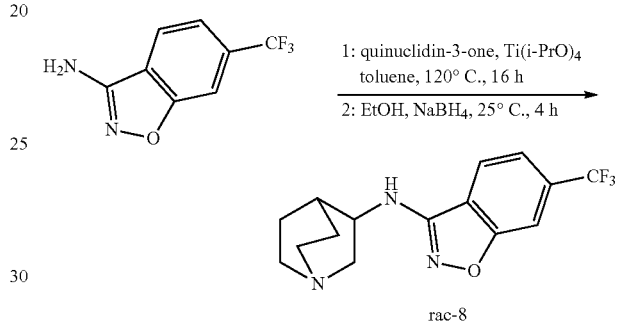

Following general procedure B1, rac-8 was prepared from 6-(trifluoromethyl)benzo[d]isoxazol-3-amine (0.40 g, 2.0 mmol) using 4 equivalents of sodium borohydride and a reaction time of 16 hours for the first step. The product was purified by prep-HPLC [Instrument: GX-A; Column: Phenomenex Gemini C18 150×25 mm, particle size: 10 μm; Mobile phase: 28-58% acetonitrile in H$_2$O (add 0.5% NH$_3$.H$_2$O, v/v)] to give rac-8 (0.15 g, 24% yield) as a white solid. LCMS (G): (ES$^+$) m/z (M+H)$^+$=312.1, tR=2.84 min.

Chiral Separation:

rac-8 (0.12 g, 0.46 mmol) was separated by SFC (Column: Chiralpak AY-H-150×4.6 mm, I.D., 5 μm; Mobile phase: ethanol (0.05% DEA) in $CO_2$) according to the chiral separation of general procedure B1 to give:

N-(quinuclidin-3-yl)-6-(trifluoromethyl)benzo[d]isoxazol-3-amine-enantiomer1 hydrochloride (compound 8-P1) (35 mg, 35% yield) as a white solid: cSFC analytical (G) tR=2.66 min., purity: 99.42%; LCMS (J): tR=1.42 min., (ES$^+$) m/z (M+H)$^+$=312.1; $^1$H-NMR (CD$_3$OD, 400 MHz): δ 8.09-8.04 (m, 1H), 7.84 (s, 1H), 7.61 (d, J=8 Hz, 1H), 4.24-4.20 (m, 1H), 3.92-3.86 (m, 1H), 3.47-3.37 (m, 5H), 2.58-2.57 (m, 1H), 2.38-2.37 (m, 1H), 2.20-2.11 (m, 2H), 2.01-1.98 (m, 1H); and N-(quinuclidin-3-yl)-6-(trifluoromethyl)benzo[d]isoxazol-3-amine-enantiomer2 hydrochloride (compound 8-P2) (45 mg, 45% yield) as a white solid: cSFC analytical (G) tR=3.70 min., purity: 99.39%; LCMS (J): tR=1.42 min., (ES$^+$) m/z (M+H)$^+$=312.1; $^1$H-NMR (CD$_3$OD, 400 MHz): δ8.09-8.05 (m, 1H), 7.83 (s, 1H), 7.61 (d, J=8 Hz, 1H), 4.23-4.20 (m, 1H), 3.91-3.86 (m, 1H), 3.47-3.37 (m, 5H), 2.59-2.56 (m, 1H), 2.38-2.34 (m, 1H), 2.19-2.11 (m, 2H), 2.01-1.95 (m, 1H).

Example 9

6,7-dichloro-N-(quinuclidin-3-yl)benzo[d]isoxazol-3-amine (rac-9)

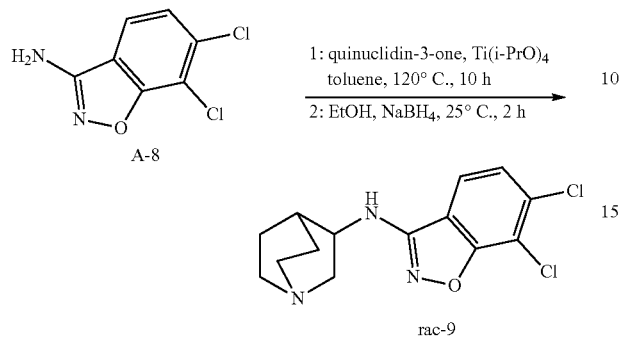

Following general procedure B1, rac-9 was prepared from A-8 (0.26 g, 1.3 mmol) using 3 equivalents of sodium borohydride and a reaction time of 10 hours for the first step and 2 hours for the second. The product was purified by prep-HPLC [Instrument: GX-A; Column: Phenomenex Gemini C18 150×25 mm, particle size: 10 μm; Mobile phase: 44-74% acetonitrile in H$_2$O (add 0.5% NH$_3$.H$_2$O, v/v)] to give rac-9 (0.10 g, 40% yield) as a white solid. LCMS (B): (ES$^+$) m/z (M+H)$^+$=311.9. tR=0.71 min.

Chiral Separation:

rac-9 (0.2 g, 0.49 mmol) was separated by SFC (Column: Chiralpak AY-H-150×4.6 mm, I.D., 5 μm; Mobile phase: ethanol (0.05% DEA) in CO$_2$) according to the chiral separation of general procedure B1 to give:

6,7-dichloro-N-(quinuclidin-3-yl)benzo[d]isoxazol-3-amine-enantiomer1 hydrochloride (compound 9-P1) (50 mg, 50% yield) as a white solid: cSFC analytical (G) tR=2.70 min., purity: 98.53%; LCMS (B): tR=0.68 min., (ES$^+$) m/z (M+H)$^+$=312.1; $^1$H-NMR (CD$_3$OD, 400 MHz): δ 7.80 (d, J=8.4 Hz, 1H), 7.47 (d, J=8.4 Hz, 1H), 4.19-4.17 (m, 1H), 3.90-3.84 (m, 1H), 3.51-3.37 (m, 5H), 2.57-2.54 (m, 1H), 2.38-2.34 (m, 1H), 2.16-2.09 (m, 2H), 1.99-1.94 (m, 1H); and 6,7-dichloro-N-(quinuclidin-3-yl)benzo[d]isoxazol-3-amine-enantiomer2 hydrochloride (compound 9-P2) (40 mg, 40% yield) as a white solid: cSFC analytical (G) tR=3.44 min., purity: 99.72%; LCMS (B): tR=0.69 min., (ES$^+$) m/z (M+H)$^+$=312.1; $^1$H-NMR (CD$_3$OD, 400 MHz): δ 7.81 (d, J=8.4 Hz, 1H), 7.45 (d, J=8 Hz, 1H), 4.19-4.17 (m, 1H), 3.90-3.84 (m, 1H), 3.50-3.45 (m, 5H), 2.57-2.54 (m, 1H), 2.39-2.35 (m, 1H), 2.16-2.09 (m, 2H), 2.00-1.97 (m, 1H).

Example 10

(R)-4-chloro-N-(quinuclidin-3-yl)benzo[d]isoxazol-3-amine hydrochloride ((R)-10)

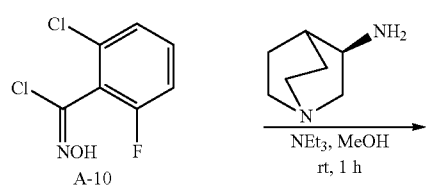

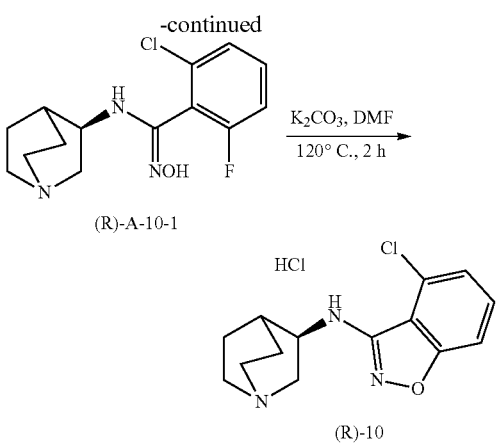

Following general procedure C1, compound (R)-10 was prepared from compound A-10:

Compound (R)-A-10-1 (0.1 g, white solid, 42% yield over two steps) was prepared from compound A-10 (0.3 g, 1.46 mmol) and (R)-quinuclidin-3-amine (0.25 g, 2.0 mmol). The product was purified by prep-HPLC [Instrument: GX-A; Column: Phenomenex Gemini C18 250×50 mm, particle size: 10 μm; Mobile phase: 22-52% acetonitrile in H$_2$O (add 0.5% NH$_3$.H$_2$O, v/v)]. LCMS (J): (ES$^+$) m/z (M+H)$^+$=298, tR=0.866 min.

A mixture of compound (R)-A-10-1 (100 mg, 0.34 mmol) and potassium carbonate (186 mg, 1.4 mmol) in N,N-dimethylformamide (3.0 mL) was stirred at 120° C. for 2 hour. On completion, the reaction mixture was filtered, concentrated in vacuo and purified by prep-HPLC [Instrument: GX-C; Column: Phenomenex Gemini C18 250×50 mm, particle size: 10 μm; Mobile phase: 38-68% acetonitrile in H$_2$O (add 0.05% ammonia-ACN, v/v)]. The resulting solid was dissolved in 0.2 M hydrochloric acid and again lyophilized to give:

Compound (R)-10 (30 mg, 29% yield) as a white solid: cSFC analytical tR=2.97 min., purity: 96.01%; LCMS (EE): tR=2.55 min., 278.1 m/z (M+1); 1H-NMR (CD$_3$OD, 400 MHz): δ 7.54-7.53 (t, J=8 Hz, 1H), 7.43 (d, J=8.4 Hz, 1H), 7.30 (d, J=8.4 Hz, 1H), 4.23-4.20 (m, 1H), 3.89-3.82 (m, 1H), 3.51-3.37 (m, 5H), 2.63-2.61 (m, 1H), 2.36-2.31 (m, 1H), 2.16-2.10 (m, 2H), 2.00-1.99 (m, 1H).

Example 11

(R)-6-fluoro-N-(quinuclidin-3-yl)benzo[d]isoxazol-3-amine hydochloride ((R)-11)

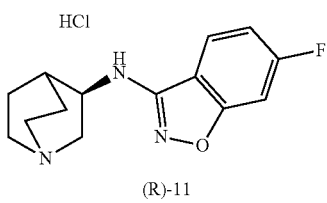

(R)-11

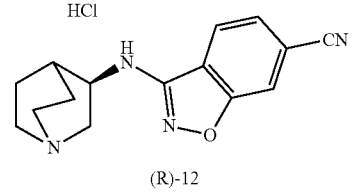

(R)-12

Following general procedure C1, compound (R)-11 was prepared from compound A-12:

Compound (R)-A-12-1 (0.10 g, white solid, 31% yield over two steps) was prepared from compound A-12 (0.20 g, 1.0 mmol) and (R)-quinuclidin-3-amine (0.25 g, 2.0 mmol), using N,N-dimethylformamide as the solvent instead of methanol. The product was purified by prep-HPLC [Instrument: GX-A; Column: Phenomenex Gemini C18 250×50 mm, particle size: 10 μm; Mobile phase: 19-49% acetonitrile in H₂O (add 0.5% NH₃.H₂O, v/v)]. LCMS (B): (ES⁺) m/z (M+H)⁺=282.1, tR=2.387 min.

A mixture of compound (R)-A-12-1 (0.10 g, 0.36 mmol) and potassium tert-butoxide (60 mg, 0.53 mmol) in N,N-dimethylacetamide (5 mL) was stirred at room temperature for 1 hour. On completion, the reaction mixture was filtered, concentrated in vacuo and purified by prep-HPLC [Instrument: GX-B; Column: YMC-Actus Pro C18 150×30 mm, particle size: 5 μm; Mobile phase: 12-42% acetonitrile in H₂O (add 0.1% TFA, v/v)]. The resulting solid was dissolved in 0.2 M hydrochloric acid and again lyophilized to give:

Compound (R)-11 (10 mg, 10% yield) as a yellow solid: cSFC analytical (A) tR=4.76 min., purity: 100%; LCMS (J): tR=1.259 min., (ES⁺) m/z (M+H)⁺=262.2; ¹H-NMR (CD₃OD, 400 MHz): δ 7.88-7.84 (m, 1H), 7.25-7.23 (d, J=8.8 Hz, 1H), 7.13-7.09 (t, J=8.8 Hz, 1H), 4.16-4.15 (m, 1H), 3.89-3.83 (t, J=11.6 Hz, 1H), 3.42-3.38 (m, 4H), 3.29 (m, 1H), 2.55-2.54 (m, 1H), 2.36 (m, 1H), 2.13-2.12 (m, 2H), 1.96 (m, 1H).

Example 12

(R)-3-(quinuclidin-3-ylamino)benzo[d]isoxazole-6-carbonitrile hydrochloride ((R)-12)

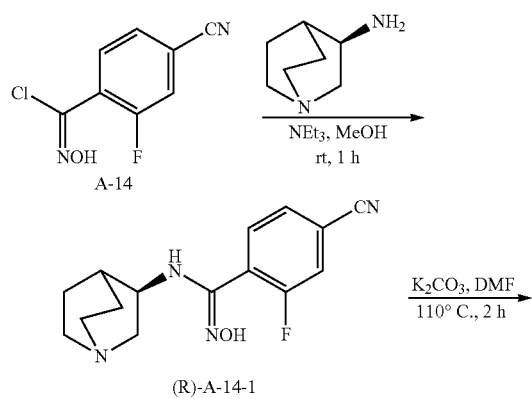

Following general procedure C1, compound (R)-12 was prepared from compound A-14:

Compound (R)-A-14-1 (0.15 g, white solid, 42% yield over two steps) was prepared from compound A-14 (0.30 g, 1.0 mmol) and (R)-quinuclidin-3-amine (0.25 g, 2.0 mmol). The product was purified by prep-HPLC [Instrument: GX-A; Column: Phenomenex Gemini C18 250 50 mm, particle size: 10 μm; Mobile phase: 19-49% acetonitrile in H₂O (add 0.5% NH₃.H₂O, v/v)]. LCMS (B): (ES⁺) m/z (M+H)⁺=289.2, tR=0.928 min.

A mixture of compound (R)-A-14-1 (0.13 g, 0.45 mmol) and potassium carbonate (0.19 g, 1.4 mmol) in N,N-dimethylformamide (3.0 mL) was stirred at 110° C. for 2 hours. On completion, the reaction mixture was filtered, concentrated in vacuo and purified by prep-HPLC [Instrument: GX-B; Column: YMC-Actus Pro C18 150×30 mm, particle size: 5 μm; Mobile phase: 17-74% acetonitrile in H₂O (add 0.5% HCl, v/v)]. The product was lyophilized to give:

Compound (R)-12 (30 mg, 23% yield) as a white solid: cSFC analytical (D) tR=2.15 min., purity: 99.44%; LCMS (EE): tR=2.39 min., 269.1 m/z (M+1); 1H-NMR (CD₃OD, 400 MHz): δ 8.08 (d, J=8 Hz, 1H), 7.94 (s, 1H), 7.64-7.62 (dd, J=8 Hz, J=0.8 Hz, 1H), 4.22-4.20 (m, 1H), 3.91-3.85 (m, 1H), 3.51-3.35 (m, 5H), 2.58-2.56 (m, 1H), 2.37-2.35 (m, 1H), 2.16-2.10 (m, 2H), 1.99-1.97 (m, 1H).

Example 13

Preparation: (R)-6-(methylsulfonyl)-N-(quinuclidin-3-yl)benzo[d]isoxazol-3-amine hydrochloride ((R)-13)

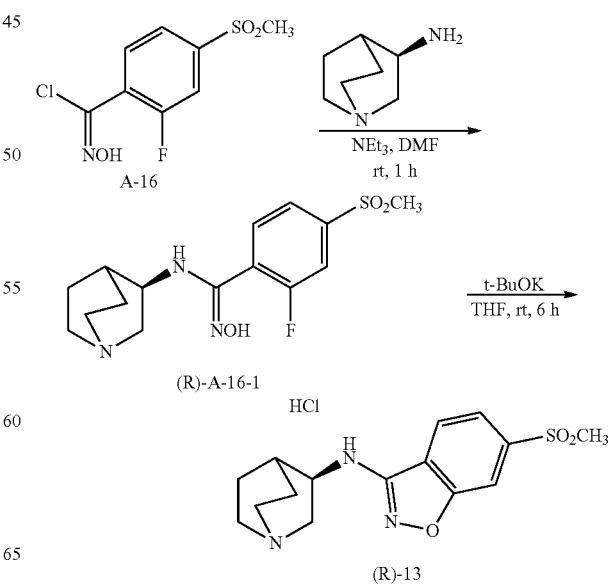

Following general procedure C1, compound (R)-13 was prepared from compound A-16:

Compound (R)-A-16-1 (0.35 g, pale yellow solid, 49% yield over two steps) was prepared from compound A-16 (0.30 g, 1.2 mmol) and (R)-quinuclidin-3-amine (0.18 g, 1.4 mmol), using N,N-dimethylformamide as the solvent instead of methanol. The product was purified by silica gel chromatography [DCM:MeOH=5:1]. LCMS (B): (ES$^+$) m/z (M+H)$^+$=342.1, tR=0.894 min.

A mixture of compound (R)-A-16-1 (0.10 g, 0.29 mmol) and potassium tert-butoxide (36 mg, 0.32 mmol) in tetrahydrofuran (5 mL) was stirred at room temperature for 6 hour. On completion, the reaction mixture was filtered, concentrated in vacuo and purified by prep-HPLC [Instrument: GX-G; Column: Phenomenex Synergi Max-RP C18 250×80 mm, particle size: 10 μm; Mobile phase: 1-31% acetonitrile in H$_2$O (add 0.2% TFA, v/v)]. The product was lyophilized, dissolved in 0.2 N hydrochloric acid and again lyophilized to give:

Compound (R)-13 (15 mg, 14% yield) as a white solid: cSFC analytical (A) tR=6.79 min., purity: 100%; LCMS (W): tR=0.740 min., (ES$^+$) m/z (M+H)$^+$=322.1; $^1$H-NMR (CD$_3$OD, 400 MHz): δ 8.12-8.09 (d, J=8.4 Hz, 1H), 8.07 (s, 1H), 7.88-7.87 (dd, J=1.2 Hz, J=8.4 Hz, 1H), 4.21-4.19 (m, 1H), 3.90-3.85 (m, 1H), 3.45-3.34 (m, 5H), 3.21 (s, 3H), 2.57-2.54 (m, 1H), 2.36-2.35 (m, 1H), 2.14-2.10 (m, 2H), 2.04-1.93 (m, 1H).

Preparation: (S)-6-(methylsulfonyl)-N-(quinuclidin-3-yl)benzo[d]isoxazol-3-amine hydrochloride ((S)-13)

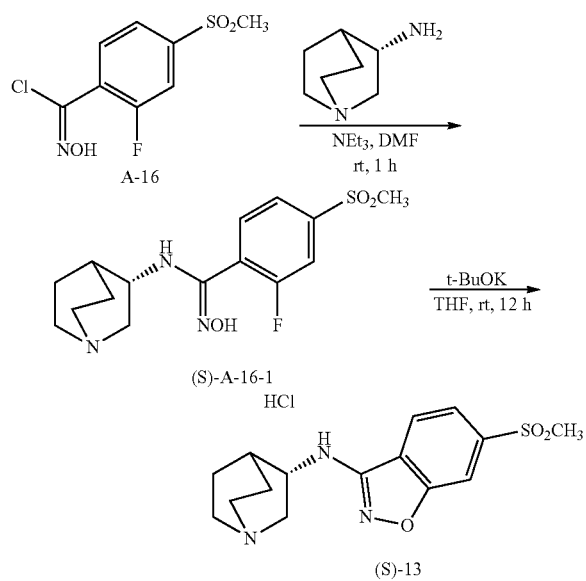

Following general procedure C1, compound (S)-13 was prepared from compound A-16:

Compound (S)-A-16-1 (0.15 g, pale yellow solid, 36% yield over two steps) was prepared from compound A-16 (0.30 g, 1.2 mmol) and (S)-quinuclidin-3-amine (0.18 g, 1.4 mmol), using N, N-dimethylformamide as the solvent instead of methanol. The product was purified by silica gel chromatography [DCM/MeOH=5/1]. LCMS (B): (ES+) m/z (M+H)$^+$=342.1, tR=0.852 min.

A mixture of compound (S)-A-16-1 (0.30 g, 0.88 mmol) and potassium tert-butoxide (0.11 g, 0.97 mmol) in tetrahydrofuran (5 mL) was stirred at room temperature for 12 hours. On completion, the reaction mixture was filtered, concentrated in vacuo and purified by prep-HPLC [Instrument: GX-G; Column: Phenomenex Synergi Max-RP C18 250×80 mm, particle size: 10 μm; Mobile phase: 1-31% acetonitrile in H$_2$O (add 0.2% TFA, v/v)]. The resulting solid was dissolved in 0.2 N hydrochloric acid and again lyophilized to give:

Compound (S)-13 (25 mg, 9% yield) as a white solid: cSFC analytical (A) tR=8.80 min., purity: 100%; LCMS (W): tR=0.708 min., (ES$^+$) m/z (M+H)$^+$=322.1; $^1$H-NMR (CD$_3$OD, 400 MHz): δ 8.11-8.09 (d, J=8.4 Hz, 1H), 8.07 (s, 1H), 7.88-7.86 (d, J=8.4 Hz, 1H), 4.16-4.14 (m, 1H), 3.84-3.78 (m, 1H), 3.35-3.25 (m, 5H), 3.20 (s, 3H), 2.52-2.50 (m, 1H), 2.30-2.29 (m, 1H), 2.10-2.06 (m, 2H), 1.91-1.89 (m, 1H).

Example 14

(R)-6-(tert-butyl)-N-(quinuclidin-3-yl)benzo[d]isoxazol-3-amine hydrochloride ((R)-14)

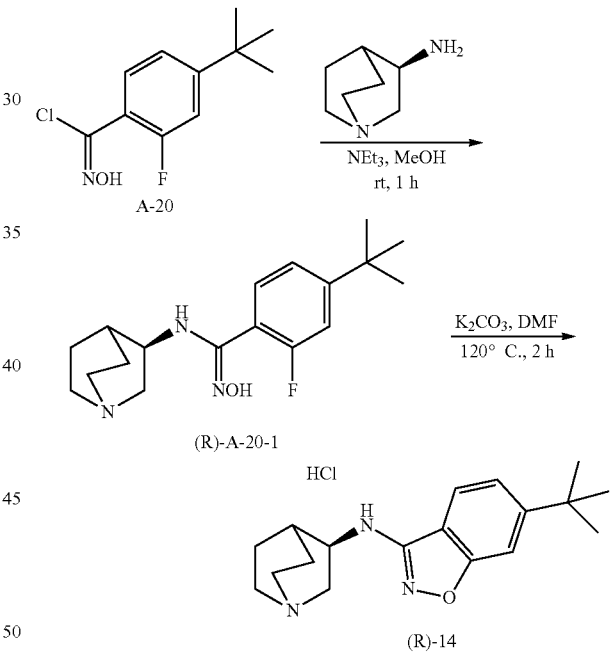

Following general procedure C1, compound (R)-14 was prepared from compound A-20:

Compound (R)-A-20-1 (60 mg, white solid, 14% yield over two steps) was prepared from compound A-20 (0.30 g, 1.3 mmol) and (R)-quinuclidin-3-amine (0.16 g, 1.3 mmol). The product was purified by prep-HPLC [Instrument: GX-C; Column: Phenomenex Synergi C18 250×50 mm, particle size: 10 μm; Mobile phase: 25-55% acetonitrile in H$_2$O (add 0.5% ammonia, v/v)]. LCMS (J): (ES$^+$) m/z (M+H)$^+$=320.2, tR=1.301 min.

A mixture of compound (R)-A-20-1 (50 mg, 0.16 mmol) and potassium carbonate (66 mg, 0.48 mmol) in N,N-dimethylformamide (4.0 mL) was stirred at 120° C. for 2 hours. On completion, the reaction mixture was filtered, concentrated in vacuo and purified by prep-HPLC [Instrument: GX-B; Column: YMC-Actus Pro C18 150×30 mm, particle size: 5 μm; Mobile phase: 17-74% acetonitrile in H$_2$O (add 0.5% HCl, v/v)]. The product was lyophilized to give:

Compound (R)-14 (6.5 mg, 14% yield) as a white solid: cSFC analytical (D) tR=2.62 min., purity: 100%; LCMS (EE): tR=2.99 min., 300.2 m/z (M+1); 1H-NMR (CD$_3$OD, 400 MHz): δ 7.79-7.77 (d, J=8.4 Hz, 1H), 7.44-7.43 (s, 1H), 7.40-7.40 (m, 1H), 4.17-4.15 (m, 1H), 3.89-3.83 (t, J=11.6 Hz, 1H), 3.43-3.33 (m, 5H), 2.55-2.54 (m, 1H), 2.36 (m, 1H), 2.15-2.11 (m, 2H), 1.96 (m, 1H), 1.40-1.36 (m, 9H).

Example 15

Preparation: (R)-5,6-dichloro-N-(quinuclidin-3-yl) benzo[d]isoxazol-3-amine hydrochloride ((R)-15)

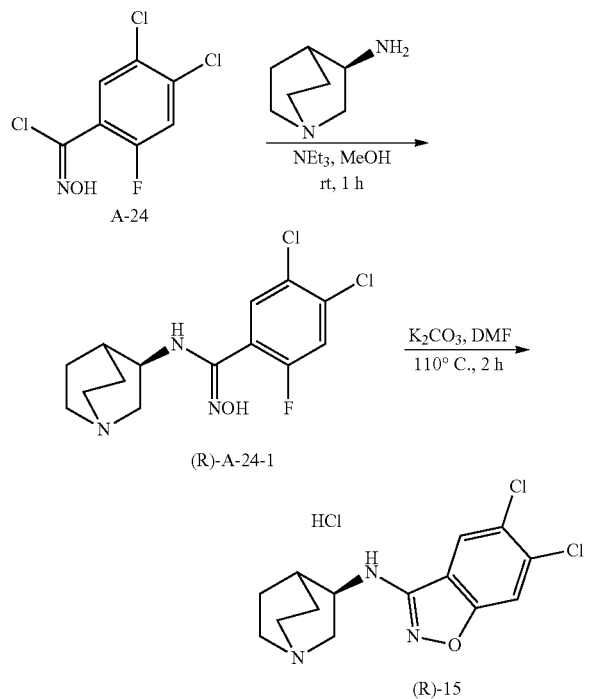

Following general procedure C1, compound (R)-15 was prepared from compound A-24:

Compound (R)-A-24-1 (30 mg, white solid, 22% yield over two steps) was prepared from compound A-24 (0.10 g, 0.41 mmol) and (R)-quinuclidin-3-amine (62 mg, 0.49 mmol). The product was purified by prep-HPLC [Instrument: GX-C; Column: Phenomenex Synergi C18 250×50 mm, particle size: 10 μm; Mobile phase: 25-55% acetonitrile in H$_2$O (add 0.5% ammonia, v/v)]. LCMS (X): (ES$^+$) m/z (M+H)$^+$=332.1, tR=1.178 min.

A mixture of compound (R)-A-24-1 (75 mg, 0.23 mmol) and potassium carbonate (94 mg, 0.68 mmol) in N,N-dimethylformamide (3.0 mL) was stirred at 110° C. for 2 hours. On completion, the reaction mixture was filtered, concentrated in vacuo and purified by prep-HPLC [Instrument: GX-B; Column: YMC-Actus Pro C18 150×30 mm, particle size: 5 μm; Mobile phase: 17-74% acetonitrile in H$_2$O (add 0.5% HCl, v/v)]. The product was lyophilized to give:

Compound (R)-15 (30 mg, 43% yield) as a white solid: cSFC analytical tR=5.47 min., purity: 100%; LCMS (X): tR=0.16 min., 312.0 m/z (M+1); 1H-NMR (CD$_3$OD, 400 MHz): δ 8.09 (s, 1H), 7.73 (s, 1H), 4.18-4.16 (m, 1H), 3.89-3.83 (m, 1H), 3.51-3.31 (m, 5H), 2.55-2.53 (m, 1H), 2.38-2.34 (m, 1H), 2.16-2.09 (m, 2H), 2.08-1.96 (m, 1H).

Preparation: (S)-5,6-dichloro-N-(quinuclidin-3-yl) benzo[d]isoxazol-3-amine hydrochloride ((S)-15)

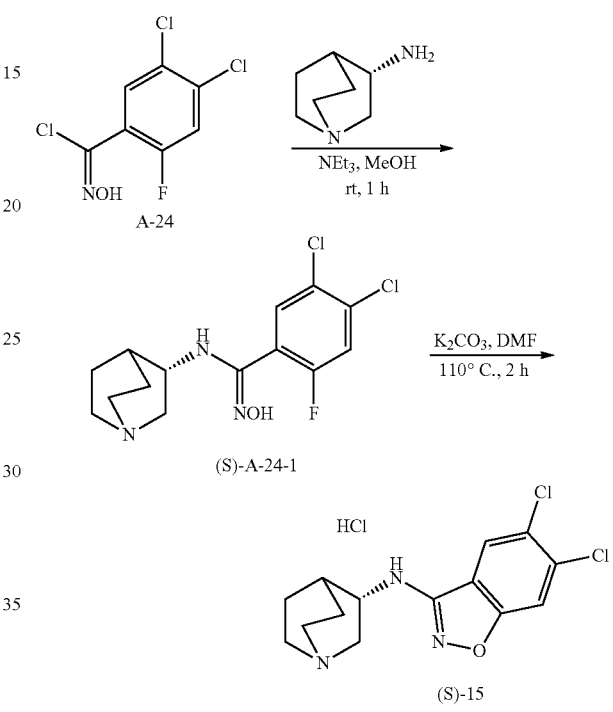

Following general procedure C1, compound (S)-15 was prepared from compound A-24:

Compound (S)-A-24-1 (0.30 g, white solid, 44% yield over two steps) was prepared from compound A-24 (0.50 g, 2.1 mmol) and (S)-quinuclidin-3-amine (0.26 g, 2.1 mmol). The product was purified by prep-HPLC [Instrument: GX-C; Column: Phenomenex Gemini C18 250×50 mm, particle size: 10 μm; Mobile phase: 25-55% acetonitrile in H$_2$O (add 0.5% ammonia, v/v)]. LCMS (J): (ES$^+$) m/z (M+H)$^+$=332.1, tR=1.166 min.

A mixture of compound (S)-A-24-1 (0.20 g, 0.60 mmol) and potassium carbonate (0.25 g, 1.8 mmol) in N,N-dimethylacetamide (8.0 mL) was stirred at 110° C. for 2 hours. On completion, the reaction mixture was filtered, concentrated in vacuo and purified by prep-HPLC [Instrument: GX-A; Column: Phenomenex Synergi C18 150×30 mm, particle size: 4 μm; Mobile phase: 25-55% acetonitrile in H$_2$O (add 0.5% HCl, v/v)]. The product was lyophilized to give:

Compound (S)-15 (0.12 g, 64% yield) as a white solid: cSFC analytical (D) tR=1.977 min., purity: 99.16%; LCMS (B): tR=0.683 min., (ES$^+$) m/z (M+H)$^+$=312.1; 1H-NMR (CD$_3$OD, 400 MHz): δ 8.06 (s, 1H), 7.75 (s, 1H), 4.18-4.15 (m, 1H), 3.89-3.83 (m, 1H), 3.49-3.27 (m, 5H), 2.55-2.53 (m, 1H), 2.38-2.34 (m, 1H), 2.16-2.09 (m, 2H), 1.99-1.96 (m, 1H).

Example 16

(R) N-(quinuclidin-3-yl)-6-(trifluoromethoxy)benzo[d]isoxazol-3-amine hydrochloride ((R)-16)

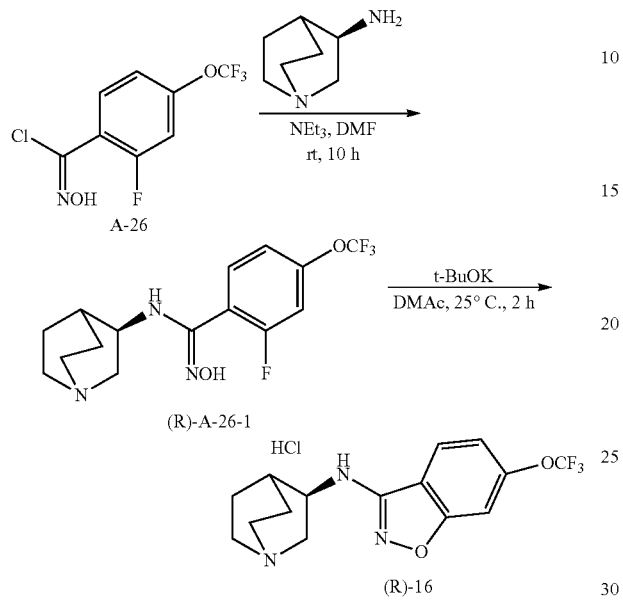

Following general procedure C1, compound (R)-16 was prepared from compound A-26:

Compound (R)-A-26-1 (0.22 g, white solid, 30% yield over three steps) was prepared from compound A-26 (0.55 g, 2.5 mmol), triethylamine (0.42 g, 4.2 mmol) and (R)-quinuclidin-3-amine (0.26 g, 2.1 mmol), using N,N-dimethylformamide as the solvent instead of methanol. The reaction time was 10 hours. The product was purified by prep-HPLC [Instrument: GX-H; Column: Waters Xbridge C18 150×25 mm, particle size: 5 μm; Mobile phase: 26-56% acetonitrile in $H_2O$ (add 0.5% $NH_3.H_2O$, v/v)]. $^1$H-NMR ($CDCl_3$, 400 MHz): δ 7.43 (t, J=8.0 Hz, 1H), 7.05 (m, 2H), 5.63 (d, J=8.0 Hz, 1H), 3.13-3.09 (m, 2H), 2.93-2.77 (m, 3H), 2.63-2.57 (m, 2H), 1.99-1.84 (m, 2H), 1.68-1.60 (m, 2H), 1.48-1.46 (m, 1H), 1.34-1.33 (m, 1H). LCMS (J): ($ES^+$) m/z $(M+H)^+$=348.0, tR=1.052 min.

A mixture of compound (R)-A-26-1 (0.25 g, 0.52 mmol) and potassium tert-butoxide (88 mg, 0.79 mmol) in N,N-dimethylacetamide (26 mL) was stirred at 25° C. for 2 hours. The mixture was diluted with ethyl acetate (260 mL), washed with brine (6×40 mL), dried with anhydrous sodium sulfate, filtered and concentrated in vacuo. The product was purified twice by prep-HPLC [Instrument: GX-D; Column: Boston Green ODS 150×30 mm, particle size: 5 μm; Mobile phase: 6-42% acetonitrile in $H_2O$ (add 0.225% FA, v/v), and Instrument: GX-B; Column: Phenomenex Synergi C18 150×30 mm, particle size: 4 μm; Mobile phase: 23-53% acetonitrile in $H_2O$ (add 0.1% TFA, v/v)], treated with 0.2 M hydrochloric acid and lyophilized to give:

Compound (R)-16 (32 mg, 17% yield) as a yellow solid: cSFC analytical (D) tR=1.64 min., purity: 100%; LCMS (EE): tR=2.820 min., ($ES^+$) m/z $(M+H)^+$=328.1; $^1$H-NMR ($CD_3OD$, 400 MHz): δ 7.95 (d, J=8.4 Hz, 1H), 7.38 (s, 1H), 7.19 (d, J=8.4 Hz, 1H), 4.14 (t, J=9.2 Hz, 1H), 3.82 (t, J=10.6 Hz, 1H), 3.47-3.28 (m, 5H), 2.51 (d, J=3.2 Hz, 1H), 2.34-2.32 (m, 1H), 2.13-2.07 (m, 2H), 1.95-1.92 (m, 1H).

Example 17

(R)-7-fluoro-N-(quinuclidin-3-yl)benzo[d]isoxazol-3-amine hydrochloride ((R)-17)

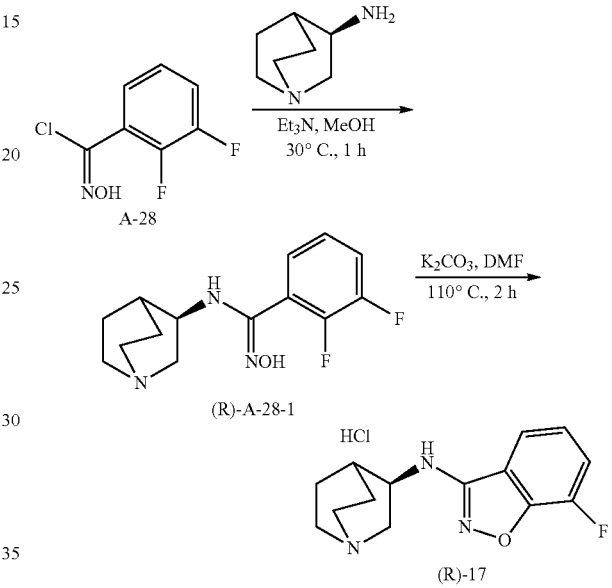

Following general procedure C1, compound (R)-17 was prepared from compound A-28:

Compound (R)-A-28-1 (0.20 g, white solid, 27% yield over two steps) was prepared from compound A-28 (0.50 g, 2.6 mmol) and (R)-quinuclidin-3-amine (0.40 g, 3.1 mmol). The product was purified by prep-HPLC [Instrument: GX-C; Column: Phenomenex Gemini C18 250×50 mm, particle size: 10 μm; Mobile phase: 20-50% acetonitrile in $H_2O$ (add 0.5% ammonia, v/v)]. LCMS (J): ($ES^+$) m/z $(M+H)^+$=282.1, tR=0.999 min.

A mixture of compound (R)-A-28-1 (0.20 g, 0.71 mmol) and potassium tert-butoxide (0.30 g, 2.0 mmol) in N,N-dimethylacetamide (5.0 mL) was stirred at 110° C. for 2 hours. On completion, the reaction mixture was filtered, concentrated in vacuo and purified by prep-HPLC [Instrument: GX-B; Column: Phenomenex Synergi C18 150×30 mm, particle size: 4 μm; Mobile phase: 10-40% acetonitrile in $H_2O$ (add 0.5% HCl, v/v)]. The product was lyophilized to give:

Compound (R)-17 (0.10 g, 47% yield) as a white solid: cSFC analytical (D) tR=2.22 min., purity: 94%; LCMS (EE): tR=2.50 min., 262.1 m/z (M+1); 1H-NMR ($CD_3OD$, 400 MHz): δ7.69-7.67 (d, J=8.0 Hz, 1H), 7.39-7.34 (m, 1H), 7.30-7.26 (m, 1H), 4.21-4.18 (m, 1H), 3.91-3.85 (m, 1H), 3.49-3.31 (m, 5H), 2.58-2.56 (m, 1H), 2.40-2.35 (m, 1H), 2.16-2.10 (m, 2H), 1.99-1.97 (m, 1H).

Example 18

(R)-5-fluoro-N-(quinuclidin-3-yl)benzo[d]isoxazol-3-amine hydrochloride ((R)-18) and (S)-5-fluoro-N-(quinuclidin-3-yl)benzo[d]isoxazol-3-amine hydrochloride ((S)-18)

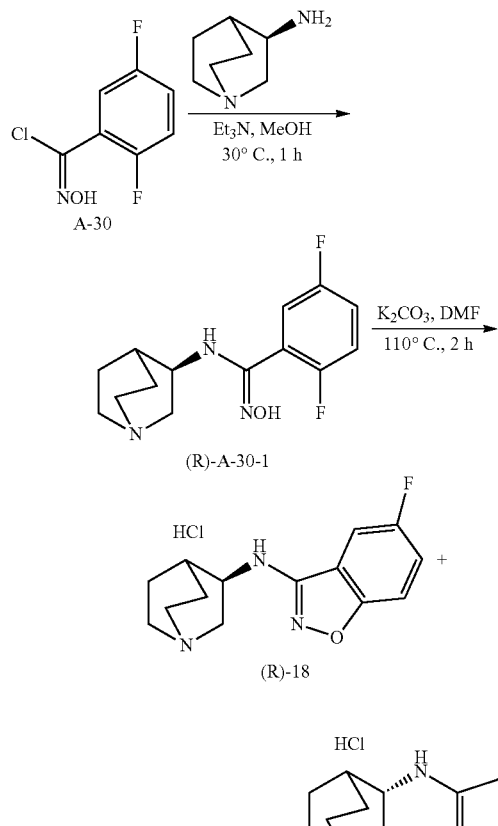

Following general procedure C1, compound (R)-18 was prepared from compound A-30:

Compound (R)-A-30-1 (0.20 g, white solid, 27% yield over three steps) was prepared from compound A-30 (0.50 g, 2.6 mmol) and (R)-quinuclidin-3-amine (0.40 g, 3.1 mmol). The product was purified by prep-HPLC [Instrument: GX-C; Column: Phenomenex Gemini C18 250×50 mm, particle size: 10 μm; Mobile phase: 20-50% acetonitrile in $H_2O$ (add 0.5% ammonia, v/v)]. LCMS (J): $(ES^+)$ m/z $(M+H)^+=282.2$, tR=0.964 min.

A mixture of compound (R)-A-30-1 (0.30 g, 1.1 mmol) and potassium carbonate (0.44 g, 3.2 mmol) in N,N-dimethylformamide (5.0 mL) was stirred at 110° C. for 2 hours. On completion, the reaction mixture was filtered, concentrated in vacuo and purified by prep-HPLC [Instrument: GX-B; Column: Phenomenex Synergi C18 150×30 mm, particle size: 4 μm; Mobile phase: 12-42% acetonitrile in $H_2O$ (add 0.5% HCl, v/v)]. The product was lyophilized to give:

Compound (R)-18 (0.15 g, 37% yield) as a white solid: cSFC analytical (D) tR=2.027 min., chiral purity: 90%;

Chiral Purification:

A solution of (R)-18 at 90% chiral purity (0.12 g, 0.46 mmol) in 3 mL of methanol was purified by cSFC (Instrument: SFC A; Column: AY-10 μm; Mobile phase: 50% methanol (0.01% $NH_3.H_2O$) in $CO_2$) at room temperature. In addition to the major product compound (R)-18, the minor product compound (S)-18 was also collected. Each set of collected fractions was concentrated at room temperature and lyophilized. The resulting solids were dissolved in 0.2 M hydrochloric acid and again lyophilized to give:

Compound (R)-18 (80 mg, 59% yield) as a white solid: cSFC analytical (D) tR=2.038 min., purity: 100%; LCMS (EE): tR=2.464 min., $(ES^+)$ m/z $(M+H)^+=262.1$; 1H-NMR ($CD_3OD$, 400 MHz): δ7.59-7.56 (dd, J=8.0 Hz, J=2.4 Hz, 1H), 7.47-7.44 (dd, J=8.8 Hz, J=4.0 Hz, 1H), 7.40-7.35 (m, 1H), 4.19-4.16 (m, 1H), 3.90-3.84 (m, 1H), 3.47-3.29 (m, 5H), 2.56-2.54 (m, 1H), 2.37-2.33 (m, 1H), 2.16-2.10 (m, 2H), 1.99-1.95 (m, 1H); and Compound (S)-18 (8.0 mg, 6% yield) as a white solid: cSFC analytical (D) tR=2.673 min., purity: 97.2%; LCMS (EE): tR=2.438 min., $(ES^+)$ m/z $(M+H)^+=262.1$; 1H-NMR ($CD_3OD$, 400 MHz): δ7.61-7.58 (dd, J=8.0 Hz, J=2.4 Hz, 1H), 7.47-7.44 (dd, J=8.4 Hz, J=4.0 Hz, 1H), 7.40-7.35 (m, 1H), 4.19-4.16 (m, 1H), 3.90-3.83 (m, 1H), 3.48-3.30 (m, 5H), 2.56-2.54 (m, 1H), 2.39-2.33 (m, 1H), 2.18-2.09 (m, 2H), 1.98-1.96 (m, 1H);

cSFC analytical conditions: Column: Chiralcel AY-3 100× 4.6 mm, I.D., 3 μm; Mobile phase: ethanol (0.05% DEA) in $CO_2$ from 5% to 40%; Flow rate: 3 mL/min.; Back pressure: 120 bar.

Example 19

(R)-4-fluoro-N-(quinuclidin-3-yl)benzo[d]isoxazol-3-amine hydrochloride ((R)-19)

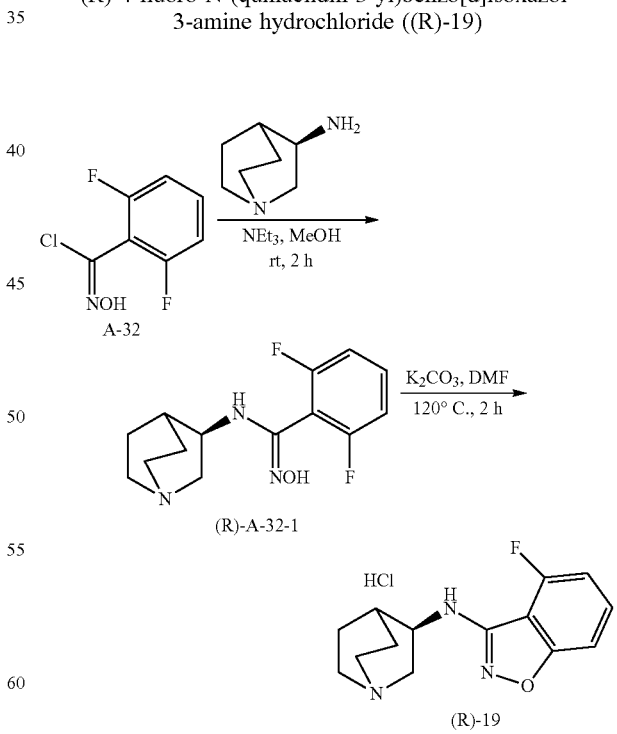

Following general procedure C1, compound (R)-19 was prepared from compound A-32:

Compound (R)-A-32-1 (0.60 g, white solid, crude) was prepared from compound A-32 (0.40 g, 2.1 mmol) and (R)-quinuclidin-3-amine (0.26 g, 2.1 mmol). The reaction time was 2 hours. LCMS (Q): (ES$^+$) m/z (M+H)$^+$=282.1, tR=2.310 min.

A mixture of compound (R)-A-32-1 (0.30 g, 1.1 mmol) and potassium carbonate (0.44 g, 3.2 mmol) in N,N-dimethylformamide (10 mL) was stirred at 120° C. for 2 hours. On completion, the reaction mixture was filtered, concentrated in vacuo and purified by prep-HPLC [Instrument: GX-A; Column: Phenomenex Gemini C18 250×50, particle size: 10 μm; Mobile phase: 29-59% acetonitrile in H$_2$O (add 0.05% NH$_3$.H$_2$O, v/v)]. The resulting solid was dissolved in 0.2 N hydrochloric acid and again lyophilized to give:

Compound (R)-19 (90 mg, 28% yield over three steps) as a yellow solid: cSFC analytical (D) tR=2.672 min., purity: 97.27%; LCMS (EE): tR=2.383 min., (ES$^+$) m/z (M+H)$^+$=262.1; $^1$H-NMR (CD$_3$OD, 400 MHz): δ 7.61-7.56 (m, 1H), 7.30-7.28 (d, J=8.0 Hz, 1H), 7.03-7.98 (t, J=10.0 Hz, 1H), 4.21-4.18 (m, 1H), 3.87-3.81 (m, 1H), 3.50-3.35 (m, 5H), 2.61-2.59 (m, 1H), 2.34-2.32 (m, 1H), 2.15-2.09 (m, 2H), 1.98-1.92 (m, 1H).

Example 20

(R)-7-fluoro-6-methyl-N-(quinuclidin-3-yl)benzo[d]isoxazol-3-amine hydrochloride ((R)-20)

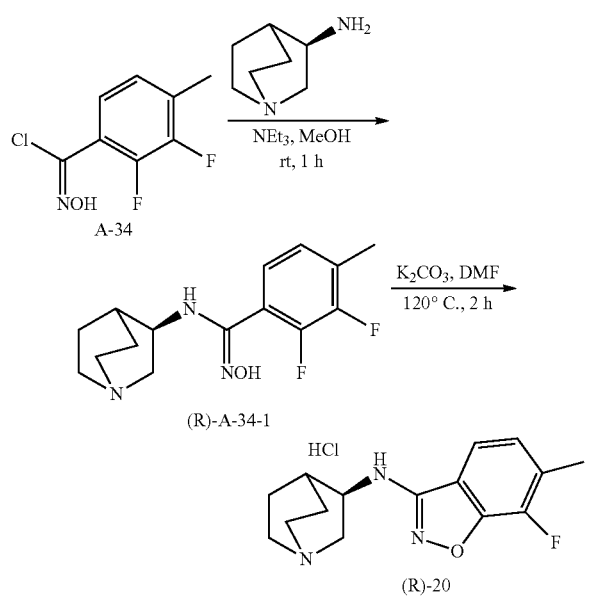

Following general procedure C1, compound (R)-20 was prepared from compound A-34:

Compound (R)-A-34-1 (0.11 g, white solid, 26% yield over two steps) was prepared from compound A-34 (0.30 g, 1.5 mmol) and (R)-quinuclidin-3-amine (0.18 g, 1.5 mmol). The product was purified by prep-HPLC [Instrument: GX-H; Waters Xbridge 150×25, particle size: 5 μm; Mobile phase: 20-50% acetonitrile in H$_2$O (add 0.05% NH$_3$.H$_2$O, v/v)]. LCMS (J): (ES$^+$) m/z (M+H)$^+$=296.1, tR=1.108 min.

A mixture of compound (R)-A-34-1 (80 mg, 0.27 mmol) and potassium carbonate (0.11 g, 0.81 mmol) in N,N-dimethylformamide (10 mL) was stirred at 120° C. for 2 hours. On completion, the reaction mixture was filtered, concentrated in vacuo and purified by prep-HPLC [Instrument: GX-C; Column: Phenomenex Gemini C18 250×50, particle size: 10 μm; Mobile phase: 30-60% acetonitrile in H$_2$O (add 0.05% NH$_3$.H$_2$O, v/v)]. The resulting product was lyophilized, dissolved in 0.2 N hydrochloric acid and again lyophilized to give:

Compound (R)-20 (30 mg, 36% yield) as a yellow solid: cSFC analytical (D) tR=2.377 min., purity: 96.68%; LCMS (EE): tR=2.659 min., (ES$^+$) m/z (M+H)$^+$=276.1; $^1$H-NMR (CD$_3$OD, 400 MHz): δ 7.52-7.50 (d, J=8.0 Hz, 1H), 7.18-7.15 (t, J=7.6 Hz, 1H), 4.18-4.15 (m, 1H), 3.90-3.83 (m, 1H), 3.46-3.38 (m, 4H), 3.29-3.28 (m, 1H), 2.56-2.54 (m, 1H), 2.43-2.42 (m, 3H), 2.38-2.34 (m, 1H), 2.16-2.09 (m, 2H), 1.99-1.95 (m, 1H).

Example 21

(R)-6,7-difluoro-N-(quinuclidin-3-yl)benzo[d]isoxazol-3-amine hydrochloride ((R)-21)

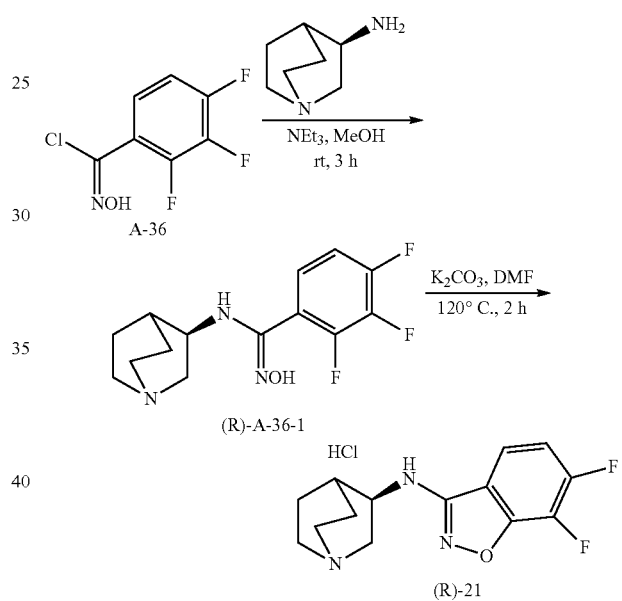

Following general procedure C1, compound (R)-21 was prepared from compound A-36:

Compound (R)-A-36-1 (0.11 g, white solid, 77% yield over two steps) was prepared from compound A-36 (0.10 g, 0.48 mmol) and (R)-quinuclidin-3-amine (0.12 g, 1.0 mmol) with a reaction time of 3 hours. The product was purified by prep-HPLC [Instrument: GX-H; Column: Waters Xbridge 150×25 mm, particle size: 5 μm; Mobile phase: 20-5% acetonitrile in H$_2$O (add 0.05% ammonia-ACN, v/v)]. LCMS (J): (ES$^+$) m/z (M+H)$^+$=300.1, tR=1.1 min.

A mixture of compound (R)-A-36-1 (0.11 g, 0.45 mmol) and potassium carbonate (0.19 g, 1.4 mmol) in N,N-dimethylformamide (3.0 mL) was stirred at 120° C. for 2 hours. On completion, the reaction mixture was filtered. The reaction mixture was concentrated in vacuo and purified by prep-HPLC [Instrument: GX-B; Column: YMC-Actus Pro C18 150×30 mm, particle size: 5 μm; Mobile phase: 17-74% acetonitrile in H$_2$O (add 0.5% HCl, v/v)]. The product was lyophilized to give:

Compound (R)-21 (35 mg, 34% yield) as a white solid: cSFC analytical tR=1.87 min., purity: 97.57%; LCMS (GG): tR=1.74 min., 280.1 m/z (M+1); 1H-NMR (CD$_3$OD, 400 MHz): δ 7.70-7.86 (m, 1H), 7.28-7.22 (m, 1H), 4.18-4.16 (m, 1H), 3.90-3.83 (m, 1H), 3.58-3.36 (m, 5H), 2.57-2.54 (m, 1H), 2.38-2.35 (m, 1H), 2.17-2.09 (m, 2H), 1.98-1.95 (m, 1H).

Example 22

(R)-5-fluoro-6-methyl-N-(quinuclidin-3-yl)benzo[d]isoxazol-3-amine hydrochloride ((R)-22)

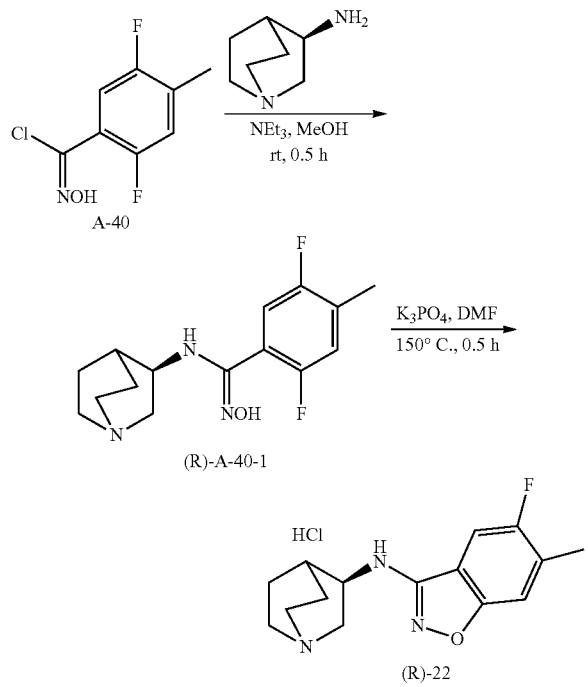

Following general procedure C1, compound (R)-22 was prepared from compound A-40:

Compound (R)-A-40-1 (0.14 g, white solid, 16% yield over four steps) was prepared from compound A-40 (0.50 g, 2.4 mmol) and (R)-quinuclidin-3-amine (0.31 g, 2.4 mmol). The reaction time was 0.5 hours. The product was purified by prep-HPLC [Instrument: GX-C; Column: Phenomenex Synergi C18 250×50 mm, particle size: 10 µm; Mobile phase: 25-55% acetonitrile in H$_2$O (add 0.05% ammonia-ACN, v/v)]. LCMS (J): (ES$^+$) m/z (M+H)$^+$=296.2, tR=1.092 min.

A mixture of compound (R)-A-40-1 (90 mg, 0.30 mmol) and potassium phosphate (0.19 g, 0.91 mmol) in N,N-dimethylformamide (3.0 mL) was stirred at 150° C. for 0.5 hour. On completion, the reaction mixture was filtered, concentrated in vacuo and purified by prep-HPLC [Instrument: GX-B; Column: YMC-Actus Pro C18 150×30 mm, particle size: 4 µm; Mobile phase: 25-55% acetonitrile in H$_2$O (add 0.1% TFA-ACN, v/v)]. The resulting solid was dissolved in 0.2 M hydrochloric acid and again lyophilized to give:

Compound (R)-22 (35 mg, 37% yield) as a white solid: cSFC analytical (D) tR=5.47 min., purity: 98.28%; LCMS (FF): tR=2.07 min., 276.1 m/z (M+1); 1H-NMR (CD$_3$OD, 400 MHz): δ 7.54 (d, J=8.8 Hz, 1H), 7.32 (d, J=5.6 Hz, 1H), 4.17-4.14 (m, 1H), 3.88-3.82 (m, 1H), 3.47-3.36 (m, 4H), 3.31-3.30 (m, 1H), 2.55-2.53 (m, 1H), 2.38-2.35 (m, 1H), 2.15-2.08 (m, 2H), 1.97-1.92 (m, 1H).

Example 23

(R)-6-chloro-7-methyl-N-(quinuclidin-3-yl)benzo[d]isoxazol-3-amine hydrochloride ((R)-23)

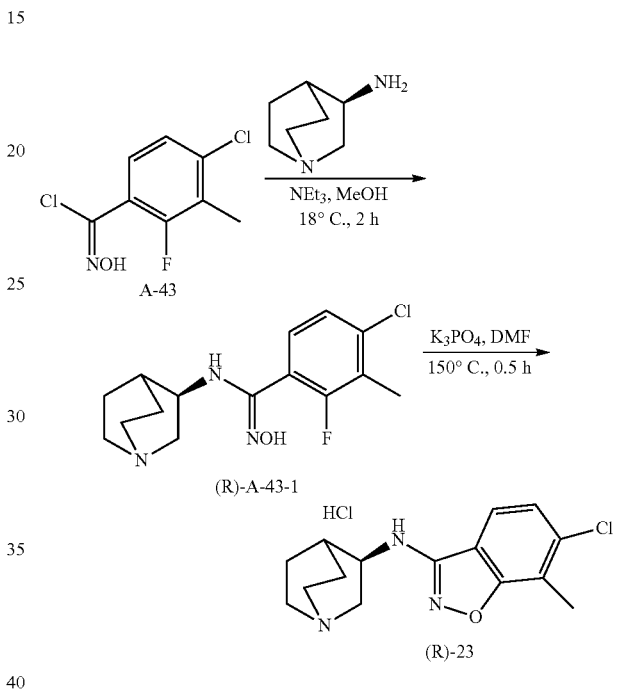

Following general procedure C1, compound (R)-23 was prepared from compound A-43:

Compound (R)-A-43-1 (0.14 g, white solid, 20% yield over four steps) was prepared from compound A-43 (0.45 g, 2.3 mmol) and (R)-quinuclidin-3-amine (0.29 g, 2.3 mmol). The reaction was stirred at 18° C. for 2 hours. The product was purified by prep-HPLC [Instrument: GX-C; Column: Phenomenex Synergi C18 250×50 mm, particle size: 10 µm; Mobile phase: 27-58% acetonitrile in H$_2$O (add 0.05% ammonia-ACN, v/v)]. LCMS (J): (ES$^+$) m/z (M+H)$^+$=312.2, tR=1.172 min.

A mixture of compound (R)-A-43-1 (90 mg, 0.30 mmol) and potassium phosphate (0.19 g, 0.91 mmol) in N,N-dimethylformamide (3.0 mL) was stirred at 150° C. for 0.5 hour. On completion, the reaction mixture was filtered, concentrated in vacuo and purified by prep-HPLC [Instrument: GX-I; Column: Welch Ultimate AQ-C18 150×30 mm, particle size: 5 µm; Mobile phase: 30-60% acetonitrile in H$_2$O (add 0.1% TFA-ACN, v/v)]. The resulting solid was dissolved in 0.2 M hydrochloric acid and again lyophilized to give:

Compound (R)-23 (55 mg, 65% yield) as a white solid: cSFC analytical (D) tR=2.74 min., purity: 100.00%; LCMS (FF): tR=2.30 min., 292.1 m/z (M+1); 1H-NMR (CD$_3$OD, 400 MHz): δ 7.65 (d, J=8.4 Hz, 1H), 7.32 (d, J=8.4 Hz, 1H), 4.19-4.16 (m, 1H), 3.90-3.83 (m, 1H), 3.50-3.36 (m, 4H), 3.30-3.29 (m, 1H), 2.56-2.54 (m, 1H), 2.50 (m, 3H), 2.36-2.32 (m, 1H), 2.16-2.09 (m, 2H), 2.00-1.93 (m, 1H).

Example 24

(R)-6-chloro-7-methoxy-N-(quinuclidin-3-yl)benzo[d]isoxazol-3-amine hydrochloride ((R)-24)

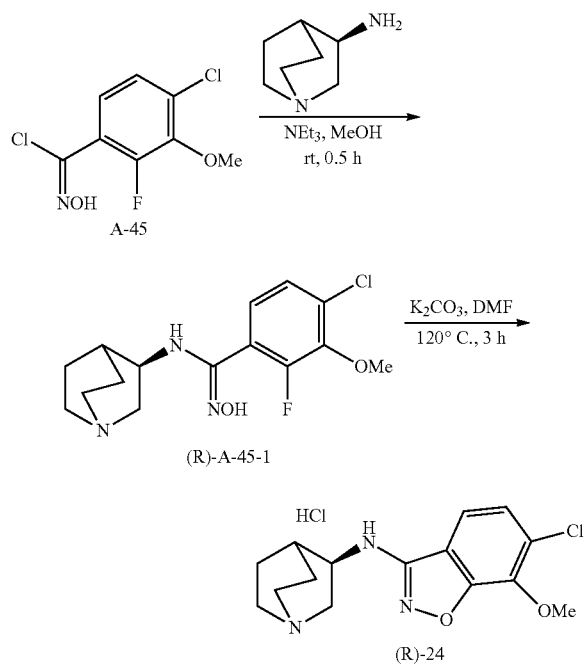

Following general procedure C1, compound (R)-24 was prepared from compound A-45:

Compound (R)-A-45-1 (0.15 g, white solid, 23% yield over three steps) was prepared from compound A-45 (0.45 g, 1.89 mmol) and (R)-quinuclidin-3-amine (0.24 g, 2.0 mmol) with a reaction time of 0.5 h. The product was purified by prep-HPLC [Instrument: GX-H; Column: Waters Xbridge 150×25 mm, particle size: 5 μm; Mobile phase: 20-50% acetonitrile in H$_2$O (add 0.5% NH$_3$.H$_2$O, v/v)]. LCMS (J): (ES$^+$) m/z (M+H)$^+$=328.1, tR=1.04 min.

A mixture of compound (R)-A-45-1 (0.14 g, 0.43 mmol) and potassium carbonate (0.19 g, 1.4 mmol) in N,N-dimethylformamide (3.0 mL) was stirred at 120° C. for 3 hours. On completion, the reaction mixture was filtered, concentrated in vacuo and purified by prep-HPLC [Instrument: GX-B; Column: Phenomenex Gemini C18 250×50 mm, particle size: 10 μm; Mobile phase: 37-67% acetonitrile in H$_2$O (add 0.05% ammonia-ACN, v/v)]. The residue solid was dissolved in 0.2 N hydrochloric acid and lyophilized again to give:

Compound (R)-24 (45 mg, 33% yield) as a white solid: cSFC analytical tR=2.51 min., purity: 97%; LCMS (FF): tR=2.25 min., (ES$^+$) m/z (M+H)$^+$=308.1; 1H-NMR (CD$_3$OD, 400 MHz): δ 7.48 (d, J=8.8 Hz, 1H), 7.30 (d, J=8.0 Hz, 1H), 4.20-4.16 (m, 4H), 3.90-3.83 (m, 1H), 3.50-3.31 (m, 5H), 2.57-2.55 (m, 1H), 2.36-2.35 (m, 1H), 2.16-2.10 (m, 2H), 1.98-1.94 (m, 1H).

Example 25

(R)-6-chloro-N-(quinuclidin-3-yl)-7-(trifluoromethyl)benzo[d]isoxazol-3-amine hydrochloride ((R)-25)

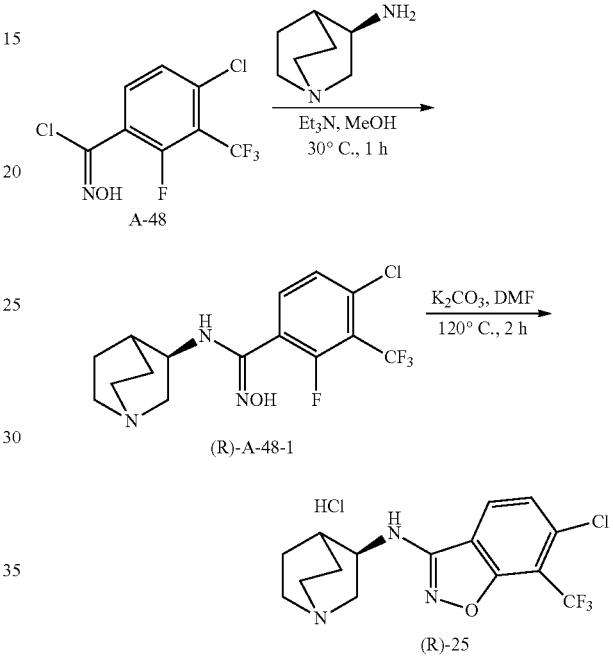

Following general procedure C1, compound (R)-25 was prepared from compound A-48:

Compound (R)-A-48-1 (0.20 g, white solid, 39% yield over two steps) was prepared from compound A-48 (0.39 g, 1.4 mmol) and (R)-quinuclidin-3-amine (0.21 g, 1.7 mmol). The product was purified by prep-HPLC [Instrument: GX-C; Column: Phenomenex Gemini C18 250×50 mm, particle size: 10 μm; Mobile phase: 30-60% acetonitrile in H$_2$O (add 0.5% ammonia, v/v)]. LCMS (J): (ES$^+$) m/z (M+H)$^+$=366.2, tR=1.239 min.

A mixture of compound (R)-A-48-1 (0.15 g, 0.41 mmol) and potassium carbonate (0.17 g, 1.2 mmol) in N,N-dimethylformamide (4.0 mL) was stirred at 120° C. for 2 hours. On completion, the reaction mixture was filtered, concentrated in vacuo and purified by prep-HPLC [Instrument: GX-A; Column: Phenomenex Synergi C18 150×30 mm, particle size: 4 μm; Mobile phase: 25-55% acetonitrile in H$_2$O (add 0.5% HCl, v/v)]. The product was lyophilized to give:

Compound (R)-25 (60 mg, 38% yield) as a white solid: cSFC analytical (D) tR=1.977 min., purity: 100%; LCMS (EE): tR=2.154 min., 346.1 m/z (M+1); 1H-NMR (D$_2$O, 400 MHz): δ7.66-7.63 (d, J=8.4 Hz, 1H), 7.25-7.23 (d, J=8.0 Hz, 1H), 4.00-3.98 (m, 1H), 3.75-3.69 (m, 1H), 3.36-3.15 (m, 5H), 2.40-2.39 (m, 1H), 2.18-1.85 (m, 4H).

Example 26

(R)-6-chloro-7-cyclopropyl-N-(quinuclidin-3-yl)benzo[d]isoxazol-3-amine ((R)-26)

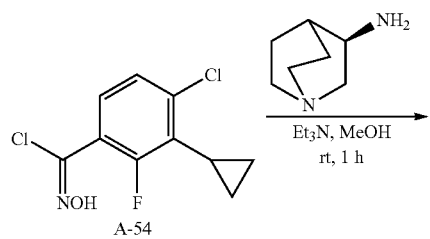

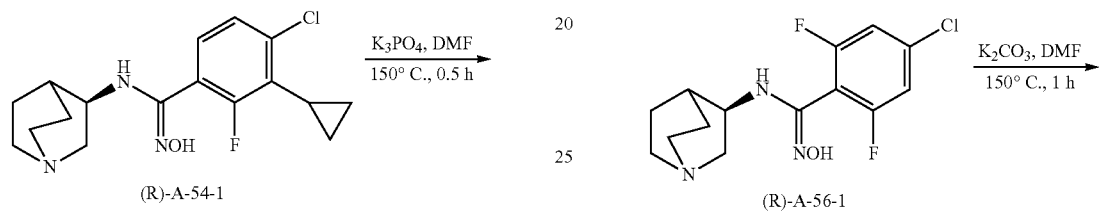

Following general procedure C1, compound (R)-26 was prepared from compound A-54:

Compound (R)-A-54-1 (0.25 g, white solid, 36% yield over two steps) was prepared from compound A-54 (0.50 g, 2.0 mmol) and (R)-quinuclidin-3-amine (0.25 g, 2.0 mmol). The product was purified by prep-HPLC [Instrument: GX-H; Column: Phenomenex Gemini C18 250×50 mm, particle size: 10 μm; Mobile phase: 27-57% acetonitrile in $H_2O$ (add 0.5% $NH_3OH.H_2O$, v/v)]. LCMS (J): ($ES^+$) m/z $(M+H)^+$=338.1, tR=1.159 min.

A mixture of compound (R)-A-54-1 (0.15 g, 0.44 mmol) and potassium phosphate (0.28 g, 1.3 mmol) in N,N-dimethylformamide (20 mL) was stirred at 150° C. for 0.5 hour. On completion, the reaction mixture was filtered and concentrated in vacuo. The residue was purified by prep-HPLC [Instrument: GX-I; Column: Welch Ultimate AQ-C18 150× 30 mm; particle size: 5 μm; Mobile phase: 25-55% acetonitrile in $H_2O$ (add 0.1% TFA, v/v)]. The resulting solid was dissolved in 0.2 N hydrochloric acid and again lyophilized to give:

Compound (R)-26 (80 mg, 50% yield) as a white solid: cSFC analytical (D) tR=3.728 min., purity: 99.57%; LCMS (GG): tR=2.152 min., ($ES^+$) m/z $(M+H)^+$=318.1; $^1H$-NMR ($CD_3OD$, 400 MHz): δ 7.18-7.13 (m, 2H), 4.22-4.20 (m, 1H), 3.89-3.83 (m, 1H), 3.50-3.36 (m, 5H), 2.63-2.60 (m, 1H), 2.35-2.31 (m, 1H), 2.21-2.10 (m, 3H), 2.00-1.98 (m, 1H), 1.12-1.07 (m, 2H), 0.95-0.93 (m, 2H).

Example 27

(R)-4-fluoro-6-chloro-N-(quinuclidin-3-yl)benzo[d]isoxazol-3-amine hydrochloride ((R)-27)

Following general procedure C1, compound (R)-27 was prepared from compound A-56:

Compound (R)-A-56-1 (1.1 g, white solid, 90% yield over two steps) was prepared from compound A-56 (0.80 g, 3.5 mmol) and (R)-quinuclidin-3-amine (0.45 g, 3.5 mmol). The product was purified by silica gel chromatography (dichloromethane/methanol=100: 1-10:1). LCMS (J): tR=1.144 min., 316.0 m/z (M+1).

A mixture of compound (R)-A-56-1 (0.30 g, 0.86 mmol) and potassium carbonate (0.35 g, 2.6 mmol) in N,N-dimethylformamide (3.0 mL) was stirred at 150° C. for 1 hour. On completion, the reaction mixture was filtered, concentrated in vacuo and purified by prep-HPLC [Instrument: GX-B; Column: Phenomenex Synergi C18 150×30 mm, particle size: 4 μm; Mobile phase: 17-47% acetonitrile in $H_2O$ (add 0.1% TFA-ACN, v/v)]. The resulting solid was dissolved in 0.2 M hydrochloric acid and again lyophilized again to give:

Compound (R)-27 (70 mg, 14% yield) as a yellow solid: cSFC analytical (D) tR=1.1 min., purity: 98%; LCMS (EE): tR=2.101 min., 296.0 m/z (M+1); 1H-NMR ($CD_3OD$, 400 MHz): δ 7.43 (s, 1H), 7.14-7.12 (d, J=9.2 Hz, 1H), 4.19-4.17 (m, 1H), 3.86-3.80 (m, 1H), 3.46-3.35 (m, 5H), 2.59-2.58 (m, 1H), 2.31 (m, 1H), 2.14-2.08 (m, 2H), 1.95 (m, 1H).

Example 28

(R)-4,6-dichloro-N-(quinuclidin-3-yl)benzo[d]isoxazol-3-amine hydrochloride ((R)-28)

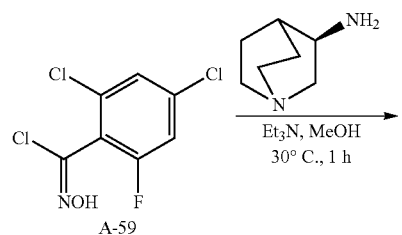

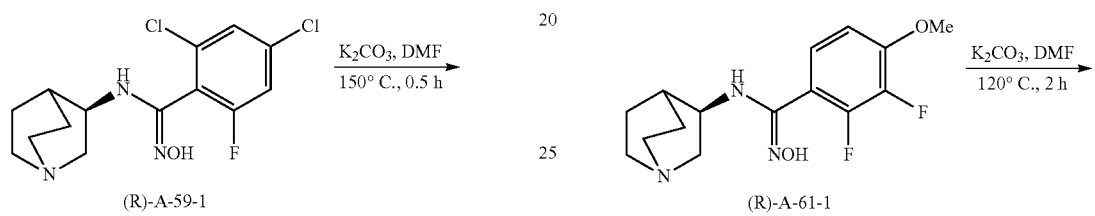

Following general procedure C1, compound (R)-28 was prepared from compound A-59:

Compound (R)-A-59-1 (0.20 g, white solid, 27% yield over two steps) was prepared from compound A-59 (0.35 g, 1.4 mmol) and (R)-quinuclidin-3-amine (0.22 g, 1.7 mmol). The product was purified by prep-HPLC [Instrument: GX-C; Column: Phenomenex Gemini C18 250×50 mm, particle size: 10 μm; Mobile phase: 22-52% acetonitrile in H$_2$O (add 0.5% ammonia, v/v)]. LCMS (J): (ES$^+$) m/z (M+H)$^+$=332.1, tR=1.125 min.

A mixture of compound (R)-A-59-1 (0.10 g, 0.30 mmol) and potassium carbonate (0.12 g, 0.90 mmol) in N,N-dimethylformamide (4.0 mL) was stirred at 150° C. for 0.5 hour. On completion, the reaction mixture was filtered, concentrated in vacuo and purified by prep-HPLC [Instrument: GX-A; Column: Phenomenex Synergi C18 150×30 mm, particle size: 10 μm; Mobile phase: 16-46% acetonitrile in H$_2$O (add 0.5% HCl, v/v)]. The product was lyophilized to give:

Compound (R)-28 (0.15 g, 37% yield) as a white solid: cSFC analytical (D) tR=3.25 min., purity: 99%; LCMS (EE): tR=2.776 min., 312.0 m/z (M+1); 1H-NMR (CD$_3$OD, 400 MHz): δ7.57-7.60 (d, J=1.6 Hz, 1H), 7.40-7.39 (d, J=1.2 Hz, 1H), 4.21-4.19 (m, 1H), 3.87-3.81 (m, 1H), 3.50-3.36 (m, 5H), 2.62-2.60 (m, 1H), 2.35-2.29 (m, 1H), 2.16-2.09 (m, 2H), 1.99-1.94 (m, 1H).

Example 29

(R)-7-fluoro-6-methoxy-N-(quinuclidin-3-yl)benzo[d]isoxazol-3-amine hydrochloride ((R)-29)

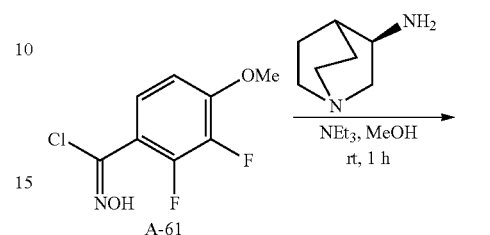

Following general procedure C1, compound (R)-29 was prepared from compound A-61:

Compound (R)-A-61-1 (0.12 g, white solid, 17% yield over two steps) was prepared from compound A-61 (0.50 g, 2.1 mmol) and (R)-quinuclidin-3-amine (0.26 g, 2.3 mmol). The product was purified by prep-HPLC [Instrument: GX-C; Column: Phenomenex Synergi C18 250×50 mm, particle size: 10 μm; Mobile phase: 25-55% acetonitrile in H$_2$O (add 0.5% ammonia, v/v)]. LCMS (J): (ES$^+$) m/z (M+H)$^+$=312.1, tR=1.161 min.

A mixture of compound (R)-A-61-1 (0.10 g, 0.32 mmol) and potassium carbonate (0.13 g, 0.56 mmol) in N,N-dimethylformamide (4.0 mL) was stirred at 120° C. for 2 hours. On completion, the reaction mixture was filtered, concentrated in vacuo and purified by prep-HPLC [Instrument: GX-B; Column: Phenomenex Synergi C18 100×21.2 mm, particle size: 4 μm; Mobile phase: 15-45% acetonitrile in H2O (add 0.1% TFA, v/v)]. The resulting solid was dissolved in 0.2 M hydrochloric acid and again lyophilized to give:

Compound (R)-29 (15 mg, 16% yield) as a yellow solid: cSFC analytical tR=2.83 min., purity: 100.00%; LCMS (FF): tR=2.08 min., 292.1 m/z (M+1); 1H-NMR (CD$_3$OD, 400 MHz): δ 7.59-7.57 (m, 1H), 7.16-7.12 (m, 1H), 4.16-4.14 (m, 1H), 4.00-3.98 (m, 3H), 3.89-3.85 (m, 1H), 3.43-3.29 (m, 5H), 2.55-2.53 (m, 1H), 2.35-2.34 (m, 1H), 2.15-2.10 (m, 2H), 1.99-1.97 (m, 1H).

Example 30

(R)-7-chloro-6-methoxy-N-(quinuclidin-3-yl)benzo[d]isoxazol-3-amine hydrochloride ((R)-30) and (S)-7-chloro-6-methoxy-N-(quinuclidin-3-yl)benzo[d]isoxazol-3-amine hydrochloride ((S)-30)

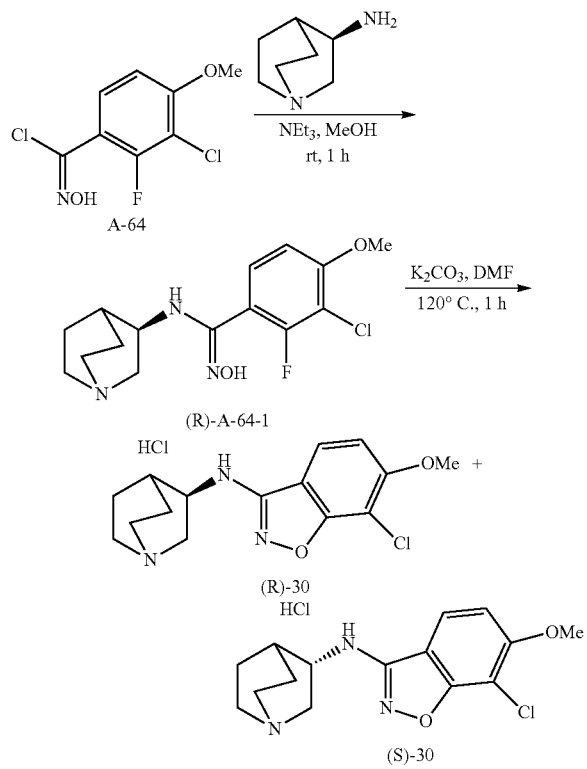

Following general procedure C1, compound (R)-30 was prepared from compound A-64:

Compound (R)-A-64-1 (0.35 g, white solid, 51% yield over three steps) was prepared from compound A-64 (0.45 g, 1.9 mmol) and (R)-quinuclidin-3-amine (0.24 g, 2.0 mmol). The product was purified by prep-HPLC [Instrument: GX-H; Column: Waters Xbridge 150×25 mm, particle size: 5 μm; Mobile phase: 20-5% acetonitrile in $H_2O$ (add 0.05% ammonia-ACN, v/v)]. LCMS (J): ($ES^+$) m/z (M+H)$^+$=328.1, tR=1.03 min.

A solution of compound (R)-A-64-1 (250 mg, 0.76 mmol) and potassium carbonate (186 mg, 1.35 mmol) in N,N-dimethylformamide (3.0 mL) was stirred at 120° C. for 1 hour. On completion, the reaction mixture was filtered, concentrated in vacuo and purified by prep-HPLC [Instrument: GX-B; Column: Phenomenex Gemini C18 250×50 mm, particle size: 10 μm; Mobile phase: 37-67% acetonitrile in $H_2O$ (add 0.05% ammonia-ACN, v/v)]. The residue was dissolved in 0.2 M hydrochloric acid and lyophilized to give:

Compound (R)-30 (50 mg, 21% yield) as a white solid: cSFC analytical (D) tR=1.045 min., chiral purity: 87%.

A solution of (R)-30 at 87% chiral purity (50 mg, 0.46 mmol) in 3 mL of methanol was purified by cSFC (Instrument: SFC A; Column: AY-10 μm; Mobile phase: 50% methanol (0.01% $NH_3 \cdot H_2O$) in $CO_2$) at room temperature. In addition to the major product compound (R)-30, the minor product compound (S)-30 was also collected. Each set of collected fractions was concentrated at room temperature and lyophilized. The resulting solids were dissolved in 0.2 M hydrochloric acid solution and again lyophilized to give:

Compound (R)-30 (35 mg, 70%) as a white solid. cSFC analytical (D) tR=1.085 min., purity: 100.00%; LCMS (FF): tR=2.15 min., ($ES^+$) m/z (M+H)$^+$=308.1; 1H-NMR ($CD_3OD$, 400 MHz): δ 7.78 (d, J=8.8 Hz, 1H), 7.13 (d, J=8.8 Hz, 1H), 4.16-4.14 (m, 1H), 4.01 (m, 3H), 3.88-3.83 (m, 1H), 3.51-3.30 (m, 5H), 2.55-2.54 (m, 1H), 2.36-2.35 (m, 1H), 2.19-2.09 (m, 2H), 1.99-1.93 (m, 1H); and Compound (S)-30 (4 mg, 10% yield) as a white solid: cSFC analytical (D) tR=2.65 min., purity: 96.44%; LCMS (FF): tR=2.15 min., ($ES^+$) m/z (M+H)$^+$=308.1; 1H-NMR ($CD_3OD$, 400 MHz): δ 7.79 (d, J=8.8 Hz, 1H), 7.12 (d, J=8.8 Hz, 1H), 4.19-4.14 (m, 1H), 4.01 (s, 3H), 3.88-3.83 (m, 1H), 3.60-3.37 (m, 5H), 2.55-2.54 (m, 1H), 2.36-2.35 (m, 1H), 2.15-2.10 (m, 2H), 1.99-1.93 (m, 1H).

Example 31

(R)-7-chloro-6-methyl-N-(quinuclidin-3-yl)benzo[d]isoxazol-3-amine hydrochloride ((R)-31)

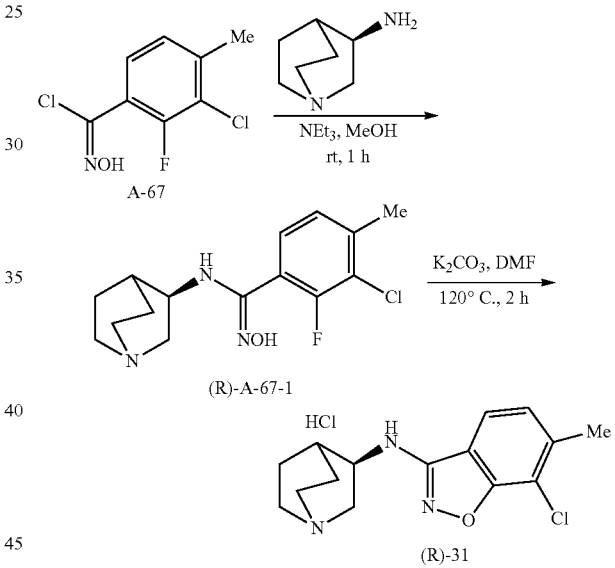

Following general procedure C1, compound (R)-31 was prepared from compound A-67:

Compound (R)-A-67-1 (0.10 g, white solid, 15% yield over two steps) was prepared from compound A-67 (0.50 g, 2.3 mmol) and (R)-quinuclidin-3-amine (0.28 g, 2.3 mmol). The product was purified by prep-HPLC [Instrument: GX-C; Column: Phenomenex Synergi C18 250×50 mm, particle size: 10 μm; Mobile phase: 25-55% acetonitrile in $H_2O$ (add 0.5% ammonia, v/v)]. LCMS (J): ($ES^+$) m/z (M+H)$^+$=312.1, tR=1.152 min.

A mixture of compound (R)-A-67-1 (80 mg, 0.26 mmol) and potassium carbonate (0.11 g, 0.77 mmol) in N,N-dimethylformamide (3.0 mL) was stirred at 120° C. for 2 hours. On completion, the reaction mixture was filtered, concentrated in vacuo and purified by prep-HPLC [Instrument: GX-B; Column: Phenomenex Synergi C18 100×21.2 mm, particle size: 4 μm; Mobile phase: 20-50% acetonitrile in $H_2O$ (add 0.1% TFA, v/v)]. The resulting solid was dissolved in 0.2 M hydrochloric acid and again lyophilized to give:

Compound (R)-31 (20 mg, 26% yield) as a white solid: cSFC analytical tR=2.90 min., purity: 94.51%; LCMS (FF): tR=2.31 min., 292.1 m/z (M+1); 1H-NMR (CD$_3$OD, 400 MHz): δ 7.68-7.66 (m, 1H), 7.26-7.24 (d, J=8.0 Hz, 1H), 4.18-4.16 (m, 1H), 3.89-3.84 (m, 1H), 3.45-3.33 (m, 5H), 2.56-2.54 (m, 1H), 2.53 (s, 3H), 2.35-2.35 (m, 1H), 2.16-2.12 (m, 2H), 1.99-1.96 (m, 1H).

Example 32

(R)-6-isopropoxy-N-(quinuclidin-3-yl)benzo[d]isoxazol-3-amine hydrochloride ((R)-32) and (S)-6-isopropoxy-N-(quinuclidin-3-yl)benzo[d]isoxazol-3-amine hydrochloride ((S)-32)

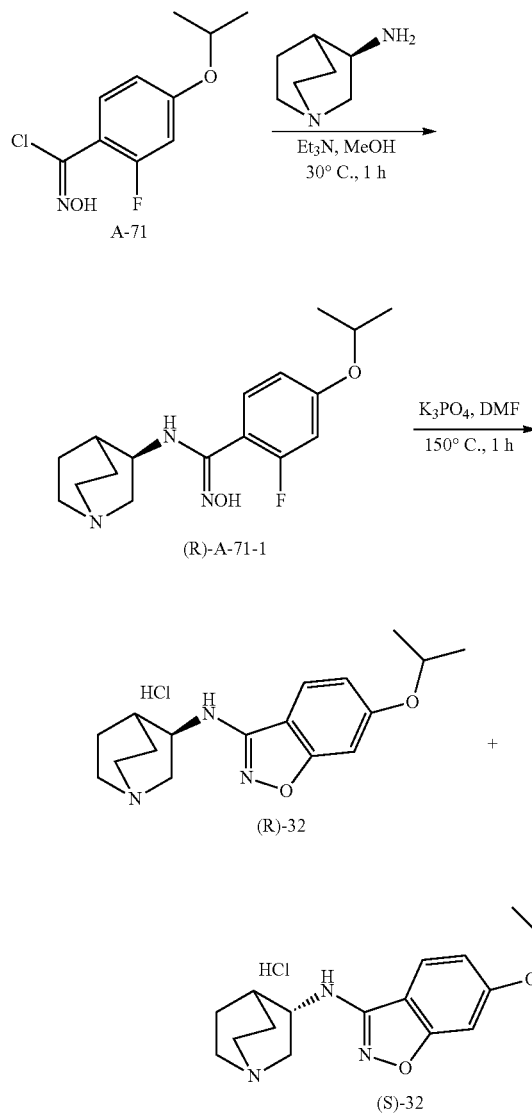

Following general procedure C1, compound (R)-32 was prepared from compound A-71:

Compound (R)-A-71-1 (0.40 g, white solid, 68% yield over two steps) was prepared from compound A-71 (0.40 g, 1.7 mmol) and (R)-quinuclidin-3-amine (0.26 g, 2.1 mmol). The product was purified by prep-HPLC [Instrument: GX-C; Column: Phenomenex Gemini C18 250×50 mm, particle size: 10 μm; Mobile phase: 22-52% acetonitrile in H$_2$O (add 0.5% ammonia, v/v)]. LCMS (J): (ES$^+$) m/z (M+H)$^+$=322.2, tR=1.166 min.

A mixture of compound (R)-A-71-1 (0.16 g, 0.50 mmol) and potassium phosphate (0.32 g, 1.5 mmol) in N,N-dimethylformamide (4.0 mL) was stirred at 150° C. for 1 hour. On completion, the reaction mixture was filtered, concentrated in vacuo and purified by prep-HPLC [Instrument: GX-A; Column: Phenomenex Synergi C18 150×30 mm, particle size: 10 μm; Mobile phase: 16-46% acetonitrile in H$_2$O (add 0.5% HCl, v/v)]. The product was lyophilized to give:

Compound (R)-32 (80 mg, 53% yield) as a white solid: cSFC analytical (D) tR=2.760 min., chiral purity: 90%;

Chiral Purification:

A solution of compound (R)-32 at 90% chiral purity (80 mg, 0.27 mmol) in 4 mL of methanol was purified by cSFC (Instrument: SFC A; Column: AY-10 μm; Mobile phase: 50% methanol (0.01% NH$_3$.H$_2$O) in CO$_2$) at room temperature. In addition to the major product compound (R)-32, the minor product compound (S)-32 was also collected. Each set of collected fractions was concentrated at room temperature and lyophilized. The resulting solids were dissolved in 0.2 M hydrochloric acid and again lyophilized to give:

Compound (R)-32 (60 mg, 67% yield) as a yellow solid: cSFC analytical (D) tR=2.684 min., purity: 100%; LCMS (EE): tR=2.264 min., (ES$^+$) m/z (M+H)$^+$=302.2; 1H-NMR (CD$_3$OD, 400 MHz): δ7.71-7.69 (d, J=8.4 Hz, 1H), 6.94-6.94 (d, J=1.6 Hz, 1H), 6.87-6.84 (dd, J=8.4 Hz, J=2.0 Hz, 1H), 4.74-4.68 (m, 1H), 4.14-4.12 (m, 1H), 3.87-3.81 (m, 1H), 3.49-3.30 (m, 5H), 2.54-2.52 (m, 1H), 2.36-2.34 (m, 1H), 2.15-2.08 (m, 2H), 1.97-1.95 (m, 1H), 1.38-1.36 (d, J=7.0 Hz, 6H); and Compound (S)-32 (6.0 mg, 7% yield) as a yellow solid: cSFC analytical (D) tR=4.131 min., purity: 97.12%; LCMS (EE): tR=2.281 min., (ES$^+$) m/z (M+H)$^+$=302.1; 1H-NMR (CD$_3$OD, 400 MHz): δ7.71-7.69 (d, J=8.4 Hz, 1H), 6.94-6.94 (d, J=1.6 Hz, 1H), 6.87-6.84 (dd, J=8.4 Hz, J=2.0 Hz, 1H), 4.74-4.68 (m, 1H), 4.14-4.12 (m, 1H), 3.87-3.82 (m, 1H), 3.47-3.28 (m, 5H), 2.54-2.52 (m, 1H), 2.36-2.32 (m, 1H), 2.15-2.08 (m, 2H), 1.98-1.92 (m, 1H), 1.38-1.36 (d, J=7.0 Hz, 6H).

Example 33

(R)-6-ethoxy-N-(quinuclidin-3-yl)benzo[d]isoxazol-3-amine ((R)-33) and (S)-6-ethoxy-N-(quinuclidin-3-yl)benzo[d]isoxazol-3-amine ((S)-33)

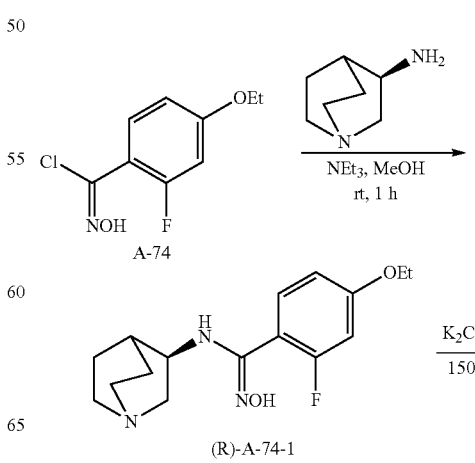

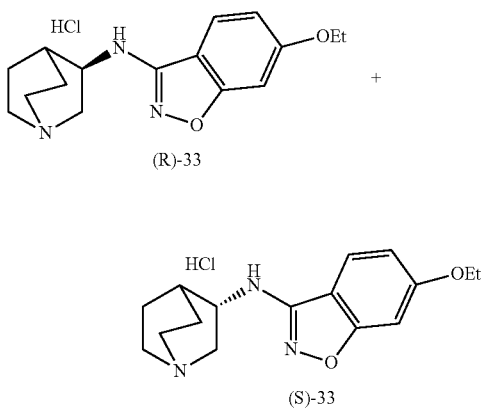

(R)-33

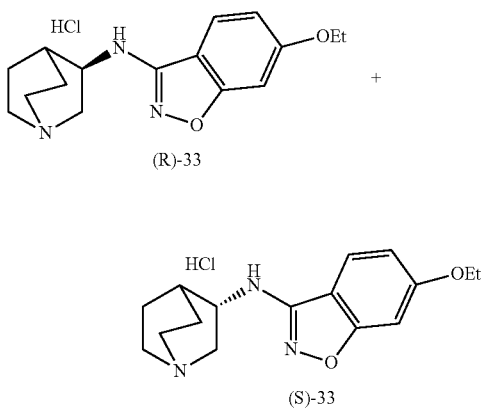

(S)-33

Following general procedure C1, compound (R)-33 was prepared from compound A-74:

Compound (R)-A-74-1 (0.30 g, white solid, 42% yield over two steps) was prepared from compound A-74 (0.50 g, 2.3 mmol) and (R)-quinuclidin-3-amine (0.29 g, 2.3 mmol). The product was purified by base prep-HPLC [Instrument: GX-A; Column: Phenomenex Gemini C18 250×50 mm, particle size: 10 μm; Mobile phase: 24-54% acetonitrile in $H_2O$ (add 0.5% $NH_3.H_2O$, v/v)]. LCMS (J): ($ES^+$) m/z $(M+H)^+$=308.2, tR=1.117 min.

A mixture of compound (R)-A-74-1 (0.15 g, 0.49 mmol) and potassium carbonate (0.20 g, 1.5 mmol) in N,N-dimethylformamide (20 mL) was stirred at 150° C. for 2 hours. On completion, the reaction mixture was filtered, concentrated in vacuo and purified by prep-HPLC [Instrument: GX-B; Column: Welch Ultimate AQ-C18 150×30 mm, particle size: 5 μm; Mobile phase: 17-47% acetonitrile in $H_2O$ (add 0.1% TFA, v/v)]. The resulting solid was dissolved in 0.2 M hydrochloric acid and again lyophilized to give compound (R)-33 (0.12 g, 81% chiral purity).

A solution of compound (R)-33 at 81% chiral purity (0.12 g, 0.39 mmol) in 5 mL ethanol was purified by SFC (Column: Chiralpak AY-H-150×4.6 mm, I.D., 5 μm; Mobile phase: ethanol (0.05% DEA) in $CO_2$) at room temperature. In addition to the major product compound (R)-33, the minor product compound (S)-33 was also collected. Each set of collected fractions was concentrated at room temperature. The residue was dissolved in 0.2 M hydrochloric acid and lyophilized to give:

Compound (R)-33 (40 mg, 32% yield) as a yellow solid: cSFC analytical (A) tR=2.73 min., purity: 100%; LCMS (GG): tR=1.969 min., ($ES^+$) m/z $(M+H)^+$=288.1; $^1$H-NMR ($CD_3OD$, 400 MHz): δ 7.70-7.68 (d, J=8.8 Hz, 1H), 6.94-6.93 (d, J=1.6 Hz, 1H), 6.89-6.87 (m, 1H), 4.14-4.09 (m, 3H), 3.87-3.81 (m, 1H), 3.47-3.36 (m, 4H), 3.33-3.30 (m, 1H), 2.54-2.52 (m, 1H), 2.36-2.34 (m, 1H), 2.15-2.08 (m, 2H), 1.97-1.95 (m, 1H), 1.46-1.43 (t, J=7.2 Hz, 3H); and Compound (S)-33 (10 mg, 8% yield) as a yellow solid: cSFC analytical (A) tR=3.86 min., purity: 100%; LCMS (GG): tR=1.935 min., ($ES^+$) m/z $(M+H)^+$=288.1; $^1$H-NMR ($CD_3OD$, 400 MHz): δ 7.71-7.69 (d, J=8.4 Hz, 1H), 6.94-6.93 (d, J=1.6 Hz, 1H), 6.89-6.86 (m, 1H), 4.14-4.09 (m, 3H), 3.87-3.81 (m, 1H), 3.50-3.37 (m, 4H), 3.33-3.28 (m, 1H), 2.54-2.52 (m, 1H), 2.36-2.34 (m, 1H), 2.15-2.08 (m, 2H), 1.97-1.95 (m, 1H), 1.46-1.43 (t, J=7.2 Hz, 3H).

Example 34

(R)-6-chloro-3-(quinuclidin-3-ylamino)benzo[d]isoxazole-7-carbonitrile hydrochloride ((R)-34)

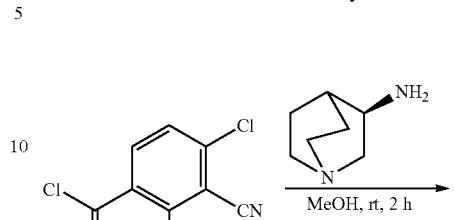

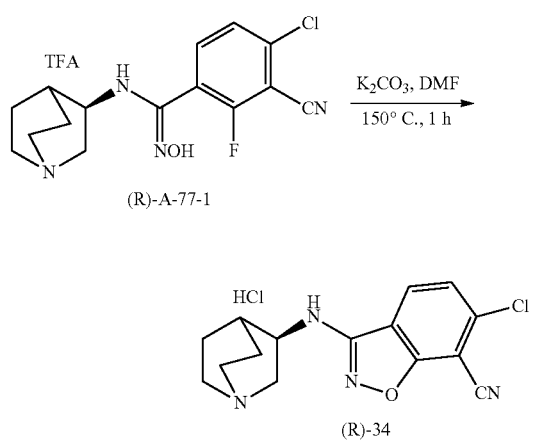

Following general procedure C1, compound (R)-34 was prepared from compound A-77:

Compound (R)-A-77-1 was prepared as follows: A solution of (R)-quinuclidin-3-amine (0.27 g, 2.2 mmol) in methanol (5 mL) was added dropwise to a solution of 4-chloro-3-cyano-2-fluoro-N-hydroxybenzimidoyl chloride compound A-77 (0.50 g, 2.2 mmol) in methanol (5 mL) at room temperature. The resulting mixture was stirred at room temperature for 2 hours. On completion, the reaction mixture was concentrated in vacuo and purified by prep-HPLC [Instrument: GX-B; Column: Atlantis Hilic Silica C18 150× 19 mm, particle size: 5 μm; Mobile phase: 11-41% acetonitrile in $H_2O$ (add 0.1% TFA-ACN, v/v)] to give compound (R)-A-77-1 (0.20 g, 28% yield over two steps) as a yellow solid. LCMS (M): tR=0.540 min., 323.1 m/z (M+1).

A solution of compound (R)-A-77-1 (0.18 g, 0.41 mmol) and potassium carbonate (0.17 g, 1.2 mmol) in N,N-dimethylformamide (2.0 mL) was stirred at 150° C. for 2 hour. On completion, the reaction mixture was filtered, concentrated in vacuo and purified by prep-HPLC [Instrument: GX-E; Column: Phenomenex Synergi C18 150×30 mm, particle size: 4 μm; Mobile phase: 12-42% acetonitrile in $H_2O$ (add 0.05% HCl-ACN, v/v)]. The resulting solution was lyophilized to give:

Compound (R)-34 (20 mg, 16% yield) as a white solid: cSFC analytical (D) tR=2.8 min., purity: 97%; LCMS (GG): tR=1.942 min., 303.1 m/z (M+1); 1H-NMR ($CD_3OD$, 400 MHz): δ 8.17 (d, J=8.8 Hz, 1H), 7.56 (d, J=8.4 Hz, 1H), 4.21-4.18 (m, 1H), 3.91-3.88 (m, 1H), 3.47-3.36 (m, 5H), 2.57-2.55 (m, 1H), 2.34 (m, 1H), 2.16-2.10 (m, 2H), 1.99-1.98 (m, 1H).

Example 35

(R)-7-chloro-6-fluoro-N-(quinuclidin-3-yl)benzo[d]isoxazol-3-amine hydrochloride ((R)-35)

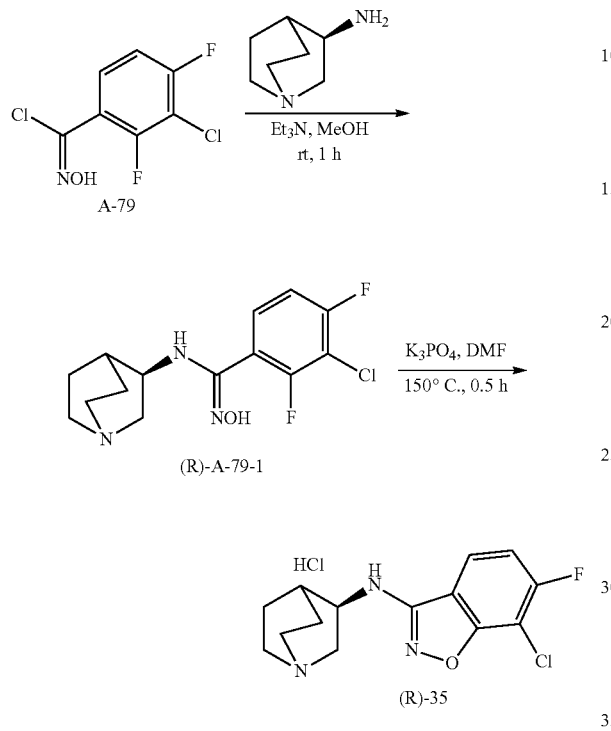

Following general procedure C1, compound (R)-35 was prepared from compound A-79:

Compound (R)-A-79-1 (0.30 g, white solid, 54% yield over two steps) was prepared from compound A-79 (0.40 g, 1.8 mmol) and (R)-quinuclidin-3-amine (0.22 g, 1.8 mmol). The product was purified by prep-HPLC [Instrument: GX-H; Column: Phenomenex Gemini C18 250×50 mm, particle size: 10 μm; Mobile phase: 24-54% acetonitrile in H$_2$O (add 0.5% ammonia, v/v)]. LCMS (J): (ES$^+$) m/z (M+H)$^+$=316.1, tR=1.084 min.

A mixture of compound (R)-A-79-1 (0.10 g, 0.32 mmol) and potassium phosphate (0.20 g, 0.95 mmol) in N,N-dimethylformamide (10 mL) was stirred at 150° C. for 0.5 hour. On completion, the reaction mixture was filtered and concentrated in vacuo. The residue was purified by prep-HPLC [Instrument: GX-I; Column: Xtimate C18 150×25 mm; particle size: 5 μm; Mobile phase: 12-42% acetonitrile in H$_2$O (add 0.1% TFA, v/v)]. The resulting solid was dissolved in 0.2 N hydrochloric acid and again lyophilized to give:

Compound (R)-35 (70 mg, 66% yield) as a white solid: cSFC analytical (D) tR=2.375 min., purity: 98.24%; LCMS (FF): tR=2.306 min., (ES$^+$) m/z (M+H)$^+$=296.1; $^1$H-NMR (CD$_3$OD, 400 MHz): δ7.84-7.81 (m, 1H), 7.28-7.23 (t, J=9.0 Hz, 1H), 4.18-4.16 (m, 1H), 3.90-3.84 (m, 1H), 3.48-3.36 (m, 4H), 3.33-3.30 (m, 1H), 2.56-2.54 (m, 1H), 2.38-2.32 (m, 1H), 2.16-2.09 (m, 2H), 1.99-1.95 (m, 1H).

Example 36

(R)-6-(1H-pyrazol-1-yl)-N-(quinuclidin-3-yl)benzo[d]isoxazol-3-amine hydrochloride ((R)-36)

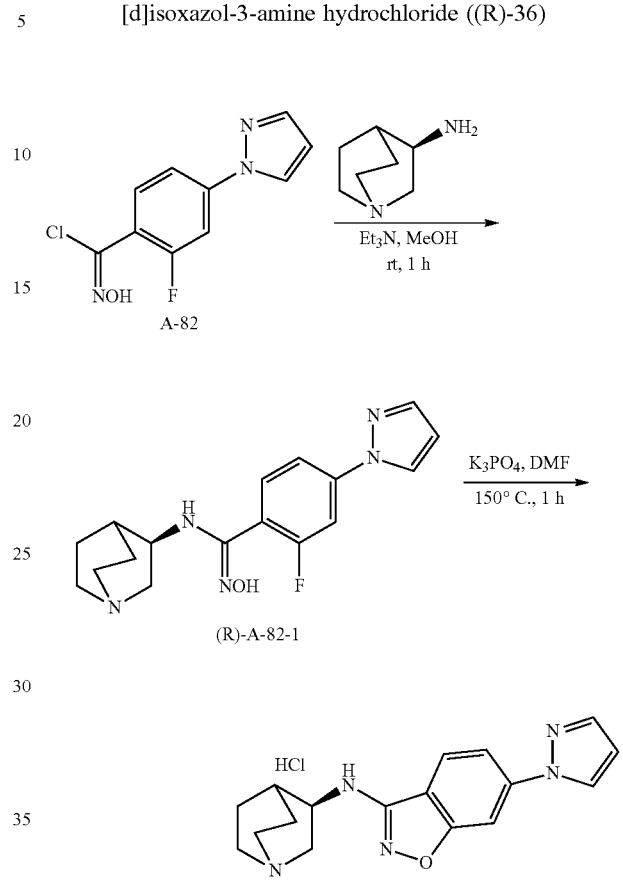

Following general procedure C1, compound (R)-36 was prepared from compound A-82:

Compound (R)-A-82-1 (0.15 g, white solid, 27% yield over two steps) was prepared from compound A-82 (0.30 g, 1.3 mmol) and (R)-quinuclidin-3-amine (0.16 g, 1.3 mmol). The product was purified by prep-HPLC [Instrument: GX-C; Column: Phenomenex Gemini C18 250×50 mm, particle size: 10 μm; Mobile phase: 22-52% acetonitrile in H$_2$O (add 0.5% ammonia, v/v)]. LCMS (J): (ES$^+$) m/z (M+H)$^+$=330.2, tR=1.044 min.

A solution of compound (R)-A-82-1 (0.10 g, 0.30 mmol) and potassium phosphate (0.19 g, 0.91 mmol) in N,N-dimethylformamide (5.0 mL) was stirred at 150° C. for 1 hour. On completion, the reaction mixture was filtered and concentrated in vacuo. The residue was purified by prep-HPLC [Instrument: GX-A; Column: Phenomenex Synergi C18 150×30 mm, particle size: 10 μm; Mobile phase: 16-46% acetonitrile in H$_2$O (add 0.5% HCl, v/v)] to give:

Compound (R)-36 (50 mg, 48% yield) as a yellow solid: cSFC analytical (D) tR=3.154 min., purity: 95.41%; LCMS (EE): tR=2.174 min., 310.1 m/z (M+1); 1H-NMR (CD$_3$OD, 400 MHz): δ8.40-8.39 (d, J=2.4 Hz, 1H), 7.99-7.97 (d, J=8.4 Hz, 1H), 7.86 (s, 1H), 7.81-7.77 (m, 2H), 6.66 (s, 1H), 4.20-4.18 (m, 1H), 3.91-3.79 (m, 1H), 3.53-3.36 (m, 5H), 2.57-2.56 (m, 1H), 2.41-2.31 (m, 1H), 2.18-2.10 (m, 2H), 2.00-1.94 (m, 1H).

Example 37

(R)-6-(5-methyl-1,3,4-oxadiazol-2-yl)-N-(quinuclidin-3-yl)benzo[d]isoxazol-3-amine hydrochloride ((R)-37)

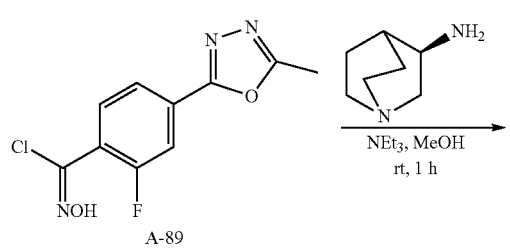

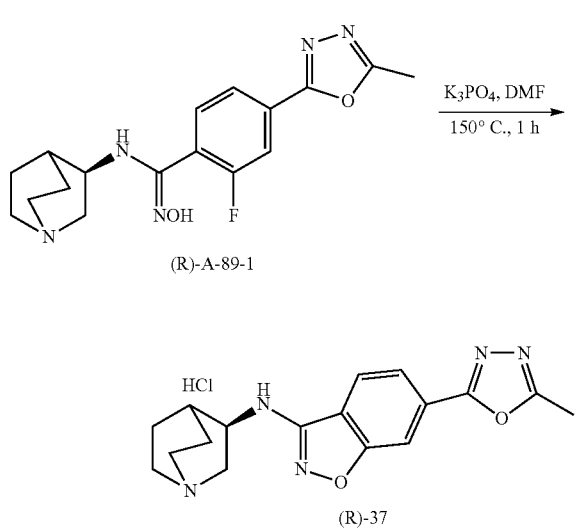

Following general procedure C1, compound (R)-37 was prepared from compound A-89:

Compound (R)-A-89-1 (0.78 g, yellow solid, crude) was prepared from compound A-89 (0.58 g, 2.3 mmol) and (R)-quinuclidin-3-amine (0.28 g, 2.3 mmol). The crude was used for the next step without purification. LCMS (J): (ES$^+$) m/z (M+H)$^+$=346.2, tR=0.931 min.

A solution of compound (R)-A-89-1 (0.78 g, crude) and potassium phosphate (1.4 g, 6.8 mmol) in N,N-dimethylformamide (20 mL) was stirred at 150° C. for 1 hour. On completion, the reaction mixture was filtered and concentrated in vacuo. The residue was purified by prep-HPLC [Instrument: GX-B; Column: Welch Ultimate AQ-C18 150× 30 mm, particle size: 5 μm; Mobile phase: 10-40% acetonitrile in H$_2$O (add 0.1% TFA, v/v)]. The resulting solid was dissolved in 0.2 N hydrochloric acid and again lyophilized to give:

Compound (R)-37 (0.13 g, 16% yield over three steps) as a yellow solid: cSFC analytical(D) tR=3.11 min., purity: 100%; LCMS (X): tR=1.78 min., 326.1 m/z (M+1); 1H-NMR (CD$_3$OD, 400 MHz): δ 8.08 (s, 1H), 8.04-8.02 (m, 1H), 7.99-7.97 (m, 1H), 4.23-4.20 (m, 1H), 3.93-3.86 (m, 1H), 3.51-3.33 (m, 5H), 2.57 (s, 3H), 2.68-2.57 (m, 1H), 2.38-2.37 (m, 1H), 2.17-2.13 (m, 2H), 2.11-1.98 (m, 1H).

Example 38

(R)-7-methoxy-6-methyl-N-(quinuclidin-3-yl)benzo[d]isoxazol-3-amine hydrochloride ((R)-38)

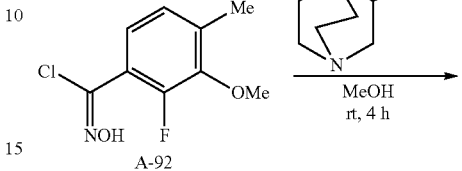

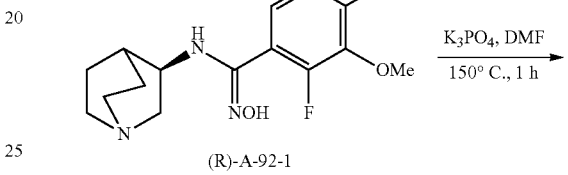

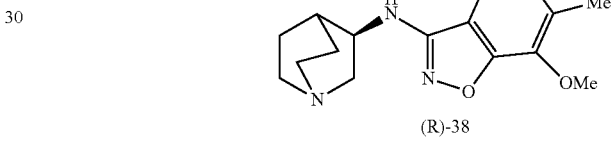

Following general procedure C1, compound (R)-38 was prepared from compound A-92:

Compound (R)-A-92-1 (0.13 g, yellow solid, 13% yield over two steps) was prepared from compound A-92 (0.50 g, 2.3 mmol) and (R)-quinuclidin-3-amine (0.4 g, 3.2 mmol) with a reaction time of 4 hours. The product was purified by prep-HPLC [Instrument: GX-C; Column: Phenomenex Gemini C18 250×50 mm, particle size: 10 μm; Mobile phase: 21-51% acetonitrile in H$_2$O (add 0.05% ammonia, v/v)]. LCMS (J): (ES$^+$) m/z (M+H)$^+$=308.2, tR=1.092 min.

A mixture of compound (R)-A-92-1 (0.13 g, 0.41 mmol) and potassium phosphate (0.26 g, 1.2 mmol) in N,N-dimethylformamide (20 mL) was stirred at 150° C. for 1 hour. On completion, the reaction mixture was filtered, concentrated in vacuo and purified by prep-HPLC [Instrument: GX-B; Column: Welch Ultimate AQ-C18 150×30 mm, particle size: 5 μm; Mobile phase: 23-53% acetonitrile in H$_2$O (add 0.1% TFA, v/v)]. The resulting solution was dissolved in 0.2 N hydrochloric acid and again lyophilized to give:

Compound (R)-38 (40 mg, 34% yield) as a white solid: cSFC analytical(D) tR=2.64 min., purity: 97.49%; LCMS (X): tR=1.90 min., 288.2 m/z (M+1); 1H-NMR (CD$_3$OD, 400 MHz): δ 7.39-7.38 (d, J=7.2 Hz, 1H), 7.10-7.08 (d, J=7.2 Hz, 1H), 4.18-4.16 (m, 1H), 4.14 (s, 3H), 3.86-3.85 (m, 1H), 3.43-3.29 (m, 5H), 2.56 (m, 1H), 2.55 (m, 1H), 2.55 (s, 3H), 2.54-2.51 (m, 2H), 2.35 (m, 1H).

Example 39

(R)-6-chloro-7-ethoxy-N-(quinuclidin-3-yl)benzo[d]isoxazol-3-amine hydrochloride ((R)-39)

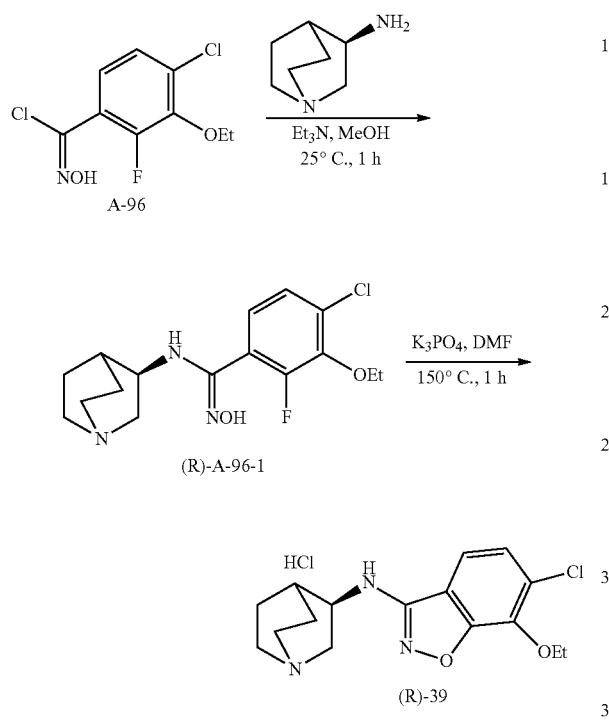

Following general procedure C1, compound (R)-39 was prepared from compound A-96:

Compound (R)-A-96-1 (0.30 g, white solid, 44% yield over two steps) was prepared from compound A-96 (0.50 g, 2.0 mmol) and (R)-quinuclidin-3-amine (0.30 g, 2.4 mmol). The product was purified by prep-HPLC [Instrument: GX-H; Column: Phenomenex Gemini C18 250×50 mm, particle size: 10 μm; Mobile phase: 30-60% acetonitrile in H$_2$O (add 0.5% ammonia, v/v)]. LCMS (J): (ES$^+$) m/z (M+H)$^+$=342.1, tR=1.223 min.

A solution of compound (R)-A-96-1 (0.20 g, 0.59 mmol) and potassium phosphate (0.37 g, 1.8 mmol) in N,N-dimethylacetamide (4.0 mL) was stirred at 150° C. for 1 hour. On completion, the reaction mixture was filtered and concentrated in vacuo. The residue was purified by prep-HPLC [Instrument: GX-A; Column: Phenomenex Synergi C18 150×30 mm, particle size: 4 μm; Mobile phase: 25-55% acetonitrile in H$_2$O (add 0.5% HCl, v/v)] to give:

Compound (R)-39 (60 mg, 29% yield) as a yellow solid: cSFC analytical (D) tR=2.600 min., purity: 96.70%; LCMS (EE): tR=2.12 min., 322.1 m/z (M+1); 1H-NMR (CD$_3$OD, 400 MHz): δ7.50-7.48 (d, J=8.4 Hz, 1H), 7.31-7.29 (d, J=8.0 Hz, 1H), 4.51-4.46 (dd, J=14 Hz, J=7.2 Hz, 1H), 4.18-4.16 (m, 1H), 3.89-3.83 (m, 1H), 3.47-3.31 (m, 5H), 2.57-2.54 (m, 1H), 2.36-2.32 (m, 1H), 2.16-2.10 (m, 2H), 1.98-1.96 (m, 1H), 1.45-1.42 (t, J=7.2 Hz, 3H).

Example 40

(R)-6,7-dimethyl-N-(quinuclidin-3-yl)benzo[d]isoxazol-3-amine hydrochloride ((R)-40) and (S)-6,7-dimethyl-N-(quinuclidin-3-yl)benzo[d]isoxazol-3-amine hydrochloride ((S)-40)

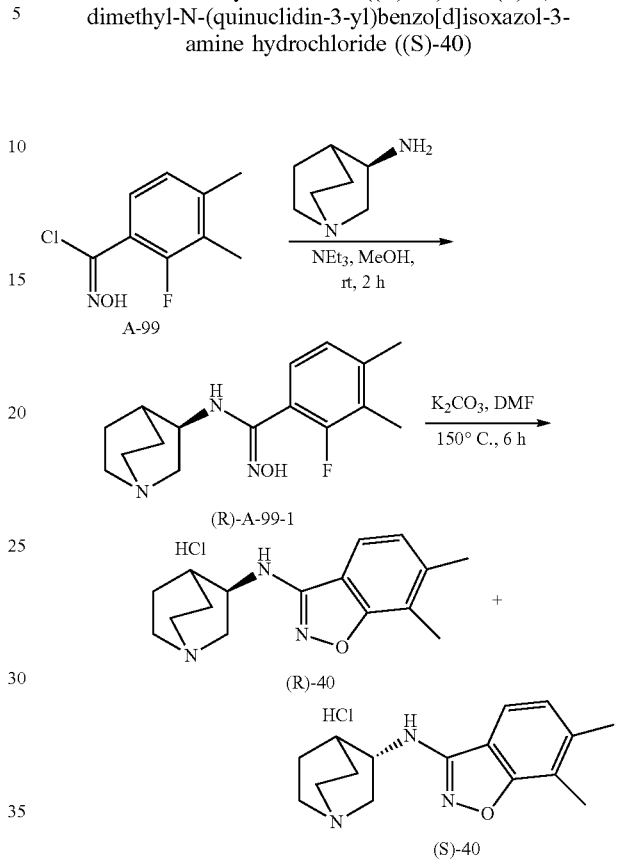

Following general procedure C1, compound (R)-40 was prepared from compound A-99:

Compound (R)-A-99-1 (0.60 g, yellow solid, 48% yield over two steps) was prepared from compound A-99 (1.9 g, 4.0 mmol) and (R)-quinuclidin-3-amine (0.50 g, 4.0 mmol) with a reaction of 2 hours. The product was purified by prep-HPLC [Instrument: GX-B; Column: Phenomenex Gemini C18 250×50 mm, particle size: 10 μm; Mobile phase: 25-48% acetonitrile in H$_2$O (add 0.05% NH$_3$.H$_2$O, v/v)]. LCMS (M): tR=0.529 min., 292.2 m/z (M+1).

A solution of compound (R)-A-99-1 (0.58 g, 1.8 mmol) and potassium carbonate (0.76 g, 5.5 mmol) in N,N-dimethylformamide (3.0 mL) was stirred at 150° C. for 6 hour. On completion, the reaction mixture was filtered, concentrated in vacuo and purified by prep-HPLC [Instrument: GX-H; Column: Phenomenex Gemini C18 150×25 mm, particle size: 10 μm; Mobile phase: 36-66% acetonitrile in H$_2$O (add 0.05% NH$_3$.H$_2$O-ACN, v/v)]. The resulting solution was lyophilized to give:

Compound (R)-40 (210 mg, 42% yield) as a white solid: cSFC analytical (D) tR=2.7 min., chiral purity: 78%;

A solution of compound (R)-40 at 78% chiral purity (210 mg, 0.77 mmol) in 4 mL of ethanol was purified by SFC (Instrument: SFC A; Column: AD-10 μm; Mobile phase: 50% ethanol (0.01% NH$_3$.H$_2$O) in CO$_2$) at room temperature. In addition to the major product compound (R)-40, the minor product compound (S)-40 was also collected. Each set of collected fractions was concentrated at room temperature and lyophilized.

The resulting solids were re-purified by prep-HPLC [Instrument: GX-C; Column: Phenomenex Gemini C18 250×50 mm, particle size: 10 μm; Mobile phase: 46-76% acetonitrile in H₂O (add 0.05% NH₃.H₂O, v/v)]. The resulting solids was dissolved in 0.2 M hydrochloric acid solution and again lyophilized to give:

Compound (R)-40 (100 mg, 48% yield) as a yellow solid: cSFC analytical (D) tR=2.789 min., purity: 99.85%; LCMS (GG): tR=1.976 min., (ES⁺) m/z (M+H)⁺=272.2; 1H-NMR (CD₃OD, 400 MHz): δ7.56-7.54 (d, J=8.4 Hz, 1H), 7.12-7.10 (d, J=8.0 Hz, 1H), 4.17-4.16 (m, 1H), 3.88-3.85 (m, 1H), 3.42-3.36 (m, 5H), 2.56-2.53 (m, 1H), 2.42-2.39 (m, 7H), 2.14-1.96 (m, 3H); and Compound (S)-40 (20 mg, 9.5% yield) as a yellow solid: cSFC analytical (D) tR=3.726 min., purity: 98.48%; LCMS (GG): tR=1.953 min., (ES+) m/z (M+H)⁺=272.2; 1H-NMR (CD3OD, 400 MHz): δ7.56-7.54 (d, J=8.0 Hz, 1H), 7.11-7.09 (d, J=8.0 Hz, 1H), 4.16-4.15 (m, 1H), 3.86-3.81 (m, 1H), 3.41-3.31 (m, 5H), 2.53-2.52 (m, 1H), 2.40-2.37 (m, 7H), 2.11-1.94 (m, 3H).

Example 41

Preparation: (R)-6-chloro-7-fluoro-N-(quinuclidin-3-yl)benzo[d]isoxazol-3-amine ((R)-41)

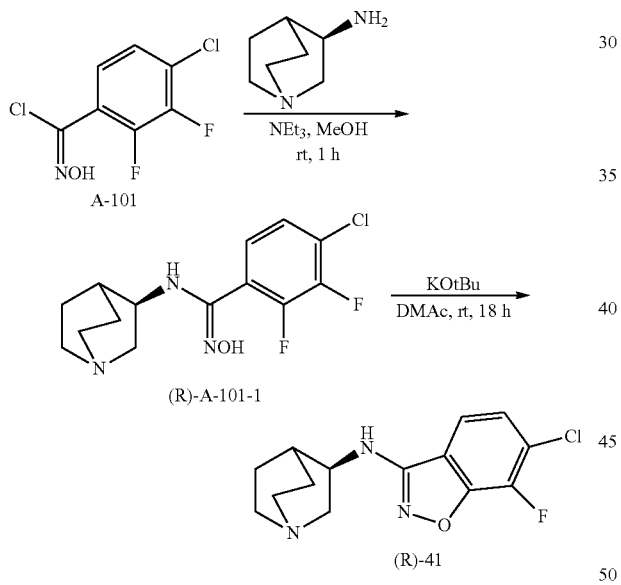

Following general procedure C2, compound (R)-41 was prepared from compound A-101:

Compound (R)-A-101-1 (88 mg, 70% yield) was prepared as a white solid from A-101 (165 mg, 0.7 mmol) and (R)-quinuclidin-3-amine (63 mg, 0.5 mmol) using 5 mL of methanol and a reaction time of 1 hour. The product purified by silica gel column chromatography [chloroform:methanol=1:0 to 17:3]. LCMS (1): tR=3.163 min., (ES⁺) m/z (M+H)⁺=316.0.

To a solution of compound (R)-A-101-1 (103 mg, 0.3 mmol) in N,N-dimethylacetamide (5 mL) was added potassium tertbutoxide (37 mg, 0.3 mmol). The mixture was stirred at room temperature for 16 hours. Additional potassium tertbutoxide (9 mg, 0.1 mmol) was added, and the mixture was stirred for an additional 2 hours. The solution was put on an SCX column and eluted with methanol. The product was eluted from the column using 7 M ammonia in methanol, concentrated and purified by silica gel column chromatography [chloroform: 7M NH₃ in methanol=99:1 to 9:1]. The resulting product was triturated with water, collected by filtration and dried in a vacuum oven to afford:

Compound (R)-41 (32 mg, 32% yield) as a white solid: cHPLC analytical [Chiralcel OD-H, 250×4.6 mm, particle size: 5 μm; Flow: 1.0 mL/min; Column temp: 25° C.; Mobile phase: 0.1% diethylamine in Heptane/Ethanol=9/1; detection: DAD (220-320 nm)] tR=6.105 min., purity: 100%; LCMS (1): tR=3.269 min., (ES+) m/z (M+H)+=296.0; 1H NMR (300 MHz, CDCl₃) δ 7.28-7.17 (m, 2H), 4.27 (d, J=5.3 Hz, 1H), 3.90-3.79 (m, 1H), 3.54-3.42 (m, 1H), 2.96-2.74 (m, 4H), 2.67-2.56 (m, 1H), 2.27-2.19 (m, 1H), 1.86-1.62 (m, 3H), 1.56-1.42 (m, 1H).

The hydrochloride salt form of compound (R)-41 was also prepared by dissolving the freebase form of compound (R)-41 in 0.2 N hydrochloric acid and subjected to lyophilization to give:

Compound (R)-41-hydrochloride as a white solid: cSFC analytical (D) tR=2.31 min., purity: 98.36%; LCMS (FF): tR=1.98 min., 296.1 m/z (M+1); 1H-NMR (CD3OD, 400 MHz): δ 7.67-7.72 (d, J=8.4 Hz 1H), 7.38-7.36 (dd, J=5.6 Hz, J=8.4 Hz, 1H), 4.18-4.16 (m, 1H), 3.88-3.82 (m, 1H), 3.41-3.34 (m, 5H), 2.55-2.53 (m, 1H), 2.37-2.30 (m, 1H), 2.18-2.04 (m, 2H), 2.00-1.93 (m, 1H).

Preparation: (S)-6-chloro-7-fluoro-N-(quinuclidin-3-yl)benzo[d]isoxazol-3-amine ((S)-41)

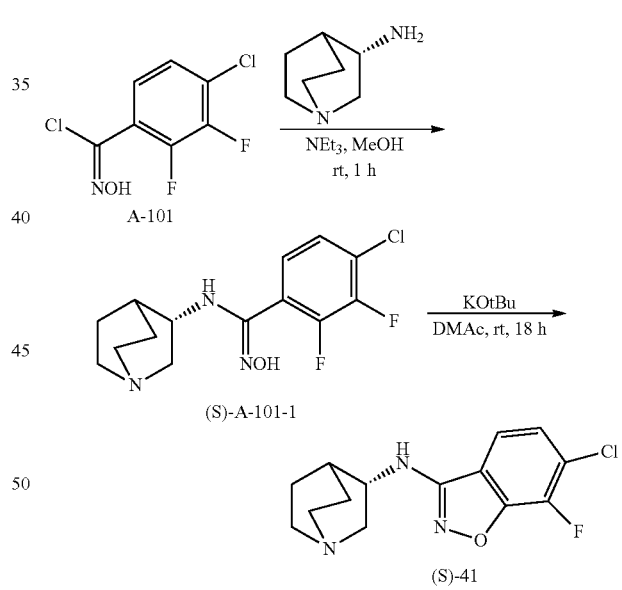

Following general procedure C2, compound (S)-41 was prepared from compound A-101:

Compound (S)-A-101-1 (171 mg, 74% yield) was prepared as a white solid from A-101 (165 mg, 0.7 mmol) and (S)-quinuclidin-3-amine (92 mg, 0.7 mmol) using 6 mL of methanol and a reaction time of 1 hour. The product purified by silica gel column chromatography [chloroform: 7M NH₃ in methanol=99:1 to 9:1]. LCMS (1): tR=2.847 min., (ES⁺) m/z (M+H)⁺=316.0.

To a solution of compound (S)-A-101-1 (171 mg, 0.5 mmol) in N,N-dimethylacetamide (5 mL) was added potassium tertbutoxide (73 mg, 0.7 mmol). The mixture was stirred at room temperature for 2 hours. Additional potassium tertbutoxide (15 mg, 0.1 mmol) was added, and the mixture was stirred for an additional 16 hours. The solution was put on an SCX column and eluted with methanol. The product was eluted from the column using 7 M ammonia in methanol, concentrated and purified by silica gel column chromatography [chloroform: 7M $NH_3$ in methanol=99/1 to 9/1]. The resulting product was further purified by preparative HPLC [Instrument: AT; Column: Phenomenex Gemini-NX C18 100×21.2 mm, particle size: 10 μm; Mobile phase A: 99% acetonitrile+1% 10 mM ammonium bicarbonate in water pH=9.0, Mobile phase B: 10 mM ammonium bicarbonate in water pH=9.0] and lyophilized to afford:

Compound (S)-41 (45 mg, 28% yield) as a white solid: cHPLC analytical [Chiralcel OD-H, 250×4.6 mm, particle size: 5 μm; Flow: 1.0 mL/min; Column temp: 25° C.; Mobile phase: 0.1% diethylamine in Heptane/Ethanol=9/1; detection: DAD (220-320 nm)] tR=17.874 min., purity: 98%; LCMS (1): tR=3.305 min., (ES+) m/z (M+H) +=296.0; H NMR (300 MHz, $CDCl_3$) δ 7.28-7.18 (m, 2H), 4.30 (d, J=5.2 Hz, 1H), 3.89-3.83 (m, 1H), 3.55-3.43 (m, 1H), 2.98-2.80 (m, 4H), 2.69-2.59 (m, 1H), 2.28-2.21 (m, 1H), 1.90-1.63 (m, 3H), 1.53-1.46 (m, 1H).

Example 42

Preparation: (R)-6-chloro-5-fluoro-N-(quinuclidin-3-yl)benzo[d]isoxazol-3-amine ((R)-42)

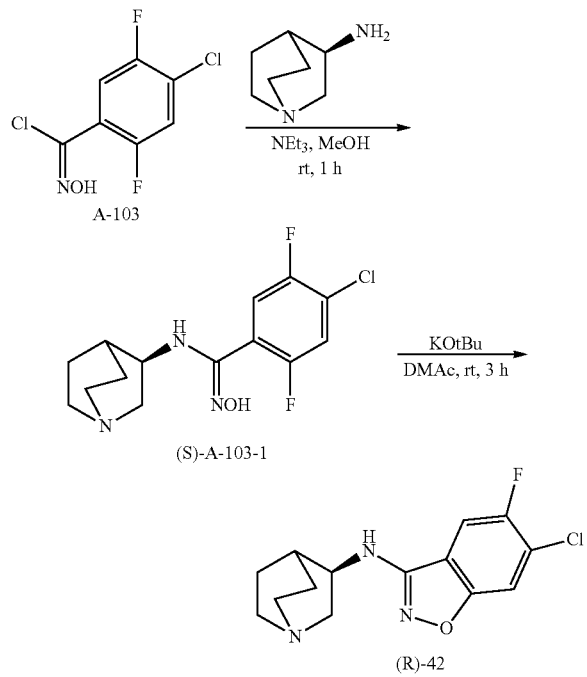

Following general procedure C2, compound (R)-42 was prepared from compound A-103:

Compound (R)-A-103-1 ((88 mg, 70% yield) was prepared as a white solid from A-103 (90 mg, 0.4 mmol) and (R)-quinuclidin-3-amine (50 mg, 0.4 mmol) using 4 mL of methanol and a reaction time of 1 hour. The product was purified by silica gel column chromatography [chloroform: methanol=1:0 to 17:3]. LCMS (1): tR=2.788 min., (ES$^+$) m/z (M+H)$^+$=316.0.

To a solution of compound (R)-A-103-1 (77 mg, 0.2 mmol) in N,N-dimethylacetamide (3 mL) was added potassium tertbutoxide (33 mg, 0.3 mmol). The mixture was stirred at room temperature for 2 hours. Additional potassium tertbutoxide (7 mg, 0.1 mmol) was added, and the mixture was stirred for an additional hour. The solution was put on an SCX column and eluted with methanol. The product was eluted from the column using 7 M ammonia in methanol, concentrated and purified by silica gel column chromatography [chloroform: 7M $NH_3$ in methanol=99:1 to 9:1]. The resulting product was lyophilized to afford:

Compound (R)-42 (30 mg, 41% yield) as a white solid: cHPLC analytical [Column: Chiralcel OD-H, 250×4.6 mm, particle size: 5 μm; Flow: 1.0 mL/min; Column temp: 25° C.; Mobile phase: 0.1% diethylamine in Heptane/Ethanol=9/1; detection: DAD (220-320 nm)] tR=5.949 min., purity: 99%; LCMS (1): tR=3.275 min., (ES+) m/z (M+H)+=296.0; $^1$H NMR (300 MHz, $CDCl_3$) δ 7.49 (d, J=5.5 Hz, 1H), 7.27 (d, J=7.8 Hz, 1H), 4.19 (d, J=5.5 Hz, 1H), 3.89-3.78 (m, 1H), 3.53-3.42 (m, 1H), 2.96-2.79 (m, 4H), 2.67-2.56 (m, 1H), 2.26-2.18 (m, 1H), 1.85-1.63 (m, 3H), 1.56-1.42 (m, 1H).

Preparation: (S)-6-chloro-5-fluoro-N-(quinuclidin-3-yl)benzo[d]isoxazol-3-amine ((S)-42)

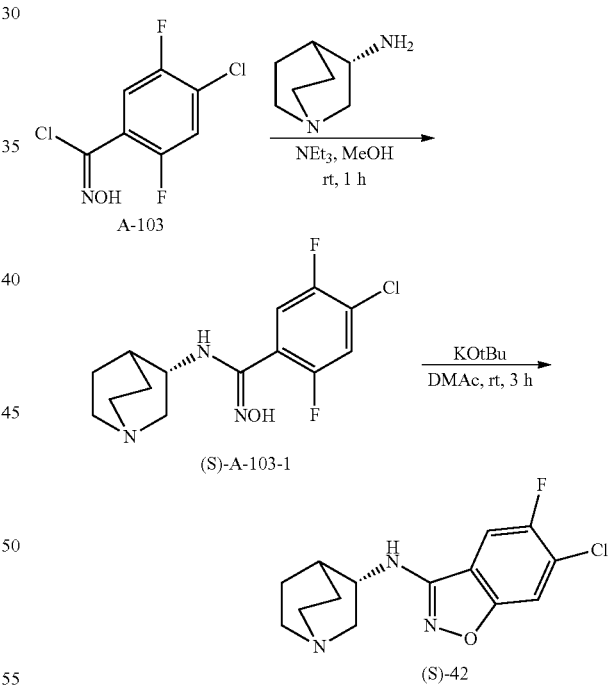

Following general procedure C2, compound (S)-42 was prepared from compound A-103:

Compound (S)-A-103-1 (167 mg, 35% yield) was prepared as a white solid from A-103 (185 mg, 0.8 mmol) and (S)-quinuclidin-3-amine (103 mg, 0.8 mmol) using 6 mL of methanol and a reaction time of 1 hour. The product was purified by silica gel column chromatography [chloroform: 7M $NH_3$ in methanol=99:1 to 9:1] to afford (S)-A-103-1 (167 mg, 65% yield) as a white solid. LCMS (1): tR=2.806 min., (ES$^+$) m/z (M+H)$^+$=316.0.

To a solution of compound (S)-A-103-1 (167 mg, 0.5 mmol) in N,N-dimethylacetamide (5 mL) was added potassium tertbutoxide (71 mg, 0.6 mmol). The mixture was stirred at room temperature for 2 hours. Additional potassium tertbutoxide (15 mg, 0.1 mmol) was added, and the mixture was stirred for an additional 16 hours. The solution was put on an SCX column and eluted with methanol. The product was eluted from the column using 7 M ammonia in methanol, concentrated and purified by silica gel column chromatography [chloroform: 7M $NH_3$ in methanol=99/1 to 9/1]. The resulting product was lyophilized to afford:

Compound (S)-42 (65 mg, 42% yield) as a white solid: cHPLC analytical [Column: Chiralcel OD-H, 250×4.6 mm, particle size: 5 μm; Flow: 1.0 mL/min; Column temp: 25° C.; Mobile phase: 0.1% diethylamine in Heptane/Ethanol=9/1; detection: DAD (220-320 nm)] tR=9.752 min., purity: 98%; LCMS (1): tR=3.244 min., (ES+) m/z (M+H)+=296.0; 1H NMR (300 MHz, $CDCl_3$) δ 7.49 (d, J=5.5 Hz, 1H), 7.27 (d, J=7.9 Hz, 1H), 4.21 (d, J=5.1 Hz, 1H), 3.93-3.75 (m, 1H), 3.56-3.41 (m, 1H), 3.03-2.72 (m, 4H), 2.71-2.53 (m, 1H), 2.28-2.16 (m, 1H), 1.92-1.59 (m, 3H), 1.58-1.40 (m, 1H).

Example 43

(R)-6-bromo-N-(quinuclidin-3-yl)benzo[d]isoxazol-3-amine ((R)-43)

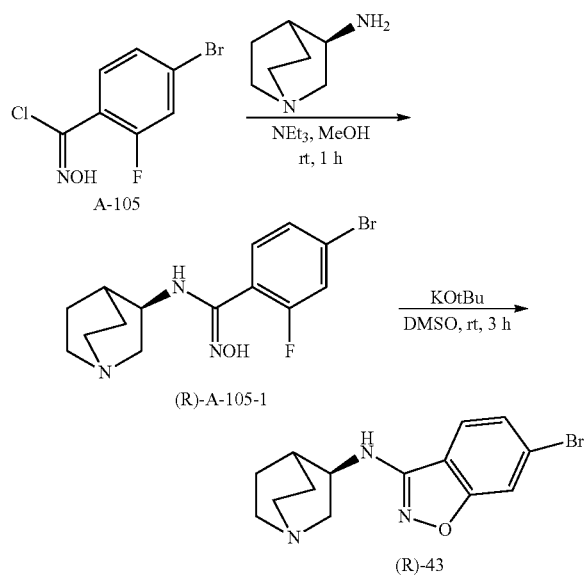

Following general procedure C2, compound (R)-43 was prepared from compound A-105:

Compound (R)-A-105-1: To a solution of (R)-quinuclidin-3-amine (634 mg, 5.0 mmol) and triethylamine (533 mg, 5.3 mmol) in methanol (12 mL) at room temperature was added a solution of compound A-105 (1.3 g, 5.3 mmol) in methanol (25 mL) over 4 hours using a syringe pump. The mixture was stirred for an additional 12 hours, then filtered and concentrated in vacuo. The residue was purified by silica gel column chromatography [chloroform: 7M $NH_3$ in methanol=99:1 to 9:1] to afford (R)-A-105-1 (1.2 g, 70% yield) as a white solid. LCMS (1): tR=2.753 min., (ES+) m/z (M+H)+=342.0/344.0.

To a solution of (R)-A-105-1 (320 mg, 0.9 mmol) in dimethylsulfoxide (5 mL) was added potassium tertbutoxide (131 mg, 1.2 mmol). The mixture was stirred at room temperature for 1.5 hours. Additional potassium tert-butoxide (60 mg, 0.5 mmol) was added, and the mixture was stirred for an additional hour. Additional potassium tertbutoxide (40 mg, 0.4 mmol) was added, and the mixture was stirred for 30 min. The solution was put on an SCX column and eluted with methanol. The product was eluted from the column using 3.5 M ammonia in methanol, concentrated and purified by silica gel column chromatography [chloroform: 7M $NH_3$ in methanol=1/0 to 9/1]. The resulting product was further purified by preparative HPLC [Instrument: AT; Column: Phenomenex Gemini-NX C18 100×21.2 mm, particle size: 10 μm; Mobile phase A: 99% acetonitrile+1% 10 mM ammonium bicarbonate in water pH=9.0, Mobile phase B: 10 mM ammonium bicarbonate in water pH=9.0] and lyophilized to afford:

Compound (R)-43 (91 mg, 21% yield) as a white solid: LCMS (1): tR=3.222 min., (ES+) m/z (M+H)+=322.0/324.0; 1H NMR (300 MHz, $CDCl_3$) δ 7.61 (dd, J=1.3, 0.8 Hz, 1H), 7.41-7.32 (m, 2H), 4.29 (d, J=5.0 Hz, 1H), 3.88-3.84 (m, 1H), 3.54-3.42 (m, 1H), 2.98-2.80 (m, 4H), 2.70-2.59 (m, 1H), 2.29-2.21 (m, 1H), 1.88-1.64 (m, 3H), 1.56-1.45 (m, 1H).

Example 44

Human α7 nAChR Binding Assay

The ability of compounds to displace binding of radioactive ligands from human α7 nAChR was determined, as a measure of the affinity of the compounds for these ligand-gated ion channels. The [$^{125}$I]-αBungarotoxin competition binding assay was performed under contract by Cerep Poitiers, France following published the methods (Sharples et al., J Neurosci. 2000; 20(8):2783-91). "SH-SY5Y cells stably expressing human α7 nicotinic acetylcholine receptors, grown to confluency in 175 $cm^2$ flasks, were washed briefly with warm PBS containing (in mm): (150 NaCl, 8 $K_2HPO_4$, 2 $KH_2PO_4$, pH 7.4, 37° C.) and scraped into cold phosphate buffer. Cells were washed by centrifugation for 3 min at 500×g and resuspended in 10 mL of ice-cold phosphate buffer. The suspension was homogenized for 10 sec using an Ultraturax and centrifuged for 30 min at 45,000×g. The pellet was resuspended in phosphate buffer (0.5 mL per original flask). SH-SY5Y membranes (30 μg protein) were incubated in a total volume of 2 mL in 50 mM phosphate buffer with 0.05 nM [$^{125}$I]-αBgt and serial dilutions of test compound. Nonspecific binding was determined in the presence of α-bungarotoxin (1 μM). Samples were incubated for 120 min at 37° C. The reaction was terminated by filtration through Whatman GFA/E filter paper (presoaked overnight in 0.3% polyethyleneimine in PBS), using a Brandel Cell Harvester. Each condition was measured in duplicate. Filters were counted for radioactivity using a scintillation counter. The results were expressed as a percent inhibition of control specific binding obtained in the presence of the test compounds where Inhibition (%)=100−[(measured specific binding/control specific binding)×100].

The $IC_{50}$ values (concentration causing a half-maximal inhibition of control specific binding) and Hill coefficients (nH) were determined by non-linear regression analysis of the competition curves generated with mean replicate values using Hill equation:

$$Y = D + \left[\frac{A - D}{1 + (C/C_{50})^{nH}}\right]$$

where Y=specific binding, A=left asymptote of the curve, D=right asymptote of the curve, C=compound concentration, $C_{50}=IC_{50}$, and nH=slope factor.

This analysis was performed using software developed at Cerep (Hill software) and validated by comparison with data generated by the commercial software SigmaPlot® 4.0 for Windows® (© 1997 by SPSS Inc.). The inhibition constants ($K_i$) were calculated using the Cheng Prusoff equation:

$$K_i = \frac{IC_{50}}{(1 + L/K_D)}$$

where L=concentration of radioligand in the assay, and $K_D$=affinity of the radioligand for the receptor.

A scatchard plot is used to determine the $K_D$. Results are provided in Table 2 (reported as h-α7 Ki (μM)).

[$^3$H]BRL 43694 competition binding (h-5HT$_3$ Ki (μM))

[$^3$H]BRL 43694 competition binding assay was performed under contract by Cerep Poitiers, France following the methods described in Hope, A. G et al., "*Characterization of a human 5-hydroxytryptamine3 receptor type A (h5-HT3R-AS) subunit stably expressed in HEK 293 cells,*" Brit. J. Pharmacol., (1996) 118: 1237-1245.

In brief, Chinese Hamster Ovary (CHO) cells stably expressing human 5-HT$_3$ serotonin receptors, grown to confluence in 175 cm$^2$ flasks. Following aspiration of the culture medium, cells were harvested by mechanical agitation in ice cold PBS containing (in mM): (150 NaCl, 8 K$_2$HPO$_4$, 2 KH$_2$PO$_4$, pH 7.4, 37° C.), centrifuged at 4,000 g for 10 min and subsequently stored as a cell pellet at −80 C. When required, the pellet was thawed and resuspended in ice cold homogenization buffer (Tris 50 mM, EGTA 5.0 mM, phenylmethylsulphonylfluoride 0.1 mM, pH 7.6) and homogenized. The homogenate was centrifuged at 48,000 g for 10 minutes at 40° C. The resulting pellet was resuspended in ice cold binding buffer comprising (in mM): NaCl 140, KCl 2.8, CaCl$_2$ 1.0; MgCl$_2$, 2.0; HEPES 10 (pH 7.4) and centrifuged as above. The pellet was resuspended in ice cold binding buffer and the protein concentration was determined by the method of Lowry et al., "*Protein measurement with the Folin phenol reagent,*" J. Biol. Chem., (1953) 193, 265-275). The membrane homogenate was adjusted to a protein concentration of approximately 600 mg/mL in binding buffer. Assay tubes were loaded with equal volumes of binding buffer containing [$^3$H]BRL 43694 and test compound and 0.5 mL of membrane homogenate in a total reaction volume of 1 ml. Binding was initiated by the addition of the membrane homogenate and allowed to proceed for 120 min. at room temperature. Bound and free radioligand were separated by the addition of 3 ml of ice-cold binding buffer and immediate vacuum filtration through pre-soaked (0.1% (v/v) polyethyleneimine) Whatman GF/B filters. Filters were washed with a further 2×3 mL applications of binding buffer and counted for radioactivity using a scintillation counter.

The results were expressed as a percent inhibition of control specific binding obtained in the presence of the test compounds where Inhibition (%)=100−[(measured specific binding/control specific binding)×100].

The IC$_{50}$ values (concentration causing a half-maximal inhibition of control specific binding) and Hill coefficients (nH) were determined by non-linear regression analysis of the competition curves generated with mean replicate values using Hill equation $$Y = D + \left[\frac{A - D}{1 + (C/C_{50})^{nH}}\right]$$

where Y=specific binding, A=left asymptote of the curve, D=right asymptote of the curve, C=compound concentration, $C_{50}$=IC$_{50}$, and nH=slope factor. This analysis was performed using software developed at Cerep (Hill software) and validated by comparison with data generated by the commercial software SigmaPlot® 4.0 for Windows® (© 1997 by SPSS Inc.).

The inhibition constants ($K_i$) were calculated using the Cheng Prusoff equation $$K_i = \frac{IC_{50}}{(1 + L/K_D)}$$

where L=concentration of radioligand in the assay, and $K_D$=affinity of the radioligand for the receptor.

A scatchard plot is used to determine the $K_D$. Results are provided in Table 2 (reported as h-5HT$_3$ Ki (μM)).

For reference, the literature reported α7 nAChR agonist AQW051 has a $K_i$ of 255 nM in the above described assay provided by Cerep (lit: $K_i$=28 nM; radioligand binding assay using recombinantly expressed human α7-nAChR and [$^{125}$I] α-BTX radioligand; Feuerbach et al., Br. J. Pharmacol., 2014, doi: 10.1111/bph.13001).

Oocyte Electrophysiology Screen (% ACh @ 10 μM Oocyte)

The Oocyte Electrophysiology Screen studies were performed under contract by HiQScreen Geneva, Switzerland. All experiments were carried out at human α7 nAChRs transiently expressed in *Xenopus laevis* oocytes using the method of cDNA expression. Currents evoked by acetylcholine or other agonist ligands were recorded using the standard two-electrode voltage-clamp configuration (TEVC). *X. laevis* oocytes were prepared and injected using standard procedures. Briefly, ovaries were harvested from *X. laevis* females that were deeply anesthetized and pithed following the animal rights rule from the Geneva canton. A small piece of ovary was isolated for immediate preparation while the remaining part was placed at 4° C. in a sterile Barth solution containing in mM: NaCl 88, KCl 1, NaHCO$_3$ 2.4, HEPES 10, MgSO$_4$.7H$_2$O 0.82, Ca(NO$_3$)$_2$.4H$_2$O 0.33, CaCl$_2$.6H$_2$O 0.41, at pH 7.4, and supplemented with 20 μg/mL of kanamycin, 100 unit/mL penicillin and 100 μg/mL streptomycin. On the second day following dissociation, oocytes were injected with 2 ng of cDNA per oocyte containing the gene encoding human α7 nicotinic acetylcholine receptor subunits using an automated injector (Hogg et al., 2008). All recordings were performed at 18° C. and cells were superfused with OR2 medium containing in mM: NaCl 82.5, KCl 2.5, HEPES 5, CaCl$_2$.2H$_2$O 2.5, pH 7.4. Cells were held at −80 mV. Data were filtered at 10 Hz, captured at 100 Hz and analyzed using proprietary data acquisition and analysis software running under Matlab (Mathworks Inc.).

Experimental Protocol and Analysis

After establishing a baseline transmembrane current, acetylcholine (ACh) was applied for 5 seconds at a concentration of 0.2 mM to establish a control ACh-evoked current response. Following a wash period of 90 s in OR2 medium (free of ACh), cells were then exposed for 30 s to the test compound applied at 0.01 mM. The same reference ACh test pulse was immediately given at the end of the compound exposure and again after 90 s of recovery in OR2 Medium (free of ACh or test compound). All data were determined in triplicate. The response evoked by the test compound was expressed as a percentage of that evoked by ACh:

Response (% $ACh$)=100×($I_{test}/I_{ACh}$)

where $I_{test}$ is the peak inward current measured during exposure to 0.01 mM of test compound and $I_{ACh}$ is the peak inward current measured in the presence of ACh.

Results are provided in Table 2 (reported as % ACh @ 10 µM Oocyte). Table 2:

TABLE 2

| Compound | h-α7 $K_i$ (µM) | h-5HT$_3$ $K_i$ (µM) | % ACh @ 10 µM Oocyte |
|---|---|---|---|
| 1-P1 | 0.815 | 1.9 | 483 |
| 1-P2 | 5.05 | 0.069 | 206 |
| 2-P1 | 0.37 | 0.019 | 418 |
| 2-P2 | 3.5 | | 363 |
| 3-P1 | 0.032 | 1.4 | 465 |
| 3-P2 | 0.4575 | 0.25 | 379 |
| (R)-3 | 0.057 | | |
| 4-P1 | 1 | | 326 |
| 4-P2 | 16 | | 17 |
| 5-P1 | 1 | 0.16 | 548 |
| 5-P2 | 0.159 | 1.85 | 645 |
| 6-P1 | 0.96 | 1.6 | 157 |
| 6-P2 | 0.41 | >10 | 355 |
| 7-P1 | 0.36 | 0.74 | 326 |
| 7-P2 | 0.032 | 4.2 | 427 |
| 8-P1 | 6.8 | | 26 |
| 8-P2 | 1.2 | | 221 |
| 9-P1 | 0.0435 | 0.0595 | |
| 9-P2 | 0.29 | 0.026 | |
| (R)-10 | >30 | | |
| (R)-11 | 0.54 | 1.9 | |
| (R)-12 | 0.74 | | |
| (R)-13 | >30 | | |
| (S)-13 | >30 | | |
| (R)-14 | >30 | | |
| (R)-15 | 0.93 | | |
| (S)-15 | 52 | | |
| (R)-16 | 2.2 | | |
| (R)-17 | 1.7 | 0.24 | |
| (R)-18 | 2 | | |
| (S)-18 | 24 | | |
| (R)-19 | 9.7 | | |
| (R)-20 | 0.22 | 0.58 | |
| (R)-21 | 0.82 | 1.5 | |
| (R)-22 | 0.14 | 3 | |
| (R)-23 | 0.071 | 0.19 | |
| (R)-24 | 0.14 | 0.4 | |
| (R)-25 | 0.245 | 4.1 | |
| (R)-26 | 11 | 1.2 | |
| (R)-27 | 0.7 | | |
| (R)-28 | 14 | | |
| (R)-29 | 0.925 | >10 | |
| (R)-30 | 2.5 | 0.28 | |
| (S)-30 | 7.4 | | |
| (R)-31 | 0.18 | 0.029 | |
| (R)-32 | 4.3 | | |
| (S)-32 | 18 | | |
| (R)-33 | 0.75 | >10 | |
| (S)-33 | 5.8 | | |
| (R)-35 | 0.18 | 0.065 | |
| (R)-36 | 0.7 | | |
| (R)-37 | 9 | | |
| (R)-39 | 0.12 | 6.9 | |
| (R)-41 | 0.046 | 1.6333 | |
| (S)-41 | 0.67 | | |
| (R)-42 | 0.26 | 1.55 | |
| (S)-42 | 0.98 | | |
| (R)-43 | 0.044 | 0.93 | |

Example 45

Novel Object Recognition Task:

The Novel Object Recognition (NOR) task is a behavioral assay commonly used to evaluate cognition, particularly recognition memory, in rodent models of CNS disorders. This test is based on the spontaneous tendency of rodents to spend more time exploring a novel object compared to a familiar one. The choice to explore the novel object reflects the use of learning and recognition memory. The assay is commonly used to evaluate potential therapeutic agents for Alzheimer's disease, other neurodegenerative diseases and psychiatric disorders.

Procedure:

Male Wistar rats (Harlan Laboratories) weighing 350-400 grams were housed under a reversed light cycle and are tested during the dark cycle. Testing was done under low lux conditions, measured to be ~2-7 lux under red light. Animals were habituated and weighed one day prior to testing. During habituation, animals were placed in a cylindrical arena and allowed to explore for 3 minutes. Training (T1) was conducted approximately 24 hours later, with one set of identical objects placed on opposite sides of the arena. Animals were allowed to explore the objects in 3-minute sessions. Animals were dosed with a designated treatment 15-60 minutes prior to testing depending on the pharmacokinetic profile of the compound before the start of T1. Drug or vehicle was dosed subcutaneously based on body weight at 5 mL/kg. Testing (T2) was done at 48 hours after T1. During testing, one familiar object is replaced with a novel object. Animals were allowed to explore both objects in 3-minute sessions.

Equipment Specification:

Animals were tracked using Noldus Ethovision XT (EthoVision XT version: 8.5, Noldus Inc. Wageningen, Netherlands) tracking software, using a 2 centimeter (cm) perimeter for each object as a separate zone. The test arena consisted of a cylinder, 80 cm diameter with 40 cm high walls of black acrylic that was opaque and matte. Objects were custom fabricated shapes (cone and bullet) similar in overall size (8 cm high×8 cm diameter) and were counterbalanced between treatment groups.

Data Analysis and Statistics:

Contact time was defined as the amount of time (seconds) an animal spent within the 2 cm perimeter of an object. All animals that had ≤5 seconds total contact time were excluded from the study. Statistical significance was determined using a Mann Whitney U-test and the criterion was set at p<0.05.

Results:

Natural forgetting in an object recognition task in male Wistar rats (n=4-20/group). Test compound was administered via sub-cutaneous administration 30 minutes before T1. Test compounds improved object recognition using a 48-hour retention interval (mean±SEM). *p<0.05=novel (N) vs. familiar (F) object. Results are illustrated in Table 3.

TABLE 3

| Compound | Active doses (mg/kg) |
|---|---|
| 3-P1 | 0.003, 0.01 |
| (R)-41 | 0.003, 0.03, 0.1 |

All publications and patent applications mentioned in this specification are herein incorporated by reference to the same extent as if each individual publication or patent application was specifically and individually indicated to be incorporated by reference.

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A compound represented by Formula (Ia) or Formula (Ib):

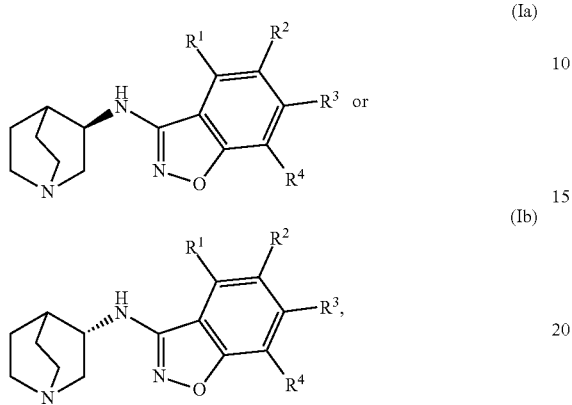

wherein:
$R^1$, $R^2$, $R^3$, and $R^4$ independently represent —H, -D, halogen radical, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —$N(R^5)(R^6)$, —$(CO)N(R^5)(R^6)$, —$NR^5(CO)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, an aryl radical, or a heteroaryl radical; wherein the alkyl portion of the unbranched $C_1$-$C_4$-alkyl radical, the branched $C_3$-$C_4$-alkyl radical, the $C_3$-$C_6$-cycloalkyl radical, the unbranched —$OC_1$-$C_4$-alkyl, the branched or cyclic —$OC_3$-$C_4$-alkyl, the —$SO_2C_1$-$C_4$-alkyl, the —$(CH_2)_mSO_2C_1$-$C_4$-alkyl, or the —$N(R^5)SO_2C_1$-$C_4$-alkyl, may be independently substituted with up to 5 radical substituents comprising: -D, halogen radical, =O, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein the aryl radical or the heteroaryl radical may be independently substituted with up to 5 radical substituents comprising: -D, halogen radical, —CN, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical;

$R^5$ and $R^6$ independently represent —H; an unbranched $C_1$-$C_6$-alkyl radical, a branched $C_3$-$C_6$-alkyl radical; a $C_3$-$C_6$-cycloalkyl radical; or the $N(R^5)(R^6)$ moiety forms a cycle, wherein $R^5$ and $R^6$ taken together represent a $C_2$-$C_6$-alkyl di-radical or a (3-6 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H, an unbranched $C_1$-$C_4$-alkyl radical, a branched $C_3$-$C_4$-alkyl radical, a $C_3$-$C_4$-cycloalkyl radical, —(CO)-unbranched $C_1$-$C_4$-alkyl, —(CO)-branched $C_3$-$C_4$-alkyl, —$(SO_2)$-unbranched $C_1$-$C_4$-alkyl, or —$(SO_2)$-branched $C_3$-$C_4$-alkyl, and with the further proviso that when the at least one ring atom is sulfur, the sulfur may be independently substituted with 0 to 2 =O; wherein the $C_2$-$C_6$-alkyl di-radical or the alkyl portion of said (3-6 membered)-heteroalkyl di-radical may be independently substituted with up to 5 radical substituents comprising: -D, halogen radical, =O, an unbranched $C_1$-$C_6$-alkyl radical, or a branched $C_3$-$C_6$-alkyl radical; and m independently represents an integer from 1 to 6; or a pharmaceutically acceptable salt thereof.

2. The compound of claim 1, wherein $R^1$ independently represents —H, -D, or halogen radical.

3. The compound of claim 1, where $R^2$ independently represents —H, -D, or halogen radical.

4. The compound of claim 1, wherein $R^3$ independently represents —H, -D, —F, —Cl, —Br, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —$N(R^5)(R^6)$, —$(CO)N(R^5)(R^6)$, —$NR^5(CO)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, an aryl radical, or a heteroaryl radical; wherein the alkyl portion of the unbranched $C_1$-$C_4$-alkyl radical, the branched $C_3$-$C_4$-alkyl radical, the $C_3$-$C_6$-cycloalkyl radical, the unbranched —$OC_1$-$C_4$-alkyl, the branched or cyclic —$OC_3$-$C_4$-alkyl, the —$SO_2C_1$-$C_4$-alkyl, the —$(CH_2)_mSO_2C_1$-$C_4$-alkyl, or the —$N(R^5)SO_2C_1$-$C_4$-alkyl, may be independently substituted with up to 5 radical substituents comprising: -D, —F, —Cl, —Br, =O, —OR, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein the aryl radical or the heteroaryl radical may be independently substituted with up to 5 radical substituents comprising: -D, —F, —Cl, —Br, —CN, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical.

5. The compound of claim 1, wherein $R^3$ independently represents —Cl, —$CH_3$, or —$OCH_3$.

6. The compound of claim 1, wherein $R^4$ independently represents —H, -D, —F, —Cl, —Br, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —$N(R^5)(R^6)$, —$(CO)N(R^5)(R^6)$, —$NR^5(CO)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, an aryl radical, or a heteroaryl radical; wherein the alkyl portion of the unbranched $C_1$-$C_4$-alkyl radical, the branched $C_3$-$C_4$-alkyl radical, the $C_3$-$C_6$-cycloalkyl radical, the unbranched —$OC_1$-$C_4$-alkyl, the branched or cyclic —$OC_3$-$C_4$-alkyl, the —$SO_2C_1$-$C_4$-alkyl, the —$(CH_2)_mSO_2C_1$-$C_4$-alkyl, or the —$N(R^5)SO_2C_1$-$C_4$-alkyl, may be independently substituted with up to 5 radical substituents comprising: -D, —F, —Cl, —Br, =O, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, —$OCF_3$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$ haloalkyl radical, or —$OC_1$-$C_2$-haloalkyl radical; and wherein aryl radical or the heteroaryl radical may be independently substituted with up to 5 radical substituents comprising: -D, —F, —Cl, —Br, —CN, —$OR^5$, —$(CH_2)_mOR^5$, —$N(R^5)(R^6)$, —$NR^5(CO)(R^6)$, —$(CH_2)_mN(R^5)(R^6)$, —$SO_2C_1$-$C_4$-alkyl, —$SO_2N(R^5)(R^6)$, —$(CH_2)_mSO_2C_1$-$C_4$-alkyl, —$(CH_2)_mSO_2N(R^5)(R^6)$, —$N(R^5)SO_2C_1$-$C_4$-alkyl, —$(CO)(CH_2)_mR^5$, —$(CO)N(R^5)(R^6)$, —$OCF_3$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical.

7. The compound of claim 1, wherein $R^4$ independently represents —H, -D, —F, —Cl, —$CH_3$, —$OCH_3$, —$OCH_2CH_3$, or —$CF_3$.

8. The compound of claim 1, wherein the compound is a single enantiomer or a single diastereomer.

9. The compound of claim 1, wherein the compound is selected from the group consisting of:
   N-(quinuclidin-3-yl)benzo[d]isoxazol-3-amine;
   7-chloro-N-(quinuclidin-3-yl)benzo[d]isoxazol-3-amine;
   6-chloro-N-(quinuclidin-3-yl)benzo[d]isoxazol-3-amine;
   5-chloro-N-(quinuclidin-3-yl)benzo[d]isoxazol-3-amine;
   6-methyl-N-(quinuclidin-3-yl)benzo[d]isoxazol-3-amine;
   6-cyclopropyl-N-(quinuclidin-3-yl)benzo[d]isoxazol-3-amine;
   6-methoxy-N-(quinuclidin-3-yl)benzo[d]isoxazol-3-amine;
   N-(quinuclidin-3-yl)-6-(trifluoromethyl)benzo[d]isoxazol-3-amine;
   6,7-dichloro-N-(quinuclidin-3-yl)benzo[d]isoxazol-3-amine;
   4-chloro-N-(quinuclidin-3-yl)benzo[d]isoxazol-3-amine;
   6-fluoro-N-(quinuclidin-3-yl)benzo[d]isoxazol-3-amine;
   3-(quinuclidin-3-ylamino)benzo[d]isoxazole-6-carbonitrile;
   6-(methylsulfonyl)-N-(quinuclidin-3-yl)benzo[d]isoxazol-3-amine;
   6-(tert-butyl)-N-(quinuclidin-3-yl)benzo[d]isoxazol-3-amine;
   5,6-dichloro-N-(quinuclidin-3-yl)benzo[d]isoxazol-3-amine;
   N-(quinuclidin-3-yl)-6-(trifluoromethoxy)benzo[d]isoxazol-3-amine;
   7-fluoro-N-(quinuclidin-3-yl)benzo[d]isoxazol-3-amine;
   5-fluoro-N-(quinuclidin-3-yl)benzo[d]isoxazol-3-amine;
   4-fluoro-N-(quinuclidin-3-yl)benzo[d]isoxazol-3-amine;
   7-fluoro-6-methyl-N-(quinuclidin-3-yl)benzo[d]isoxazol-3-amine;
   6,7-difluoro-N-(quinuclidin-3-yl)benzo[d]isoxazol-3-amine;
   5-fluoro-6-methyl-N-(quinuclidin-3-yl)benzo[d]isoxazol-3-amine;
   6-chloro-7-methyl-N-(quinuclidin-3-yl)benzo[d]isoxazol-3-amine;
   6-chloro-7-methoxy-N-(quinuclidin-3-yl)benzo[d]isoxazol-3-amine;
   6-chloro-N-(quinuclidin-3-yl)-7-(trifluoromethyl)benzo[d]isoxazol-3-amine;
   6-chloro-7-cyclopropyl-N-(quinuclidin-3-yl)benzo[d]isoxazol-3-amine;
   4-fluoro-6-chloro-N-(quinuclidin-3-yl)benzo[d]isoxazol-3-amine;
   4,6-dichloro-N-(quinuclidin-3-yl)benzo[d]isoxazol-3-amine;
   7-fluoro-6-methoxy-N-(quinuclidin-3-yl)benzo[d]isoxazol-3-amine;
   7-chloro-6-methoxy-N-(quinuclidin-3-yl)benzo[d]isoxazol-3-amine;
   7-chloro-6-methyl-N-(quinuclidin-3-yl)benzo[d]isoxazol-3-amine;
   6-isopropoxy-N-(quinuclidin-3-yl)benzo[d]isoxazol-3-amine;
   6-ethoxy-N-(quinuclidin-3-yl)benzo[d]isoxazol-3-amine;
   6-chloro-3-(quinuclidin-3-ylamino)benzo[d]isoxazole-7-carbonitrile;
   7-chloro-6-fluoro-N-(quinuclidin-3-yl)benzo[d]isoxazol-3-amine;
   6-(1H-pyrazol-1-yl)-N-(quinuclidin-3-yl)benzo[d]isoxazol-3-amine;
   6-(5-methyl-1,3,4-oxadiazol-2-yl)-N-(quinuclidin-3-yl)benzo[d]isoxazol-3-amine;
   7-methoxy-6-methyl-N-(quinuclidin-3-yl)benzo[d]isoxazol-3-amine;
   6-chloro-7-ethoxy-N-(quinuclidin-3-yl)benzo[d]isoxazol-3-amine;
   6,7-dimethyl-N-(quinuclidin-3-yl)benzo[d]isoxazol-3-amine;
   6-chloro-7-fluoro-N-(quinuclidin-3-yl)benzo[d]isoxazol-3-amine;
   6-chloro-5-fluoro-N-(quinuclidin-3-yl)benzo[d]isoxazol-3-amine; and
   6-bromo-N-(quinuclidin-3-yl)benzo[d]isoxazol-3-amine;
and single enantiomers and pharmaceutically acceptable salts thereof.

10. The compound of claim 1, wherein the compound is selected from the group consisting of:
   (R)-N-(quinuclidin-3-yl)benzo[d]isoxazol-3-amine;
   (S)-N-(quinuclidin-3-yl)benzo[d]isoxazol-3-amine;
   (R)-7-chloro-N-(quinuclidin-3-yl)benzo[d]isoxazol-3-amine;
   (S)-7-chloro-N-(quinuclidin-3-yl)benzo[d]isoxazol-3-amine;
   (R)-6-chloro-N-(quinuclidin-3-yl)benzo[d]isoxazol-3-amine;
   (S)-6-chloro-N-(quinuclidin-3-yl)benzo[d]isoxazol-3-amine;
   (R)-5-chloro-N-(quinuclidin-3-yl)benzo[d]isoxazol-3-amine;
   (S)-5-chloro-N-(quinuclidin-3-yl)benzo[d]isoxazol-3-amine;
   (R)-6-methyl-N-(quinuclidin-3-yl)benzo[d]isoxazol-3-amine;
   (S)-6-methyl-N-(quinuclidin-3-yl)benzo[d]isoxazol-3-amine;
   (R)-6-cyclopropyl-N-(quinuclidin-3-yl)benzo[d]isoxazol-3-amine;
   (S)-6-cyclopropyl-N-(quinuclidin-3-yl)benzo[d]isoxazol-3-amine;
   (R)-6-methoxy-N-(quinuclidin-3-yl)benzo[d]isoxazol-3-amine;

(S)-6-methoxy-N-(quinuclidin-3-yl)benzo[d]isoxazol-3-amine;
(R) N-(quinuclidin-3-yl)-6-(trifluoromethyl)benzo[d]isoxazol-3-amine;
(S)-N-(quinuclidin-3-yl)-6-(trifluoromethyl)benzo[d]isoxazol-3-amine;
(R)-6,7-dichloro-N-(quinuclidin-3-yl)benzo[d]isoxazol-3-amine;
(S)-6,7-dichloro-N-(quinuclidin-3-yl)benzo[d]isoxazol-3-amine;
(R)-4-chloro-N-(quinuclidin-3-yl)benzo[d]isoxazol-3-amine;
(S)-4-chloro-N-(quinuclidin-3-yl)benzo[d]isoxazol-3-amine;
(R)-6-fluoro-N-(quinuclidin-3-yl)benzo[d]isoxazol-3-amine;
(S)-6-fluoro-N-(quinuclidin-3-yl)benzo[d]isoxazol-3-amine;
(R)-3-(quinuclidin-3-ylamino)benzo[d]isoxazole-6-carbonitrile;
(S)-3-(quinuclidin-3-ylamino)benzo[d]isoxazole-6-carbonitrile;
(R)-6-(methylsulfonyl)-N-(quinuclidin-3-yl)benzo[d]isoxazol-3-amine;
(S)-6-(methylsulfonyl)-N-(quinuclidin-3-yl)benzo[d]isoxazol-3-amine;
(R)-6-(tert-butyl)-N-(quinuclidin-3-yl)benzo[d]isoxazol-3-amine;
(S)-6-(tert-butyl)-N-(quinuclidin-3-yl)benzo[d]isoxazol-3-amine;
(R)-5,6-dichloro-N-(quinuclidin-3-yl)benzo[d]isoxazol-3-amine;
(S)-5,6-dichloro-N-(quinuclidin-3-yl)benzo[d]isoxazol-3-amine;
(R) N-(quinuclidin-3-yl)-6-(trifluoromethoxy)benzo[d]isoxazol-3-amine;
(S)-N-(quinuclidin-3-yl)-6-(trifluoromethoxy)benzo[d]isoxazol-3-amine;
(R)-7-fluoro-N-(quinuclidin-3-yl)benzo[d]isoxazol-3-amine;
(S)-7-fluoro-N-(quinuclidin-3-yl)benzo[d]isoxazol-3-amine;
(R)-5-fluoro-N-(quinuclidin-3-yl)benzo[d]isoxazol-3-amine;
(S)-5-fluoro-N-(quinuclidin-3-yl)benzo[d]isoxazol-3-amine;
(R)-4-fluoro-N-(quinuclidin-3-yl)benzo[d]isoxazol-3-amine;
(S)-4-fluoro-N-(quinuclidin-3-yl)benzo[d]isoxazol-3-amine;
(R)-7-fluoro-6-methyl-N-(quinuclidin-3-yl)benzo[d]isoxazol-3-amine;
(S)-7-fluoro-6-methyl-N-(quinuclidin-3-yl)benzo[d]isoxazol-3-amine;
(R)-6,7-difluoro-N-(quinuclidin-3-yl)benzo[d]isoxazol-3-amine;
(S)-6,7-difluoro-N-(quinuclidin-3-yl)benzo[d]isoxazol-3-amine;
(R)-5-fluoro-6-methyl-N-(quinuclidin-3-yl)benzo[d]isoxazol-3-amine;
(S)-5-fluoro-6-methyl-N-(quinuclidin-3-yl)benzo[d]isoxazol-3-amine;
(R)-6-chloro-7-methy-N-(quinuclidin-3-yl)benzo[d]isoxazol-3-amine;
(S)-6-chloro-7-methyl-N-(quinuclidin-3-yl)benzo[d]isoxazol-3-amine;
(R)-6-chloro-7-methoxy-N-(quinuclidin-3-yl)benzo[d]isoxazol-3-amine;
(S)-6-chloro-7-methoxy-N-(quinuclidin-3-yl)benzo[d]isoxazol-3-amine;
(R)-6-chloro-N-(quinuclidin-3-yl)-7-(trifluoromethyl)benzo[d]isoxazol-3-amine;
(S)-6-chloro-N-(quinuclidin-3-yl)-7-(trifluoromethyl)benzo[d]isoxazol-3-amine;
(R)-6-chloro-7-cyclopropyl-N-(quinuclidin-3-yl)benzo[d]isoxazol-3-amine;
(S)-6-chloro-7-cyclopropyl-N-(quinuclidin-3-yl)benzo[d]isoxazol-3-amine;
(R)-4-fluoro-6-chloro-N-(quinuclidin-3-yl)benzo[d]isoxazol-3-amine;
(S)-4-fluoro-6-chloro-N-(quinuclidin-3-yl)benzo[d]isoxazol-3-amine;
(R)-4,6-dichloro-N-(quinuclidin-3-yl)benzo[d]isoxazol-3-amine;
(S)-4,6-dichloro-N-(quinuclidin-3-yl)benzo[d]isoxazol-3-amine;
(R)-7-fluoro-6-methoxy-N-(quinuclidin-3-yl)benzo[d]isoxazol-3-amine;
(S)-7-fluoro-6-methoxy-N-(quinuclidin-3-yl)benzo[d]isoxazol-3-amine;
(R)-7-chloro-6-methoxy-N-(quinuclidin-3-yl)benzo[d]isoxazol-3-amine;
(S)-7-chloro-6-methoxy-N-(quinuclidin-3-yl)benzo[d]isoxazol-3-amine;
(R)-7-chloro-6-methyl-N-(quinuclidin-3-yl)benzo[d]isoxazol-3-amine;
(S)-7-chloro-6-methyl-N-(quinuclidin-3-yl)benzo[d]isoxazol-3-amine;
(R)-6-isopropoxy-N-(quinuclidin-3-yl)benzo[d]isoxazol-3-amine;
(S)-6-isopropoxy-N-(quinuclidin-3-yl)benzo[d]isoxazol-3-amine;
(R)-6-ethoxy-N-(quinuclidin-3-yl)benzo[d]isoxazol-3-amine;
(S)-6-ethoxy-N-(quinuclidin-3-yl)benzo[d]isoxazol-3-amine;
(R)-6-chloro-3-(quinuclidin-3-ylamino)benzo[d]isoxazole-7-carbonitrile;
(S)-6-chloro-3-(quinuclidin-3-ylamino)benzo[d]isoxazole-7-carbonitrile;
(R)-7-chloro-6-fluoro-N-(quinuclidin-3-yl)benzo[d]isoxazol-3-amine;
(S)-7-chloro-6-fluoro-N-(quinuclidin-3-yl)benzo[d]isoxazol-3-amine;
(R)-6-(1H-pyrazol-1-yl)-N-(quinuclidin-3-yl)benzo[d]isoxazol-3-amine;
(S)-6-(1H-pyrazol-1-yl)-N-(quinuclidin-3-yl)benzo[d]isoxazol-3-amine;
(R)-6-(5-methyl-1,3,4-oxadiazol-2-yl)-N-(quinuclidin-3-yl)benzo[d]isoxazol-3-amine;
(S)-6-(5-methyl-1,3,4-oxadiazol-2-yl)-N-(quinuclidin-3-yl)benzo[d]isoxazol-3-amine;
(R)-7-methoxy-6-methyl-N-(quinuclidin-3-yl)benzo[d]isoxazol-3-amine;
(S)-7-methoxy-6-methyl-N-(quinuclidin-3-yl)benzo[d]isoxazol-3-amine;
(R)-6-chloro-7-ethoxy-N-(quinuclidin-3-yl)benzo[d]isoxazol-3-amine;
(S)-6-chloro-7-ethoxy-N-(quinuclidin-3-yl)benzo[d]isoxazol-3-amine;
(R)-6,7-dimethyl-N-(quinuclidin-3-yl)benzo[d]isoxazol-3-amine;

(S)-6,7-dimethyl-N-(quinuclidin-3-yl)benzo[d]isoxazol-3-amine;
(R)-6-chloro-7-fluoro-N-(quinuclidin-3-yl)benzo[d]isoxazol-3-amine;
(S)-6-chloro-7-fluoro-N-(quinuclidin-3-yl)benzo[d]isoxazol-3-amine;
(R)-6-chloro-5-fluoro-N-(quinuclidin-3-yl)benzo[d]isoxazol-3-amine;
(S)-6-chloro-5-fluoro-N-(quinuclidin-3-yl)benzo[d]isoxazol-3-amine;
(R)-6-bromo-N-(quinuclidin-3-yl)benzo[d]isoxazol-3-amine; and
(S)-6-bromo-N-(quinuclidin-3-yl)benzo[d]isoxazol-3-amine;
and pharmaceutically acceptable salts thereof.

11. The compound of claim 1, wherein the compound is selected from the group consisting of:
(R)-6-chloro-N-(quinuclidin-3-yl)benzo[d]isoxazol-3-amine;
(S)-6-chloro-N-(quinuclidin-3-yl)benzo[d]isoxazol-3-amine;
(R)-6-methyl-N-(quinuclidin-3-yl)benzo[d]isoxazol-3-amine;
(R)-6-methoxy-N-(quinuclidin-3-yl)benzo[d]isoxazol-3-amine;
(S)-6-methoxy-N-(quinuclidin-3-yl)benzo[d]isoxazol-3-amine;
(R)-6,7-dichloro-N-(quinuclidin-3-yl)benzo[d]isoxazol-3-amine;
(R)-7-fluoro-6-methyl-N-(quinuclidin-3-yl)benzo[d]isoxazol-3-amine;
(R)-5-fluoro-6-methyl-N-(quinuclidin-3-yl)benzo[d]isoxazol-3-amine;
(R)-6-chloro-7-methyl-N-(quinuclidin-3-yl)benzo[d]isoxazol-3-amine;
(R)-6-chloro-7-methoxy-N-(quinuclidin-3-yl)benzo[d]isoxazol-3-amine;
(R)-6-chloro-N-(quinuclidin-3-yl)-7-(trifluoromethyl)benzo[d]isoxazol-3-amine;
(R)-6-chloro-7-fluoro-N-(quinuclidin-3-yl)benzo[d]isoxazol-3-amine; and
(R)-6-chloro-5-fluoro-N-(quinuclidin-3-yl)benzo[d]isoxazol-3-amine;
and pharmaceutically acceptable salts thereof.

12. The compound of claim 1, wherein the compound is selected from the group consisting of:
(R)-6-chloro-N-(quinuclidin-3-yl)benzo[d]isoxazol-3-amine;
(R)-6-methyl-N-(quinuclidin-3-yl)benzo[d]isoxazol-3-amine;
(R)-6,7-dichloro-N-(quinuclidin-3-yl)benzo[d]isoxazol-3-amine;
(R)-7-fluoro-6-methyl-N-(quinuclidin-3-yl)benzo[d]isoxazol-3-amine;
(R)-6-chloro-7-methyl-N-(quinuclidin-3-yl)benzo[d]isoxazol-3-amine;
(R)-6-chloro-7-methoxy-N-(quinuclidin-3-yl)benzo[d]isoxazol-3-amine;
(R)-6-chloro-N-(quinuclidin-3-yl)-7-(trifluoromethyl)benzo[d]isoxazol-3-amine; and
(R)-6-chloro-7-fluoro-N-(quinuclidin-3-yl)benzo[d]isoxazol-3-amine;
and pharmaceutically acceptable salts thereof.

13. A pharmaceutical composition, comprising:
i) the compound, or pharmaceutically acceptable salt thereof, of claim 1; and
ii) at least one pharmaceutically acceptable carrier, excipient or diluent.

* * * * *